(12) United States Patent
Hatakeyama et al.

(10) Patent No.: US 11,711,970 B2
(45) Date of Patent: *Jul. 25, 2023

(54) ORGANIC ELECTROLUMINESCENT DEVICE

(71) Applicants: KWANSEI GAKUIN EDUCATIONAL FOUNDATION, Hyogo (JP); SK MATERIALS JNC CO., LTD., Gyeonggi-Do (KR)

(72) Inventors: Takuji Hatakeyama, Hyogo (JP); Yukihiro Fujita, Chiba (JP); Guofang Wang, Chiba (JP)

(73) Assignees: KWANSEI GAKUIN EDUCATIONAL FOUNDATION, Hyogo (JP); SK MATERIALS JNC CO., LTD., Gyeonggi-Do (KR)

( * ) Notice: Subject to any disclaimer, the term of this patent is extended or adjusted under 35 U.S.C. 154(b) by 553 days.

This patent is subject to a terminal disclaimer.

(21) Appl. No.: 16/778,121

(22) Filed: Jan. 31, 2020

(65) Prior Publication Data

US 2020/0259096 A1   Aug. 13, 2020

(30) Foreign Application Priority Data

Feb. 12, 2019 (JP) .................................. 2019-022857

(51) Int. Cl.
*H10K 85/60* (2023.01)
*C09K 11/06* (2006.01)
(Continued)

(52) U.S. Cl.
CPC .......... *H10K 85/626* (2023.02); *C07C 15/28* (2013.01); *C07C 211/61* (2013.01); *C07D 307/77* (2013.01); *C07D 307/91* (2013.01); *C07F 5/027* (2013.01); *C07F 7/081* (2013.01); *C09K 11/06* (2013.01); *H10K 50/11* (2023.02); *H10K 85/322* (2023.02); *H10K 85/40* (2023.02);
(Continued)

(58) Field of Classification Search
CPC ............. H01L 51/0058; H01L 51/0052; H01L 51/006; H01L 51/0061; H01L 51/0073; H01L 51/008; H01L 51/0094; H01L 51/5012; H01L 51/0054; H01L 51/5024; H01L 51/5048; C07C 15/28; C07C 211/61; C07C 2603/24; C07C 2603/40; C07C 2603/48; C07C 2603/50; C07D 307/77; C07D 307/91; C07F 5/027; C07F 7/081; C09K 11/06; C09K 2211/1011; C09K 2211/1014; C09K 2211/1018
See application file for complete search history.

(56) References Cited

U.S. PATENT DOCUMENTS 10,811,613 B2    10/2020   Hatakeyama et al.
2014/0058099 A1*   2/2014   Wakamiya .......... H01L 51/0072
                                                        544/347
(Continued)

FOREIGN PATENT DOCUMENTS

JP      2008-291006     12/2008
JP      2012-104806      5/2012
(Continued)

OTHER PUBLICATIONS

Nat. Photonics 13, 540-546 (2019). https://doi.org/10.1038/s41566-019-0415-5. (Year: 2019).*

(Continued)

*Primary Examiner* — Dawn L Garrett
(74) *Attorney, Agent, or Firm* — Wenderoth, Lind & Ponack, L.L.P.

(57) ABSTRACT

To provide an organic electroluminescent device in which energy efficiency is improved. An organic electroluminescent device includes a pair of electrode layers formed of an anode layer and a cathode layer, and a luminescent layer arranged between the pair of electrode layers, in which the luminescent layer includes a host material and a dopant material, and the dopant material is an anthracene-based compound represented by formula (1), and the luminescent layer further includes a polycyclic aromatic compound represented by formula (2) or a multimer of a polycyclic aromatic compound having a plurality of structures represented by formula (2).

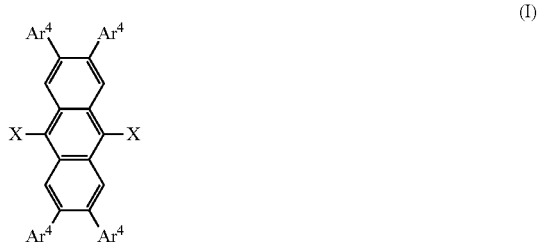

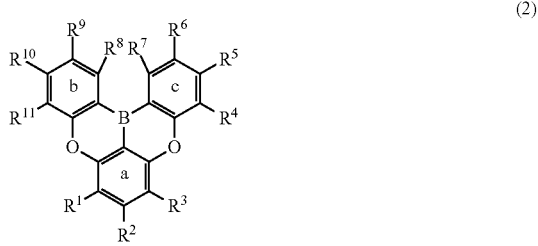

20 Claims, 1 Drawing Sheet

(51) Int. Cl.
  *C07D 307/77* (2006.01)
  *C07F 5/02* (2006.01)
  *C07C 211/61* (2006.01)
  *C07F 7/08* (2006.01)
  *C07D 307/91* (2006.01)
  *C07C 15/28* (2006.01)
  *H10K 50/11* (2023.01)
  *H10K 85/40* (2023.01)
  *H10K 85/30* (2023.01)
  *H10K 50/12* (2023.01)

(52) U.S. Cl.
  CPC ......... *H10K 85/615* (2023.02); *H10K 85/633* (2023.02); *H10K 85/636* (2023.02); *H10K 85/6574* (2023.02); *C07C 2603/24* (2017.05); *C07C 2603/40* (2017.05); *C07C 2603/48* (2017.05); *C07C 2603/50* (2017.05); *C09K 2211/1011* (2013.01); *C09K 2211/1014* (2013.01); *C09K 2211/1018* (2013.01); *H10K 50/12* (2023.02); *H10K 85/622* (2023.02)

(56) References Cited

U.S. PATENT DOCUMENTS

| | | |
|---|---|---|
| 2014/0319510 A1 | 10/2014 | Kageyama |
| 2015/0236274 A1 | 8/2015 | Hatakeyama et al. |
| 2018/0301629 A1 | 10/2018 | Hatakeyama et al. |
| 2019/0207112 A1 | 7/2019 | Hatakeyama et al. |
| 2020/0176680 A1* | 6/2020 | Hatakeyama .......... C09K 11/06 |

FOREIGN PATENT DOCUMENTS

| | | |
|---|---|---|
| JP | 2016-88927 | 5/2016 |
| WO | 2015/102118 | 7/2015 |
| WO | 2016/152544 | 9/2016 |
| WO | 2017/126443 | 7/2017 |
| WO | 2017/188111 | 11/2017 |

OTHER PUBLICATIONS

Hirai, M., Tanaka, N., Sakai, M., & Yamaguchi, S. (2019). Structurally constrained boron-, nitrogen-, silicon-, and phosphorus-centered polycyclic π-conjugated systems. Chemical reviews, 119(14), 8291-8331. (Year: 2019).*

Office Action dated Jun. 14, 2022 in Japanese Patent Application No. 2019-022857, with English-language translation.

Office Action dated Dec. 20, 2022 in corresponding Japanese Patent Application No. 2019-022857, with English language machine translation.

* cited by examiner

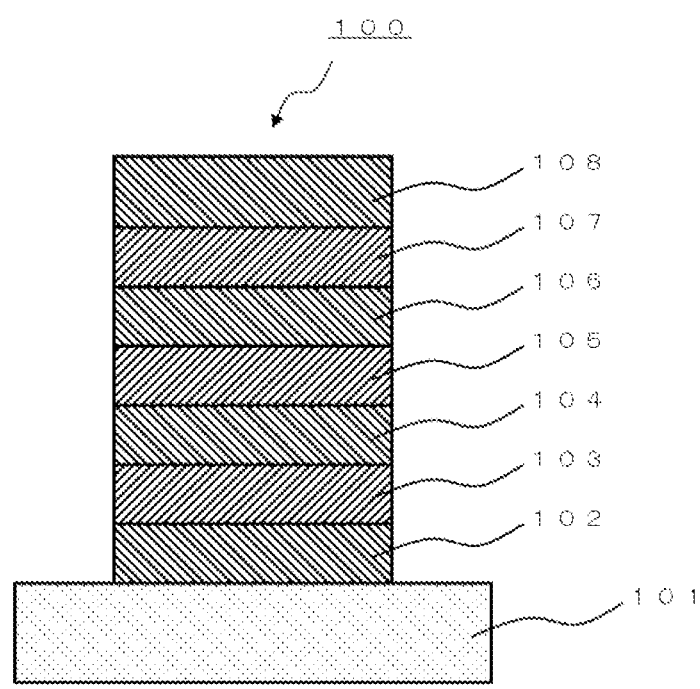

ORGANIC ELECTROLUMINESCENT DEVICE

CROSS-REFERENCE TO RELATED APPLICATIONS

This application is related to and claims priority under 35 U.S.C § 119 to Japanese Patent Application No. 2019-22857 filed on Feb. 12, 2019, the disclosure of which is expressly incorporated by reference herein in its entirety.

TECHNICAL FIELD

The invention relates to an organic electroluminescent device, and a display apparatus and a lighting apparatus.

BACKGROUND ART

A display apparatus using a luminescent device causing electroluminescence can achieve power saving or thickness reduction, and therefore various studies have been conducted so far thereon. Further, an organic electroluminescent device (hereinafter, referred to as an organic EL device in several cases) formed of an organic material has been actively studied because weight reduction or large size is easily achieved. In particular, active studies have been conducted so far on development of an organic material having luminescence characteristics for blue light which is one of primary colors of light, or the like, and a combination of a plurality of materials having optimum luminescence characteristics, irrespective of whether the organic material is a high-molecular-weight compound or a low-molecular-weight compound.

The organic EL device has a structure configured of a pair of electrodes formed of an anode and a cathode, and a single layer or a plurality of layers containing an organic compound arranged between the pair of electrodes. The layer including the organic compound includes a luminescent layer, a charge transport and injection layer for transporting or injecting a charge such as a hole and an electron, and various organic materials suitable for the layers have been developed.

As a luminescent layer material, a benzofluorene-based compound and the like have been developed (Patent literature No. 1 and the like). Moreover, in recent years, a polycyclic aromatic compound obtained by fusing a plurality of aromatic rings using boron or the like as a central atom has been reported (Patent literature No. 2). Further, Patent literature No. 3 reports that an excellent organic EL device is obtained by arranging a luminescent layer including, as a dopant material, the polycyclic aromatic compound, and further containing, as a host material, a specific anthracene-based compound between a pair of electrodes to form an organic EL device.

CITATION LIST

Patent Literature

Patent literature No. 1: JP 2008-291006 A.
Patent literature No. 2: WO 2015/102118 A.
Patent literature No. 3: WO 2016/152544 A.

SUMMARY OF INVENTION

Technical Problem

As disclosed in Patent literature described above, as a material used for an organic EL device, various materials and a combination thereof have been developed. Further, a specific combination or an additive material is studies, whereby provision of an organic EL device having desired coloring characteristics and also having further practically preferred characteristics is expected. An object of the invention is to provide an organic EL device having improved energy efficiency.

Solution to Problem

The present inventors have diligently continued to conduct studies for achieving the object described above, and as a result, have found that, in an organic EL device configured by arranging a luminescent layer including an anthracene-based compound as a host material, and a dopant material between a pair of electrodes, a polycyclic aromatic compound having a specific structure is added to the luminescent layer to thus improve energy efficiency, and have completed the invention based on the finding.

Item 1. An organic electroluminescent device comprising a pair of electrode layers formed of an anode layer and a cathode layer, and a luminescent layer arranged between the pair of electrode layers, wherein the luminescent layer includes a host material and a dopant material, the host material contains an anthracene-based compound represented by formula (1), and the luminescent layer further includes a polycyclic aromatic compound represented by formula (2) or a multimer of a polycyclic aromatic compound having a plurality of structures represented by formula (2):

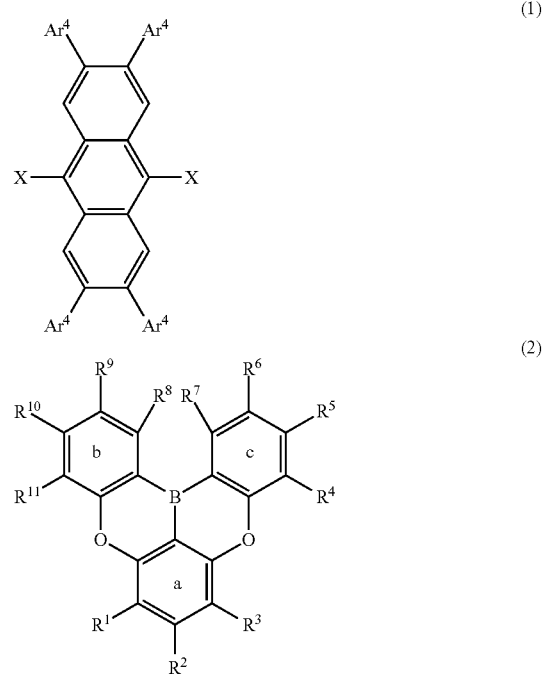

wherein, in formula (1),

X and $Ar^4$ are independently hydrogen, aryl which may be subjected to substitution, heteroaryl which may be subjected to substitution, diarylamino which may be subjected to substitution, diheteroarylamino which may be subjected to substitution, arylheteroarylamino which may be subjected to substitution, alkyl which may be subjected to substitution, alkenyl which may be subjected to substitution, alkoxy which may be subjected to substitution, aryloxy which may be subjected to substitution, arylthio which may be subjected to substitution, or silyl which may be subjected to substitution, and a case where all of X and $Ar^4$ simultaneously become hydrogen is excluded, and at least one hydrogen in the compound represented by formula (1) may be replaced by halogen, cyano, deuterium, or heteroaryl which may be subjected to substitution, in formula (2), $R^1$, $R^2$, $R^3$, $R^4$, $R^5$, $R^6$, $R^7$, $R^8$, $R^9$, $R^{10}$ and $R^{11}$ are independently hydrogen, aryl, heteroaryl, diarylamino, diheteroarylamino, arylheteroarylamino, alkyl, cycloalkyl, alkoxy, trialkylsilyl or aryloxy, and at least one hydrogen in the groups may be replaced by aryl, heteroaryl or alkyl, and adjacent groups of $R^1$ to $R^{21}$ may be bonded to each other to form an aryl ring or a heteroaryl ring together with an a ring, a b ring or a c ring, and at least one hydrogen in the ring formed may be replaced by aryl, heteroaryl, diarylamino, diheteroarylamino, arylheteroarylamino, alkyl, alkoxy or aryloxy, and at least one hydrogen in the groups may be replaced by aryl, heteroaryl or alkyl, and at least one hydrogen in the compound represented by formula (2) may be replaced by halogen or deuterium.

Item 2. The organic electroluminescent device according to item 1, wherein, in formula (1), X is independently a group represented by formula (1-X1), (1-X2) or (1-X3), $Ar^4$ is independently hydrogen, phenyl, biphenylyl, terphenylyl, naphthyl, or silyl which is subjected to substitution for alkyl having 1 to 4 carbons, and at least one hydrogen in the compound represented by formula (1) may be replaced by halogen, cyano, deuterium, or a group represented by formula (A):

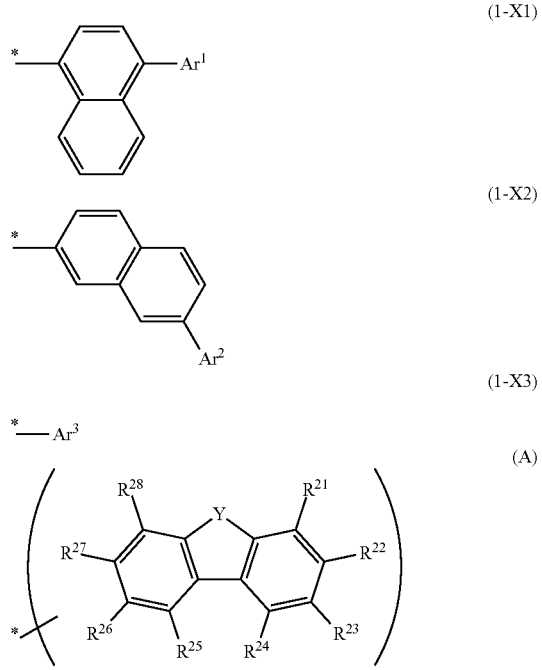

wherein, in formulas (1-X1), (1-X2) and (1-X3), $Ar^1$, $Ar^2$ and $Ar^3$ are independently hydrogen (excluding $Ar^3$), phenyl, biphenylyl, terphenylyl, quaterphenylyl, naphthyl, phenanthryl, fluorenyl, benzofluorenyl, chrysenyl, triphenylenyl, pyrenyl, or a group represented by formula (A), and at least one hydrogen in $Ar^3$ may be further replaced by phenyl, biphenylyl, terphenylyl, naphthyl, phenanthryl, fluorenyl, chrysenyl, triphenylenyl, pyrenyl, or a group represented by formula (A), a naphthylene site in formulas (1-X1) and (1-X2) may be fused by one benzene ring, a group represented by formula (1-X1), (1-X2) or (1-X3) is bonded to an anthracene ring of formula (1) at a position "*", in formula (A), Y is —O—, —S— or >N—$R^{29}$, and $R^{29}$ is hydrogen, or aryl which may be subjected to substitution, $R^{21}$ to $R^{28}$ are independently hydrogen, alkyl which may be subjected to substitution, aryl which may be subjected to substitution, heteroaryl which may be subjected to substitution, alkoxy which may be subjected to substitution, aryloxy which may be subjected to substitution, arylthio which may be subjected to substitution, trialkylsilyl, amino which may be subjected to substitution, halogen, hydroxy or cyano, adjacent groups of $R^{21}$ to $R^{28}$ may be bonded to each other to form a hydrocarbon ring, an aryl ring or a heteroaryl ring, and a group represented by formula (A) is bonded, by applying any of positions in the structure as a bonding position "*," to a naphthalene ring of formula (1-X1) or (1-X2), a single bond of formula (1-X3) or $Ar^3$ of formula (1-X3), or is replaced by at least one hydrogen in the compound represented by formula (1).

Item 3. The organic electroluminescent device according to item 1 or 2, wherein, in formula (1), X is independently a group represented by formula (1-X1), (1-X2) or (1-X3), $Ar^4$ is independently hydrogen, phenyl or naphthyl, and at least one hydrogen in the compound represented by formula (1) may be replaced by halogen, cyano or deuterium:

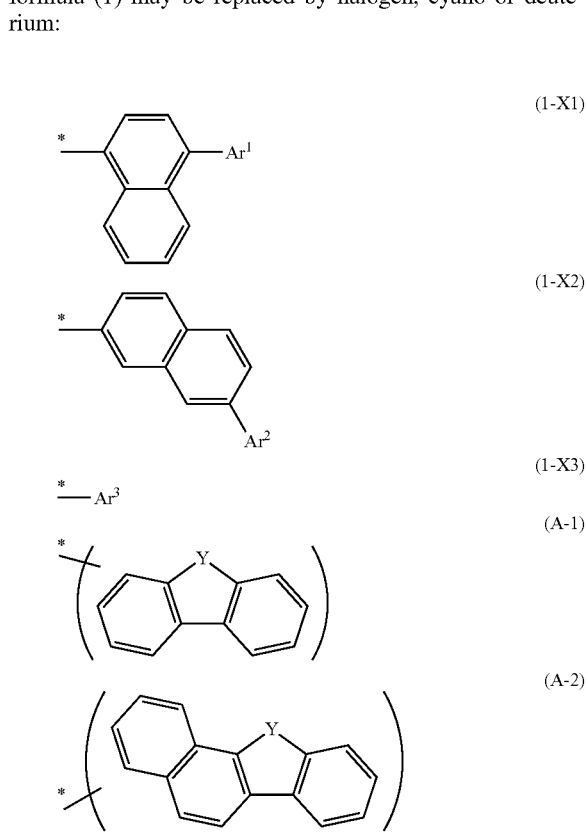

-continued (A-3)
(A-4)
(A-5)
(A-6)
(A-7)
(A-8)
(A-9)
(A-10)

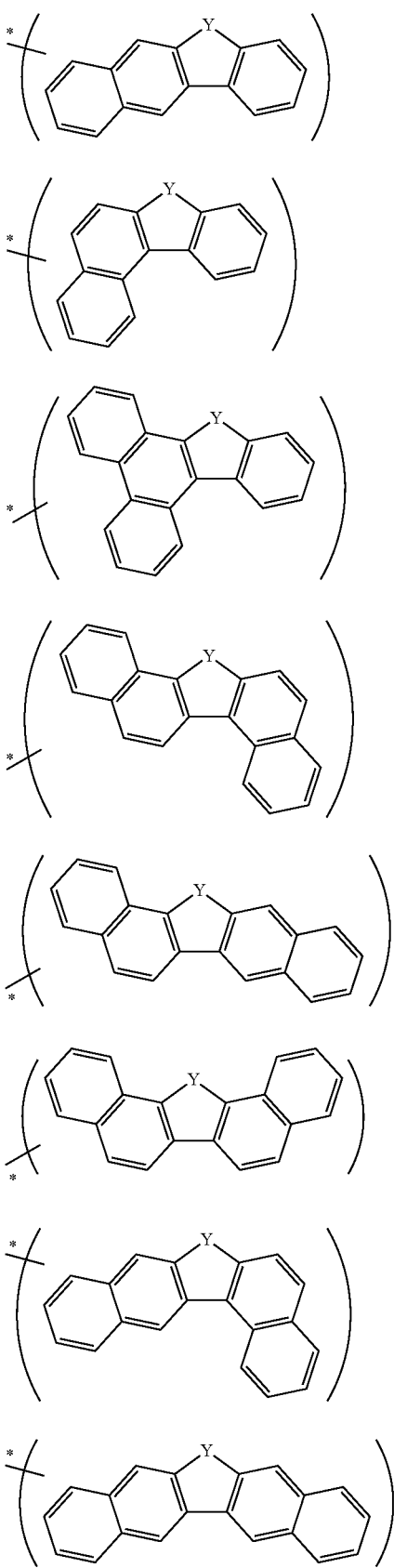

-continued (A-11)

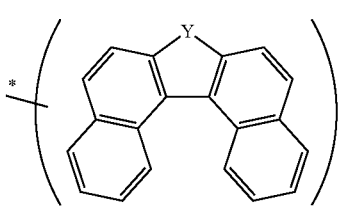

wherein, in formulas (1-X1), (1-X2) and (1-X3), $Ar^1$, $Ar^2$ and $Ar^3$ are independently hydrogen (excluding $Ar^3$), phenyl, biphenylyl, terphenylyl, naphthyl, phenanthryl, fluorenyl, chrysenyl, triphenylenyl, pyrenyl, or a group represented by any of formulas (A-1) to (A-11), at least one hydrogen in $Ar^3$ may be further replaced by phenyl, biphenylyl, terphenylyl, naphthyl, phenanthryl, fluorenyl, chrysenyl, triphenylenyl, pyrenyl, or a group represented by any of formulas (A-1) to (A-11), a group represented by formula (1-X1), (1-X2) or (1-X3) is bonded to an anthracene ring of formula (1) at a position "*", in formulas (A-1) to (A-11), Y is —O—, —S— or >N—$R^{29}$, and $R^{29}$ is hydrogen or aryl, and at least one hydrogen in the groups represented by formulas (A-1) to (A-11) may be replaced by alkyl, aryl, heteroaryl, alkoxy, aryloxy, arylthio, trialkylsilyl, diaryl-substituted amino, diheteroaryl-substituted amino, arylheteroaryl-substituted amino, halogen, hydroxy or cyano, and a group represented by formulas (A-1) to (A-11) is bonded, by applying any of positions in the structure as a bonding position "*," to a naphthalene ring of formula (1-X1) or (1-X2), a single bond of formula (1-X3), or $Ar^3$ of formula (1-X3).

Item 4. The organic electroluminescent device according to item 3, wherein, in formula (1), X is independently a group represented by formula (1-X1), (1-X2) or (1-X3), and a group represented by formula (1-X1), (1-X2) or (1-X3) is bonded to an anthracene ring of formula (1) at a position "*," and $Ar^1$, $Ar^2$ and $Ar^3$ are independently hydrogen (excluding $Ar^3$), phenyl, biphenylyl, terphenylyl, naphthyl, phenanthryl, fluorenyl, or a group represented by any of formulas (A-1) to (A-4), and at least one hydrogen in $Ar^3$ may be further replaced by phenyl, naphthyl, phenanthryl, fluorenyl, or a group represented by any of formulas (A-1) to (A-4), and $Ar^4$ is independently hydrogen, phenyl or naphthyl.

Item 5. The organic electroluminescent device according to any one of items 1 to 4, wherein the anthracene-based compound is represented by the following structural formula:

(1-199)

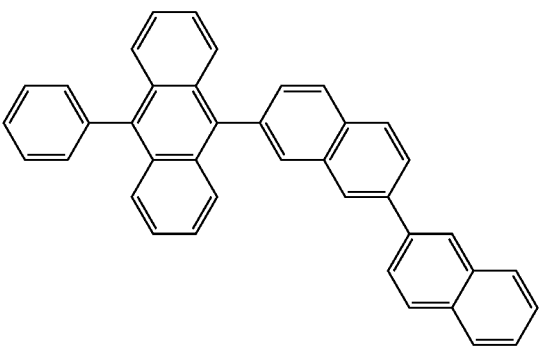

(1-192)
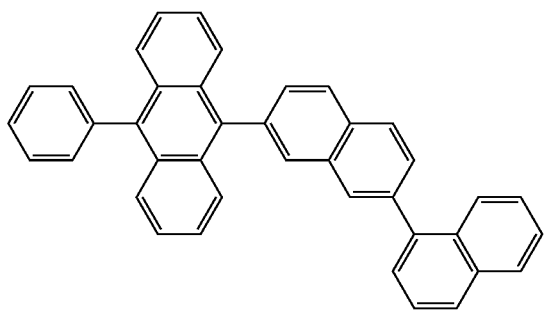

(1-222)
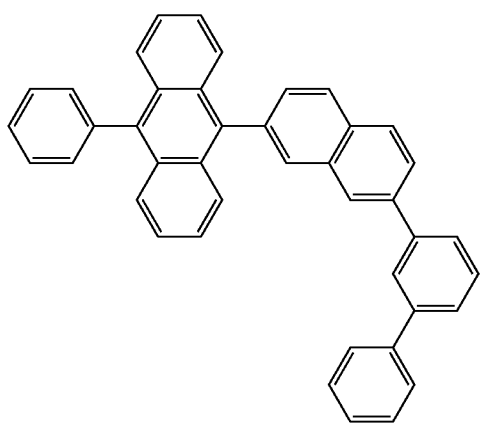

(1-221)
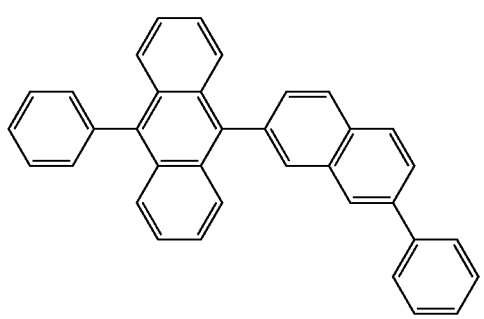

(1-195)
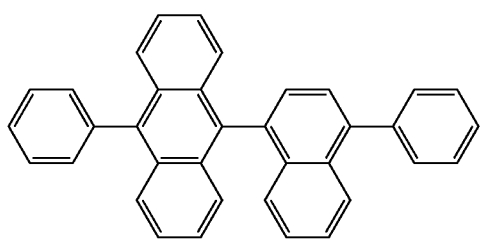

(1-134-O)
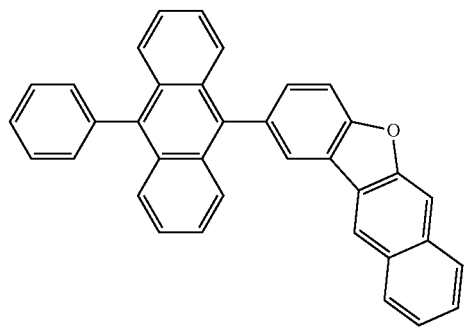

Item 6. The organic electroluminescent device according to any one of items 1 to 5, wherein the polycyclic aromatic compound represented by formula (2) is a polycyclic aromatic compound represented by formula (2A):

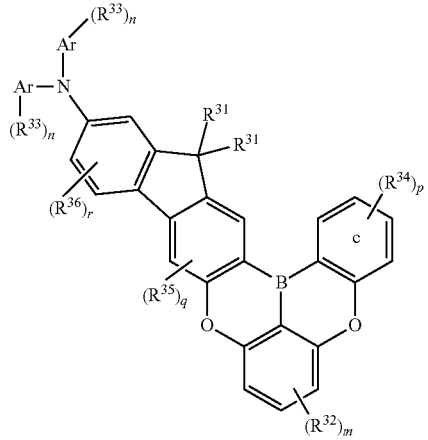

(2A)

wherein, in formula (2A),

Ar is independently aryl or heteroaryl, $R^{31}$ to $R^{36}$ are independently hydrogen, aryl, heteroaryl, diarylamino, diheteroarylamino, arylheteroarylamino, alkyl, cycloalkyl, alkoxy, trialkylsilyl or aryloxy, and at least one hydrogen in the groups may be replaced by aryl, heteroaryl, diarylamino or alkyl, when $R^{34}$ is plural, adjacent $R^{34}$'s may be bonded to each other to form an aryl ring or a heteroaryl ring together with a c ring, and at least one hydrogen in the ring formed may be replaced by aryl, heteroaryl, diarylamino, diheteroarylamino, arylheteroarylamino, alkyl, alkoxy, trialkylsilyl or aryloxy, and at least one hydrogen in the groups may be replaced by aryl, heteroaryl, diarylamino or alkyl, when $R^{33}$ and $R^{36}$ are adjacent to each other, both may be bonded by —O—, —S—, —C(—R)$_2$— or a single bond, and R of the —C(—R)$_2$— is hydrogen or alkyl having 1 to 6 carbons, m is an integer from 0 to 3, and n is independently an integer from 0 to the maximum replaceable number to Ar, p is an integer from 0 to 4, q is independently an integer from 0 to 2, and r is independently an integer from 0 to 3, and at least one hydrogen in the compound represented by formula (2A) may be replaced by halogen or deuterium.

Item 7. The organic electroluminescent device according to item 6, wherein, in formula (2A), Ar is independently aryl, $R^{31}$ to $R^{34}$ are independently hydrogen, aryl, heteroaryl, alkyl, cycloalkyl, alkoxy, trialkylsilyl or aryloxy, and at least one hydrogen in the groups may be replaced by aryl, heteroaryl or alkyl, when $R^{34}$ is plural, adjacent $R^{34}$'s may be bonded to each other to form an aryl ring or a heteroaryl ring together with a c ring, and at least one hydrogen in the ring formed may be replaced by aryl, heteroaryl, alkyl, alkoxy, trialkylsilyl or aryloxy, and at least one hydrogen in the groups may be replaced by aryl, heteroaryl or alkyl, and q is 0 and r is 0.

Item 8. The organic electroluminescent device according to any one of items 1 to 7, wherein the polycyclic aromatic compound represented by formula (2) is a polycyclic aromatic compound represented by formula (2A'):

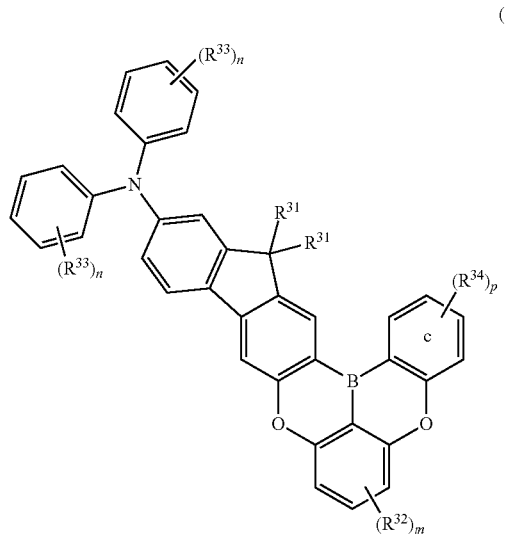

(2A')

wherein, in formula (2A'), $R^{31}$ to $R^{34}$ are independently hydrogen, aryl, heteroaryl, alkyl, cycloalkyl, alkoxy, trialkylsilyl or aryloxy, and at least one hydrogen in the groups may be replaced by aryl, heteroaryl or alkyl, when $R^{34}$ is plural, adjacent $R^{34}$'s may be bonded to each other to form an aryl ring or a heteroaryl ring together with a c ring, and at least one hydrogen in the ring formed may be replaced by aryl, heteroaryl, alkyl, alkoxy, trialkylsilyl or aryloxy, and at least one hydrogen in the groups may be replaced by aryl, heteroaryl or alkyl, and m is an integer from 0 to 3, n is independently an integer from 0 to the maximum replaceable number to Ar, and p is an integer from 0 to 4.

Item 9. The organic electroluminescent device according to item 8, wherein, in formula (2A'), $R^{31}$ is independently hydrogen, aryl having 6 to 30 carbons or alkyl having 1 to 24 carbons, $R^{32}$ to $R^{34}$ are independently hydrogen, aryl having 6 to 30 carbons, heteroaryl having 2 to 30 carbons, alkyl having 1 to 24 carbons, alkoxy having 1 to 24 carbons, trialkylsilyl having alkyl having 1 to 4 carbons, or aryloxy having 6 to 30 carbons, and at least one hydrogen in the groups may be replaced by aryl having 6 to 16 carbons, heteroaryl having 2 to 25 carbons or alkyl having 1 to 18 carbons, and m is an integer from 0 to 3, n is independently an integer from 0 to 6, and p is an integer from 0 to 2.

Item 10. The organic electroluminescent device according to item 8, wherein, in formula (2A'), $R^{31}$ is independently hydrogen, aryl having 6 to 12 carbons or alkyl having 1 to 12 carbons, $R^{32}$ to $R^{34}$ are independently hydrogen, aryl having 6 to 30 carbons, heteroaryl having 2 to 30 carbons, alkyl having 1 to 24 carbons or trialkylsilyl having alkyl having 1 to 4 carbons, and m is 0 or 1, n is independently 0 or 1, and p is 0 or 1.

Item 11. The organic electroluminescent device according to any one of items 1 to 10, wherein the polycyclic aromatic compound represented by formula (2) is a polycyclic aromatic compound represented by formula (2A-1):

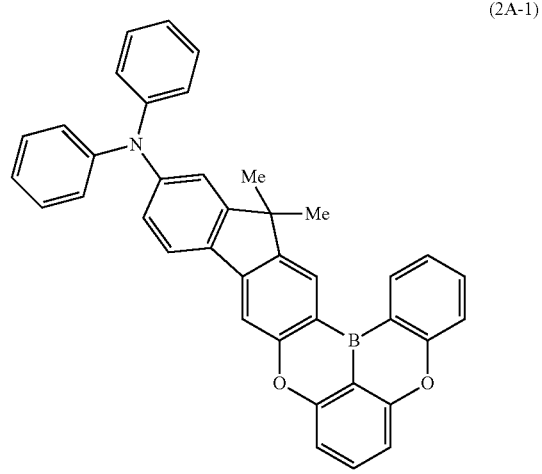 [SMILES: CC1(C)c2cc(N(c3ccccc3)c3ccccc3)ccc2-c2cc3c(cc21)B1c2ccccc2Oc2cccc(c21)O3]

(2A-1)

wherein, in formula (2A-1), "Me" represents methyl.

Item 12. The organic electroluminescent device according to any one of items 1 to 11, wherein the dopant material is a polycyclic aromatic compound represented by formula (3), or a dimer or a trimer of a polycyclic aromatic compound having a plurality of structures represented by formula (3), or a compound represented by formula (4):

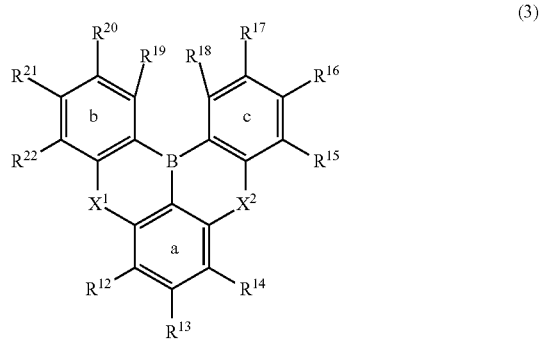

(3)

(4)

wherein, in formula (3), $R^{12}$ to $R^{22}$ are independently hydrogen, aryl, heteroaryl, diarylamino, diheteroarylamino, arylheteroarylamino, alkyl, cycloalkyl, alkoxy or aryloxy, and at least one hydrogen in the groups may be replaced by aryl, heteroaryl or alkyl, and adjacent groups of $R^{12}$ to $R^{22}$ may be bonded to each other to form an aryl ring or a heteroaryl ring together with an a ring, a b ring or a c ring, and at least one hydrogen in the ring formed may be replaced by aryl, heteroaryl, diarylamino, diheteroarylamino, arylheteroarylamino, alkyl, alkoxy or aryloxy, and at least one hydrogen in the groups may be replaced by aryl, heteroaryl or alkyl, and $X^1$ and $X^2$ are independently >O, >N—R, >C(—R)$_2$, >S or >Se, in which, at least one of $X^1$ and $X2$ is >N—R, and R of the >N—R is aryl having 6 to 12 carbons which may be subjected to substitution for alkyl having 1 to 6 carbons, heteroaryl having 2 to 15 carbons which may be subjected to substitution for alkyl having 1 to 6 carbons, or alkyl having 1 to 6 carbons, and R of the >C(—R)$_2$ is hydrogen, aryl having 6 to 12 carbons which may be subjected to substitution for alkyl having 1 to 6 carbons, or alkyl having 1 to 6 carbons, and R of the >N—R and/or R of the >C(—R)$_2$ may be bonded with the a ring, the b ring and/or the c ring by —O—, —S—, —C(—R)$_2$— or a single bond, and R of the —C(—R)$_2$— is alkyl having 1 to 6 carbons, and at least one hydrogen in the compound or the structure represented by formula (3) may be replaced by deuterium, cyano or halogen, wherein, in formula (4), Z is a pyrene ring, a benzofluorene ring or a chrysene ring which may be subjected to substitution, and $Ar^4$, $Ar^5$ $Ar^6$ and $Ar^7$ are independently hydrogen, aryl, heteroaryl, diarylamino, diheteroarylamino, arylheteroarylamino, alkyl, cycloalkyl, alkoxy or aryloxy, and at least one hydrogen in the groups may be replaced by aryl, heteroaryl, alkyl, cycloalkyl, alkoxy, aryloxy or trialkylsilyl, and adjacent groups of $Ar^4$ to $Ar^7$ may be bonded to each other to form a ring, and at least one hydrogen in the ring formed may be replaced by aryl, heteroaryl, diarylamino, diheteroarylamino, arylheteroarylamino, alkyl, alkoxy, aryloxy or trialkylsilyl, and u is an integer from 0 to 3, and at least one hydrogen in the compound represented by formula (4) may be replaced by halogen, cyano or deuterium.

Item 13. The organic electroluminescent device according to item 12, wherein, in formula (3), $R^{12}$ to $R^{22}$ are independently hydrogen, aryl having 6 to 30 carbons which may be subjected to substitution for alkyl having 1 to 6 carbons, heteroaryl having 2 to 30 carbons which may be subjected to substitution for alkyl having 1 to 6 carbons, diarylamino (in which, aryl is aryl having 6 to 12 carbons which may be subjected to substitution for alkyl having 1 to 6 carbons), alkyl having 1 to 24 carbons or cycloalkyl having 3 to 24 carbons, and adjacent groups of $R^{12}$ to $R^{22}$ may be bonded to each other to form an aryl ring having 9 to 16 carbons or a heteroaryl ring having 6 to 15 carbons together with an a ring, a b ring or a c ring, and at least one hydrogen in the ring formed may be replaced by aryl having 6 to 30 carbons which may be subjected to substitution for alkyl having 1 to 6 carbons, a heteroaryl having 2 to 30 carbons which may be subjected to substitution for alkyl having 1 to 6 carbons, diarylamino (in which, aryl is aryl having 6 to 12 carbons which may be subjected to substitution for alkyl having 1 to 6 carbons), or alkyl having 1 to 24 carbons, and $X^1$ and $X^2$ are independently >O, >N—R, >C(—R)$_2$ or >S, in which, at least one of $X^1$ and $X^2$ is >N—R, and R of the >N—R is aryl having 6 to 10 carbons which may be subjected to substitution for alkyl having 1 to 4 carbons, heteroaryl having 2 to 12 carbons which may be subjected to substitution for alkyl having 1 to 4 carbons or alkyl having 1 to 4 carbons, and R of the >C(—R)$_2$ is hydrogen, aryl having 6 to 10 carbons which may be subjected to substitution for alkyl having 1 to 4 carbon, or alkyl having 1 to 4 carbons, at least one hydrogen in the compound or the structure represented by formula (3) may be replaced by deuterium, cyano or halogen, and in the case of a multimer, the multimer is a dimer having two structures represented by formula (3), and the compound represented by formula (4) is a compound represented by each of formulas (4-A) to (4-C):

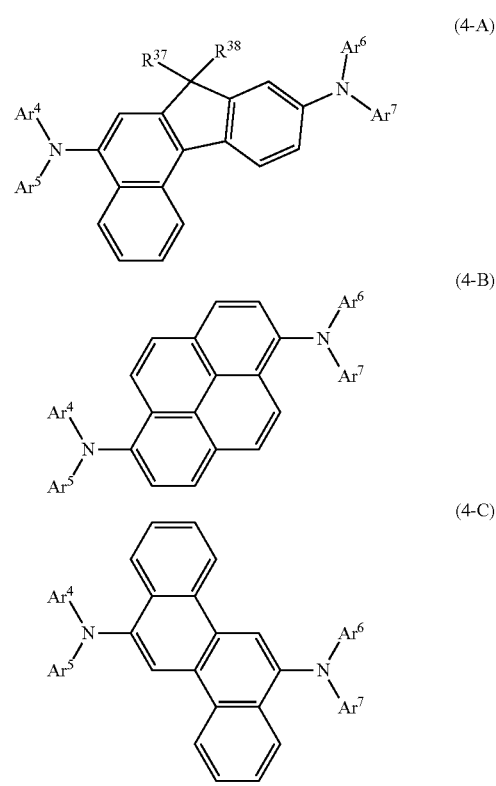

wherein, in formulas (4-A) to (4-C), $Ar^4$ $Ar^5$, $Ar^6$ and $Ar^7$ are independently aryl having 6 to 30 carbons or heteroaryl having 5 to 30 carbons, and at least one hydrogen in the groups may be replaced by aryl having 6 to 10 carbons, heteroaryl having 5 to 12 carbons, alkyl having 1 to 6 carbons, cycloalkyl having 3 to 10 carbons, alkoxy having 1 to 6 carbons, aryloxy having 6 to 10 carbon or trialkylsilyl having 3 to 12 carbons, and adjacent groups of $Ar^4$ to $Ar^7$ may be bonded to each other to form a ring, and $R^{37}$ and $R^{38}$ are independently hydrogen, aryl having 6 to 30 carbons, heteroaryl having 5 to 30 carbons, alkyl having 1 to 10 carbons, cycloalkyl having 3 to 12 carbons or trialkylsilyl having 3 to 12 carbons, and at least one hydrogen in the groups may be replaced by aryl having 6 to 10 carbons, heteroaryl having 5 to 12 carbons, alkyl having 1 to 6 carbons, cycloalkyl having 3 to 10 carbons or trialkylsilyl having 3 to 12 carbons, and $R^{37}$ and $R^{38}$ may be bonded to each other to form a ring, and at least one hydrogen in the compound represented by each of formulas (4-A) to (4-C) may be replaced by halogen, cyano or deuterium.

Item 14. The organic electroluminescent device according to item 13, wherein, in formula (3), $R^{12}$ to $R^{22}$ are independently hydrogen, aryl having 6 to 16 carbons which may be subjected to substitution for alkyl having 1 to 4 carbons, heteroaryl having 2 to 20 carbons which may be subjected to substitution for alkyl having 1 to 4 carbons, diarylamino (in which, aryl is aryl having 6 to 10 carbons which may be subjected to substitution for alkyl having 1 to 4 carbons), alkyl having 1 to 12 carbons or cycloalkyl having 3 to 12 carbons, and $X^1$ and $X^2$ are independently >O, >N—R, or >C(—R)$_2$, in which, at least one of $X^1$ and $X^2$ is >N—R, and R of the >N—R is aryl having 6 to 10 carbons which may be subjected to substitution for alkyl having 1 to 4 carbons, or alkyl having 1 to 4 carbons, and R of the >C(—R)$_2$ is hydrogen, aryl having 6 to 10 carbons which may be subjected to substitution for alkyl having 1 to 4 carbons, or alkyl having 1 to 4 carbons, at least one hydrogen in the compound represented by formula (3) may be replaced by deuterium, cyano or halogen, in formulas (4-A) to (4-C), $Ar^4$, $Ar^5$, $Ar^6$ and $Ar^7$ are independently aryl having 6 to 10 carbons or heteroaryl having 5 to 12 carbons, and at least one hydrogen in the groups may be replaced by aryl having 6 to 10 carbons, heteroaryl having 5 to 12 carbons, alkyl having 1 to 6 carbons, cycloalkyl having 3 to 6 carbons or trialkylsilyl having 3 to 12 carbons, and adjacent groups of $Ar^4$ to $Ar^7$ may be bonded to each other to form a ring, and $R^{37}$ and $R^{38}$ are independently hydrogen, aryl having 6 to 10 carbons, heteroaryl having 5 to 12 carbons, alkyl having 1 to 6 carbons, cycloalkyl having 3 to 6 carbons or trialkylsilyl having 3 to 6 carbons, and at least one hydrogen in the groups may be replaced by aryl having 6 to 10 carbons, heteroaryl having 5 to 12 carbons, alkyl having 1 to 6 carbons, cycloalkyl having 3 to 6 carbons or trialkylsilyl having 3 to 6 carbons, and $R^{37}$ and $R^{38}$ may be bonded to form a ring.

Item 15. The organic electroluminescent device according to item 13, wherein, in formula (3), $R^{12}$ to $R^{22}$ are independently hydrogen, aryl having 6 to 16 carbons which may be subjected to substitution for alkyl having 1 to 4 carbons, heteroaryl having 2 to 20 carbons which may be subjected to substitution for alkyl having 1 to 4 carbons, diarylamino (in which, aryl is aryl having 6 to 10 carbons which may be subjected to substitution for alkyl having 1 to 4 carbons), alkyl having 1 to 12 carbons or cycloalkyl having 3 to 12 carbons, and $X^1$ and $X^2$ are independently >O or >N—R, in which, at least one of X1 and $X^2$ is >N—R, and R of the >N—R is aryl having 6 to 10 carbons which may be subjected to substitution for alkyl having 1 to 4 carbons, or alkyl having 1 to 4 carbons, and at least one hydrogen in the compound represented by formula (3) may be replaced by deuterium, cyano or halogen, in formulas (4-A) to (4-C), $Ar^4$, $Ar^5$, $Ar^6$ and $Ar^7$ are independently phenyl, naphthyl, or a group represented by formula (4-X), and at least one hydrogen in the groups may be replaced by phenyl, naphthyl, methyl, isopropyl, tertiary butyl or trimethylsilyl, and in formula (4-X), $Y^1$ is —O—, —S— or >N—$R^{39}$, and $R^{39}$ is hydrogen or phenyl, and is bonded to a nitrogen atom in formulas (4-A) to (4-C) at any of positions in formula (4-X), and $R^{37}$ and $R^{38}$ are independently phenyl or methyl.

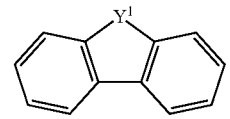

(4-X)

Item 16. The organic electroluminescent device according to any one of items 1 to 15, wherein the dopant material contains any one or more of compounds represented by the following structural formula:

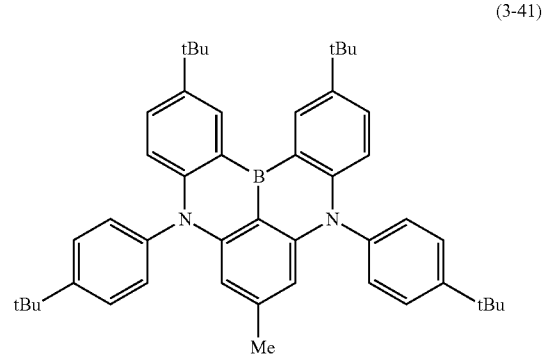

(3-41)

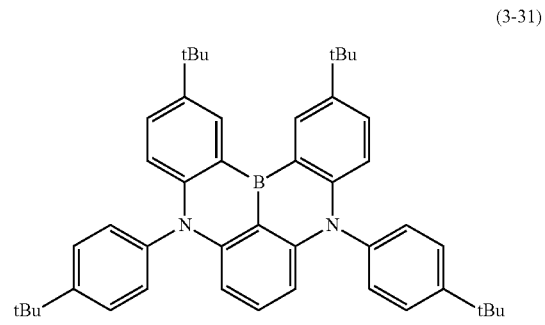

(3-31)

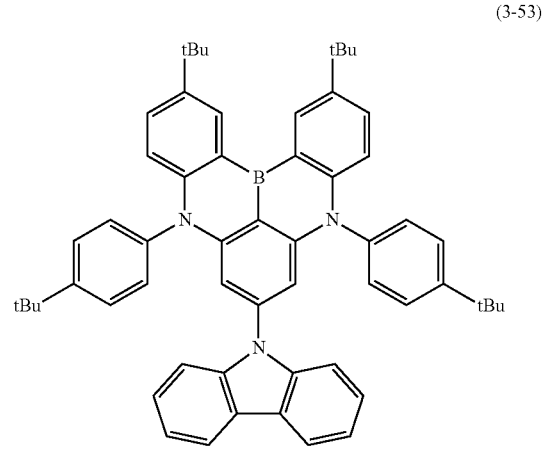

(3-53)

(3-37)
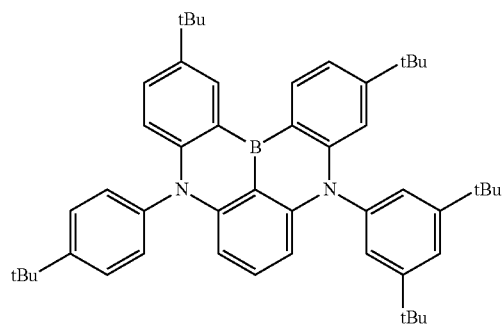
(3-46)
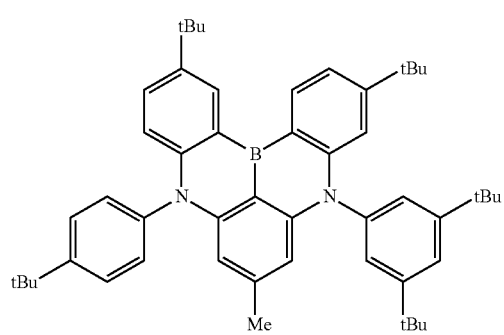
(3-50)
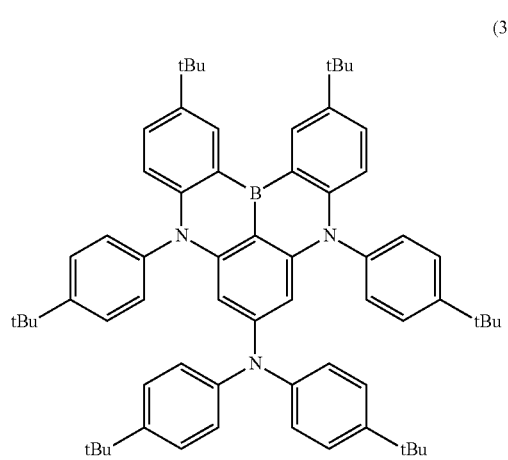
(3-49)
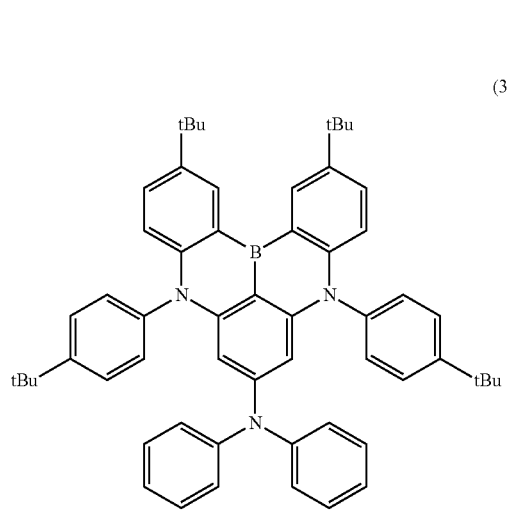
(3-A-1)
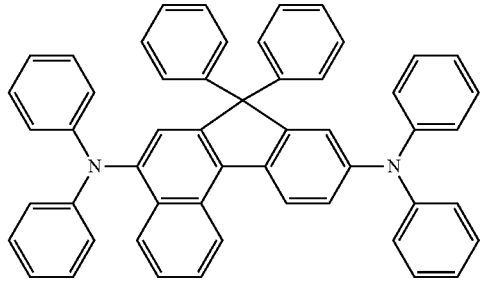
(3-A-2)
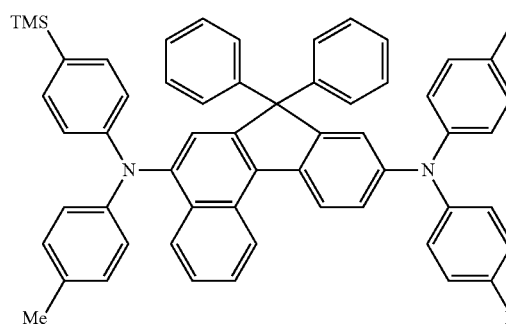
(3-A-3)
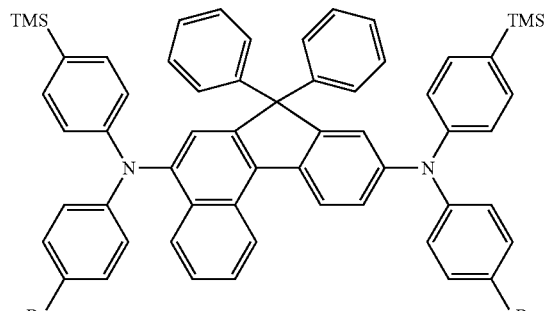
(3-A-4)
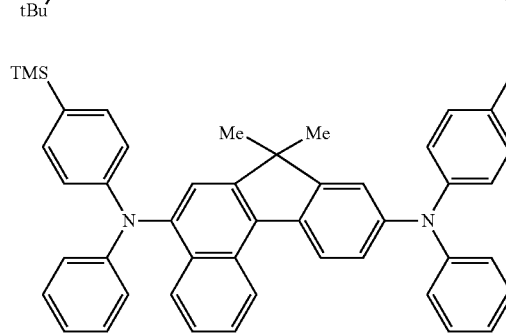
(3-A-5)
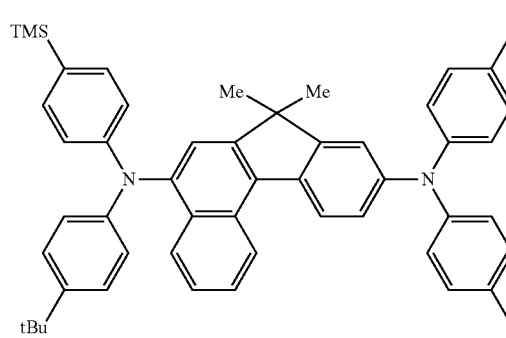

(3-B-1)
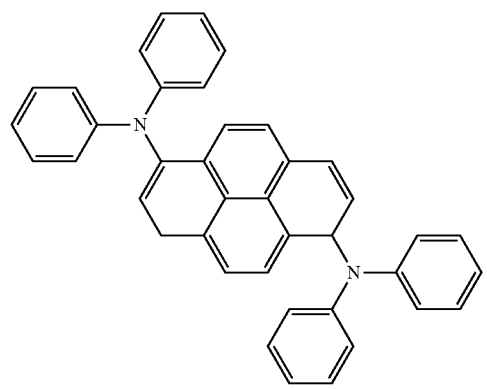
(3-B-4)
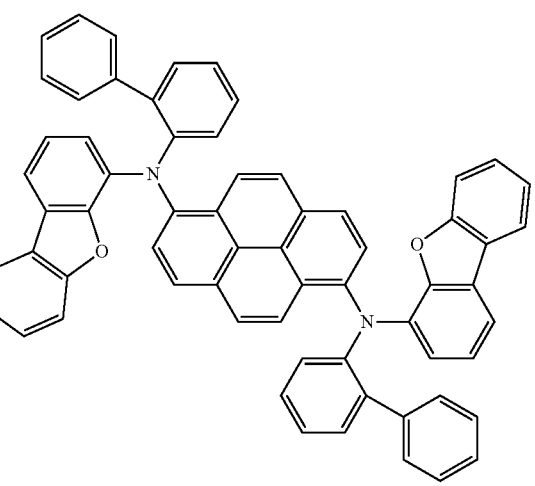
(3-B-2)
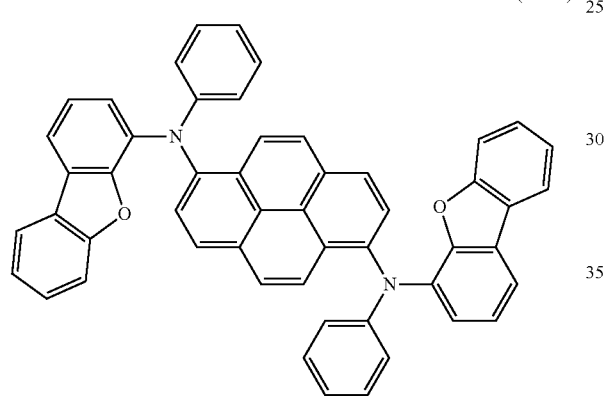
(3-C-1)
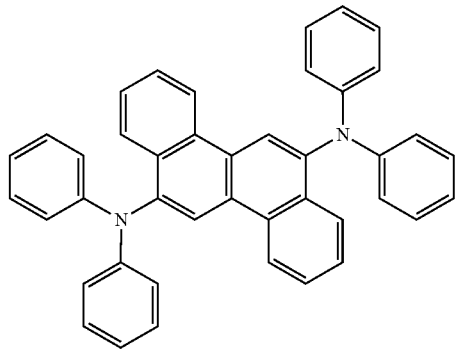
(3-B-3)
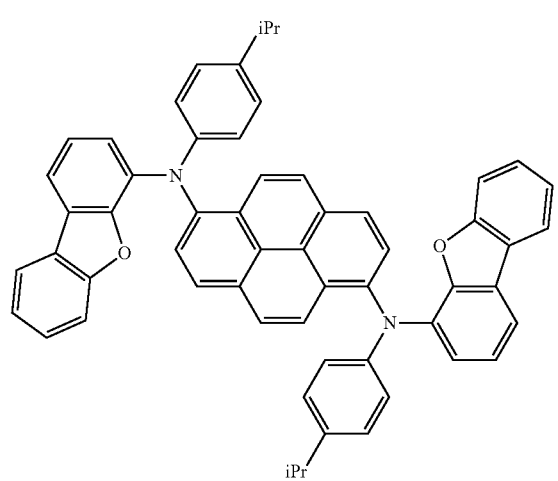
(3-C-2)
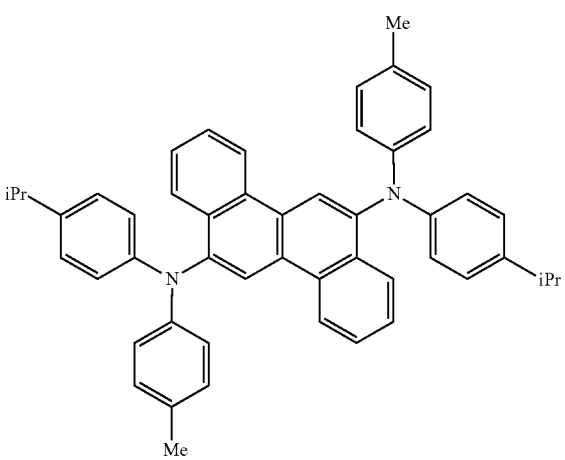

(3-C-3)

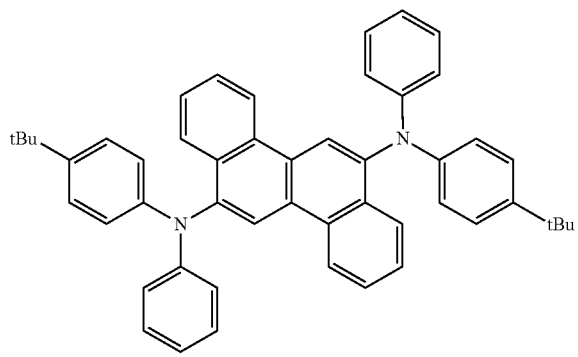

wherein, in the structural formulas, "Me" represents methyl, "iPr" represents isopropyl, "tBu" represents tertiary butyl, and "TMS" represents trimethylsilyl.

Item 17. The organic electroluminescent device according to any one of items 1 to 16, comprising an electron transport layer and/or an electron injection layer arranged between the cathode and the luminescent layer, wherein at least one of the electron transport layer and the electron injection layer includes at least one selected from the group of a borane derivative, a pyridine derivative, a fluoranthene derivative, a BO-based derivative, an anthracene derivative, a benzofluorene derivative, a phosphine oxide derivative, a pyrimidine derivative, a carbazole derivative, a triazine derivative, a benzimidazole derivative, a phenanthroline derivative and a quinolinol-based metal complex.

Item 18. The organic electroluminescent device according to item 17, wherein the electron transport layer and/or the electron injection layer further includes at least one selected from the group of alkali metal, alkaline earth metal, rare earth metal, an oxide of alkali metal, a halide of alkali metal, an oxide of alkaline earth metal, a halide of alkaline earth metal, an oxide of rare earth metal, a halide of rare earth metal, an organic complex of alkali metal, an organic complex of alkaline earth metal and an organic complex of rare earth metal.

Item 19. A display apparatus, comprising the organic electroluminescent device according to any one of items 1 to 18.

Item 20. A lighting apparatus, comprising the organic electroluminescent device according to any one of items 1 to 18.

Advantageous Effects of Invention

The invention can provide an organic EL device having improved energy efficiency.

BRIEF DESCRIPTION OF DRAWINGS

The FIGURE is a schematic cross-sectional view showing an organic electroluminescent device.

DESCRIPTION OF EMBODIMENTS

Hereinafter, the invention will be described in detail. Description of constituent features described below is made on the basis of typified embodiments or specific examples in several cases, but the invention is not limited to such embodiments. The numerical range represented by using "to" in the specification means a range including numerical values described before and after "to" as a lower limit and an upper limit. Moreover, "hydrogen" as used herein in description of a structural formula means a "hydrogen atom (H)." Further, "Me," "tBu," "iPr," "Ph" and "TMS" used herein represent methyl, tertiary butyl, isopropyl, phenyl and trimethylsilyl, respectively.

A chemical structure or a substituent is represented herein by using the number of carbon atoms in several cases. However, the number of carbon atoms when an atom of the chemical structure is replaced by the substituent in, when an atom of the substituent is further replaced by a substituent, or the like means the number of carbon atoms of each chemical structure or each substituent, and does not mean the total number of carbon atoms of each chemical structure and the substituent thereof or the total number of carbon atoms of each substituent and the substituent thereof. For example, an expression "substituent B having Y carbons which is subjected to substitution for substituent A having X carbos" means that hydrogen of "substituent B having Y carbons" is replaced by "substituent A having X carbons," and the Y carbons do not represent the number of carbon atoms of a total of the substituent A and the substituent B. For example, an expression "substituent B having Y carbons which is subjected to substitution for substituent A" means that hydrogen of "substituent B having Y carbons" is replaced by "substituent A (in which the number of carbon atoms is not specified), and the Y carbons do not mean the number of carbon atoms of a total of the substituent A and the substituent B.

Organic Electroluminescent Device

An organic electroluminescent device according to the invention includes a pair of electrodes formed of an anode and cathode, and a luminescent layer arranged between the pair of electrodes. The luminescent layer includes an anthracene-based compound represented by formula (1) as a host material, a dopant material, and at least one of a polycyclic aromatic compound represented by formula (2) or a multimer thereof having a plurality of structures represented by formula (2).

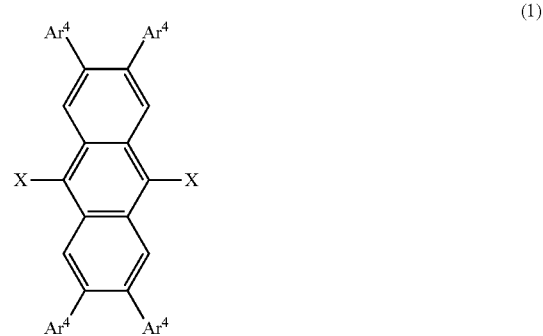

(1)

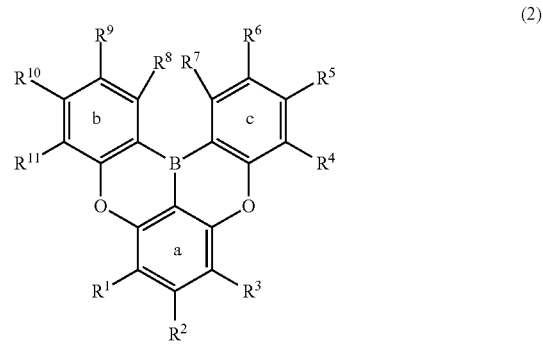

(2)

As shown in Examples described later, the present inventors have found that the polycyclic aromatic compound represented by formula (2) or the multimer thereof having the plurality of structures represented by formula (2) is added to the luminescent layer including the anthracene-based compound represented by formula (1) as the host material, and the dopant material, whereby the same luminance can be provided at lower driving voltage without influencing a color and external quantum efficiency.

Without sticking to any theory, excitation energy generated in the host material is considered to efficiently move as intermolecular energy to the dopant material through the polycyclic aromatic compound represented by formula (2) or the multimer thereof having the plurality of structures represented by formula (2). More specifically, the polycyclic aromatic compound represented by formula (2) or the multimer thereof having the plurality of structures represented by formula (2) does not produce luminescence, and the dopant mainly produces luminescence, and the polycyclic aromatic compound represented by formula (2) or the multimer thereof having the plurality of structures represented by formula (2) is considered to act as an assist dopant.

Luminescent Layer Forming Material: A Polycyclic Aromatic Compound Represented by Formula (2) or a Multimer Thereof Having a Plurality of Structures Represented by Formula (2) (Assist Dopant)

The polycyclic aromatic compound represented by formula (2) or the multimer of the polycyclic aromatic compound having the plurality of structures represented by formula (2) is as described below.

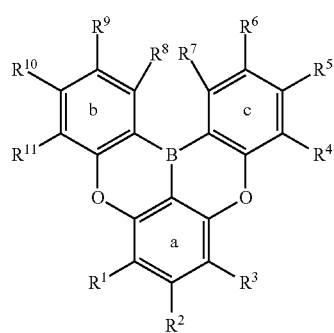

(2)

In formula (2), $R^1$, $R^2$, $R^3$, $R^4$, $R^5$, $R^6$, $R^7$, $R^8$, $R^9$, $R^{10}$ and $R^{11}$ are independently hydrogen, aryl, heteroaryl, diarylamino, diheteroarylamino, arylheteroarylamino, alkyl, cycloalkyl, alkoxy, trialkylsilyl or aryloxy, and at least one hydrogen in the groups may be replaced by aryl, heteroaryl or alkyl, and adjacent groups of $R^1$ to $R^{11}$ may be bonded to each other to form an aryl ring or a heteroaryl ring together with an a ring, a b ring or a c ring, and at least one hydrogen in the ring formed may be replaced by aryl, heteroaryl, diarylamino, diheteroarylamino, arylheteroarylamino, alkyl, alkoxy or aryloxy, and at least one hydrogen in the groups may be replaced by aryl, heteroaryl or alkyl, and at least one hydrogen in the compound represented by formula (2) may be replaced by halogen or deuterium.

Adjacent groups of substituents $R^1$ to $R^{11}$ of the a ring, the b ring and the c ring may be bonded to each other to form the aryl ring or the heteroaryl ring together with the a ring, the b ring or the c ring, and at least one hydrogen in the ring formed may be replaced by aryl, heteroaryl, diarylamino, diheteroarylamino, arylheteroarylamino, alkyl, alkoxy or aryloxy, and at least one hydrogen in the groups may be replaced by aryl, heteroaryl or alkyl. Accordingly, in the polycyclic aromatic compound represented by formula (2), as shown in formula (2-1) and formula (2-2), a ring structure constituting the compound is changed by a mutual bonding form of the substituents in the a ring, the b ring and the c ring.

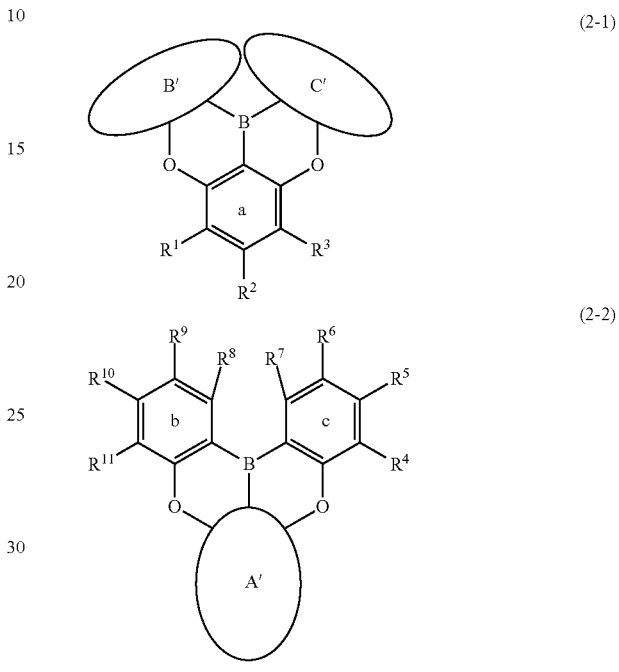

An A' ring and a B' ring and a C' ring in formula (2-1) and formula (2-2) show an aryl ring or a heteroaryl ring which is formed with the a ring, the b ring and the c ring by bonding adjacent groups of substituents $R^1$ to $R^{11}$ to each other, respectively (also referred to as a fused ring formed by fusing another ring structure to the a ring, the b ring and the c ring). In addition, although not shown in the formula, the polycyclic aromatic compound may be a compound in which only the a ring is changed to the A' ring, or a compound in which all of the a ring, the b ring and the c ring are changed to the A' ring, the B' ring and the C' ring, respectively. Moreover, as found from formulas (2-1) to (2-2), for example, $R^6$ of the b ring and $R^7$ of the c ring, $R^{11}$ of the b ring and $R^1$ of the a ring, $R^4$ of the c ring and $R^3$ of the a ring and so forth do not correspond to the "adjacent groups," and the above-described groups are not bonded to each other. More specifically, the term "adjacent groups" means adjacent groups on the same ring.

For example, if a benzene ring, an indole ring, a pyrrole ring, a benzofuran ring or a benzothiophene ring, a cyclohexane ring or an indan ring is fused with a benzene ring being the a ring (or the b ring or the c ring), and a ring is formed, the fused ring A' (or the fused ring B' or the fused ring C') formed is a naphthalene ring, a carbazole ring, an indole ring, a dibenzofuran ring or a dibenzothiophene ring, a tetralin ring or a fluorene ring, respectively.

In formula (2), "alkyl" as a first substituent in $R^1$, $R^2$, $R^3$, $R^4$, $R^5$, $R^6$, $R^7$, $R^8$, $R^9$, $R^{10}$ and $R^{11}$ may be either a straight chain or a branched chain, and specific examples thereof include straight-chain alkyl having 1 to 24 carbons or branched-chain alkyl having 3 to 24 carbons. Alkyl having 1 to 18 carbons (branched-chain alkyl having 3 to 18 carbons) is preferred, and alkyl having 1 to 12 carbons (branched-chain alkyl having 3 to 12 carbons) is further preferred, and alkyl having 1 to 6 carbons (branched-chain alkyl having 3 to 6 carbons) is still further preferred, and alkyl having 1 to 4 carbons (branched-chain alkyl having 3 to 4 carbons) is particularly preferred.

Specific examples of the alkyl include methyl, ethyl, n-propyl, isopropyl, n-butyl, isobutyl, s-butyl, t-butyl, n-pentyl, isopentyl, neopentyl, t-pentyl, n-hexyl, 1-methylpentyl, 4-methyl-2-pentyl, 3,3-dimethylbutyl, 2-ethylbutyl, n-heptyl, 1-methylhexyl, n-octyl, t-octyl, 1-methylheptyl, 2-ethylhexyl, 2-propylpentyl, n-nonyl, 2,2-dimethylheptyl, 2,6-dimethyl-4-heptyl, 3,5,5-trimethylhexyl, n-decyl, n-undecyl, 1-methyldecyl, n-dodecyl, n-tridecyl, 1-hexylheptyl, n-tetradecyl, n-pentadecyl, n-hexadecyl, n-heptadecyl, n-octadecyl and n-eicosyl.

"Cycloalkyl" (first substituent) as a first substituent may be any of cycloalkyl formed of one ring, cycloalkyl formed of a plurality of rings, cycloalkyl containing a nonconjugated double bond in the ring and cycloalkyl containing a branched chain outside the ring, and is cycloalkyl having 3 to 14 carbons, for example. Cycloalkyl having 5 to 10 carbons is preferred, and cycloalkyl having 6 to 10 carbons is further preferred.

Specific examples of the cycloalkyl include cyclopropyl, cyclobutyl, cyclopentyl, cyclohexyl, cycloheptyl, cyclooctyl, bicyclo[1.0.1]butyl, bicyclo[1.1.1]pentyl, bicyclo[2.0.1]pentyl, bicyclo[1.2.1]hexyl, bicyclo[3.0.1]hexyl, bicyclo[2.2.1]heptyl, bicyclo[2.2.2]octyl, decahydronaphthyl, adamantyl (particularly, 1-adamantyl), diamantyl and decahydroazulenyl. In addition, specific examples of cycloalkyl which is subjected to substitution for a second substituent described later include methylcyclopropyl, methylcyclobutyl, methylcyclopentyl, methylcyclohexyl, methylcycloheptyl and methylcyclooctyl.

Moreover, specific examples of "alkoxy" as a first substituent include straight-chain alkoxy having 1 to 24 carbons or branched-chain alkoxy having 3 to 34 carbons. Alkoxy (branched-chain alkoxy having 3 to 18 carbons), and alkoxy having 1 to 12 carbons (branched-chain alkoxy having 3 to 12 carbons) is further preferred, and alkoxy having 1 to 6 carbons (branched-chain alkoxy having 3 to 6 carbons) is still further preferred, and alkoxy having 1 to 4 carbons (branched-chain alkoxy having 3 to 4 carbons) is particularly preferred.

Specific examples of the alkoxy include methoxy, ethoxy, propoxy, isopropoxy, butoxy, isobutoxy, s-butoxy, t-butoxy, pentyloxy, hexyloxy, heptyloxy and octyloxy.

Moreover, specific examples of "trialkylsilyl" as a first substituent include a structure in which three hydrogens in a silyl group are independently replaced by alkyl, and specific examples of the alkyl include a group described in a column of "alkyl" as a first substituent. Alkyl by which hydrogen is preferably replaced is alkyl having 1 to 4 carbons, and specific examples thereof include methyl, ethyl, propyl, i-propyl, butyl, sec-butyl, t-butyl and cyclobutyl.

Specific examples of the trialkylsilyl include trimethylsilyl, triethylsilyl, tripropylsilyl, triisopropylsilyl, tributylsilyl, trisec-butylsilyl, trit-butylsilyl, ethyldimethylsilyl, propyldimethylsilyl, i-propyldimethylsilyl, butyldimethylsilyl, sec-butyldimethylsilyl, t-butyldimethylsilyl, methyldiethylsilyl, propyldiethylsilyl, i-propyldiethylsilyl, butyldiethylsilyl, sec-butyldiethylsilyl, t-butyldiethylsilyl, methyldipropylsilyl, ethyldipropylsilyl, butyldipropylsilyl, sec-butyldipropylsilyl, t-butyldipropylsilyl, methyldiisopropylsilyl, ethyldiisopropylsilyl, butyldiisopropylsilyl, sec-butyldiisopropylsilyl and t-butyldiisopropylsilyl.

Specific examples of aryl, heteroaryl, aryl of diarylamino, heteroaryl of diheteroarylamino, aryl and heteroaryl of arylheteroarylamino or aryl of aryloxy in $R^1$ to $R^{11}$ in formula (2) include a monovalent group of an "aryl ring" or a "heteroaryl ring" described below.

Specific examples of the "aryl ring" include a monocyclic benzene ring, a bicyclic biphenyl ring, a fused bicyclic naphthalene ring, a tricyclic terphenyl ring (m-terphenyl, o-terphenyl, p-terphenyl), a fused tricyclic acenaphthylene ring, fluorene ring, phenalene ring and phenanthrene ring, a fused tetracyclic triphenylene ring, pyrene ring and naphthacene ring, a fused pentacyclic perylene ring and pentacene ring.

Specific examples of the "heteroaryl ring" include a heteroaryl ring having 2 to 30 carbons, and a heteroaryl ring having 2 to 25 carbons is preferred, and a heteroaryl ring having 2 to 20 carbons is further preferred, and a heteroaryl ring having 2 to 15 carbons is still further preferred, and a heteroaryl ring having 2 to 10 carbons is particularly preferred. Moreover, specific examples of the "heteroaryl ring" include a heterocyclic ring containing, in addition to carbon, 1 to 5 hetero atoms selected from oxygen, sulfur and nitrogen as a ring-forming atom.

Specific examples of the "heteroaryl ring" include a pyrrole ring, an oxazole ring, an isoxazol ring, a thiazole ring, an isothiazole ring, an imidazole ring, an oxadiazole ring, a thiadiazole ring, a triazole ring, a tetrazole ring, a pyrazole ring, a pyridine ring, a pyrimidine ring, a pyridazine ring, a pyrazine ring, a triazine ring, an indole ring, an isoindole ring, a 1H-indazole ring, a benzimidazole ring, a benzooxazole ring, a benzothiazole ring, a 1H-benzotriazol ring, a quinoline ring, an isoquinoline ring, a cinnoline ring, a quinazoline ring, a quinoxaline ring, a phthalazine ring, a naphthyridine ring, a purine ring, a pteridine ring, a carbazole ring, an acridine ring, a phenoxathiin ring, a phenoxazine ring, a phenothiazine ring, a phenazine ring, an indolizine ring, a furan ring, a benzofuran ring, an isobenzofuran ring, a dibenzofuran ring, a thiophene ring, a benzothiophene ring, a dibenzothiophene ring, a furazan ring, an oxadiazole ring and a thianthrene ring.

In aryl, heteroaryl, diarylamino, diheteroarylamino, arylheteroarylamino, alkyl, cycloalkyl, alkoxy, trialkylsilyl and aryloxy, which are the first substituent, at least one hydrogen therein may be replaced by the second substituent. Specific examples of the second substituent include aryl, heteroaryl or alkyl, and specific examples thereof can be referred to the above-described description of the monovalent group of the "aryl ring" and the "heteroaryl ring," and the "alkyl" as the first substituent. Moreover, aryl or heteroaryl as the second substituent also includes a group in which, at least one hydrogen therein is replaced by aryl such as phenyl (specific examples include the above-described groups), or alkyl such as methyl (specific examples include the above-described groups). As one example, when the second substituent is a carbazolyl group, a carbazolyl group in which, at least one hydrogen in a 9-position is replaced by aryl such as phenyl or alkyl such as methyl is also included in heteroaryl as the second substituent.

When adjacent groups of $R^1$ to $R^{11}$ are bonded to each other to form the aryl ring or the heteroaryl ring together with the a ring, the b ring or the c ring, heteroaryl, diarylamino, diheteroarylamino, arylheteroarylamino, alkyl, alkoxy or aryloxy, which are substituents to the above rings, and aryl, heteroaryl or alkyl, which are further substituents, can also be referred to the description of the "alky" or the "alkoxy" as the first substituent in the above-described description for formula (2).

Moreover, as a multimer of a polycyclic aromatic compound having a plurality of unit structures represented by formula (2), a dimer to a hexamer are preferred, and a dimer to a trimer are further preferred, and a dimer is particularly preferred. The multimer only needs have a form having the plurality of unit structures in one compound, and for example, the multimer may have, in addition to a form in which the plurality of unit structures are bonded by a linking group such as a single bond, an alkylene group having 1 to 3 carbons, a phenylene group, a naphthylene group, a form in which arbitrary rings (a ring, b ring or c ring) contained in the unit structure are bonded so as to be shared in the plurality of unit structures, or a form in which arbitrary rings (a ring, b ring or c ring) contained in the unit structure are bonded so as to be fused to each other.

Specific examples of such a multimer include multimer compounds represented by formula (2-4), formulas (2-5-1) to (2-5-4) or formula (2-6). The multimer compound represented by formula (2-4) is a multimer compound having, in one compound, unit structures represented by a plurality of formulas (2) in such a manner that a benzenes ring being an a ring is shared. Moreover, the multimer compounds represented by formulas (2-5-1) to (2-5-4) are a multimer compound having, in one compound, unit structures represented by a plurality of formulas (2) in such a manner that a benzene ring being a b ring (or c ring) is shared. Moreover, the multimer compound represented by formula (2-6) corresponds to a compound represented by formula (1A-431) described later, for example. More specifically, if described in formula (2), for example, the multimer compound is a multimer compound having, in one compound, the unit structures represented by a plurality of formulas (2) in such a manner that a benzene ring being a b ring (or a ring or c ring) having a certain unit structure is fused to a benzene ring being a b ring (or a ring or c ring) having a certain unit structure.

In addition, each symbol in formula (2-4), formulas (2-5-1) to (2-5-4) or formula (2-6) is the same as the definition in formula (2).

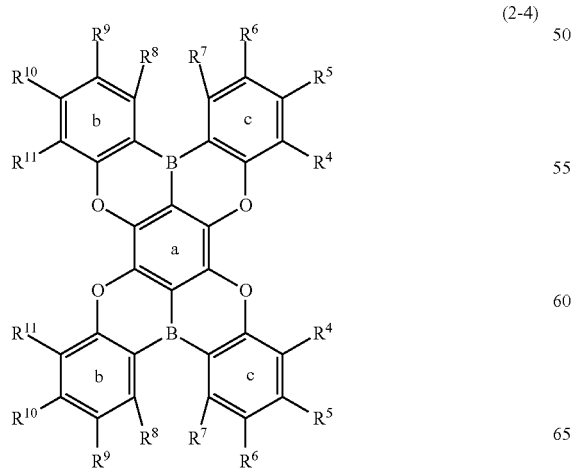

(2-4)

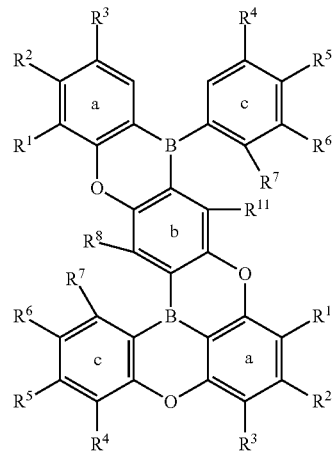

(2-5-1)

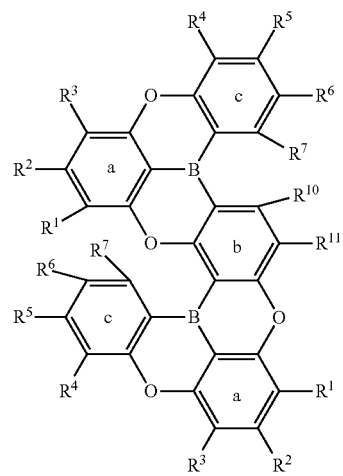

(2-5-2)

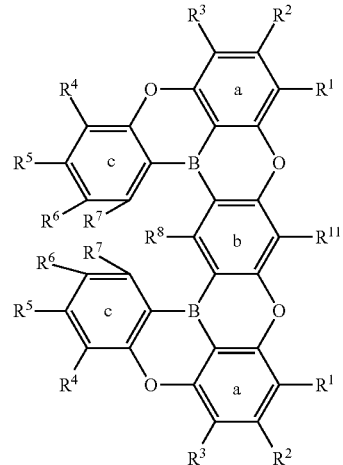

(2-5-3)

-continued (2-5-4)

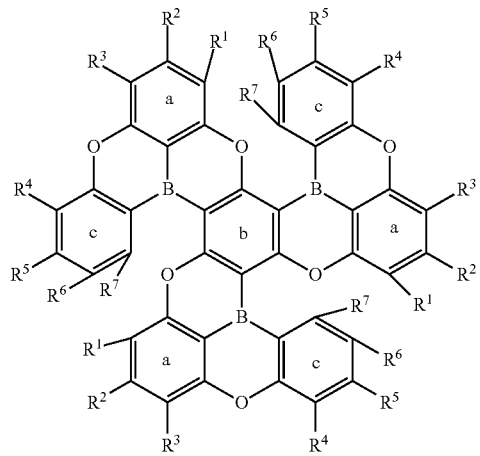

(2-6)

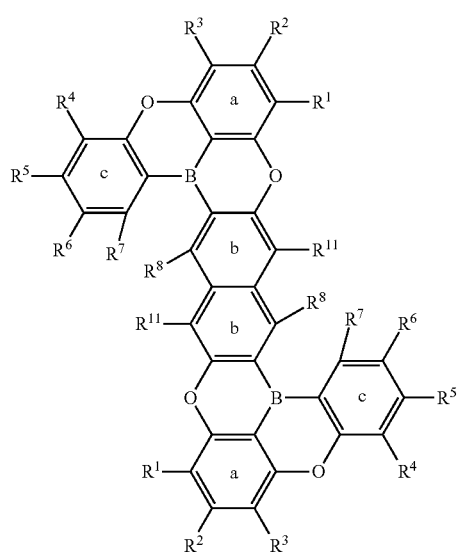

The multimer compound may be a multimer in which a multimerized form represented by formula (2-4) is combined with a multimerized form represented by any of formulas (2-5-1) to (2-5-4), or formula (2-6), or a multimer in which a multimerized form represented by any of formulas (2-5-1) to (2-5-4) is combined with a multimerized form represented by formula (2-6), or a multimer in which a multimerized form represented by formula (2-4) and a multimerized form represented by any of formulas (2-5-1) to (2-5-4) and a multimerized form represented by formula (2-6) are combined with each other.

Moreover, a hydrogen in the polycyclic aromatic compound represented by formula (2) and the chemical structure of the multimer thereof may be wholly or partly deuterium.

The polycyclic aromatic compound represented by formula (2) and the multimer of the polycyclic aromatic compound having the plurality of structures represented by formula (2) are preferably a polycyclic aromatic compound represented by formula (2A) and a multimer of a polycyclic aromatic compound having a plurality of structures represented by formula (2A).

(2A)

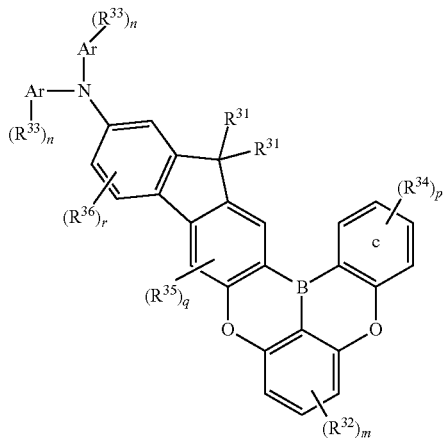

The polycyclic aromatic compound represented by formula (2A) is preferably a polycyclic aromatic compound represented by formula (2A').

(2A')

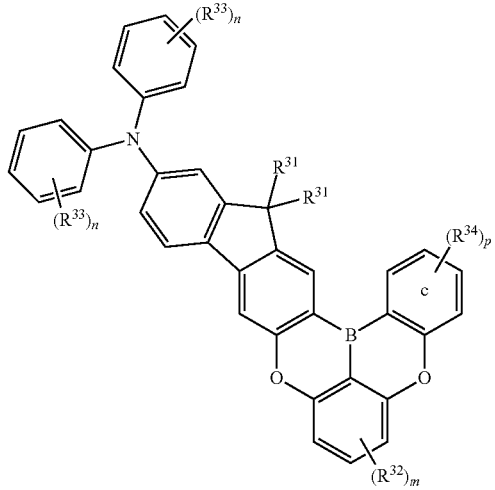

In formula (2A) and formula (2A'),

Ar is independently aryl or heteroaryl, and when $R^{34}$ is plural, adjacent $R^{34}$'s may be bonded to each other to form an aryl ring or a heteroaryl ring together with a c ring, and at least one hydrogen in the ring formed may be replaced by aryl, heteroaryl, diarylamino, diheteroarylamino, arylheteroarylamino, alkyl, alkoxy, trialkylsilyl or aryloxy, and at least one hydrogen in the groups may be replaced by aryl, heteroaryl, diarylamino or alkyl, and when $R^{33}$ and $R^{36}$ are adjacent to each other, $R^{33}$ and $R^{36}$ may be bonded to each other by —O—, —S—, —C(—R)$_2$— or a single bond, and R of the —C(—R)$_2$— is hydrogen or alkyl having 1 to 6 carbons.

In formula (2A), Ar is independently aryl or heteroaryl. More accurately, Ar is a (1+n)-valent group formed of aryl or heteroaryl.

$R^{31}$ to $R^{36}$ in formula (2A) and formula (2A') are independently hydrogen, aryl, heteroaryl, diarylamino, diheteroarylamino, arylheteroarylamino, alkyl, cycloalkyl, alkoxy, trialkylsilyl or aryloxy, and at least one hydrogen in the groups may be replaced by aryl, heteroaryl, diarylamino or alkyl.

Aryl and heteroaryl as $R^{31}$ to $R^{36}$ in formula (2A) and formula (2A') are as described below.

Specific examples of the aryl include aryl having 6 to 30 carbons, and aryl having 6 to 16 carbons is preferred, aryl having 6 to 12 carbons is further preferred, and aryl having 6 to 10 carbons is particularly preferred.

Specific examples of the aryl include phenyl as monocyclic aryl, biphenylyl as bicyclic aryl, naphthyl as fused bicyclic aryl, terphenylyl (m-terphenylyl, o-terphenylyl, p-terphenylyl) as tricyclic aryl, acenaphthylenyl, fluorenyl, phenalenyl and phenanthrenyl as fused tricyclic aryl, triphenylenyl, pyrenyl and naphthacenyl as fused tetracyclic aryl, and perylenyl and pentacenyl as fused pentacyclic aryl.

Specific examples of the heteroaryl include heteroaryl having 2 to 30 carbons or heteroaryl having 2 to 25 carbons is preferred, heteroaryl having 2 to 20 carbons is further preferred, heteroaryl having 2 to 15 carbons is still further preferred, and heteroaryl having 2 to 10 carbons is particularly preferred. Moreover, specific examples of the heteroaryl include a heterocyclic ring containing, in addition to carbon, 1 to 5 hetero atoms selected from oxygen, sulfur and nitrogen as a ring-forming atom.

Specific examples of the heteroaryl include pyrrolyl, oxazolyl, isoxazolyl, thiazolyl, isothiazolyl, imidazolyl, oxadiazolyl, thiadiazolyl, triazoryl, tetrazoryl, pyrazolyl, pyridyl, pyrimidinyl, pyridazinyl, pyrazinyl, thoriadinyl, indolyl, isoindolyl, 1H-indazolyl, benzimidazolyl, benzoxazolyl, benzothiazolyl, 1H-benzotriazoryl, quinolyl, isoquinolyl, cinnolyl, quinazolyl, quinoxalinyl, phthalazinyl, naphthyridinyl, purinyl, pteridinyl, carbazolyl, acridinyl, phenoxathiinyl, phenoxazinyl, phenothiazinyl, phenazinyl, indolizinyl, furyl, benzofuranyl, isobenzofuranyl, dibenzofuranyl, thienyl, benzo[b]thienyl, dibenzothienyl, furazanyl, oxadiazolyl, thianthrenyl, naphthobenzofuranyl and naphthobenzothienyl.

Diarylamino, diheteroarylamin and arylheteroarylamino as $R^{31}$ to $R^{36}$ in formula (2A) and formula (2A') each is a group in which an amino group is replaced by two aryl groups, two heteroaryl groups, and one aryl group and one heteroaryl group, and for the aryl and the heteroaryl herein, the above-mentioned description can be quoted.

Alkyl as $R^{31}$ to $R^{36}$ in formula (2A) and formula (2A') may be any of straight-chain alkyl and branched-chain alkyl, and specific examples thereof include straight-chain alkyl having 1 to 24 carbons and branched-chain alkyl having 3 to 24 carbons. Alkyl having 1 to 18 carbons (branched-chain alkyl having 3 to 18 carbons) is preferred, alkyl having 1 to 12 carbons (branched-chain alkyl having 3 to 12 carbons) is further preferred, alkyl having 1 to 6 carbons (branched-chain alkyl having 3 to 6 carbons) is still further preferred, and alkyl having 1 to 4 carbons (branched-chain alkyl having 3 to 4 carbons) is particularly preferred.

Specific examples of the alkyl include methyl, ethyl, n-propyl, isopropyl, n-butyl, isobutyl, s-butyl, t-butyl, n-pentyl, isopentyl, neopentyl, t-pentyl, n-hexyl, 1-methylpentyl, 4-methyl-2-pentyl, 3,3-dimethylbutyl, 2-ethylbutyl, n-heptyl, 1-methylhexyl, n-octyl, t-octyl, 1-methylheptyl, 2-ethylhexyl, 2-propylpentyl, n-nonyl, 2,2-dimethylheptyl, 2,6-dimethyl-4-heptyl, 3,5,5-trimethylhexyl, n-decyl, n-undecyl, 1-methyldecyl, n-dodecyl, n-tridecyl, 1-hexylheptyl, n-tetradecyl, n-pentadecyl, n-hexadecyl, n-heptadecyl, n-octadecyl and n-eicosyl.

Cycloalkyl as $R^{31}$ to $R^{36}$ in formula (2A) and formula (2A') may be any of cycloalkyl formed of one ring, cycloalkyl formed of a plurality of rings, cycloalkyl containing a nonconjugated double bond in the ring, and cycloalkyl containing a branched chain outside the ring, and is cycloalkyl having 3 to 14 carbons, for example. Cycloalkyl having 5 to 10 carbons is preferred, and cycloalkyl having 6 to 10 carbons is further preferred.

Specific examples of the cycloalkyl include cyclopropyl, cyclobutyl, cyclopentyl, cyclohexyl, cycloheptyl, cyclooctyl, bicyclo[1.0.1]butyl, bicyclo[1.1.1]pentyl, bicyclo[2.0.1] pentyl, bicyclo[1.2.1]hexyl, bicyclo[3.0.1]hexyl, bicyclo [2.2.1]heptyl, bicyclo[2.2.2]octyl, decahydro naphthyl, adamanthyl (particularly 1-adamanthyl), diamantyl and decahydroazulenyl. In addition, particular examples of cycloalkyl which is subjected to substitution for a second substituent described later include methylcyclopropyl, methylcyclobutyl, methylcyclopentyl, methylcyclohexyl, methylcycloheptyl and methylcyclooctyl.

Specific examples of the alkoxy as $R^{31}$ to $R^{36}$ in formula (2A) and formula (2A') include straight-chain alkoxy having 1 to 24 carbons or branched-chain alkoxy having 3 to 24 carbons. Alkoxy having 1 to 18 carbons (branched-chain alkoxy having 3 to 18 carbons) is preferred, alkoxy having 1 to 12 carbons (branched-chain alkoxy having 3 to 12 carbons) is further preferred, alkoxy having 1 to 6 carbons (branched-chain alkoxy having 3 to 6 carbons) is still further preferred, and alkoxy having 1 to 4 carbons (branched-chain alkoxy having 3 to 4 carbons) is particularly preferred.

Specific examples of the alkoxy include methoxy, ethoxy, propoxy, isopropoxy, butoxy, isobutoxy, s-butoxy, t-butoxy, pentyloxy, hexyloxy, heptyloxy and octyloxy.

Specific examples of the trialkylsilyl as $R^{31}$ to $R^{36}$ in formula (2A) and formula (2A') include a structure in which three hydrogens in a silyl group are independently replaced by alkyl, and specific examples of the alkyl include the group described in the column of the alkyl as $R^1$ to $R^6$. Specific examples of the alkyl by which hydrogen is preferably replaced is alkyl having 1 to 4 carbons, and specific examples thereof include methyl, ethyl, propyl, i-propyl, butyl, sec-butyl, t-butyl and cyclobutyl.

Specific examples of the trialkylsilyl include trimethylsilyl, triethylsilyl, tripropylsilyl, triisopropylsilyl, tributylsilyl, trisec-butylsilyl, trit-butylsilyl, ethyldimethylsilyl, propyldimethylsilyl, i-propyldimethylsilyl, butyldimethylsilyl, sec-butyldimethylsilyl, t-butyldimethylsilyl, methyldiethylsilyl, propyldiethylsilyl, i-propyldiethylsilyl, butyldiethylsilyl, sec-butyldiethylsilyl, t-butyldiethylsilyl, methyldipropylsilyl, ethyldipropylsilyl, butyldipropylsilyl, sec-butyldipropylsilyl, t-butyldipropylsilyl, methyldiisopropylsilyl, ethyldiisopropylsilyl, butyldiisopropylsilyl, sec-butyldiisopropylsilyl and t-butyldiisopropylsilyl.

Aryloxy as $R^{31}$ to $R^{36}$ in formulas (2A) and (2A') is a group in which hydrogen of a hydroxyl group is replaced by aryl, and also for the aryl herein, the above-mentioned description can be quoted.

Moreover, at least one hydrogen in $R^3$ to $R^{36}$ in formulas (2A) and (2A') may be replaced by aryl, heteroaryl, diarylamino or alkyl, and also for the above substituents, the above-mentioned description can be quoted.

When $R^{34}$ in formulas (2A) and (2A') is plural, adjacent $R^{34}$'s may be bonded to each other to form an aryl ring or a heteroaryl ring together with a c ring, and at least one hydrogen in the ring formed may be replaced by aryl, heteroaryl, diarylamino, diheteroarylamino, arylheteroarylamino, alkyl, cycloalkyl, alkoxy, trialkylsilyl or aryloxy, and at least one hydrogen in the groups may be replaced by aryl, heteroaryl, diarylamino or alkyl.

Here, the above-mentioned description can be quoted for the substituent in the ring formed (aryl, heteroaryl, diarylamino, diheteroarylamino, arylheteroarylamino, alkyl, cycloalkyl, alkoxy, trialkylsilyl or aryloxy), and the further substituent to the above substituent (aryl, heteroaryl, diarylamino or alkyl).

The case where the substituents $R^{34}$'s are adjacent means the case where two substituents $R^{34}$'s are substituted on adjacent carbons on a c ring (benzene ring). For example, benzene rings are fused and formed for a c ring, a fused ring c' formed is a naphthalene ring. In addition thereto, specific examples thereof include a carbazole ring (also including a ring in which hydrogen on N is replaced by the alkyl or the aryl), an indole ring (also including a ring in which hydrogen on N is replaced by the alkyl or the aryl), a dibenzofuran ring or a dibenzothiophene ring, in which an indole ring, a pyrrole ring, a benzofuran ring or a benzothiophene ring each is fused to a benzene ring being a c ring.

$R^{33}$ in formulas (2A) and (2A') may be bonded to a fluorene ring in the structure by —O—, —S—, —C(—R)$_2$— or a single bond, and R of the —C(—R)$_2$— is hydrogen or alkyl having 1 to 6 carbons (particularly, alkyl having 1 to 4 carbons (for example, methyl, ethyl or the like)).

One example in which $R^{33}$ is bonded with the fluorene ring in the structural formula is described below. A bonding place in the fluorene ring is shown by $R^{36}$.

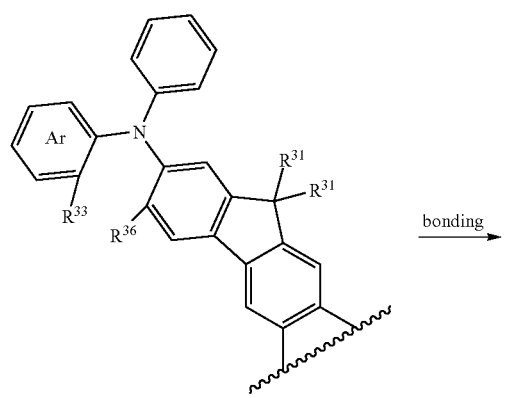

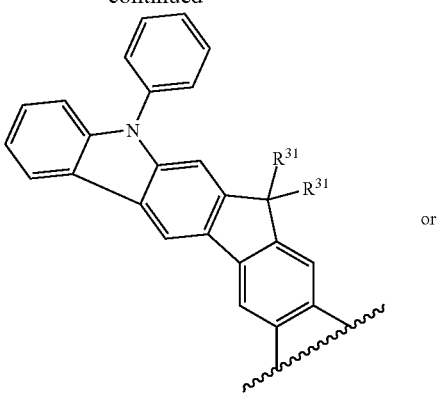

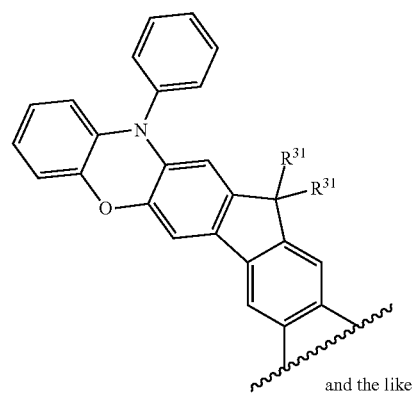

and the like

In formula (2A), m is an integer from 0 to 3, n is independently an integer from 0 to the maximum replaceable number to Ar (an integer from 0 to 5), p is an integer from 0 to 4, q is an integer from 0 to 2, and r is an integer from 0 to 3.

At least one hydrogen in a compound represented by formula (2A) may be replaced by halogen or deuterium.

Then, m is preferably an integer from 0 to 2, further preferably 0 or 1, and particularly preferably 0. Moreover, n is independently preferably an integer from 0 to 3, further preferably an integer from 0 to 2, still further preferably 0 or 1, and most preferably 0. Then, p is preferably an integer from 0 to 2, further preferably 0 or 1, and particularly preferably 0. Then, q is an integer from 0 to 2, preferably 0 or 1, and further preferably 0. Then, r is an integer from 0 to 3, preferably an integer from 0 to 2, further preferably 0 or 1, and particularly preferably 0.

Further specific examples of the polycyclic aromatic compound represented by formula (2) and the multimer thereof include compounds represented by the following structural formulas. In addition, "Me," "tBu," "iPr" and "Ph" in the following structural formula represent methyl, tertiary butyl, isopropyl and phenyl, respectively.

(2A-1)
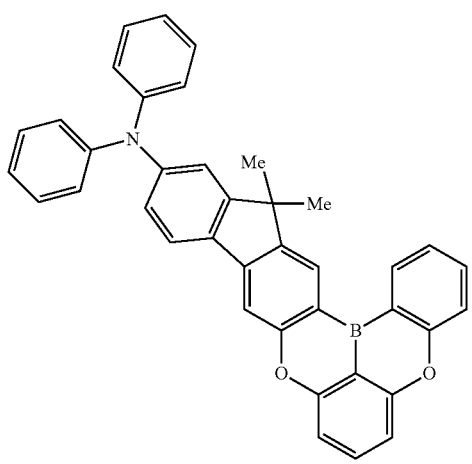
(2A-2)
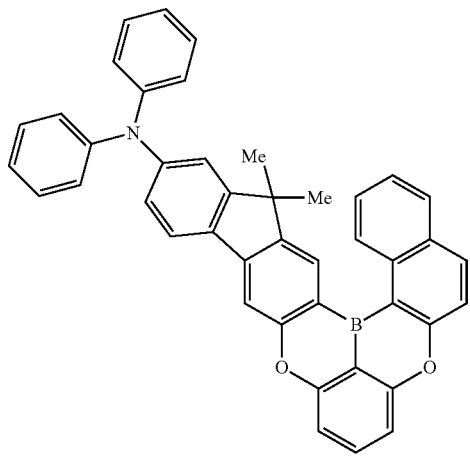
(2A-3)
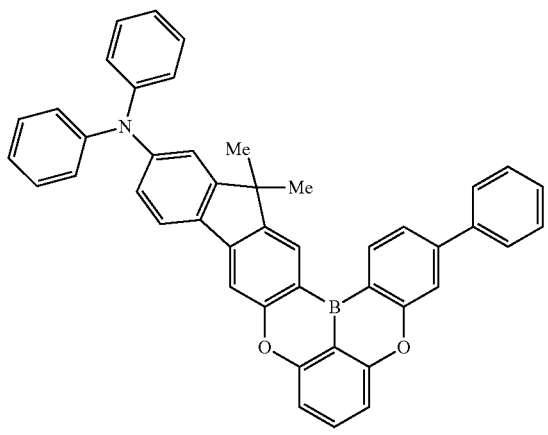
(2A-4)
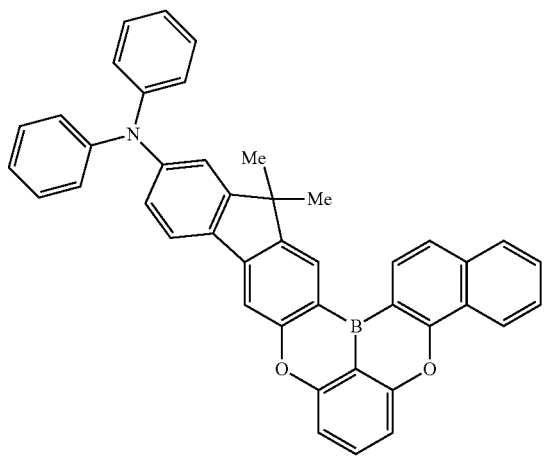
(2A-5)
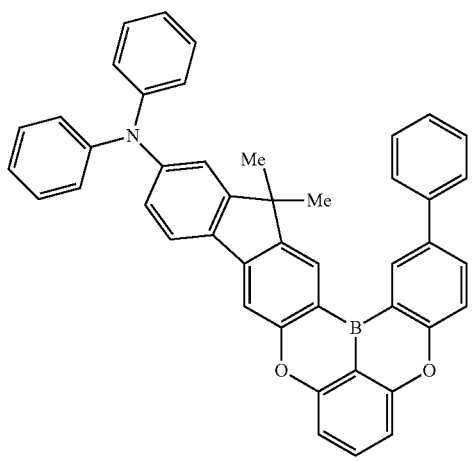
(2A-6)
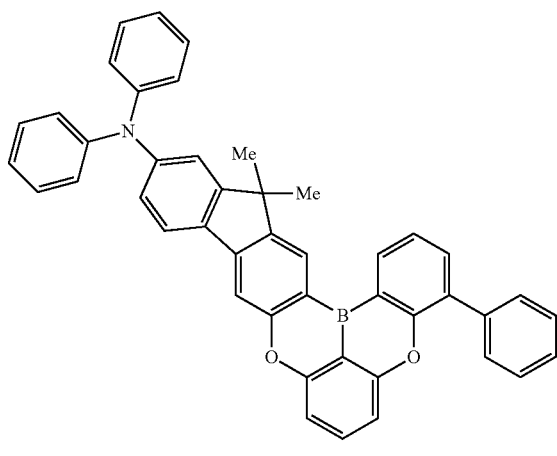

(2A-7)
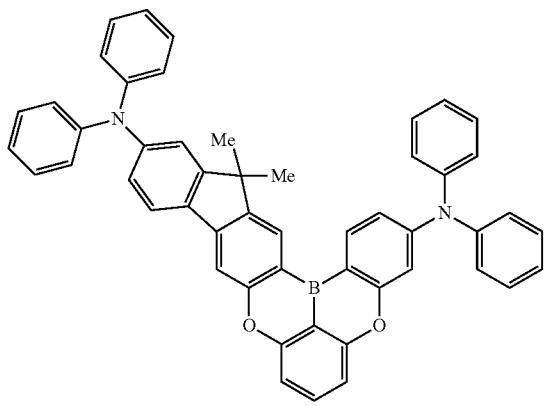
(2A-8)
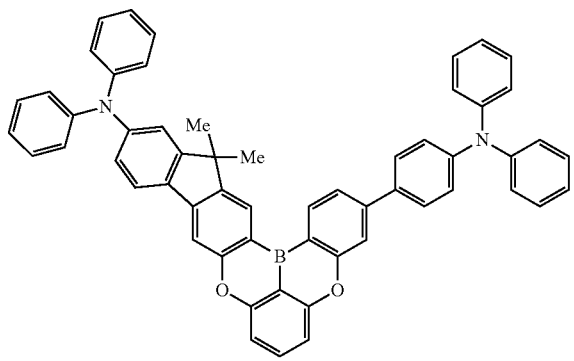
(2A-9)
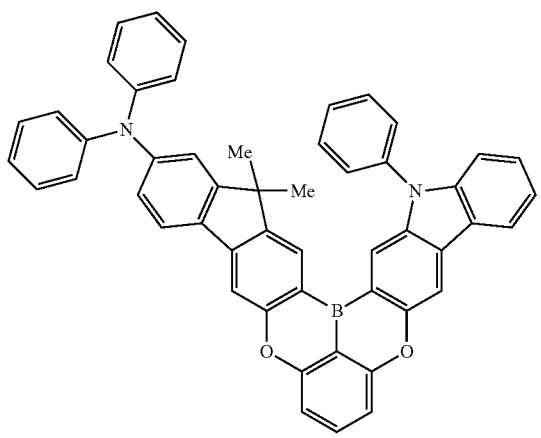
(2A-10)
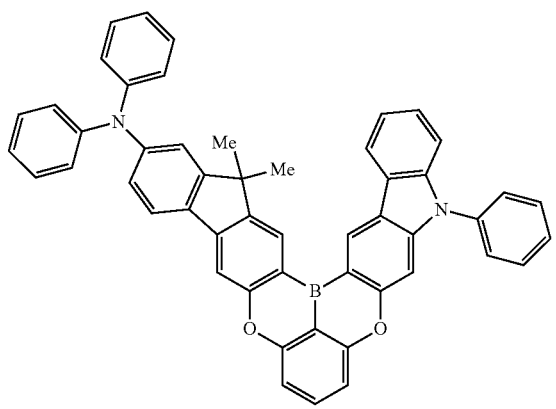
(2A-11)
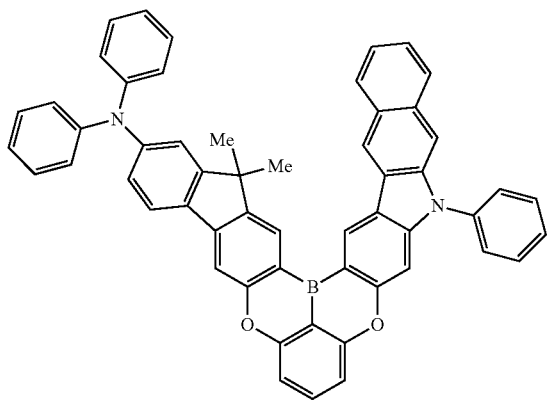
(2A-12)
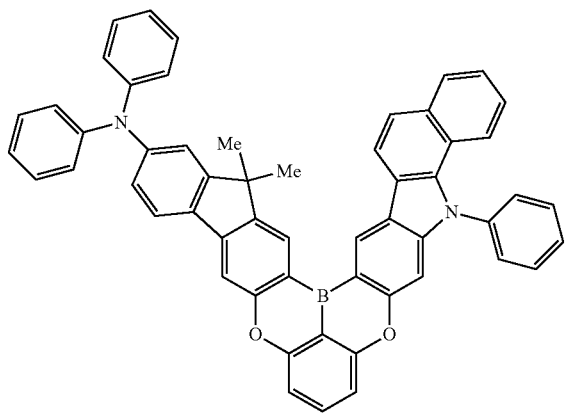

-continued
(2A-13)
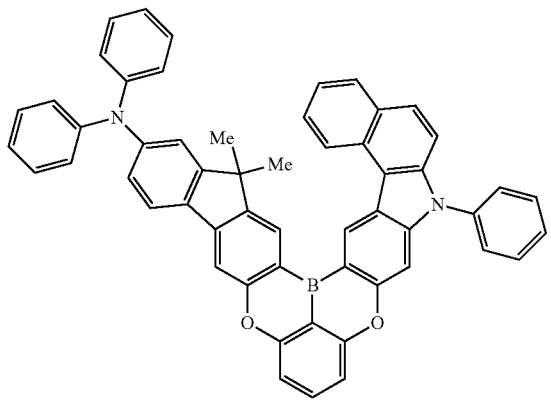
(2A-14)
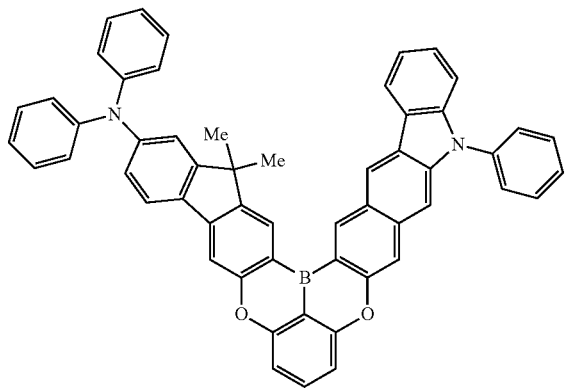
(2A-15)
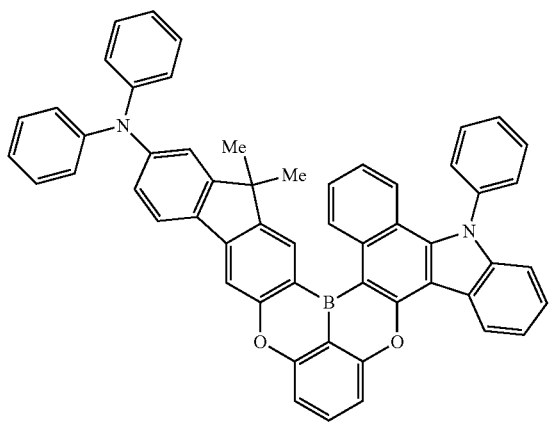
(2A-16)
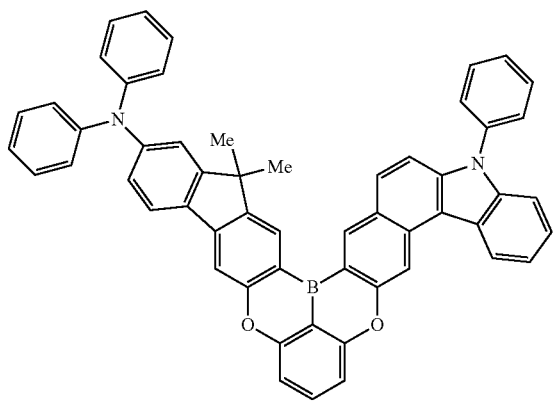
(2-1)
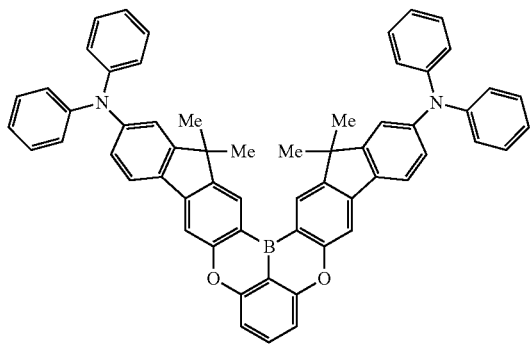
(2-2)
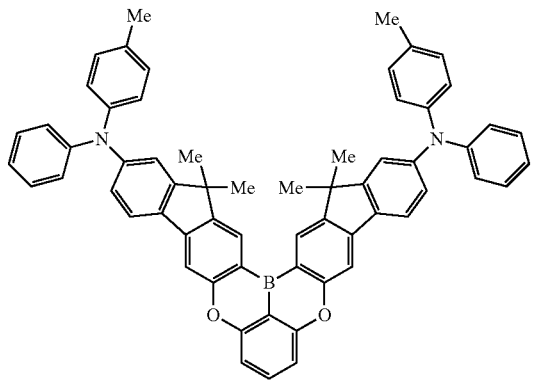

-continued
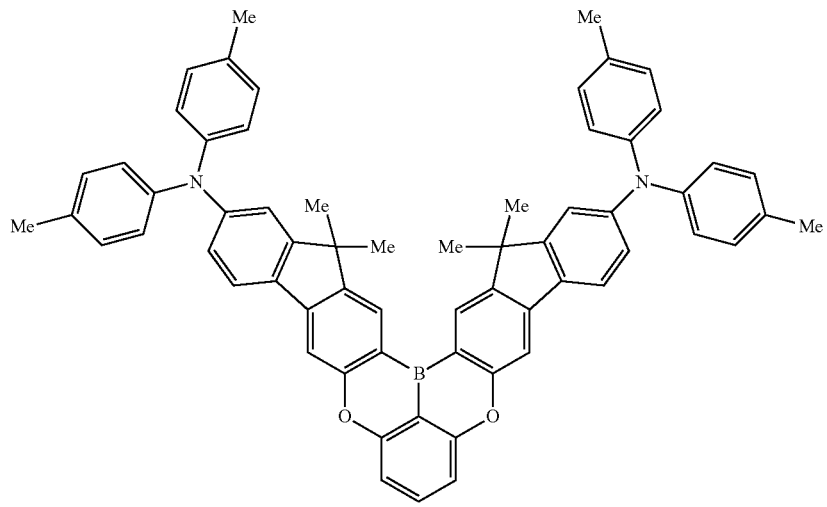
(2-3)
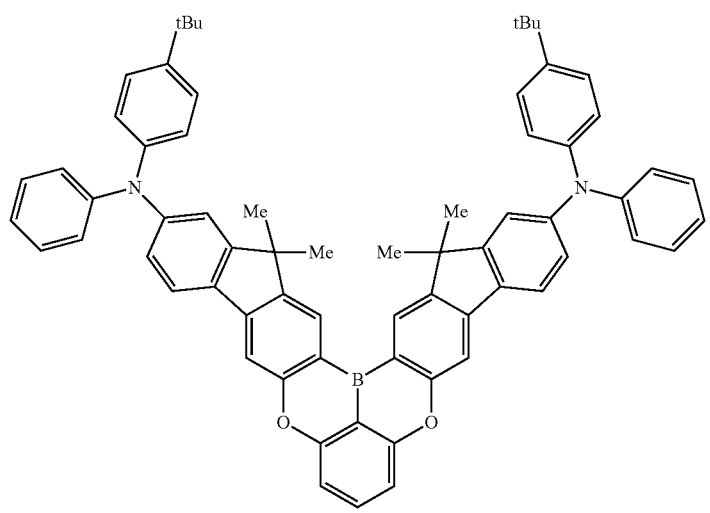
(2-4)
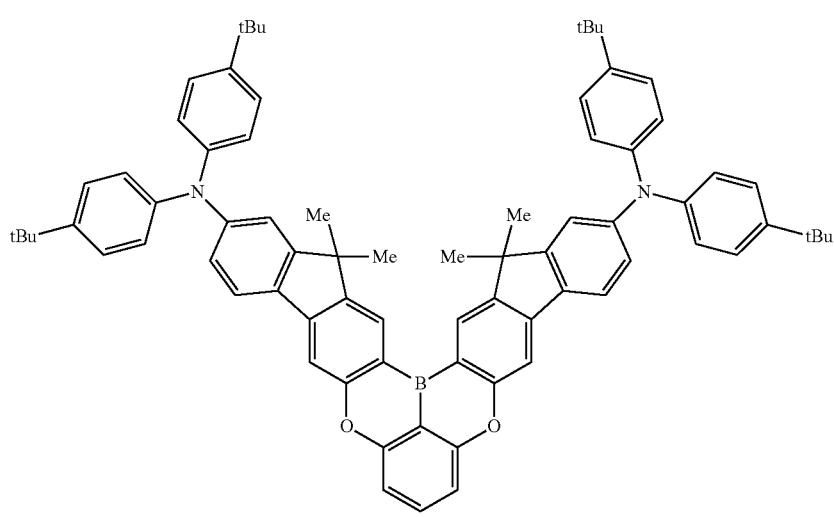
(2-5)

-continued
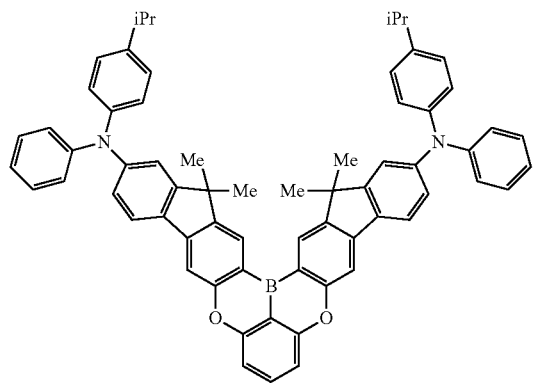
(2-6)
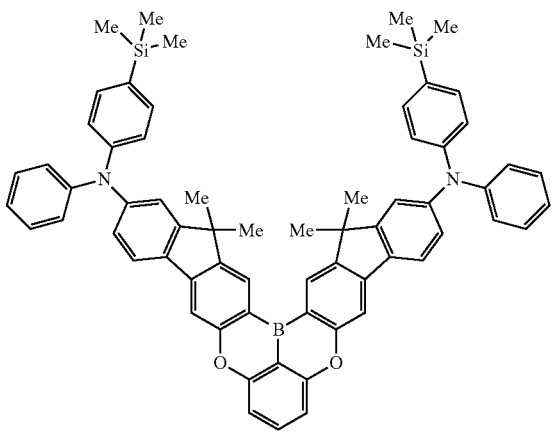
(2-7)
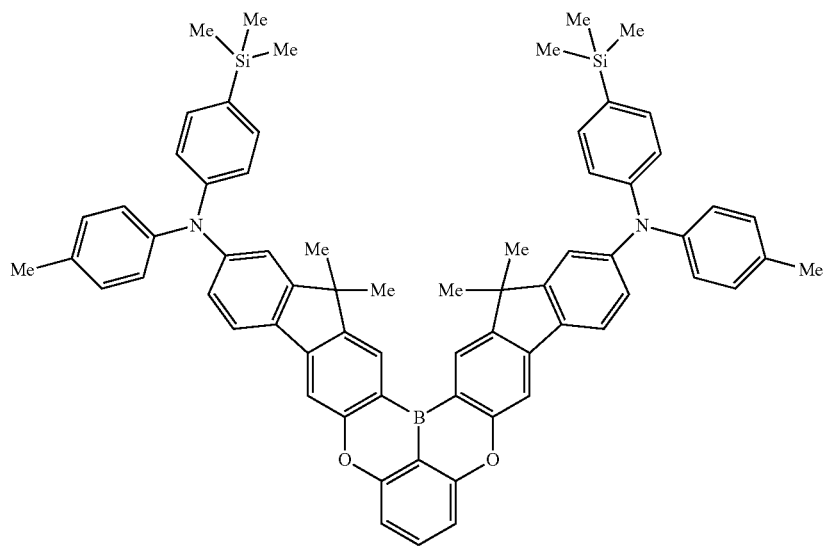
(2-8)
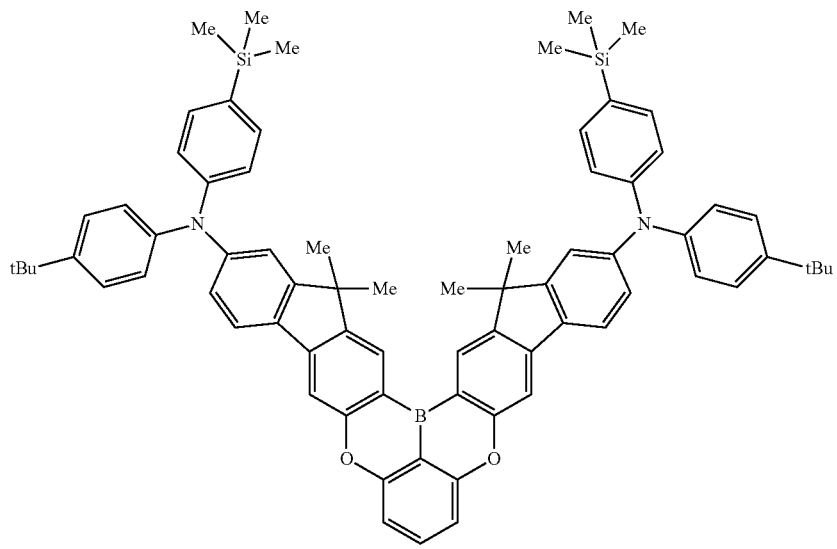
(2-9)

(2-10)
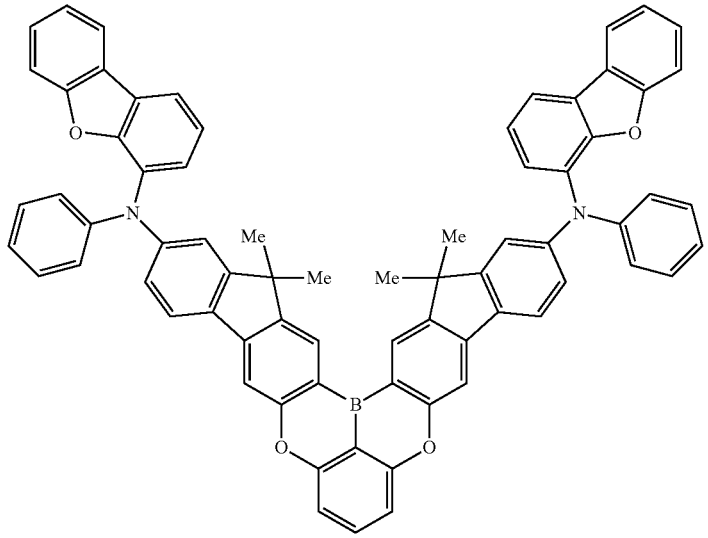
(2-11)
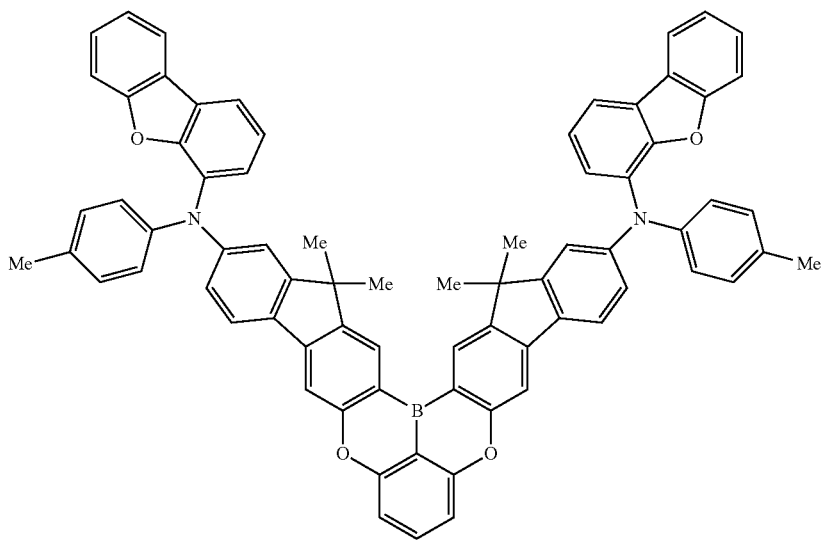
(2-12) (2-13)
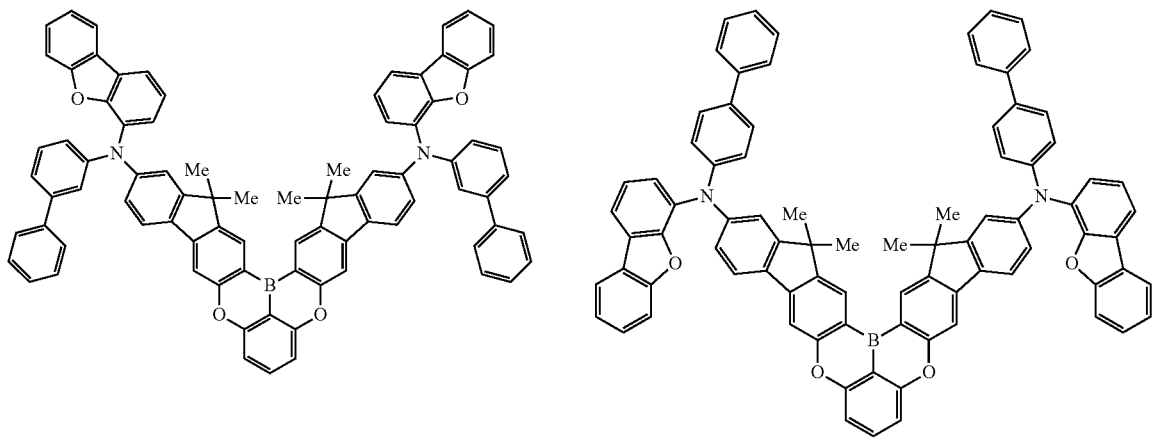

-continued
(2-14)
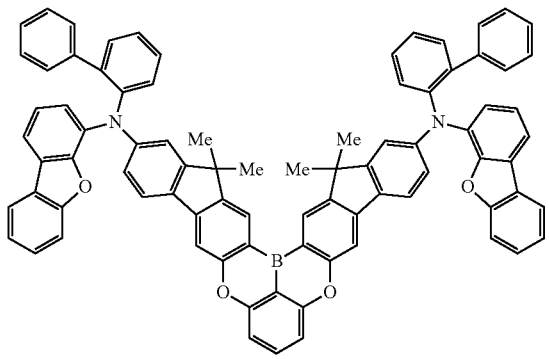
(2-15)
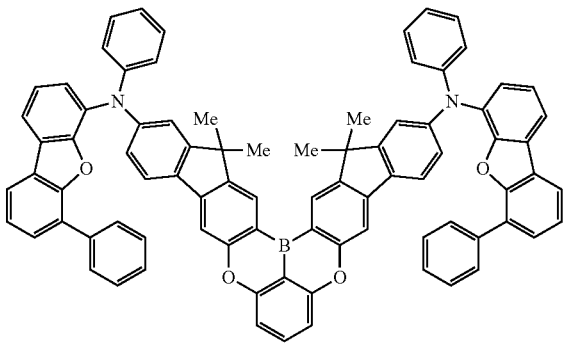
(2-16)
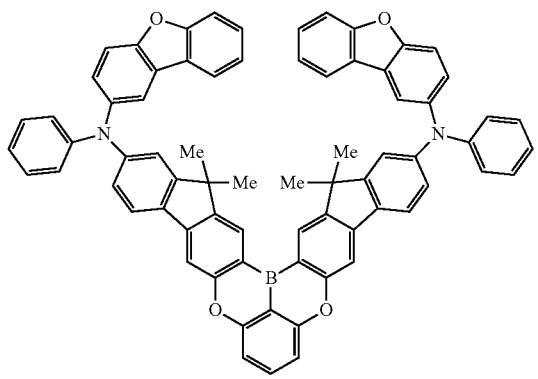
(2-17)
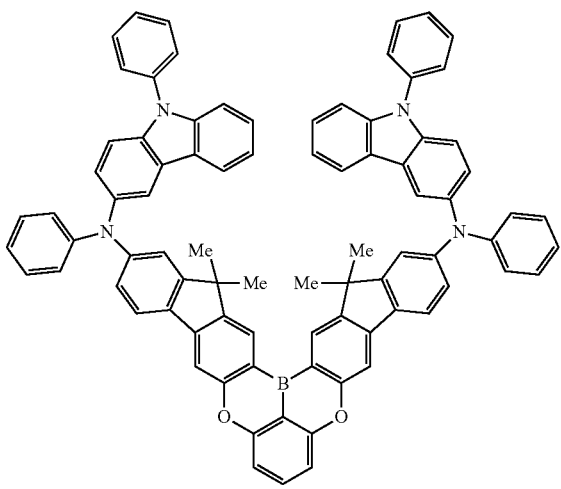
(2-18)
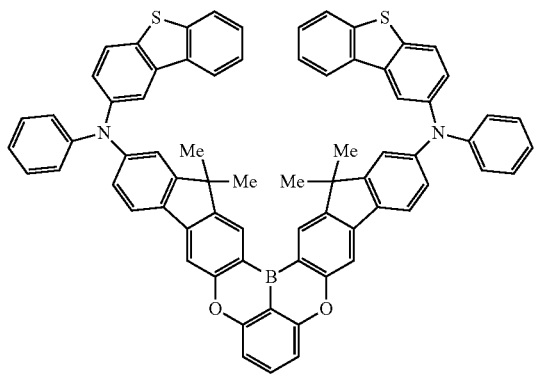
(2-19)
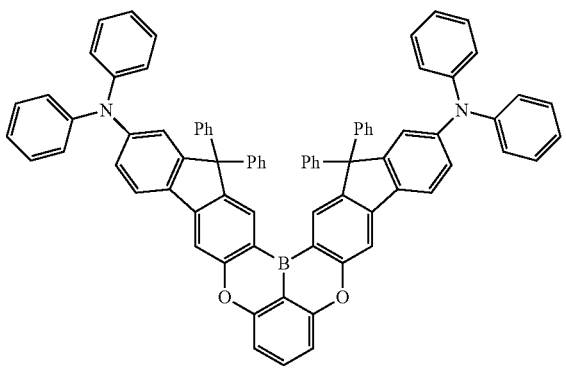

-continued
(2-20)
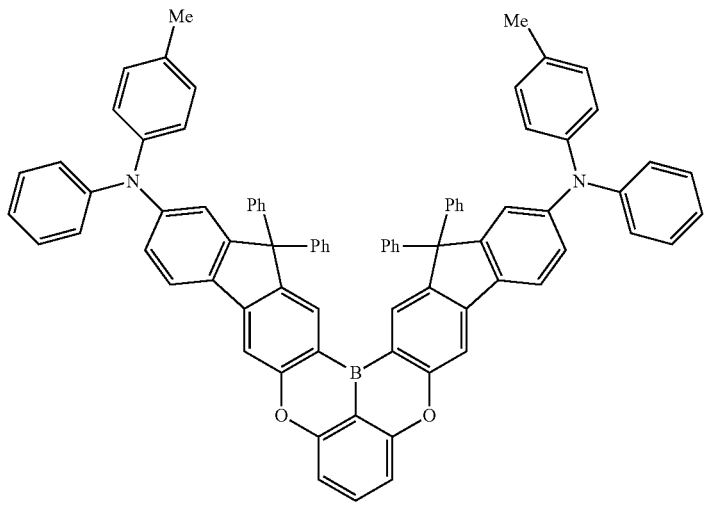
(2-21)
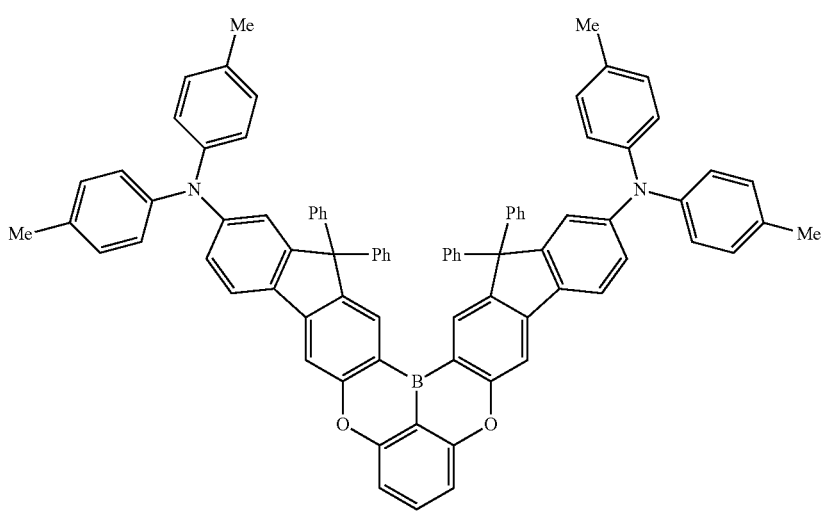
(2-22)
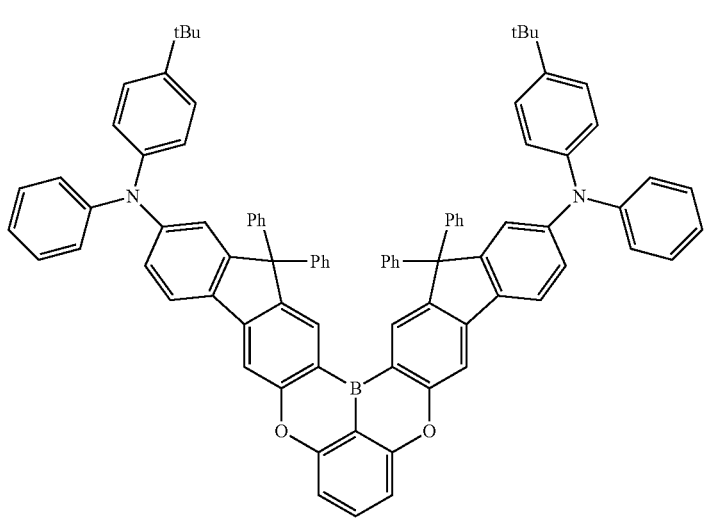

(2-23)
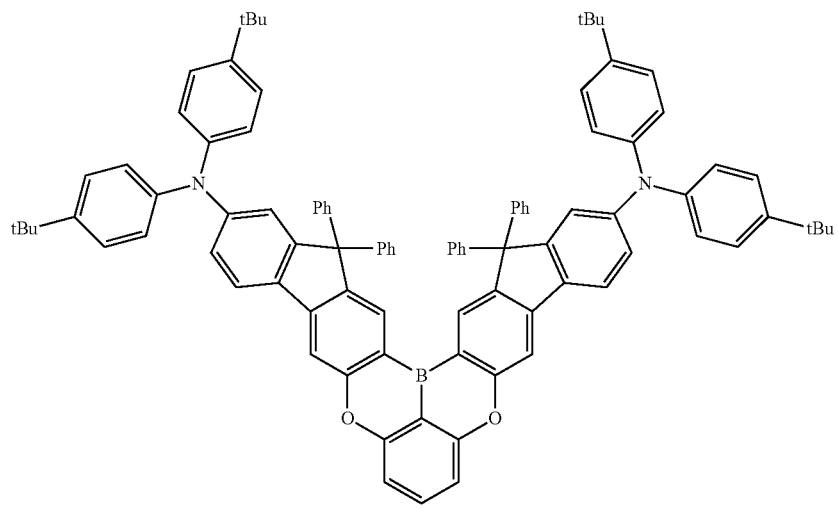
(2-24) (2-25)
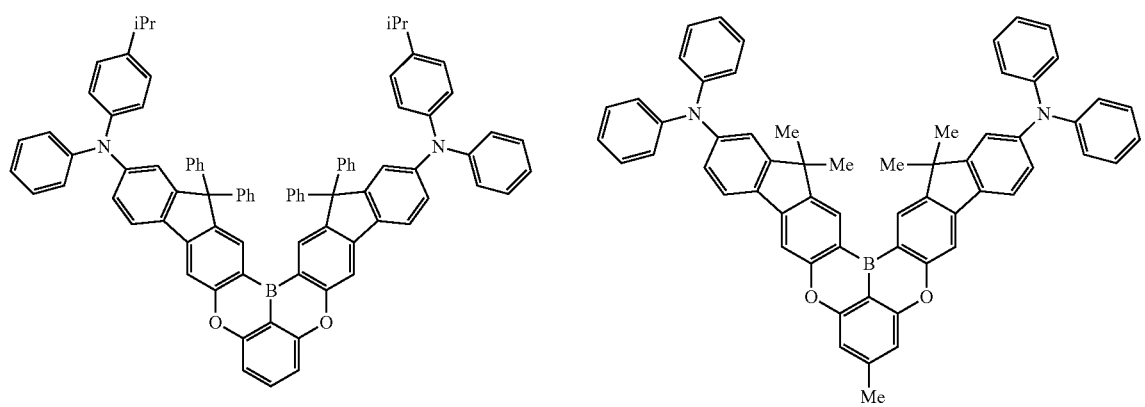
(2-26) (2-27)
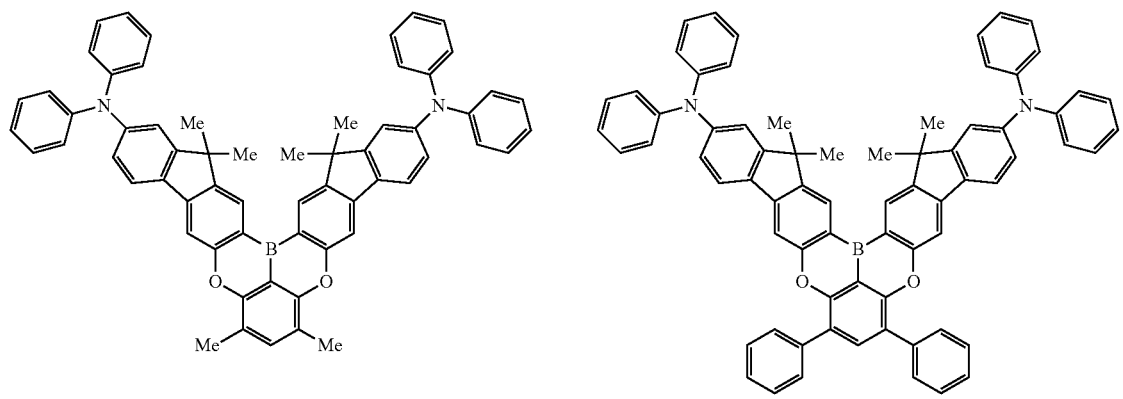

-continued
(2-28)
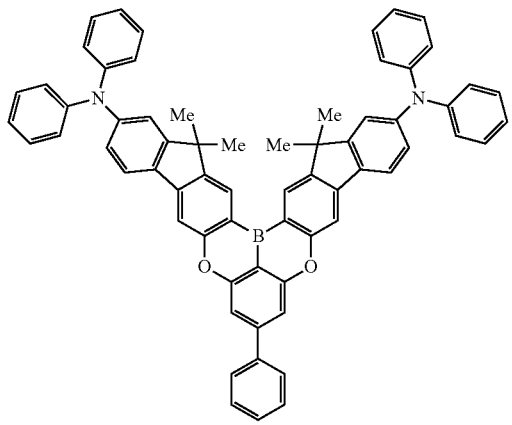
(2-101)
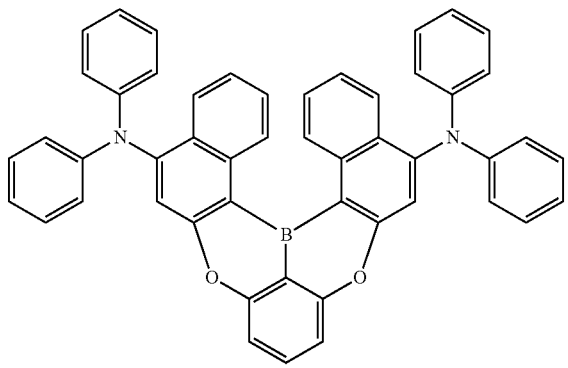
(2-102)
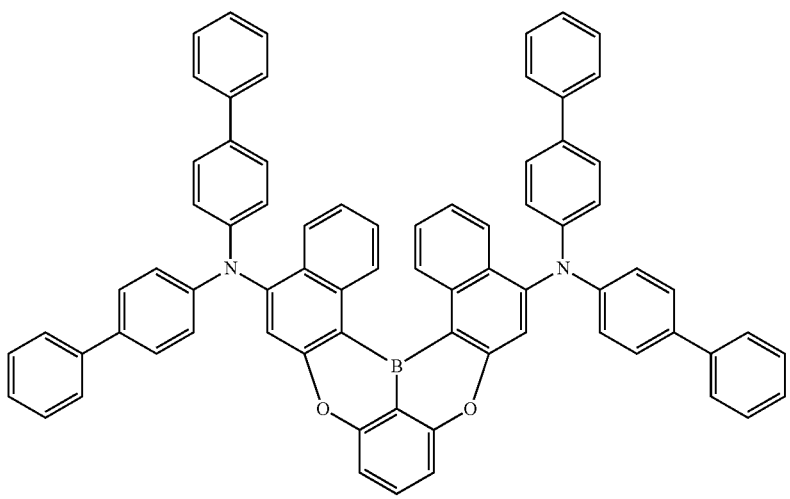
(2-103)
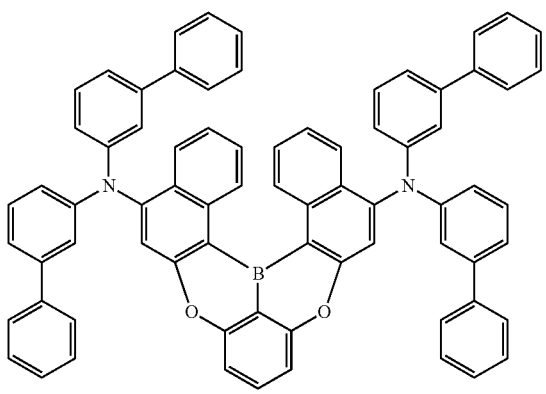
(2-104)
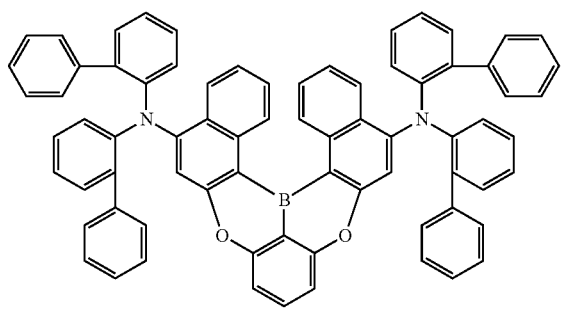

-continued
(2-105)
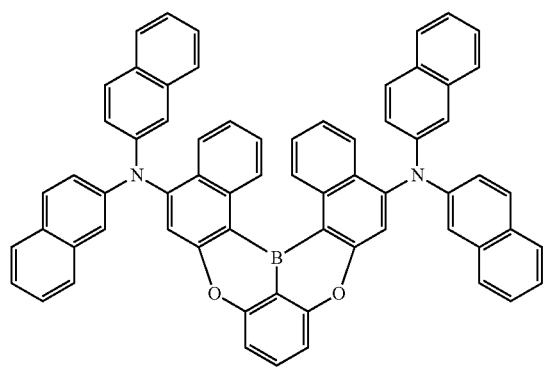
(2-106)
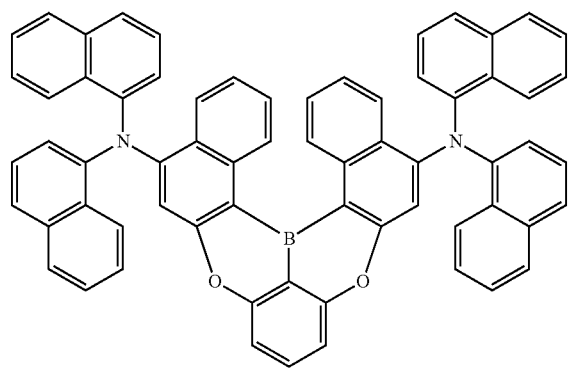
(2-111)
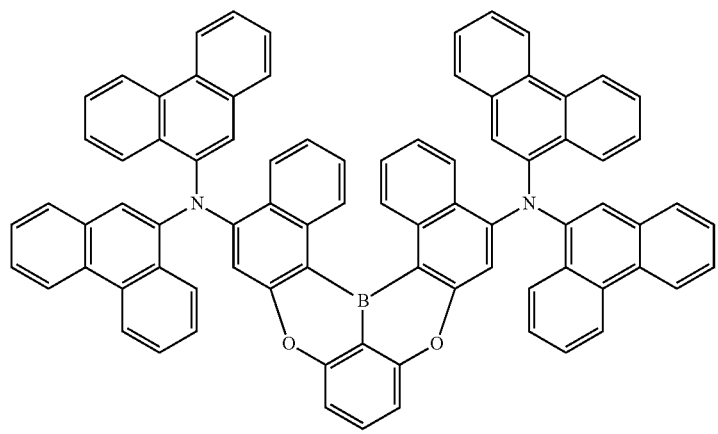
(2-112)
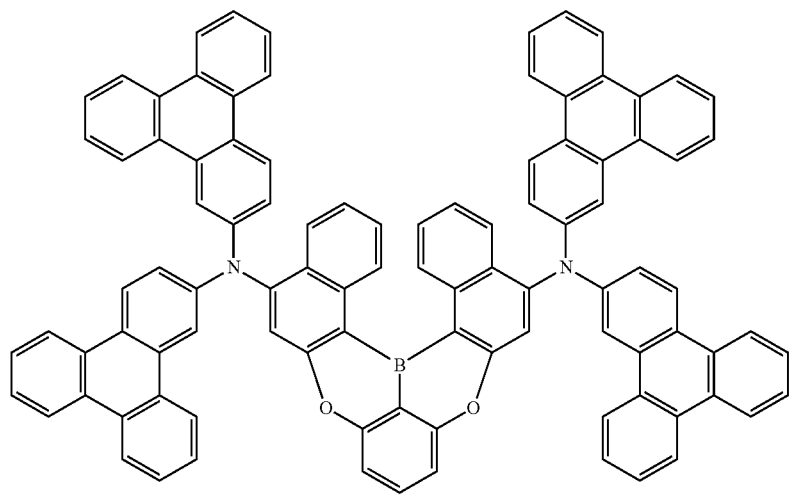

(2-113)
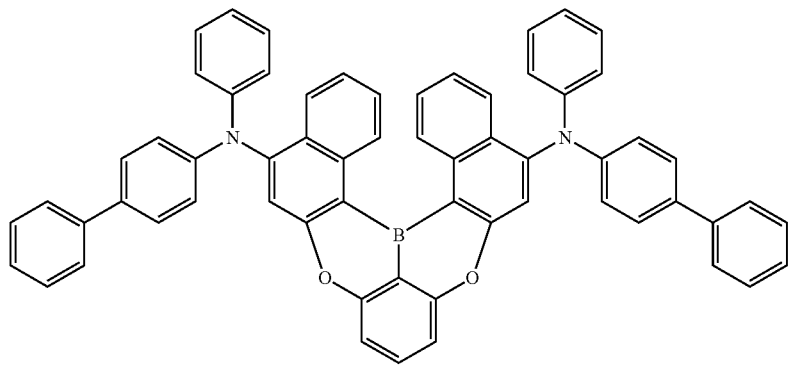
(2-114)
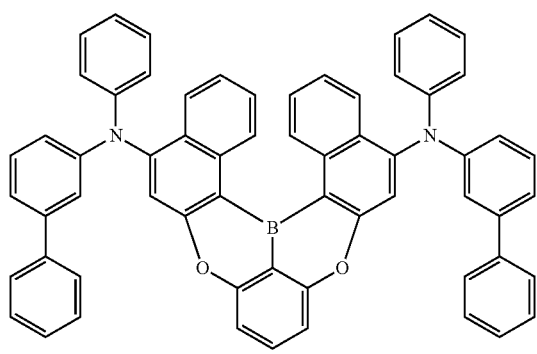
(2-115)
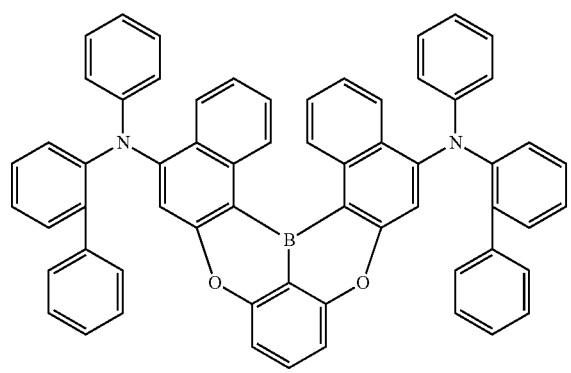
(2-116)
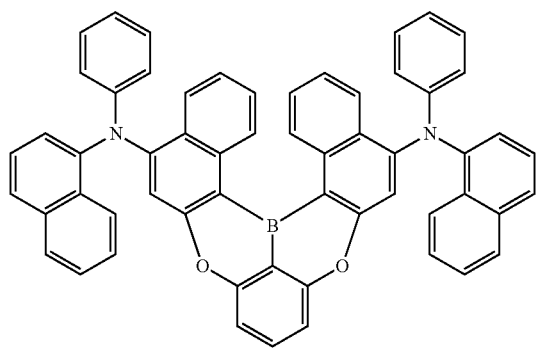
(2-121)
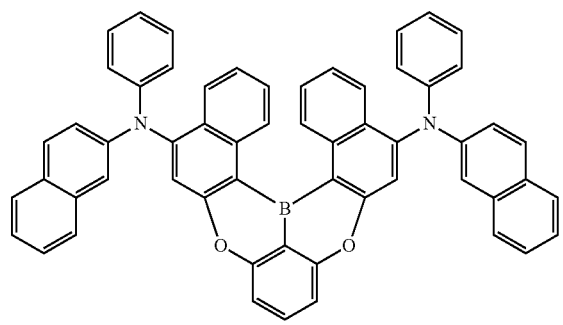
(2-122)
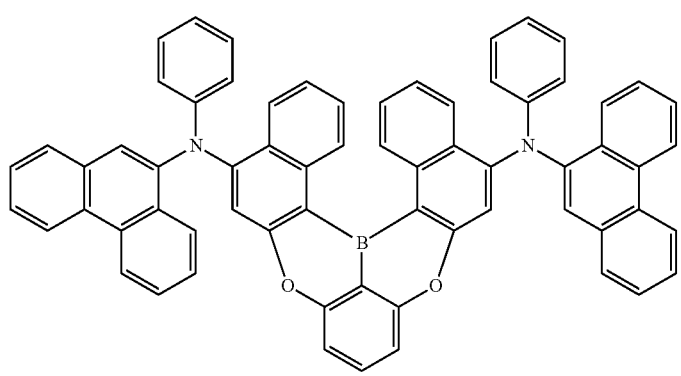

(2-123)
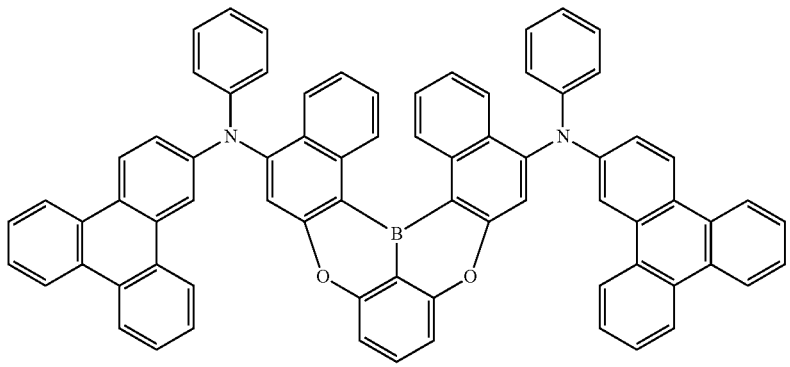
(2-124)
(2-125)
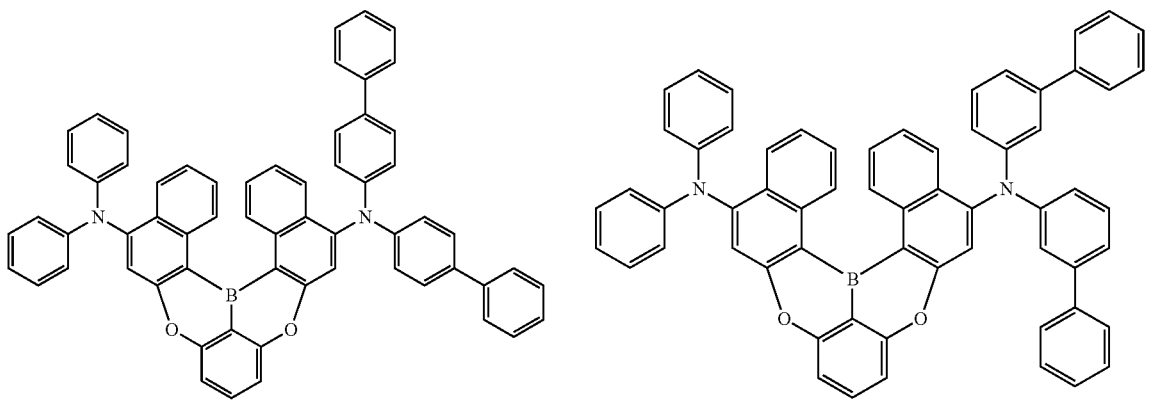
(2-126)
(2-131)
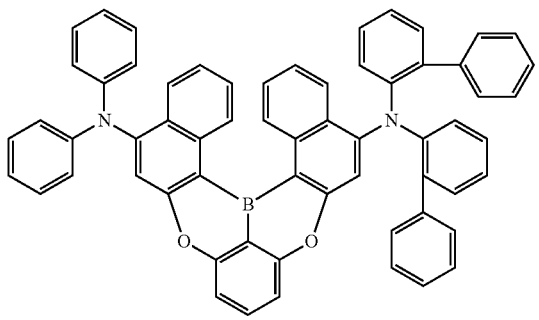
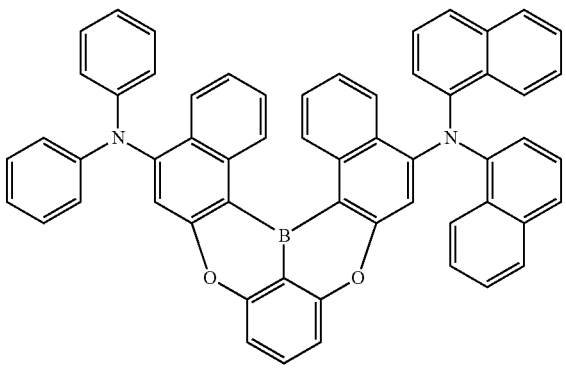
(2-132)
(2-133)
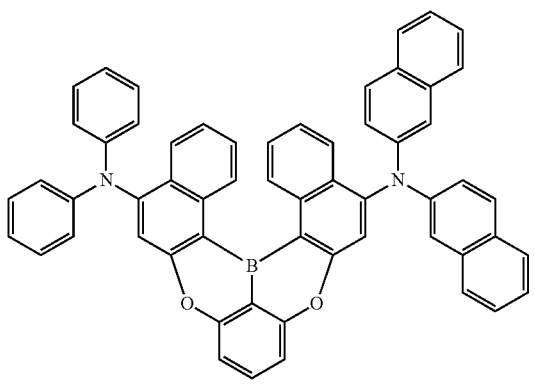
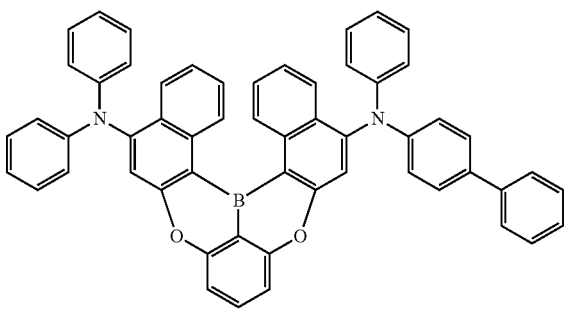

-continued
(2-134)
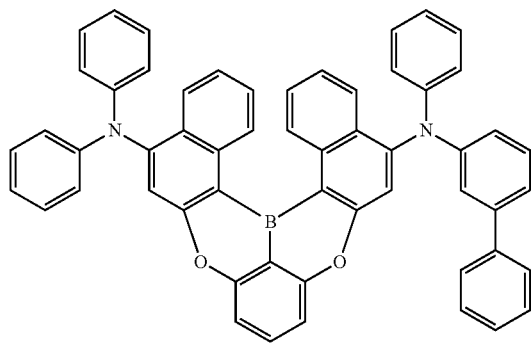
(2-135)
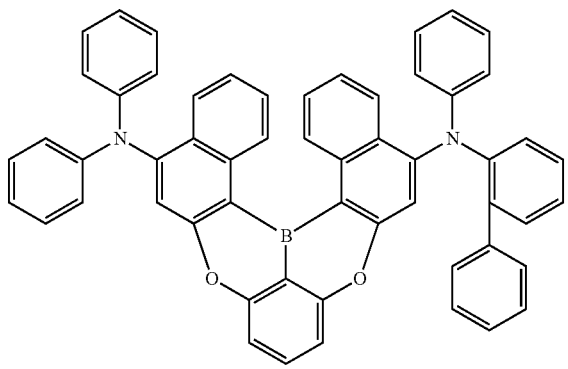
(2-136)
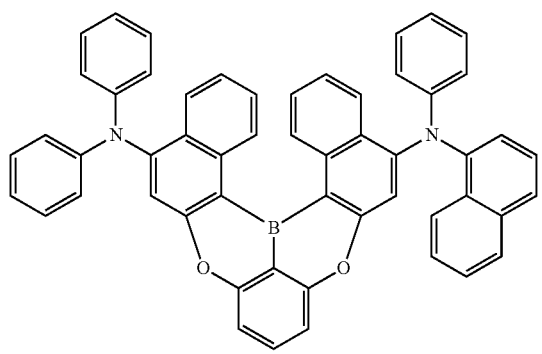
(2-141)
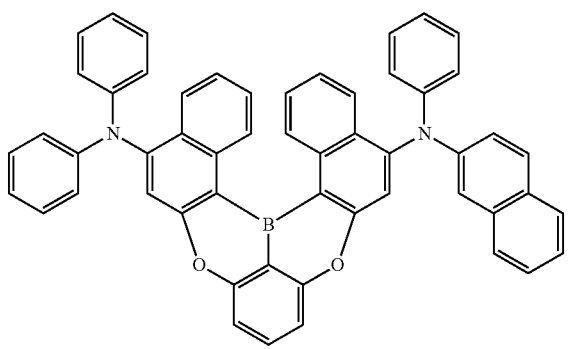
(2-142)
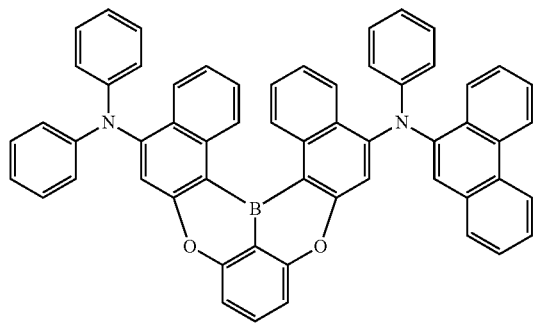
(2-143)
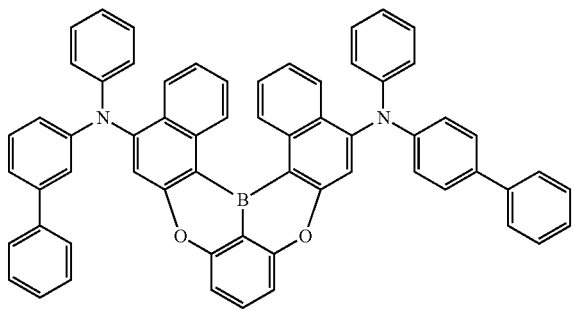
(2-144)
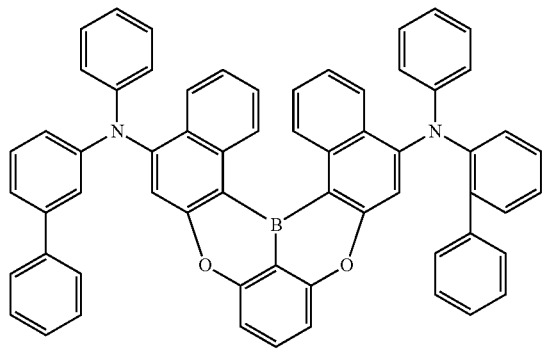
(2-145)
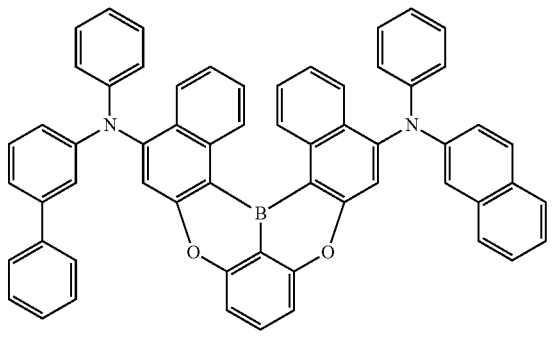

-continued
(2-146)
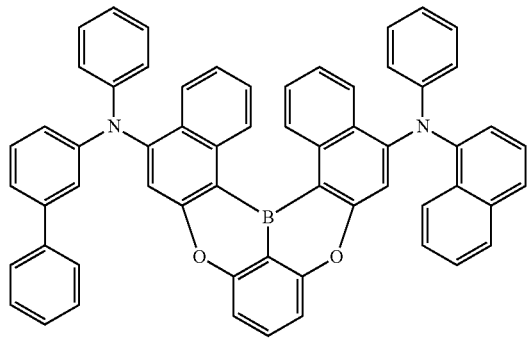
(2-151)
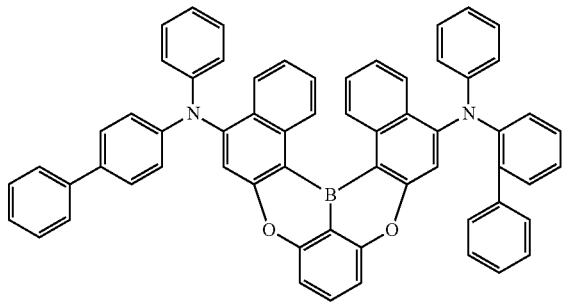
(2-152)
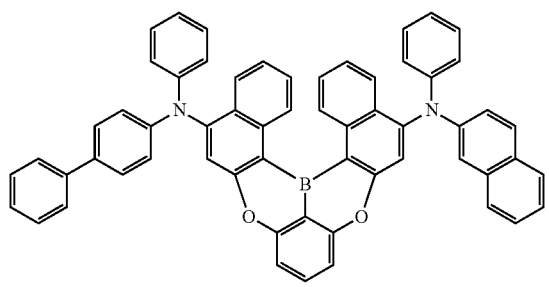
(2-153)
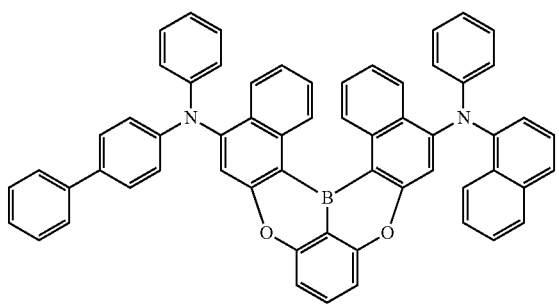
(2-154)
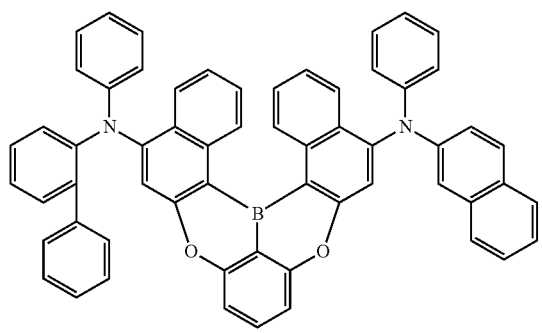
(2-155)
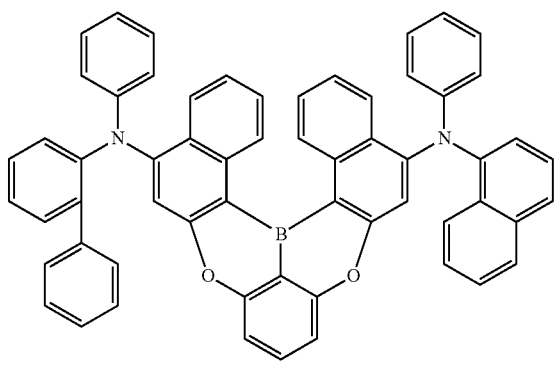
(2-156)
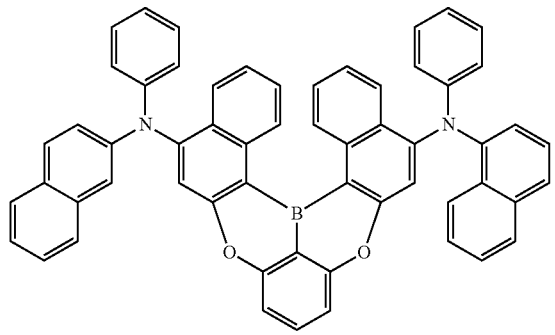
(2-161)
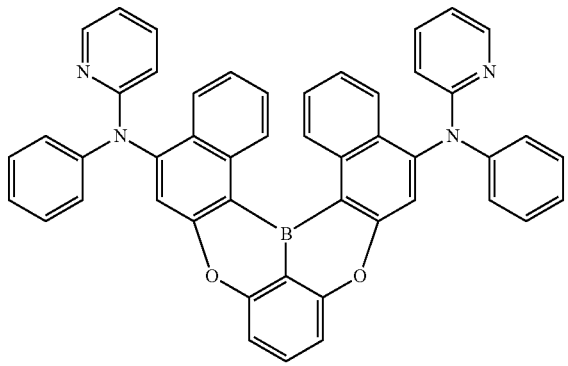

(2-162)
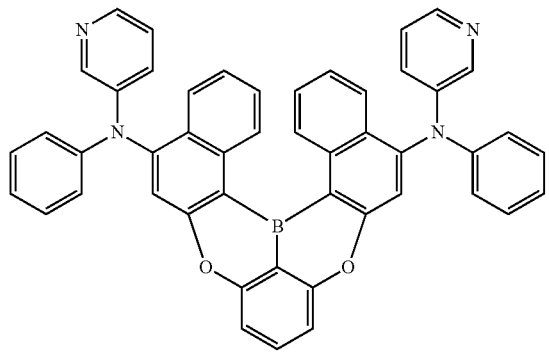
(2-163)
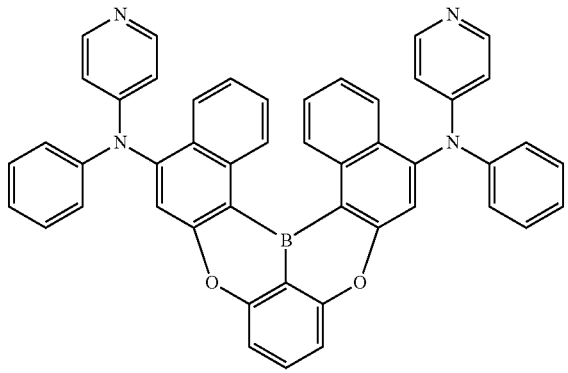
(2-164)
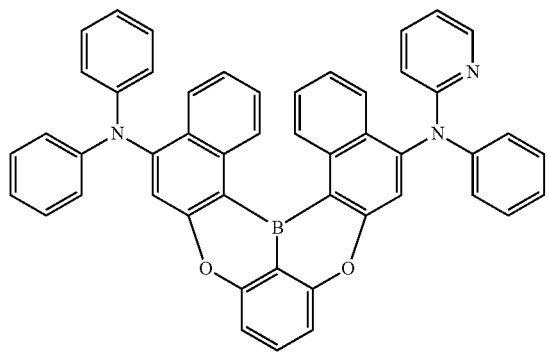
(2-165)
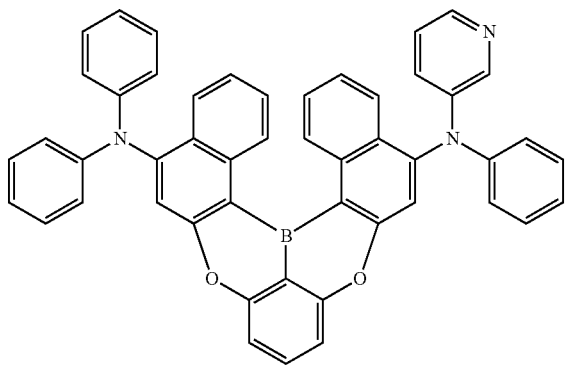
(2-166)
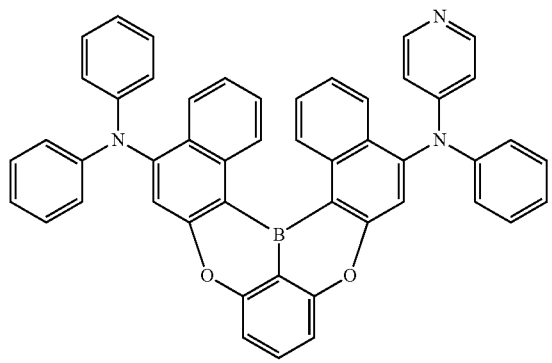
(2-171)
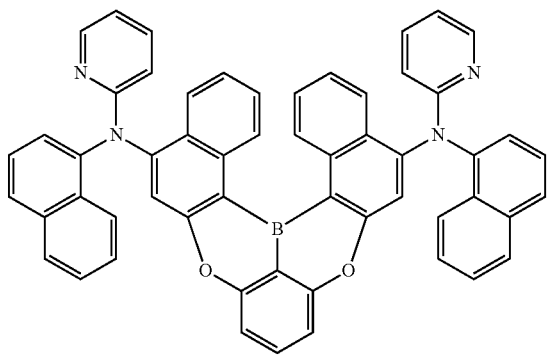
(2-172)
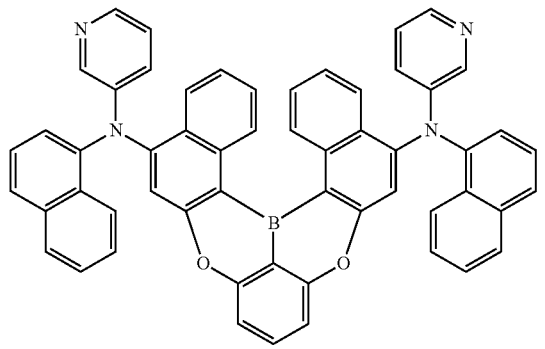
(2-173)
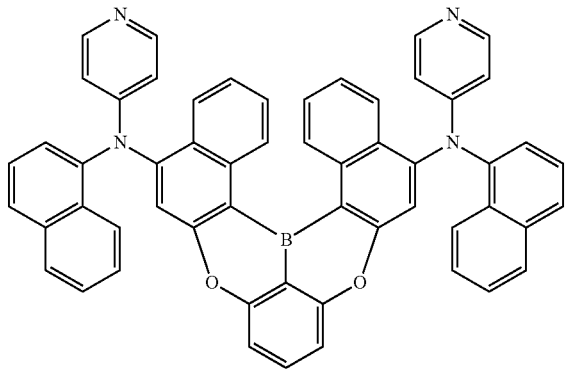

-continued
(2-174)
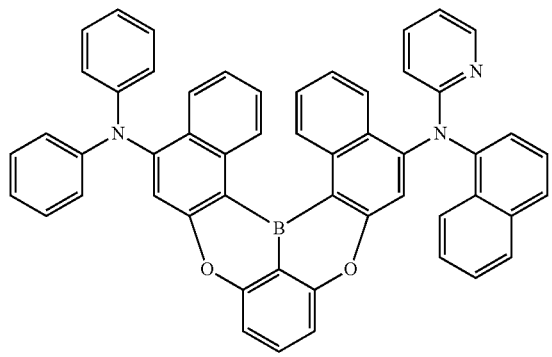
(2-175)
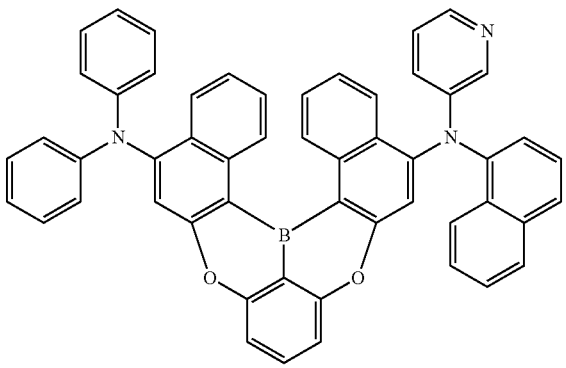
(2-176)
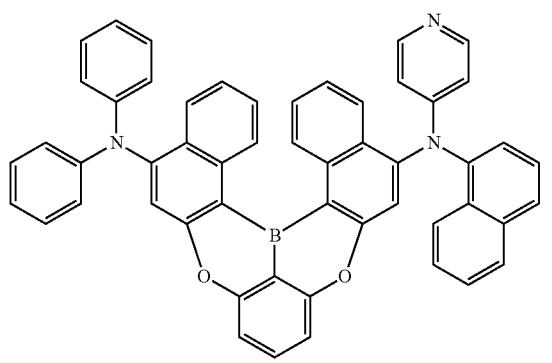
(2-181)
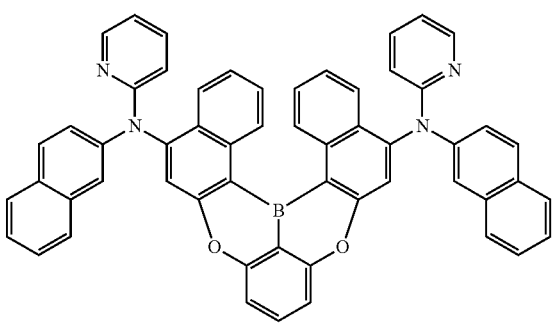
(2-182)
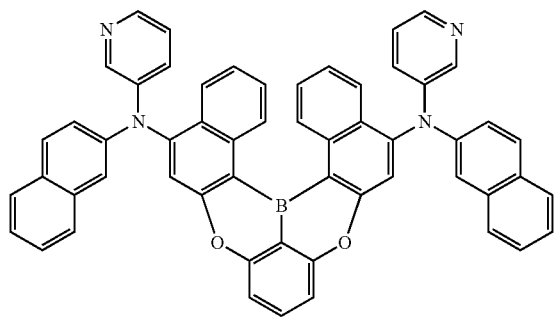
(2-183)
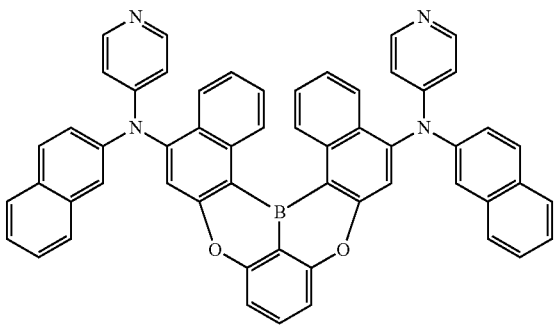
(2-184)
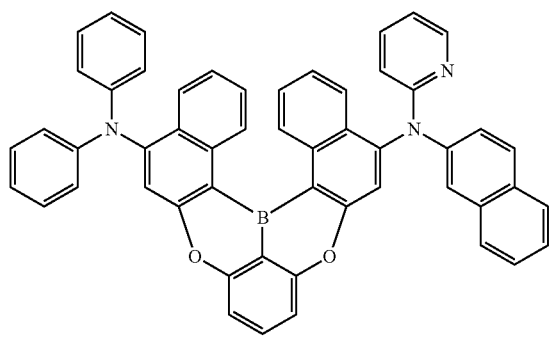
(2-185)
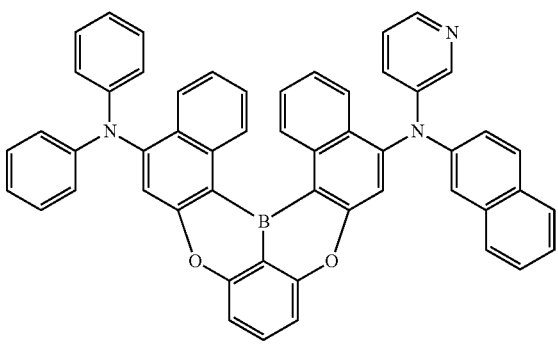

(2-186)
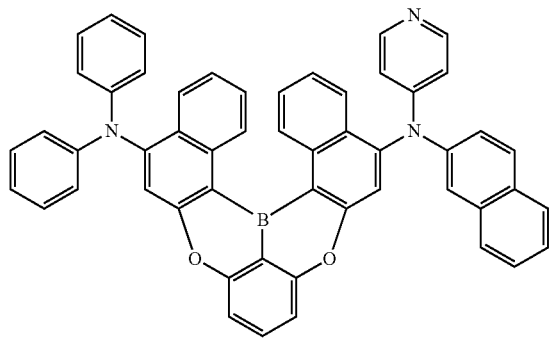
(2-191)
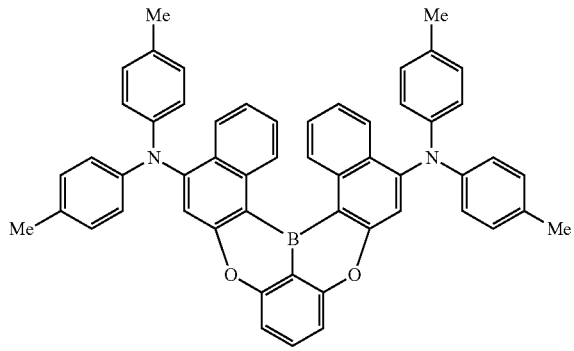
(2-192)
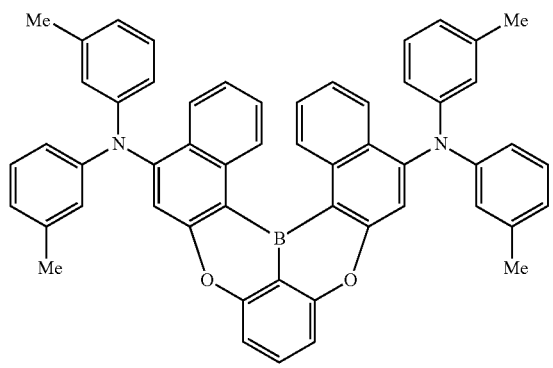
(2-193)
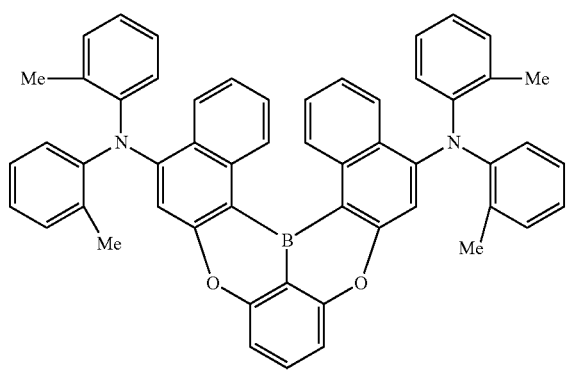
(2-194)
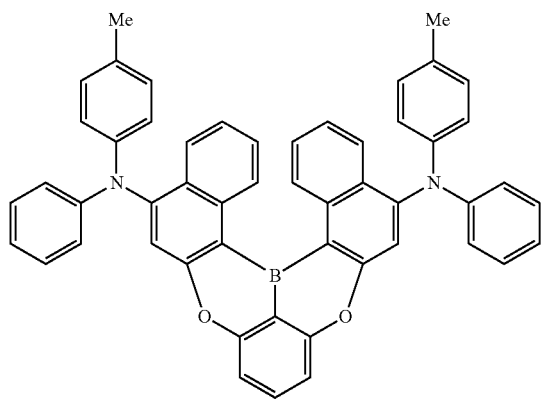
(2-195)
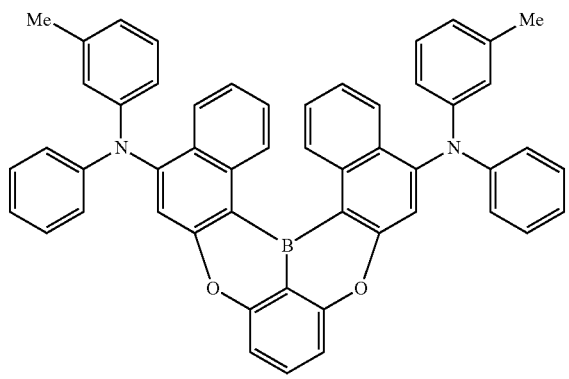

-continued
(2-196)
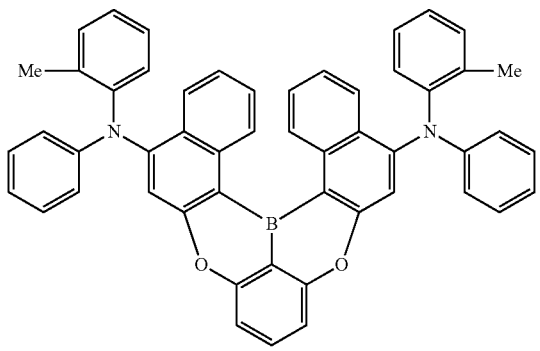
(2-201)
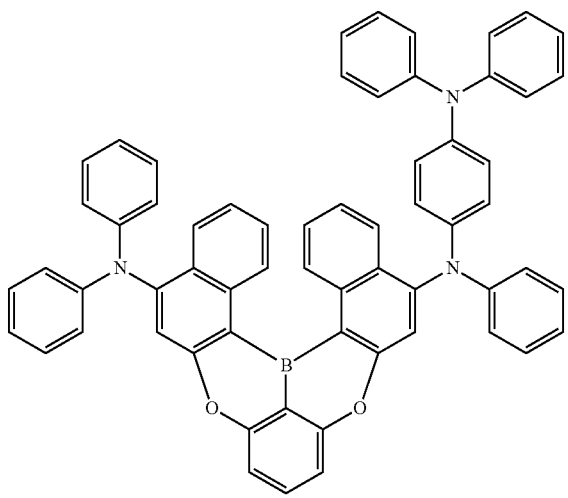
(2-202)
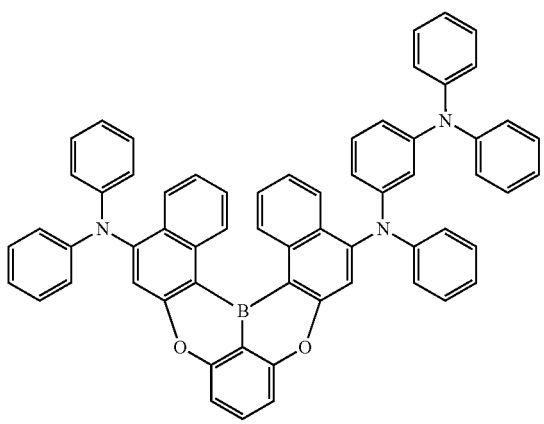
(2-203)
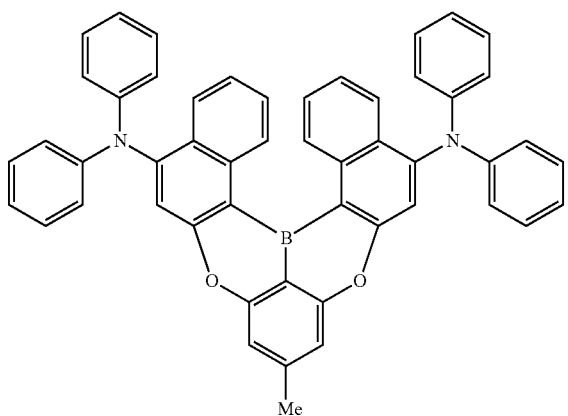
(2-204)
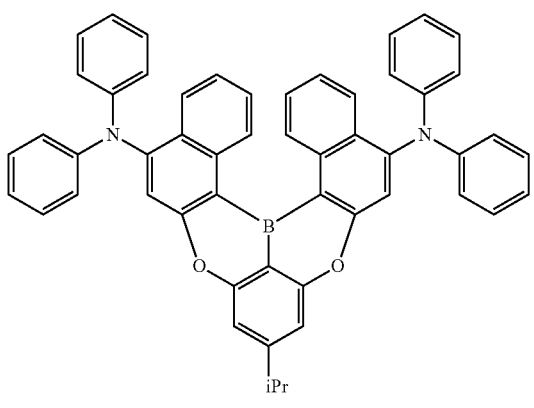
(2-205)
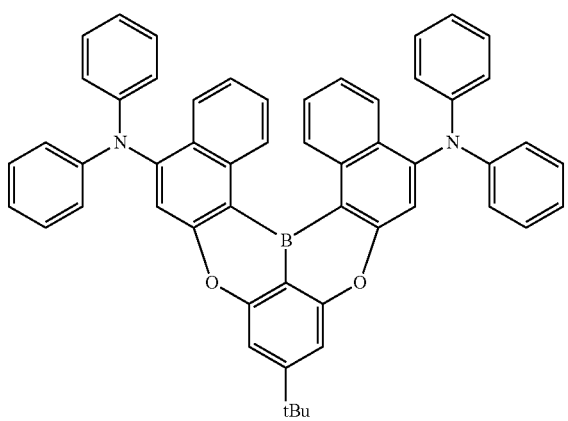

-continued
(2-206)
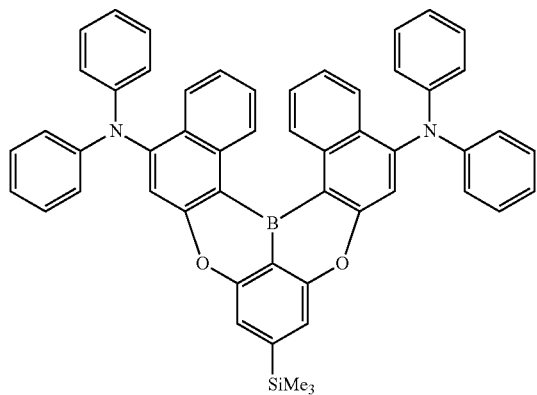
(2-211)
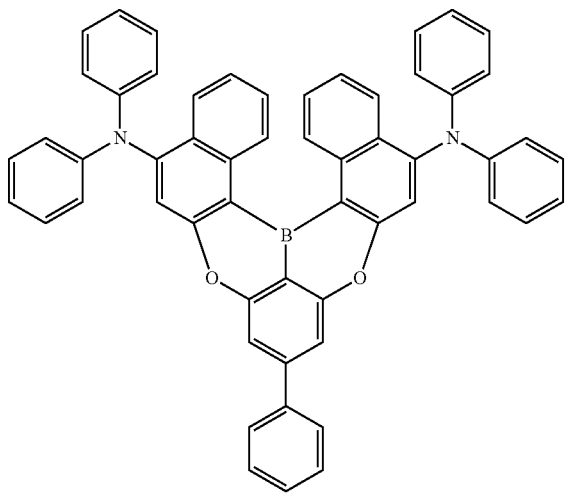
(2-212)
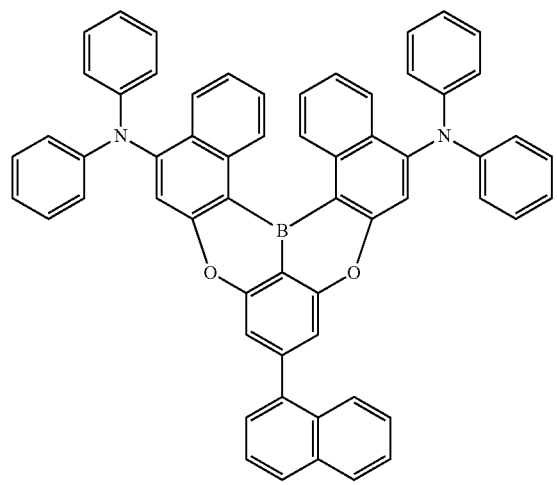
(2-213)
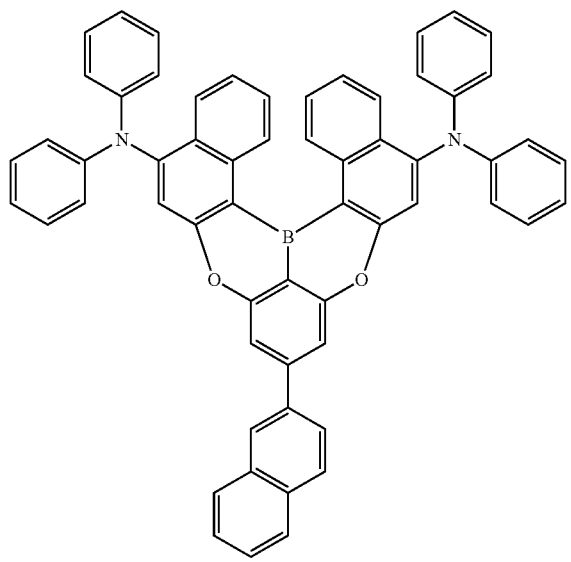
(2-214)
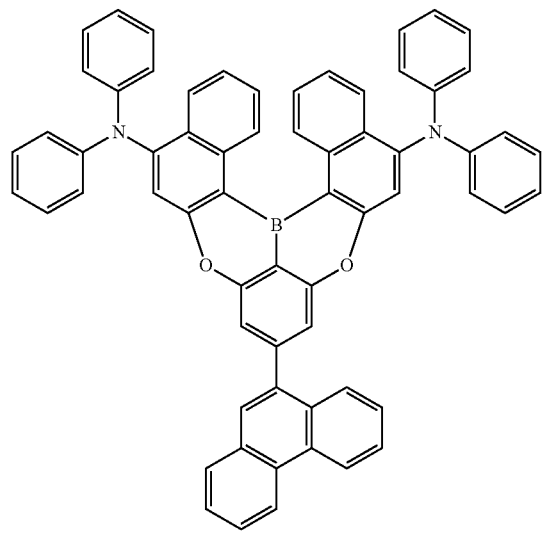
(2-215)
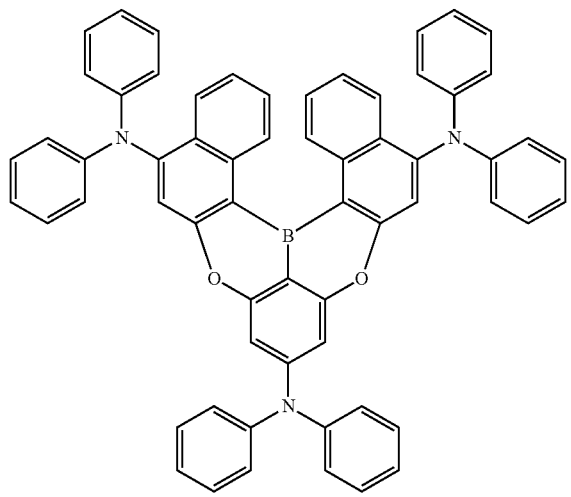

-continued
(2-216)
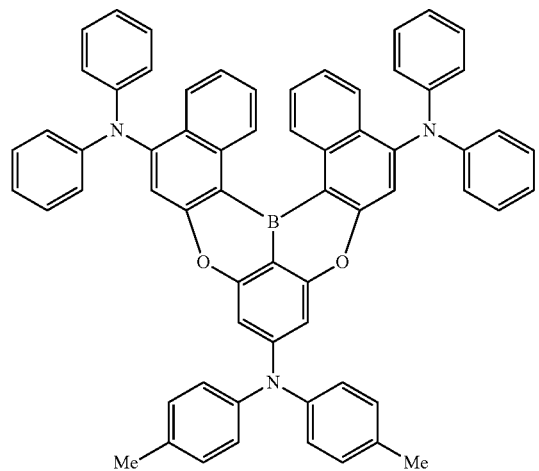
(2-221)
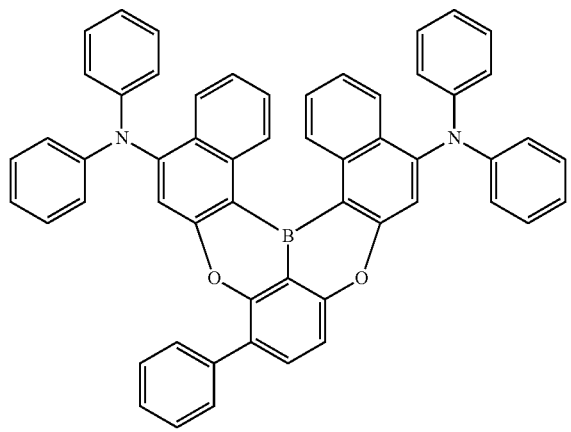
(2-222)
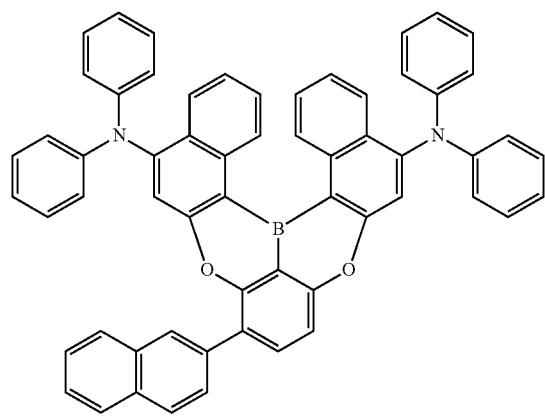
(2-223)
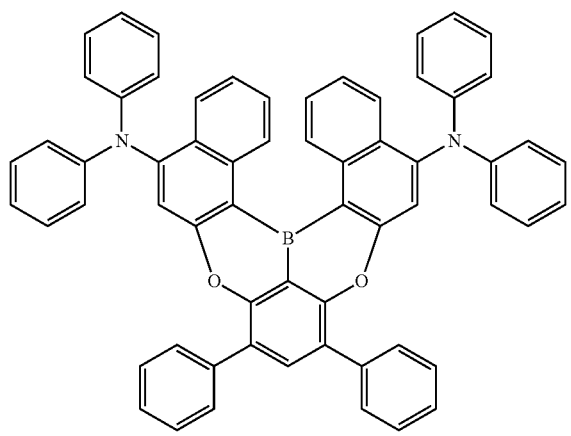
(2-224)
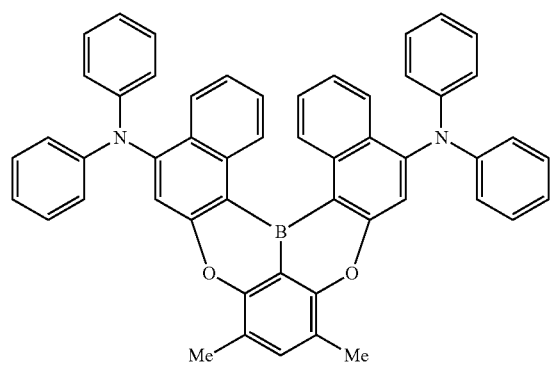
(2-225)
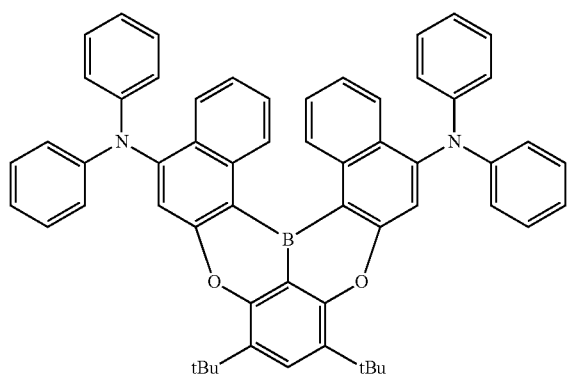

(2-226)
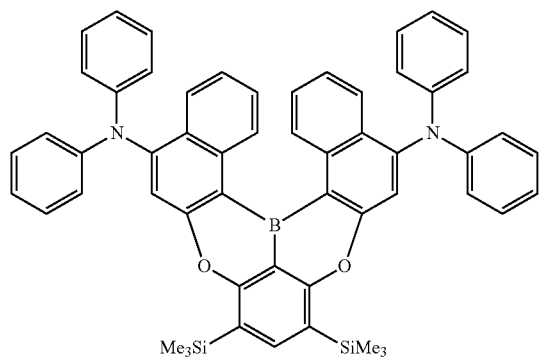
(2-231)
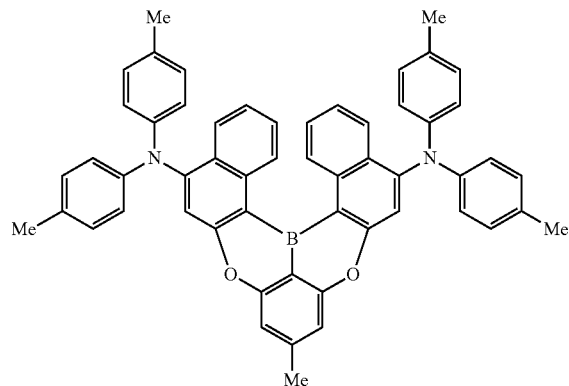
(2-232)
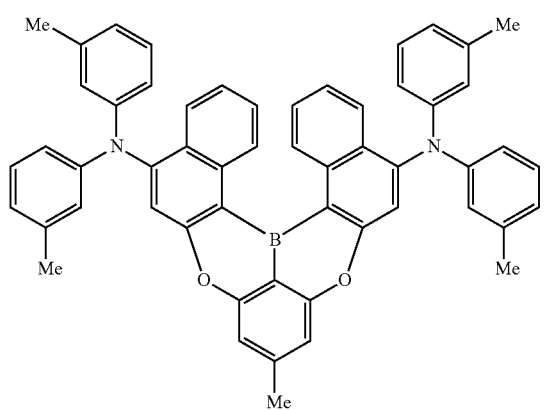
(2-233)
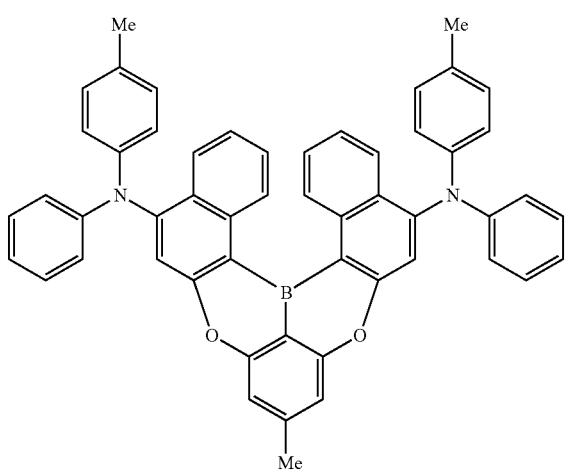
(2-234)
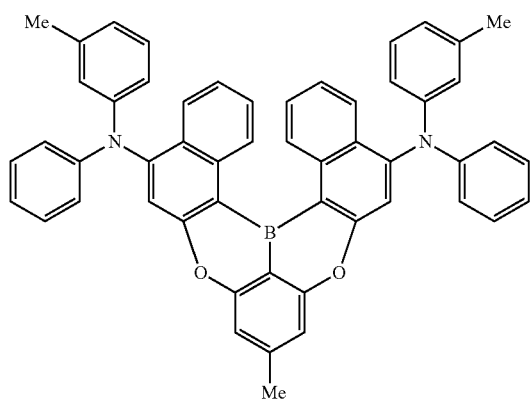
(2-235)
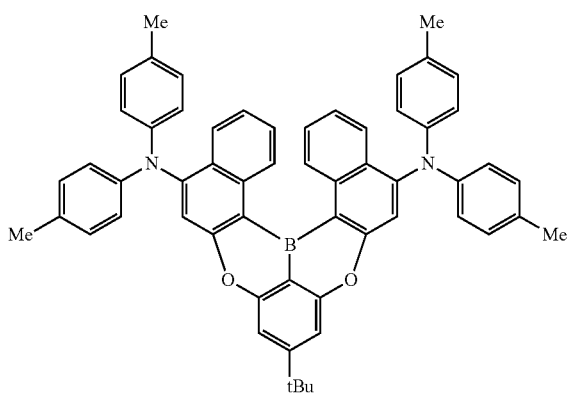

-continued
(2-236)
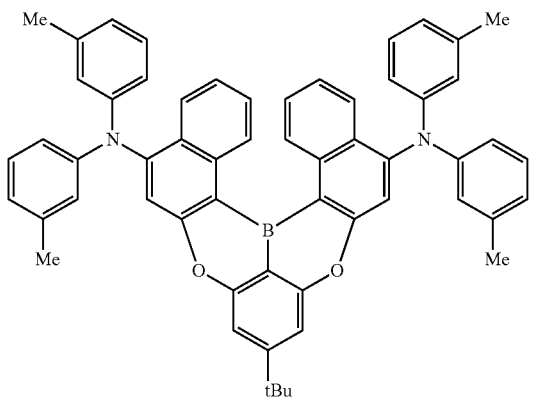
(2-241)
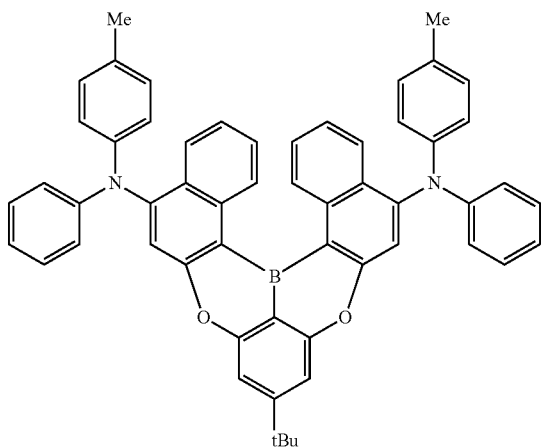
(2-242)
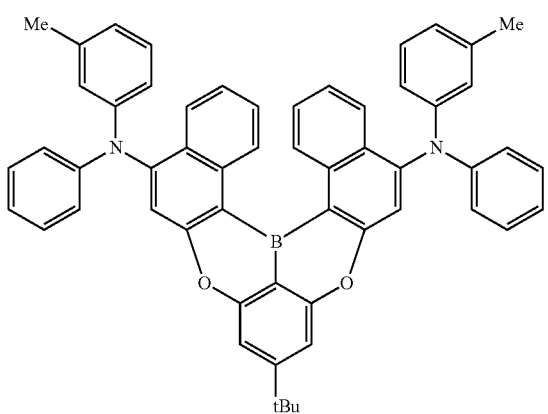
(2-243)
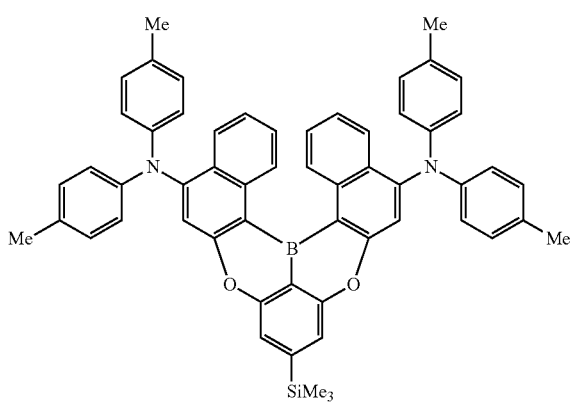
(2-244)
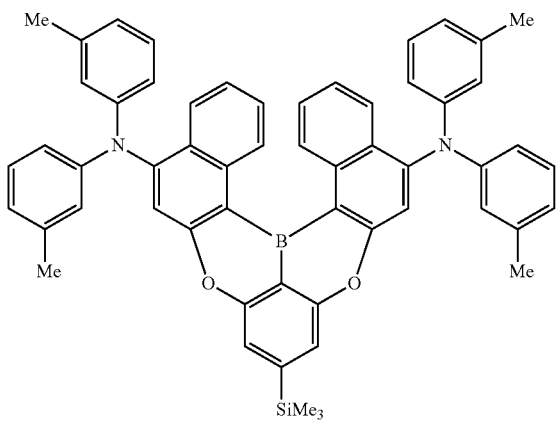
(2-245)
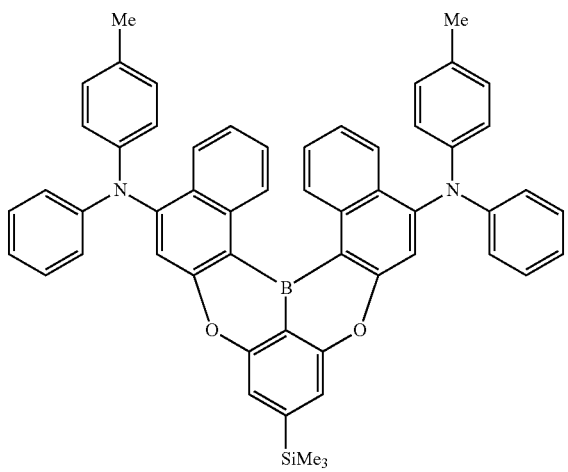

-continued
(2-246)
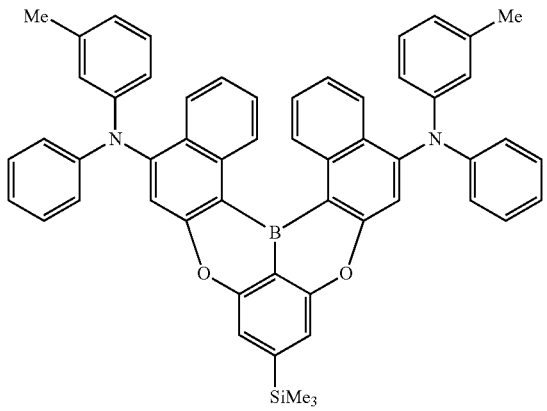
(2-251)
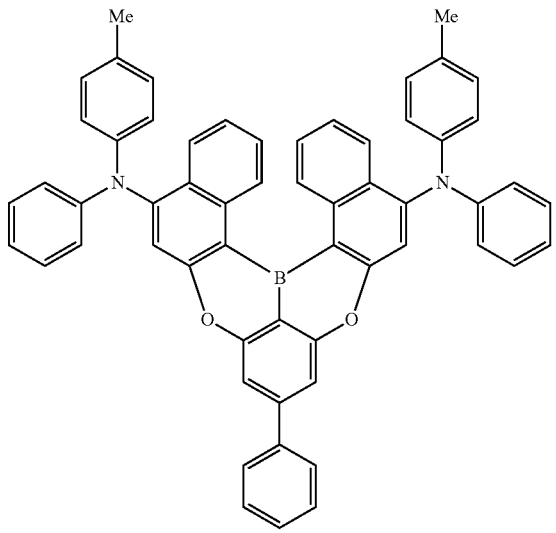
(2-252)
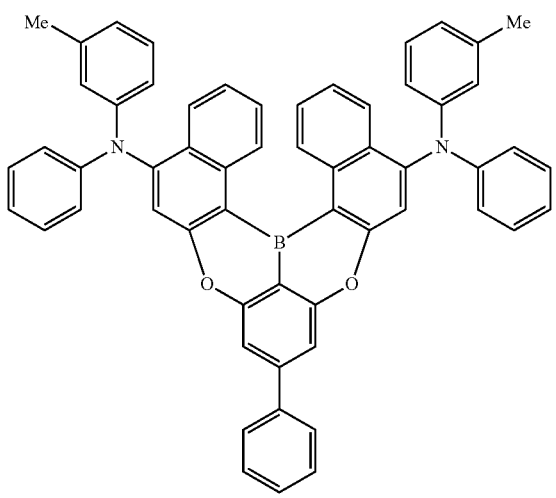
(2-253)
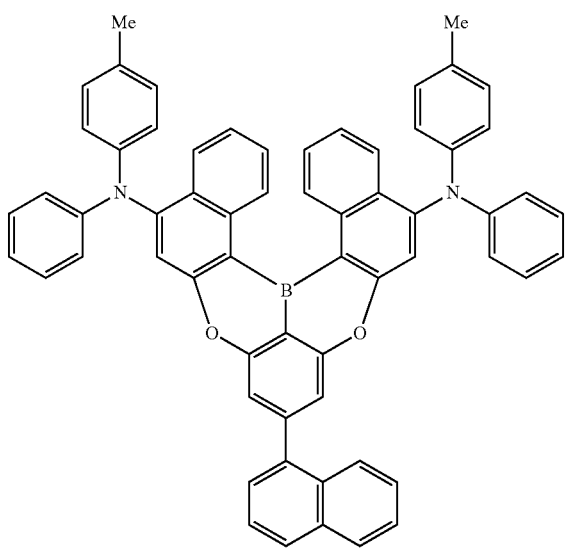
(2-254)
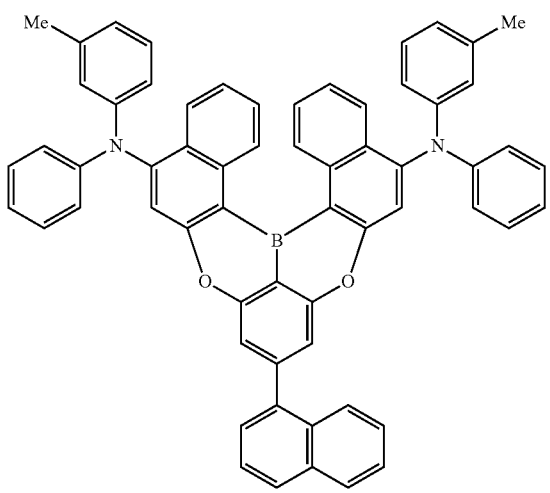
(2-255)
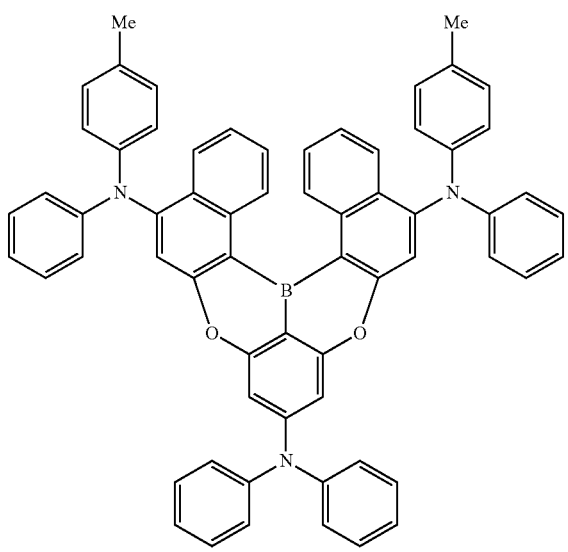

(2-256)
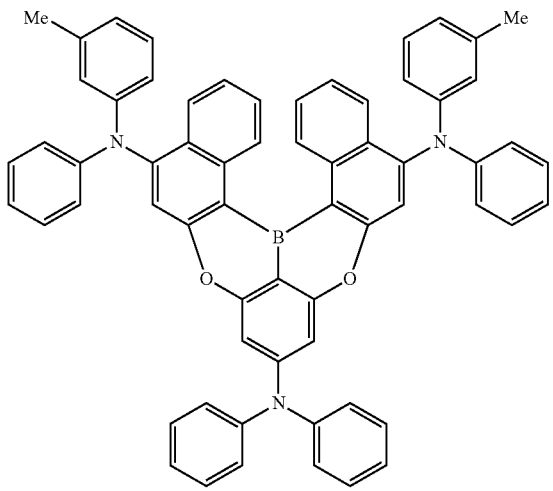
(2-301)
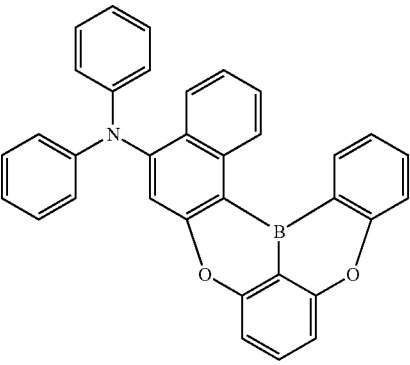
(2-302)
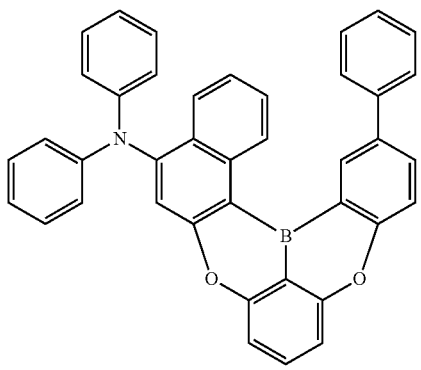
(2-303)
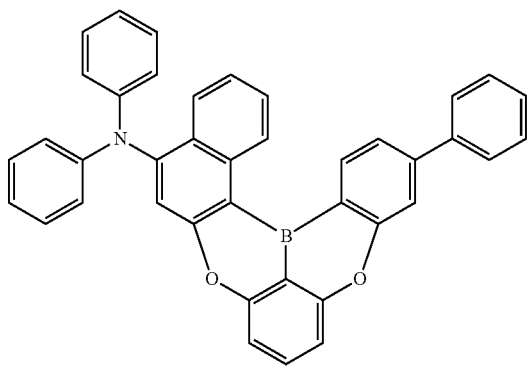
(2-304)
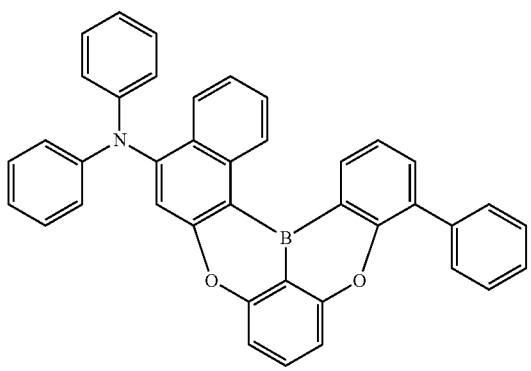
(2-305)
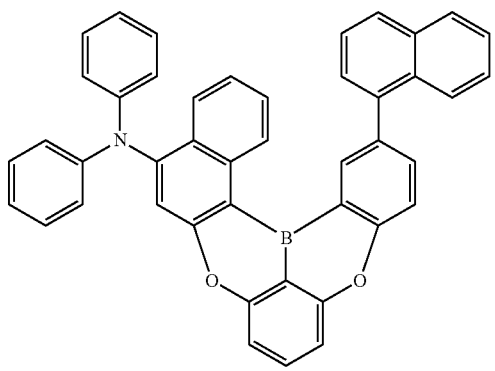

(2-306)
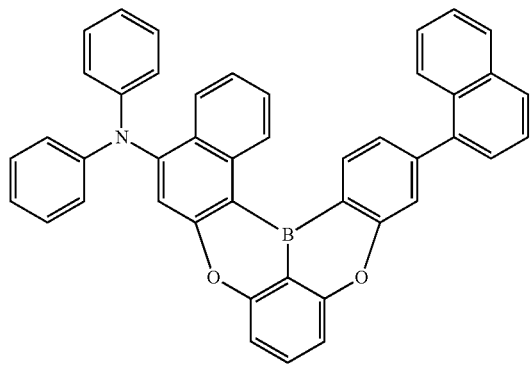
(2-311)
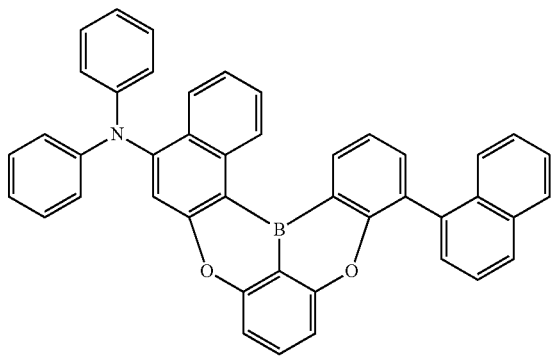
(2-312)
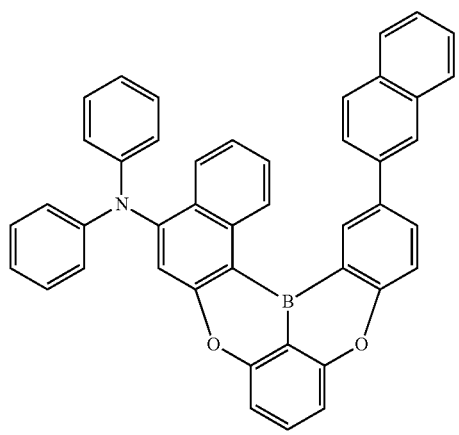
(2-313)
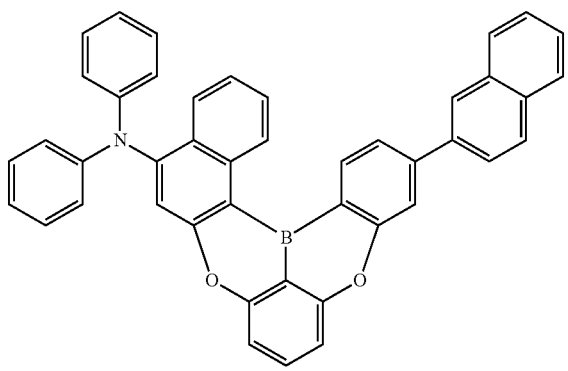
(2-314)
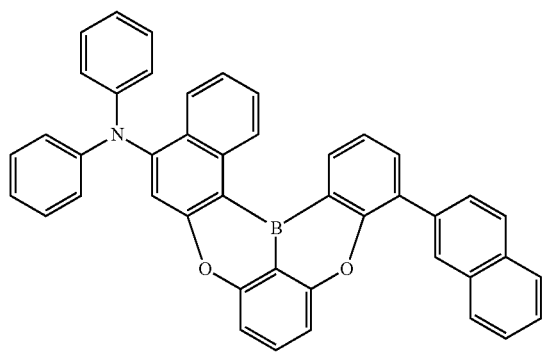
(2-315)
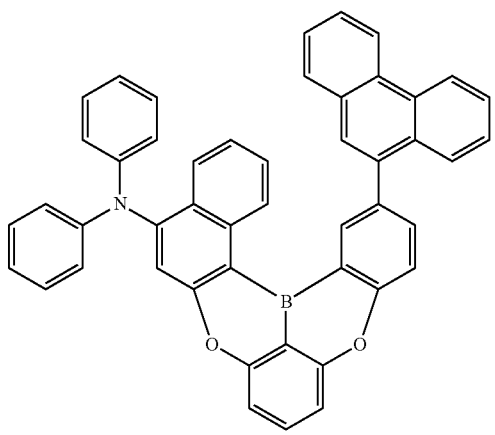

-continued
(2-316)
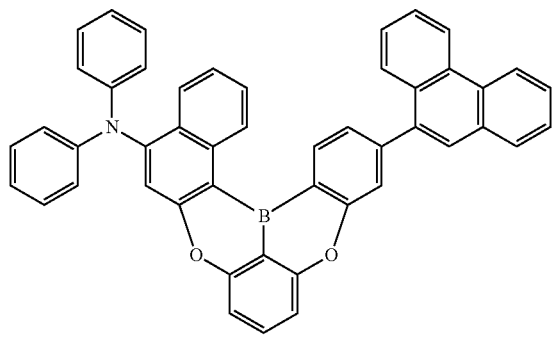
(2-321)
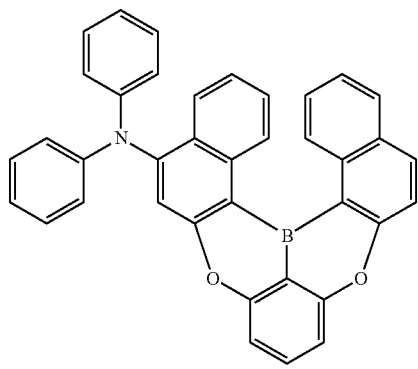
(2-322)
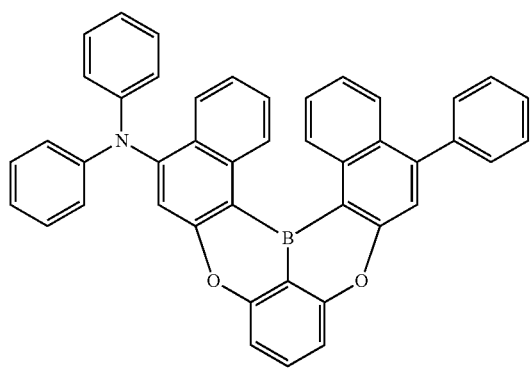
(2-323)
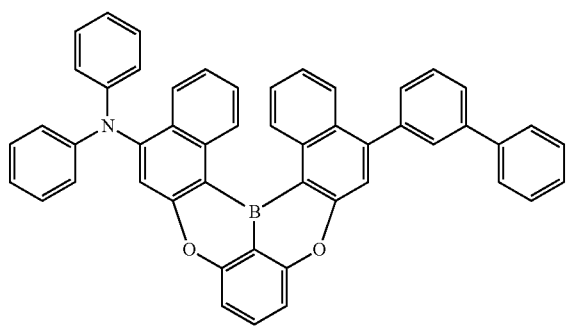
(2-324)
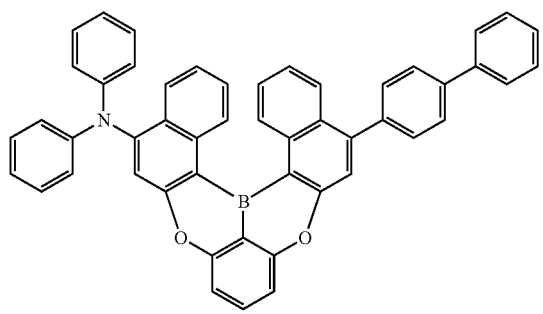
(2-325)
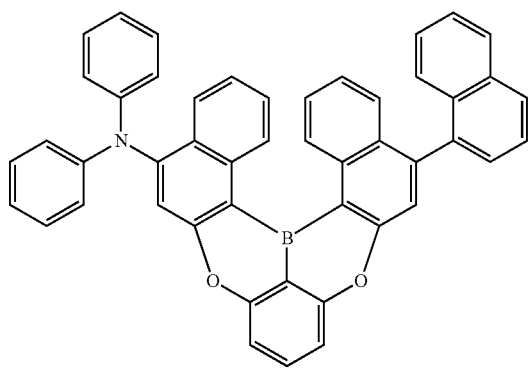
(2-326)
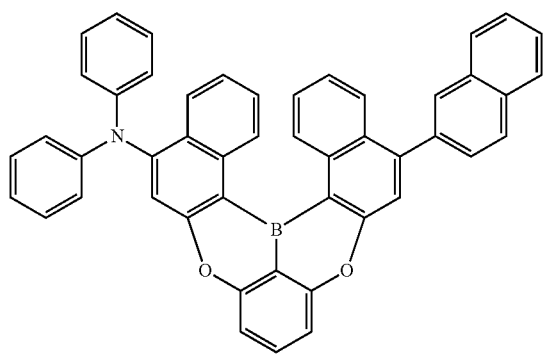
(2-331)
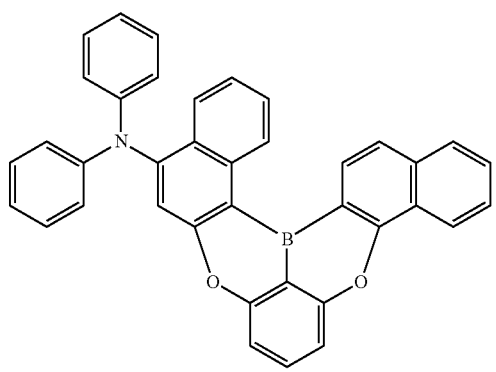

-continued
(2-332)
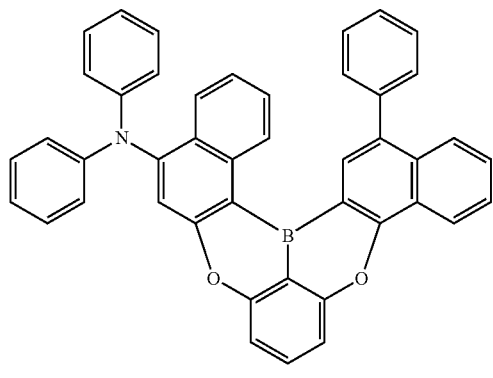
(2-333)
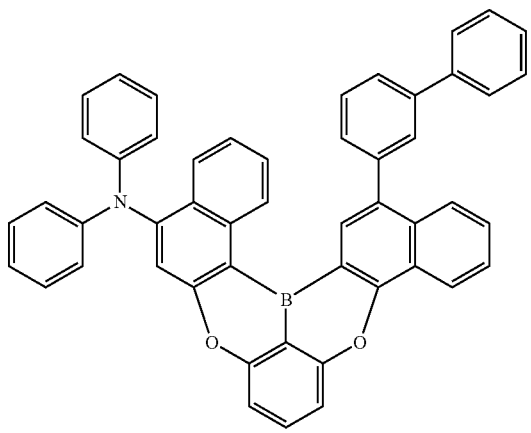
(2-334)
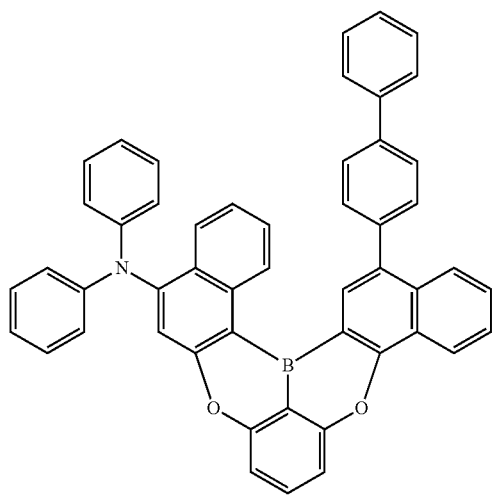
(2-335)
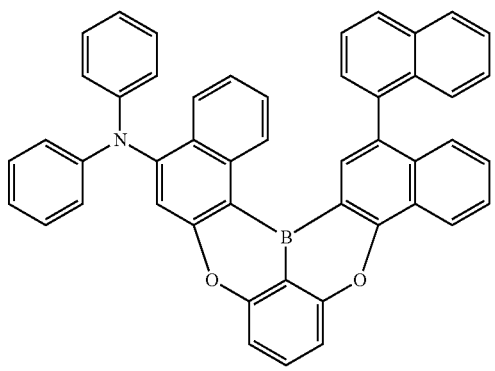
(2-336)
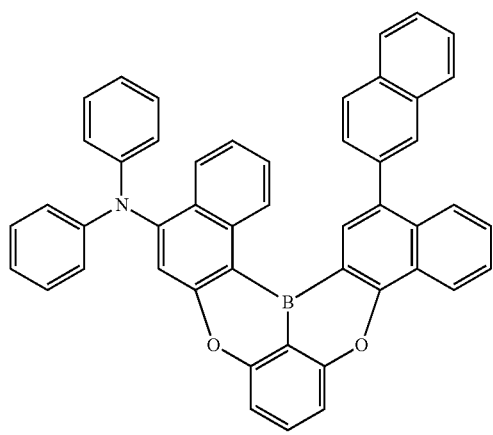
(2-341)
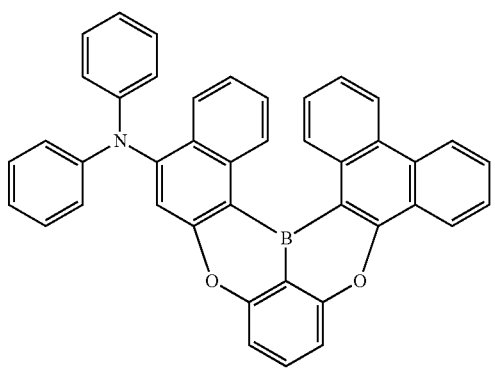

-continued
(2-342)
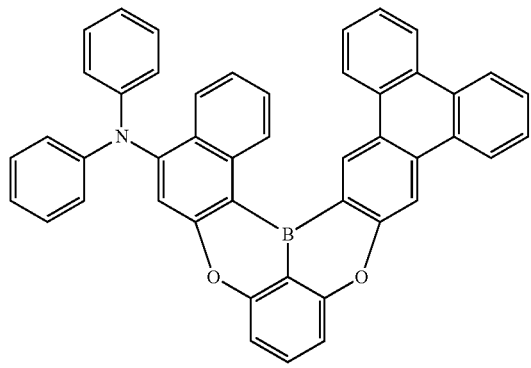
(2-343)
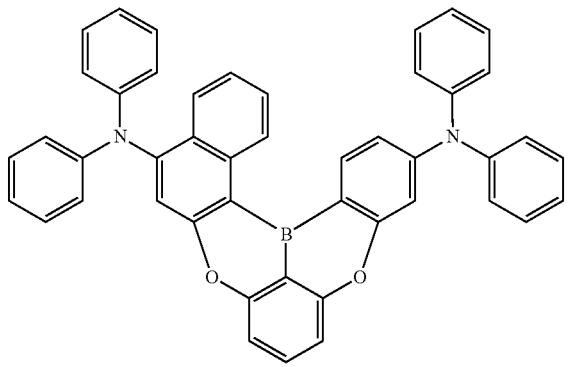
(2-344)
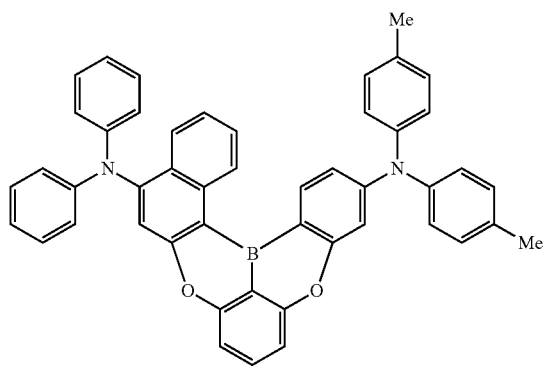
(2-345)
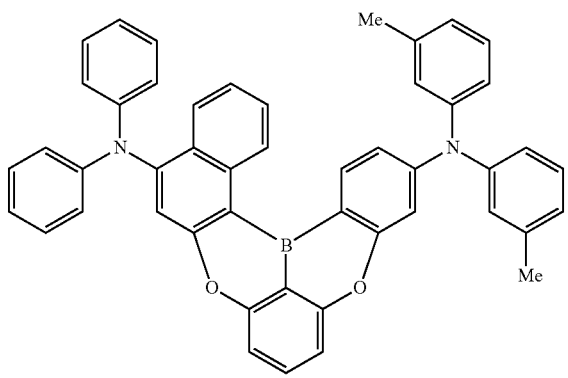
(2-346)
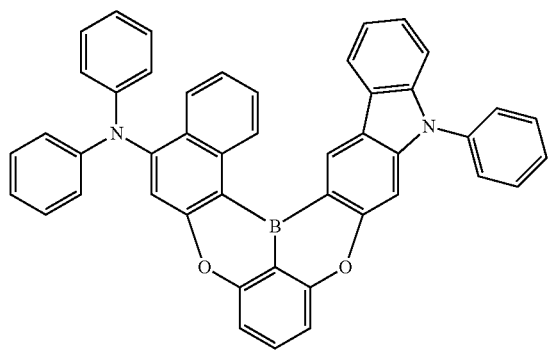
(2-351)
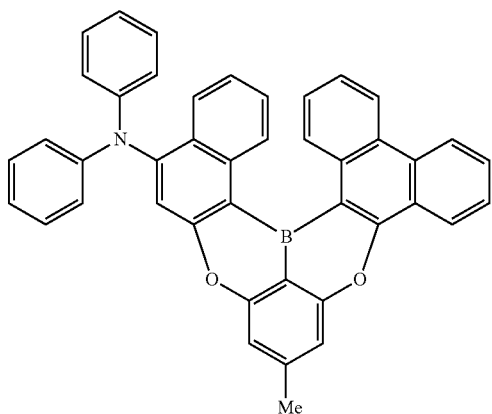
(2-352)
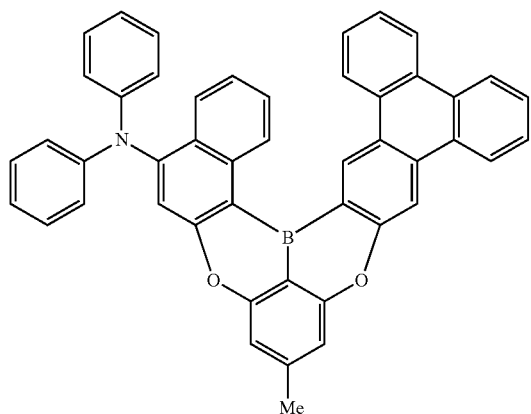
(2-353)
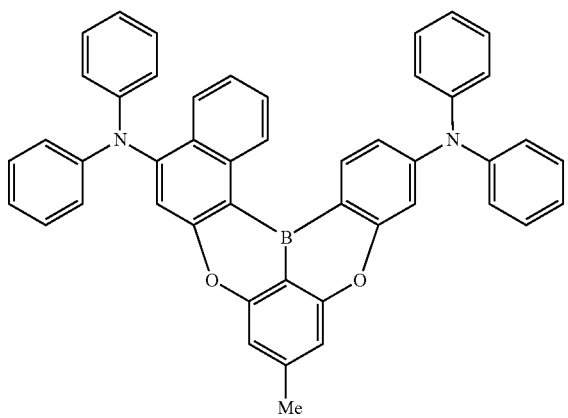

-continued
(2-354)
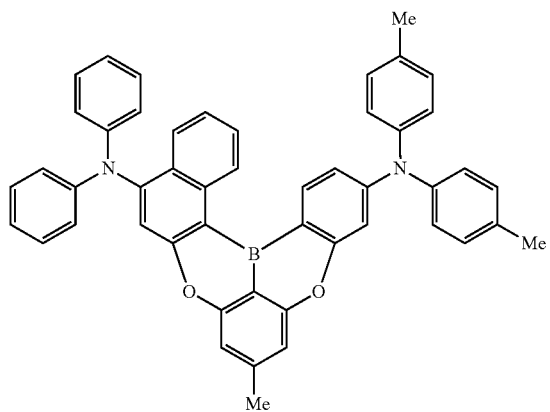
(2-355)
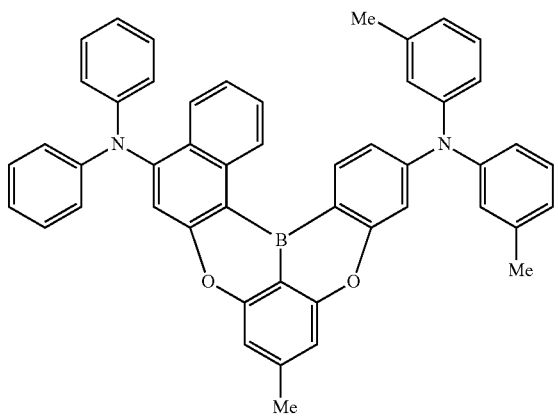
(3-356)
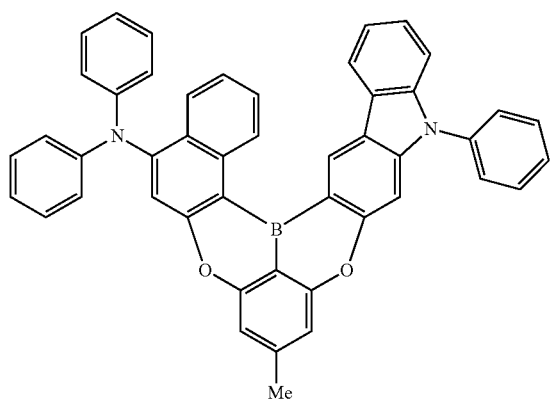
(2-361)
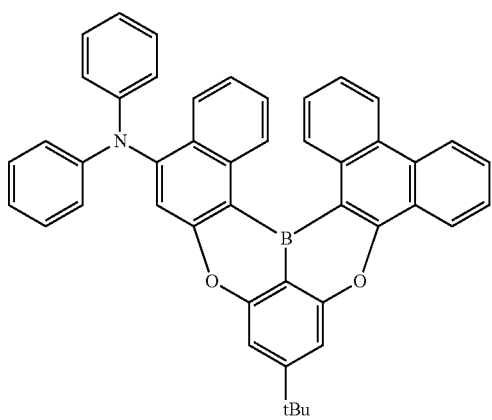
(3-362)
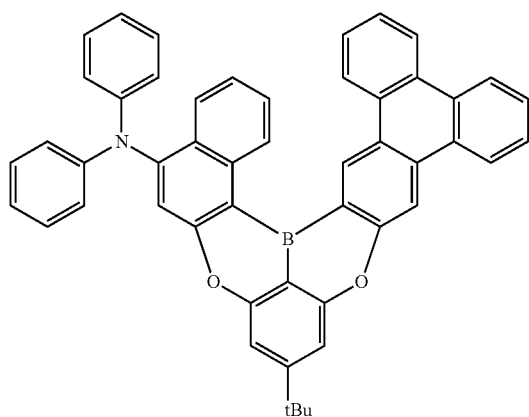
(3-363)
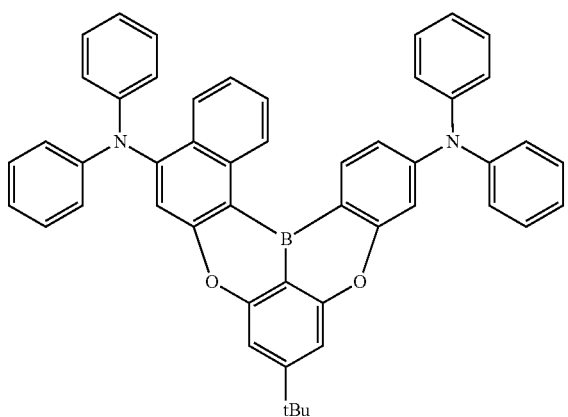

-continued
(3-364)
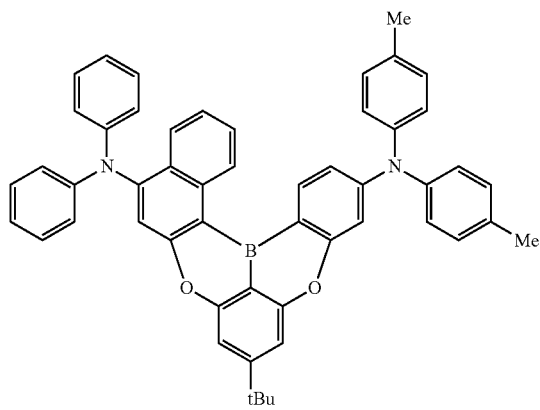
(3-365)
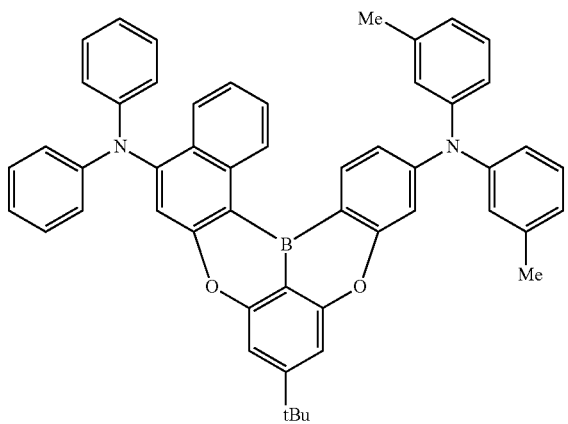
(3-366)
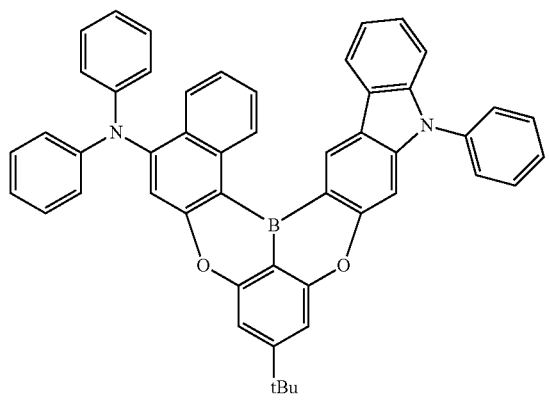
(3-371)
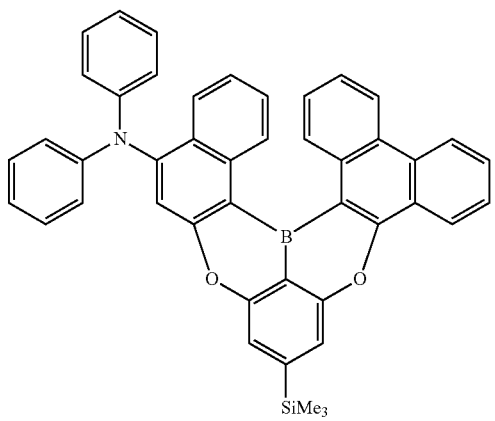
(3-372)
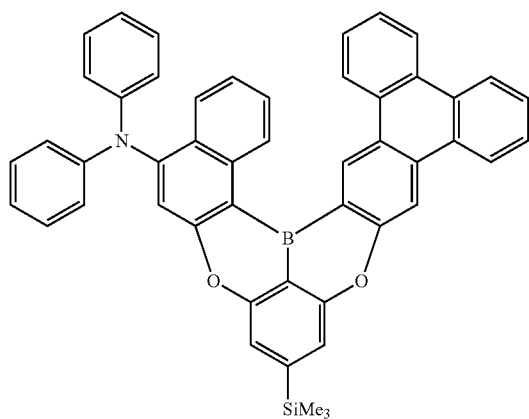
(3-373)
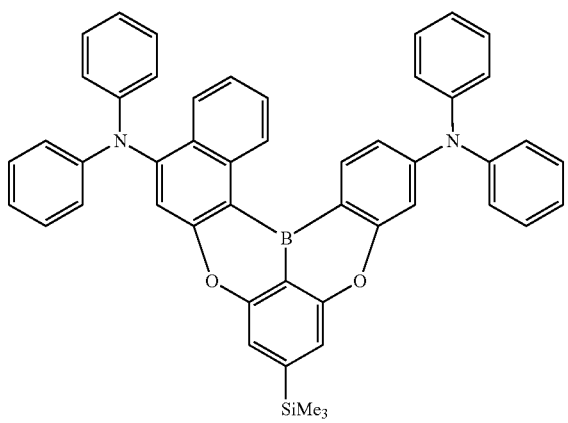

-continued
(3-374)
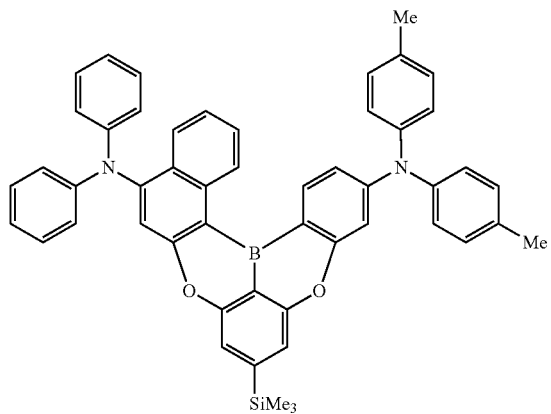
(3-375)
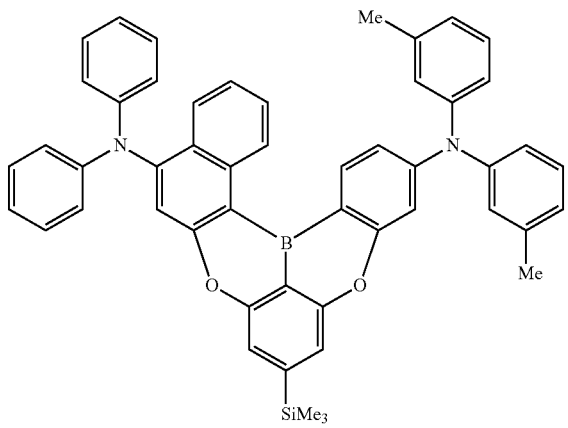
(3-376)
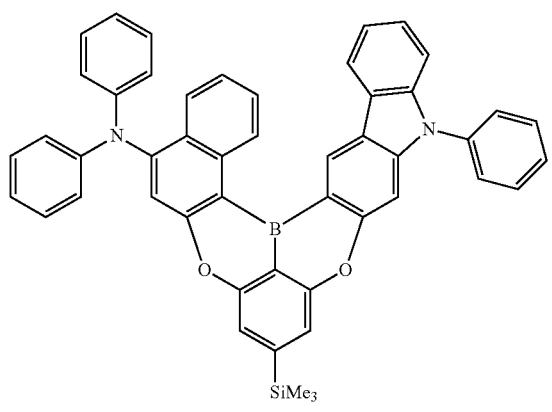
(3-381)
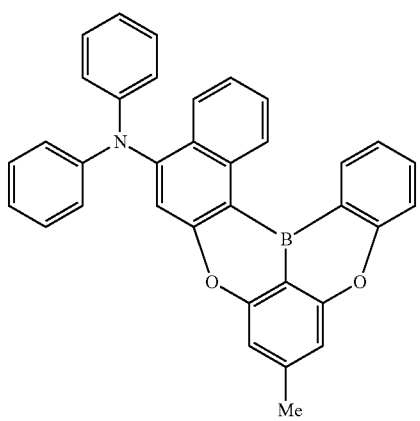
(3-382)
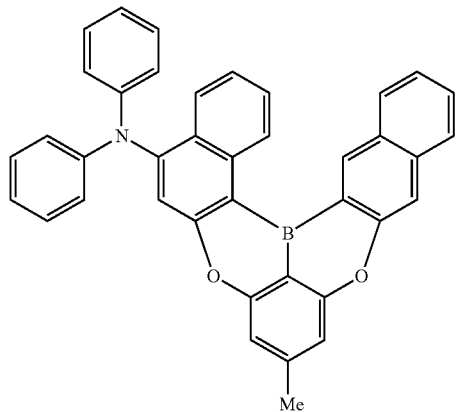
(3-383)
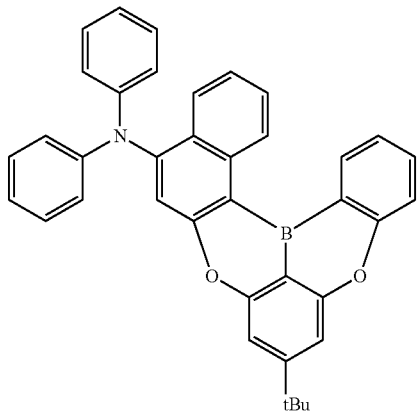

-continued

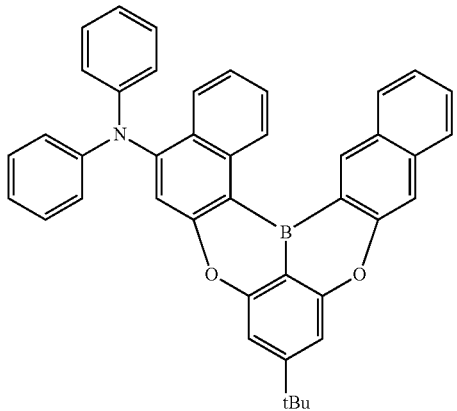
(3-384)

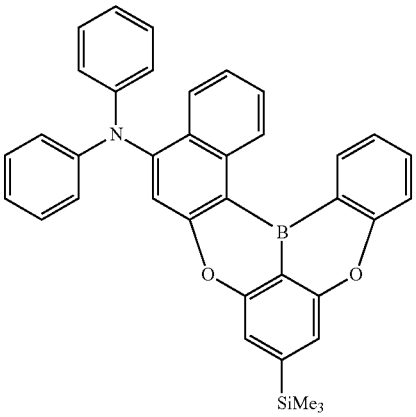
(3-385)

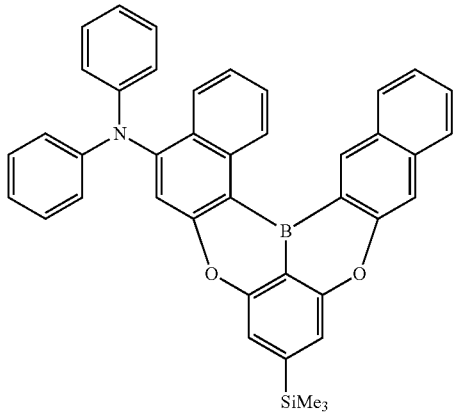
(3-386)

The polycyclic aromatic compound represented by formula (2) is preferably a compound represented by the following structural formula:

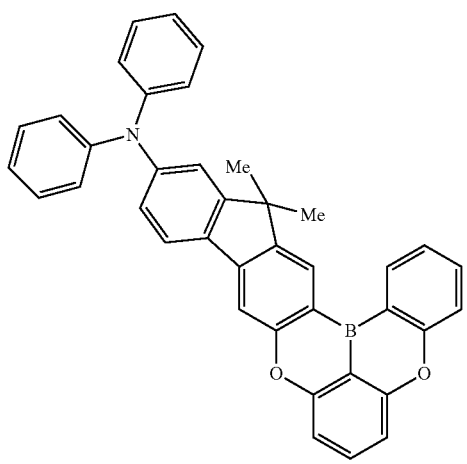
(2A-1)

The luminescent layer of the organic electroluminescent device of the invention may contain one kind or two or more kinds of the polycyclic aromatic compound represented by formula (2) as the assist dopant or the multimer thereof. Moreover, in the luminescent layer, a content of the assist dopant is preferably about 1 to 30 times, further preferably about 2 to 20 times, and still further preferably about 4 to 10 times, based on mass of the dopant material. A change in luminescent color by the assist dopant can be prevented by adjusting the content of the assist dopant to an amount equal to or more than an amount of the dopant material. Reduction of the external quantum efficiency can be suppressed by adjusting the content of the assist dopant to an amount equal to or less than about 15 times the amount of the dopant material.

Luminescent Layer Forming Material: A Host Material: An Anthracene-Based Compound Represented by Formula (1)

The host material in the luminescent layer of the organic electroluminescent device of the invention contains at least one kind of anthracene-based compound represented by formula (1).

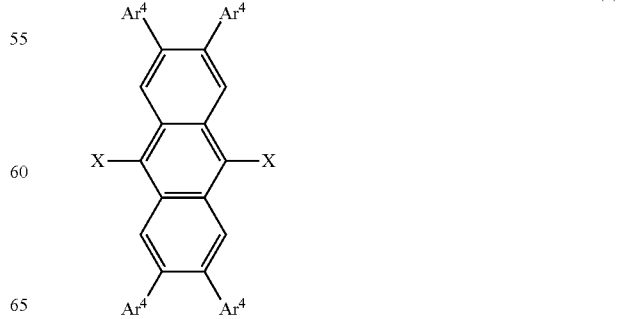
(1)

X is independently or Ar$^4$ is independently hydrogen, aryl which may be subjected to substitution, heteroaryl which may be subjected to substitution, diarylamino which may be subjected to substitution, diheteroarylamino which may be subjected to substitution, arylheteroarylamino which may be subjected to substitution, alkyl which may be subjected to substitution, alkenyl which may be subjected to substitution, alkoxy which may be subjected to substitution, aryloxy which may be subjected to substitution, arylthio which may be subjected to substitution or silyl which may be subjected to substitution, and a case where all of X and Ar$^4$ simultaneously become hydrogen is excluded, and at least one hydrogen in the compound represented by formula (1) may be replaced by halogen, cyano, deuterium or heteroaryl which may be subjected to substitution.

Specific examples of the "aryl" of the "aryl which may be subjected to substitution" in Ar$^4$ and X in formula (1) include aryl having 6 to 30 carbons, and aryl having 6 to 20 carbons is preferred, aryl having 6 to 16 carbons is further preferred, and aryl having 6 to 10 carbons is particularly preferred.

Specific examples of the "aryl" include phenyl as monocyclic aryl, biphenylyl as bicyclic aryl, naphthyl as fused bicyclic aryl, terphenylyl (m-terphenylyl, o-terphenylyl, p-terphenylyl) as tricyclic aryl, acenaphthylenyl, fluorenyl, phenalenyl and phenanthrenyl as fused tricyclic aryl, triphenylenyl, pyrenyl and naphthacenyl as fused tetracyclic aryl, and perylenyl and pentacenyl as fused pentacyclic aryl.

Specific examples of the "heteroaryl" of the "heteroaryl which may be subjected to substitution" in Ar$^4$ and X in formula (1) include heteroaryl having 2 to 30 carbons or heteroaryl having 2 to 25 carbons is preferred, heteroaryl having 2 to 20 carbons is further preferred, heteroaryl having 2 to 15 carbons is still further preferred, and heteroaryl having 2 to 10 carbons is particularly preferred. Moreover, specific examples of the heterocycle include a heterocyclic ring containing, in addition to carbon, 1 to 5 hetero atoms selected from oxygen, sulfur and nitrogen as a ring-forming atom.

Specific examples of the "heteroaryl" include pyrrolyl, oxazolyl, isoxazolyl, thiazolyl, isothiazolyl, imidazolyl, oxadiazolyl, thiadiazolyl, triazoryl, tetrazoryl, pyrazolyl, pyridyl, pyrimidinyl, pyridazinyl, pyrazinyl, thoriadinyl, indolyl, isoindolyl, 1H-indazolyl, benzimidazolyl, benzoxazolyl, benzothiazolyl, 1H-benzotriazoryl, quinolyl, isoquinolyl, cinnolyl, quinazolyl, quinoxalinyl, phthalazinyl, naphthyridinyl, purinyl, pteridinyl, carbazolyl, acridinyl, phenoxathiinyl, phenoxazinyl, phenothiazinyl, phenazinyl, indolizinyl, furyl, benzofuranyl, isobenzofuranyl, dibenzofuranyl, thienyl, benzo[b]thienyl, dibenzothienyl, furazanyl, oxadiazolyl, thianthrenyl, naphthobenzofuranyl and naphthobenzothienyl.

As the aryl or the heteroaryl in each of the "diarylamino which may be subjected to substitution," the "diheteroarylamino which may be subjected to substitution," and the "arylheteroarylamino which may be subjected to substitution" in Ar$^4$ and X in formula (1), the description described as the "aryl" and the "heteroaryl" in Ar$^4$ and X can be quoted.

Specific examples thereof include diphenylamino, dinaphthylamino, phenylnaphthylamino, dipyridylamino, phenylpyridylamino and naphthylpyridylamino.

The "alkyl" of the "alkyl which may be subjected to substitution" in Ar$^4$ and X in formula (1) may be any of straight-chain alkyl and branched-chain alkyl, and specific examples thereof include straight-chain alkyl having 1 to 24 carbons or branched-chain alkyl having 3 to 24 carbons. The alkyl having 3 to 18 carbons (branched-chain alkyl having 3 to 18 carbons) is preferred, alkyl having 1 to 12 carbons (branched-chain alkyl having 3 to 12 carbons) is further preferred, alkyl having 1 to 6 carbons (branched-chain alkyl having 3 to 6 carbons) is still further preferred, and alkyl having 1 to 4 carbons (branched-chain alkyl having 3 to 4 carbons) is particularly preferred.

Specific examples of the "alkyl" include methyl, ethyl, n-propyl, isopropyl, n-butyl, isobutyl, s-butyl, t-butyl, n-pentyl, isopentyl, neopentyl, t-pentyl, n-hexyl, 1-methylpentyl, 4-methyl-2-pentyl, 3,3-dimethylbutyl, 2-ethylbutyl, n-heptyl, 1-methylhexyl, n-octyl, t-octyl, 1-methylheptyl, 2-ethylhexyl, 2-propylpentyl, n-nonyl, 2,2-dimethylheptyl, 2,6-dimethyl-4-heptyl, 3,5,5-trimethylhexyl, n-decyl, n-undecyl, 1-methyldecyl, n-dodecyl, n-tridecyl, 1-hexylheptyl, n-tetradecyl, n-pentadecyl, n-hexadecyl, n-heptadecyl, n-octadecyl and n-eicosyl.

Specific examples of the "alkenyl" of the "alkenyl which may be subjected to substitution" in Ar$^4$ and X in formula (1) include straight-chain alkenyl having 2 to 24 carbons or branched-chain alkenyl having 4 to 24 carbons. Alkenyl having 2 to 18 carbons is preferred, alkenyl having 2 to 12 carbons is further preferred, alkenyl having 2 to 6 carbons is still further preferred, and alkenyl having 2 to 4 carbons is particularly preferred.

Specific examples of the "alkenyl" include vinyl, allyl and butadienyl.

Specific examples of the "alkoxy" of the "alkoxy which may be subjected to substitution" in Ar$^4$ and X in formula (1) include straight-chain alkoxy having 1 to 24 carbons or branched-chain alkoxy having 3 to 24 carbons. Alkoxy having 1 to 18 carbons (branched-chain alkoxy having 3 to 18 carbons) is preferred, alkoxy having 1 to 12 carbons (branched-chain alkoxy having 3 to 12 carbons) is further preferred, alkoxy having 1 to 6 carbons (branched-chain alkoxy having 3 to 6 carbons) is still further preferred, and alkoxy having 1 to 4 carbons (branched-chain alkoxy having 3 to 4 carbons) is particularly preferred.

Specific examples of the "alkoxy" include methoxy, ethoxy, propoxy, isopropoxy, butoxy, isobutoxy, s-butoxy, t-butoxy, pentyloxy, hexyloxy, heptyloxy and octyloxy.

Specific examples of the "aryloxy" of the "aryloxy which may be subjected to substitution" in Ar$^4$ and X in formula (1) include a group in which hydrogen of an —OH group is replaced by aryl, and for the above aryl, the description described as the "aryl" in Ar$^4$ and X can be quoted.

Specific examples of the "arylthio" of the "arylthio which may be subjected to substitution" in Ar$^4$ and X in formula (1) include a group in which hydrogen of an —SH group is replaced by aryl, and as the aryl, the description described as the "aryl" in Ar$^4$ and X can be quoted.

Specific examples of the "silyl which may be subjected to substitution" in Ar$^4$ and X in formula (1) include trialkylsilyl. Specific examples of the "trialkylsilyl" include a group in which three hydrogens in a silyl group are independently replaced by alkyl, and for the above alkyl, the description described as the "alkyl" in Ar$^4$ and X can be quoted. Alkyl by which hydrogen is preferably replaced is alkyl having 1 to 4 carbons, and specific examples thereof include methyl, ethyl, propyl, i-propyl, butyl, sec-butyl, t-butyl and cyclobutyl.

Specific examples of the "trialkylsilyl" include trimethylsilyl, triethylsilyl, tripropylsilyl, triisopropylsilyl, tributylsilyl, trisec-butylsilyl, trit-butylsilyl, ethyldimethylsilyl, propyldimethylsilyl, i-propyldimethylsilyl, butyldimethylsilyl, sec-butyldimethylsilyl, t-butyldimethylsilyl, methyldiethylsilyl, propyldiethylsilyl, i-propyldiethylsilyl, butyldiethylsilyl, sec-butyl-diethylsilyl, t-butyldiethylsilyl, methyldipropylsilyl, ethyldipropylsilyl, butyldipropylsilyl, sec-butyldipropylsilyl, t-butyldipropylsilyl, methyldiisopropylsilyl, ethyldiisopropylsilyl, butyldiisopropylsilyl, sec-butyldiisopropylsilyl and t-butyldiisopropylsilyl.

At least one hydrogen in the compound represented by formula (1) may be replaced by halogen, cyano, deuterium, or heteroaryl which may be subjected to substitution. Specific examples of the "halogen" in the above case include fluorine, chlorine, bromine and iodine. As the "heteroaryl" in the "heteroaryl which may be subjected to substitution," the above-mentioned description can be quoted.

Specific examples of the substituent in the above case include alkyl, aryl or heteroaryl. Specific examples of the substituent in the "heteroaryl which may be subjected to substitution" include alkyl, aryl or heteroaryl. For the above alkyl and aryl or heteroaryl, the description described as the "alkyl," the "aryl," and the "heteroaryl" in $Ar^4$ and X can be quoted.

In formula (1), X is preferably independently a group represented by formula (1-X1), formula (1-X2) or formula (1-X3). The group represented by formula (1-X1), formula (1-X2) or formula (1-X3) is bonded to an anthracene ring in formula (1) at a position "*," and a case where two X's simultaneously become a group represented by formula (1-X3) is excluded. Moreover, a case where two X's simultaneously become a group represented by formula (1-X2) is preferably excluded.

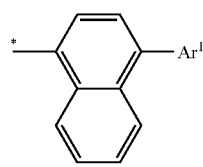
(1-X1)

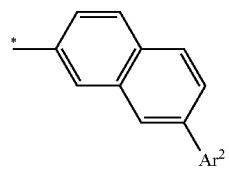
(1-X2)

*—$Ar^3$ (1-X3)

A naphthylene site in formula (1-X1) and formula (1-X2) may be fused by one benzene ring. A structure thus fused is as described below.

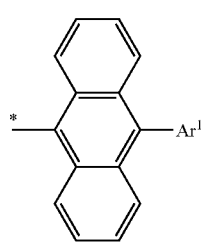
(1-X1-1)

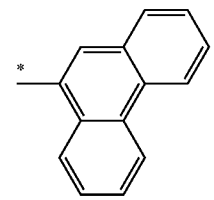
(1-X1-2)

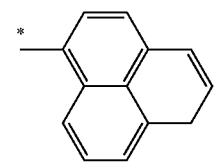
(I-X1-3)

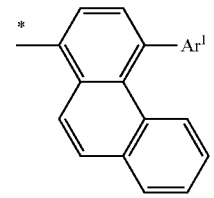
(1-X1-4)

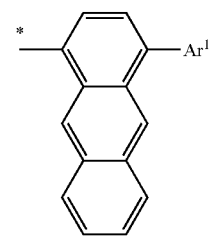
(1-X1-5)

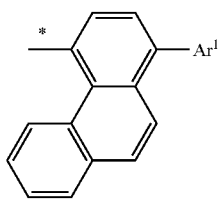
(1-X1-6)

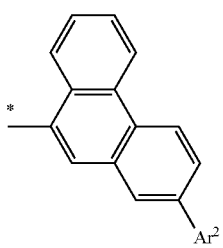
(1-X2-1)

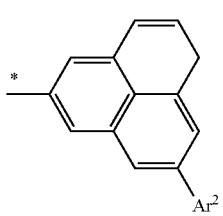
(1-X2-2)

-continued

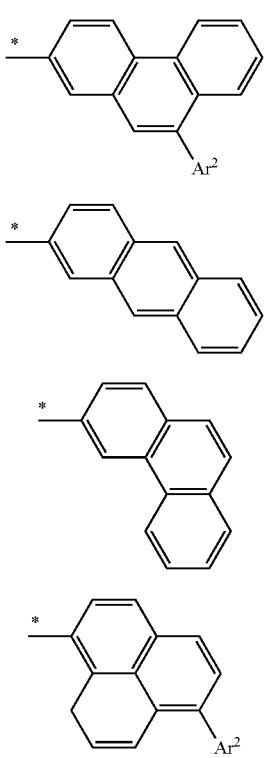

(1-X2-3)

(1-X2-4)

(1-X2-5)

(1-X2-6)

Ar¹ and Ar² are independently hydrogen, phenyl, biphenylyl, terphenylyl, quaterphenylyl, naphthyl, phenanthryl, fluorenyl, benzofluorenyl, chrysenyl, triphenylenyl, pyrenyl, or a group represented by formula (A) (also including a carbazolyl group, a benzo carbazolyl group and a phenyl-substituted carbazolyl group). In addition, when Ar¹ or Ar² is a group represented by formula (A), the group represented by formula (A) is bonded to a naphthalene ring in formula (1-X1) or formula (1-X2) at a position "*."

Ar³ is phenyl, biphenylyl, terphenylyl, quaterphenylyl, naphthyl, phenanthryl, fluorenyl, benzofluorenyl, chrysenyl, triphenylenyl, pyrenyl, or a group represented by formula (A) (also including a carbazolyl group, a benzocarbazolyl group and a phenyl-substituted carbazolyl group). In addition, when Ar³ is a group represented by formula (A), the group represented by formula (A) is bonded to a single bond represented by a straight line in formula (1-X3) at a position "*." More specifically, the anthracene ring in formula (1) is directly bonded to the group represented by formula (A).

Moreover, Ar³ may have a substituent, and at least one hydrogen in Ar³ may be replaced by phenyl, biphenylyl, terphenylyl, naphthyl, phenanthryl, fluorenyl, chrysenyl, triphenylenyl, pyrenyl, or a group represented by formula (A) (also including a carbazolyl group and a phenyl-substituted carbazolyl group). In addition, when the substituent of Ar³ is the group represented by formula (A), the group represented by formula (A) is bonded to Ar³ in formula (1-X3) at a position "*."

In addition, when formula (1-X1) and formula (1-X3) are selected as two X's, a case where both Ar¹ and Ar³ are phenyl in the formulas is excluded.

Ar⁴ is preferably independently hydrogen, phenyl, biphenylyl, terphenylyl, naphthyl, or silyl which is subjected to substitution for alkyl having 1 to 4 carbons.

Specific example of the alkyl having 1 to 4 carbons by which silyl is replaced include methyl, ethyl, propyl, i-propyl, butyl, sec-butyl, t-butyl and cyclobutyl, and three hydrogens in silyl are independently replaced by alkyl.

Specific examples of the "silyl which is subjected to substitution for alkyl having 1 to 4 carbons" include trimethylsilyl, triethylsilyl, tripropylsilyl, triisopropylsilyl, tributylsilyl, trisec-butylsilyl, trit-butylsilyl, ethyldimethylsilyl, propyldimethylsilyl, i-propyldimethylsilyl, butyldimethylsilyl, sec-butyldimethylsilyl, t-butyldimethylsilyl, methyldiethylsilyl, propyldiethylsilyl, i-propyldiethylsilyl, butyldiethylsilyl, sec-butyldiethylsilyl, t-butyldiethylsilyl, methyldipropylsilyl, ethyldipropylsilyl, butyldipropylsilyl, sec-butyldipropylsilyl, t-butyldipropylsilyl, methyldiisopropylsilyl, ethyldiisopropylsilyl, butyldiisopropylsilyl, sec-butyldiisopropylsilyl and t-butyldiisopropylsilyl.

Moreover, hydrogen in a chemical structure of the anthracene-based compound represented by formula (1) may be replaced by the group represented by formula (A). When hydrogen is replaced by the group represented by formula (A), at least one hydrogen in the compound represented by formula (1) is replaced by the group represented by formula (A) at a position "*."

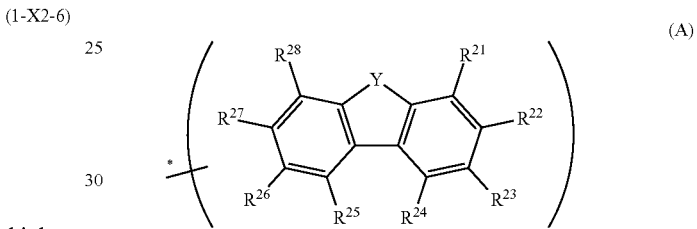

(A)

In formula (A), Y is —O—, —S— or >N—R²⁹, and R²⁹ is hydrogen or aryl which may be subjected to substitution, and R²¹ to R²⁸ are independently hydrogen, alkyl which may be subjected to substitution, aryl which may be subjected to substitution, heteroaryl which may be subjected to substitution, alkoxy which may be subjected to substitution, aryloxy which may be subjected to substitution, arylthio which may be subjected to substitution, trialkylsilyl, amino which may be subjected to substitution, halogen, hydroxy or cyano, and adjacent groups of R²¹ to R²⁸ may be bonded to each other to form a hydrocarbon ring, an aryl ring or a heteroaryl ring.

The "alkyl" of the "alkyl which may be subjected to substitution" in R²¹ to R²⁸ in formula (A) may be any of straight-chain alkyl and branched-chain alkyl, and specific examples thereof include straight-chain alkyl having 1 to 24 carbons or branched-chain alkyl having 3 to 24 carbons. Alkyl having 1 to 18 carbons (branched-chain alkyl having 3 to 18 carbons) is preferred, alkyl having 1 to 12 carbons (branched-chain alkyl having 3 to 12 carbons) is further preferred, alkyl having 1 to 6 carbons (branched-chain alkyl having 3 to 6 carbons) is still further preferred, and alkyl having 1 to 4 carbons (branched-chain alkyl having 3 to 4 carbons) is particularly preferred.

Specific examples of the "alkyl" include methyl, ethyl, n-propyl, isopropyl, n-butyl, isobutyl, s-butyl, t-butyl, n-pentyl, isopentyl, neopentyl, t-pentyl, n-hexyl, 1-methylpentyl, 4-methyl-2-pentyl, 3,3-dimethylbutyl, 2-ethylbutyl, n-heptyl, 1-methylhexyl, n-octyl, t-octyl, 1-methylheptyl, 2-ethylhexyl, 2-propylpentyl, n-nonyl, 2,2-dimethylheptyl, 2,6-dimethyl-4-heptyl, 3,5,5-trimethylhexyl, n-decyl, n-undecyl, 1-methyldecyl, n-dodecyl, n-tridecyl, 1-hexylheptyl, n-tetradecyl, n-pentadecyl, n-hexadecyl, n-heptadecyl, n-octadecyl and n-eicosyl.

Specific examples of the "aryl" of the "aryl which may be subjected to substitution" in $R^{21}$ to $R^{28}$ in formula (A) include aryl having 6 to 30 carbons, and aryl having 6 to 16 carbons is preferred, aryl having 6 to 12 carbons is further preferred, and aryl having 6 to 10 carbons is particularly preferred.

Specific examples of the "aryl" include phenyl as monocyclic aryl, biphenylyl as bicyclic aryl, naphthyl as fused bicyclic aryl, terphenylyl (m-terphenylyl, o-terphenylyl, p-terphenylyl) as tricyclic aryl, acenaphthylenyl, fluorenyl, phenalenyl and phenanthrenyl as fused tricyclic aryl, triphenylenyl, pyrenyl and naphthacenyl as fused tetracyclic aryl, and perylenyl and pentacenyl as fused pentacyclic aryl.

Specific examples of the "heteroaryl" of the "heteroaryl which may be subjected to substitution" in $R^{21}$ to $R^{28}$ in formula (A) include heteroaryl having 2 to 30 carbons or heteroaryl having 2 to 25 carbons is preferred, heteroaryl having 2 to 30 carbons is further preferred, heteroaryl having 2 to 15 carbons is still further preferred, and heteroaryl having 2 to 10 carbons is particularly preferred. Moreover, specific examples of the heterocycle include a heterocyclic ring containing, in addition to carbon, 1 to 5 hetero atoms selected from oxygen, sulfur and nitrogen as a ring-forming atom.

Specific examples of the "heteroaryl" include pyrrolyl, oxazolyl, isoxazolyl, thiazolyl, isothiazolyl, imidazolyl, oxadiazolyl, thiadiazolyl, triazoryl, tetrazoryl, pyrazolyl, pyridyl, pyrimidinyl, pyridazinyl, pyrazinyl, thoriadinyl, indolyl, isoindolyl, 1H-indazolyl, benzimidazolyl, benzoxazolyl, benzothiazolyl, 1H-benzotriazoryl, quinolyl, isoquinolyl, cinnolyl, quinazolyl, quinoxalinyl, phthalazinyl, naphthyridinyl, purinyl, pteridinyl, carbazolyl, acridinyl, phenoxathiinyl, phenoxazinyl, phenothiazinyl, phenazinyl, indrizinyl, furyl, benzofuranyl, isobenzofuranyl, dibenzofuranyl, thienyl, benzo[b]thienyl, dibenzothienyl, furazanyl, thianthrenyl, naphthobenzofuranyl and naphthobenzothienyl.

Specific examples of the "alkoxy" of the "alkoxy which may be subjected to substitution" in $R^{21}$ to $R^{28}$ in formula (A) include straight-chain alkoxy having 1 to 24 carbons or branched-chain alkoxy having 3 to 24 carbons. Alkoxy having 1 to 18 carbons (branched-chain alkoxy having 3 to 18 carbons) is preferred, alkoxy having 1 to 12 carbons (branched-chain alkoxy having 3 to 12 carbons) is further preferred, alkoxy having 1 to 6 carbons (branched-chain alkoxy having 3 to 6 carbons) is still further preferred, and alkoxy having 1 to 4 carbons (branched-chain alkoxy having 3 to 4 carbons) is particularly preferred.

Specific examples of the "alkoxy" include methoxy, ethoxy, propoxy, isopropoxy, butoxy, isobutoxy, s-butoxy, t-butoxy, pentyloxy, hexyloxy, heptyloxy and octyloxy.

Specific examples of the "aryloxy" of the "aryloxy which may be subjected to substitution" in $R^{21}$ to $R^{28}$ in formula (A) include a group in which hydrogen of an —OH group is replaced by aryl, and for the above aryl, the groups described as the "aryl" in $R^{21}$ to $R^{28}$ can be quoted.

Specific examples of the "arylthio" of the "arylthio which may be subjected to substitution" in $R^{21}$ to $R^{28}$ in formula (A) include a group in which hydrogen of an —SH group is replaced by aryl, and for the above aryl, the groups described as the "aryl" in $R^{21}$ to $R^{28}$ can be quoted.

Specific examples of the "trialkylsilyl" in $R^{21}$ to $R^{28}$ in formula (A) include a group in which three hydrogens in a silyl group are independently replaced by alkyl, and for the above alkyl, the groups described as the "alkyl" in $R^{21}$ to $R^{28}$ can be quoted. Alkyl by which hydrogen is preferably replaced is alkyl having 1 to 4 carbons, and specific examples thereof include methyl, ethyl, propyl, i-propyl, butyl, sec-butyl, t-butyl and cyclobutyl.

Specific examples of the "trialkylsilyl" include trimethylsilyl, triethylsilyl, tripropylsilyl, triisopropylsilyl, tributylsilyl, trisec-butylsilyl, trit-butylsilyl, ethyldimethylsilyl, propyldimethylsilyl, i-propyldimethylsilyl, butyldimethylsilyl, sec-butyldimethylsilyl, t-butyldimethylsilyl, methyldiethylsilyl, propyldiethylsilyl, i-propyldiethylsilyl, butyldiethylsilyl, sec-butyldiethylsilyl, t-butyldiethylsilyl, methyldipropylsilyl, ethyldipropylsilyl, butyldipropylsilyl, sec-butyldipropylsilyl, t-butyldipropylsilyl, methyldiisopropylsilyl, ethyldiisopropylsilyl, butyldiisopropylsilyl, sec-butyldiisopropylsilyl and t-butyldiisopropylsilyl.

Specific examples of the "substituted amino" of the "amino which may be subjected to substitution" in $R^{21}$ to $R^{28}$ in formula (A) include an amino group in which two hydrogens are replaced by aryl or heteroaryl. Amino in which two hydrogens are replaced by aryl is diaryl-substituted amino, amino in which two hydrogens are replaced by heteroaryl is diheteroaryl-substituted amino, and amino in which two hydrogens are replaced by aryl and heteroaryl is aryl heteroaryl-substituted amino. For the above aryl or heteroaryl, the groups described as the "aryl" or the "heteroaryl" in $R^{21}$ to $R^{28}$ can be quoted.

Specific examples of the "substituted amino" include diphenylamino, dinaphthylamino, phenylnaphthylamino, dipyridylamino, phenylpyridylamino and naphthylpyridylamino.

Specific examples of the "halogen" in $R^{21}$ to $R^{28}$ in formula (A) include fluorine, chlorine, bromine and iodine.

Several of the groups described as $R^{21}$ to $R^{28}$ in formula (A) may be replaced as described above, and specific examples of the substituent in the above case include alkyl, aryl or heteroaryl. For the above alkyl, aryl or heteroaryl, the groups described as the "alkyl," "aryl" or "heteroaryl" in $R^{21}$ to $R^{28}$ can be quoted.

$R^{29}$ in ">N—$R^{29}$" as Y in formula (A) is hydrogen or aryl which may be subjected to substitution, and as the above aryl, the groups described as the "aryl" in $R^{21}$ to $R^{28}$ can be quoted, and as the substituent, the groups described as the substituent to $R^{21}$ to $R^{28}$ can be quoted.

Adjacent groups of $R^{21}$ to $R^{28}$ in formula (A) may be bonded to each other to form a hydrocarbon ring, an aryl ring or a heteroaryl ring. Specific examples thereof include a group represented by formula (A-1) in the case where the ring is not formed, and groups represented by formulas (A-2) to (A-11) in the case where the ring is formed. In addition, at least one hydrogen in the group represented by any one of formulas (A-1) to (A-11) may be replaced by alkyl, aryl, heteroaryl, alkoxy, aryloxy, arylthio, trialkylsilyl, diaryl-substituted amino, diheteroaryl-substituted amino, arylheteroaryl-substituted amino, halogen and hydroxy or cyano, and for the above groups, the groups described as each group in $R^{21}$ to $R^{28}$ can be quoted.

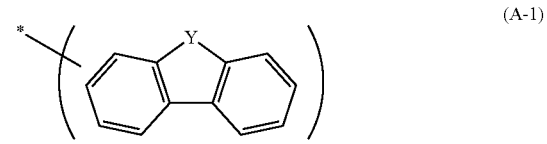

(A-1)

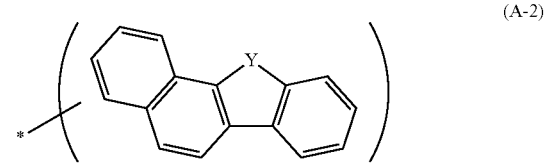

(A-2)

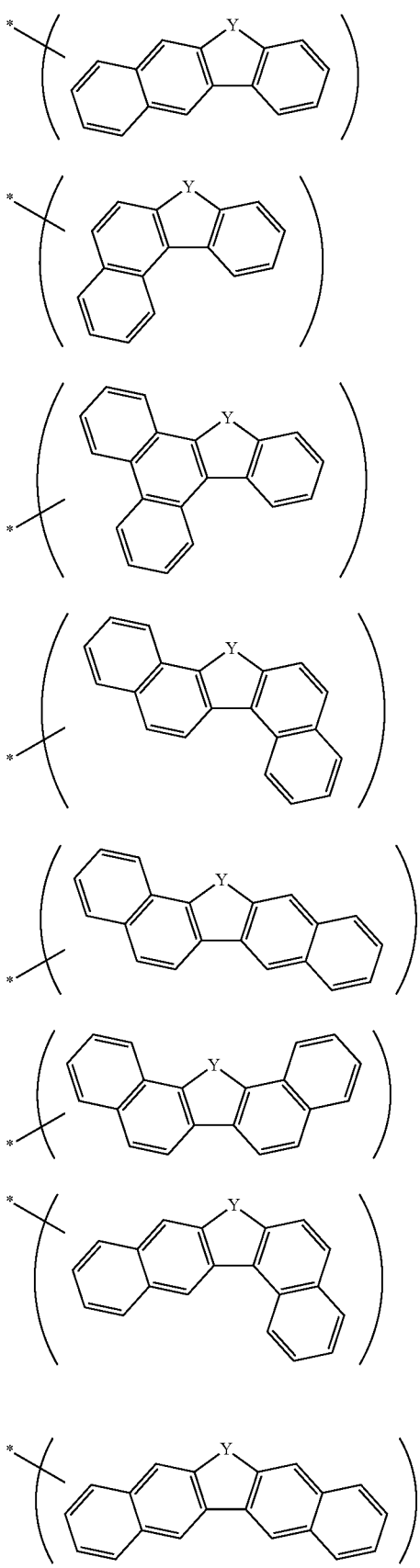

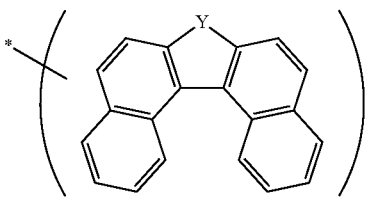

Specific examples of the ring formed by bonding adjacent groups to each other include a cyclohexane ring, if the ring is a hydrocarbon ring, and the ring structure described as the "aryl" or the "heteroaryl" in $R^{21}$ to $R^{28}$, if the ring is the aryl ring or the heteroaryl ring, in which the above rings are formed so as to be fused to one or two benzene rings in formula (A-1).

Specific examples of the group represented by formula (A) include a group represented by any one of formulas (A-1) to (A-11), and a group represented by any one of formulas (A-1) to (A-4) is preferred, a group represented by any one of formula (A-1), formulas (A-3) and (A-4) is further preferred, and a group represented by formula (A-1) is still further preferred.

As described above, the group represented by formula (A) is bonded to the naphthalene ring in formula (1-X1) or formula (1-X2), the single bond in formula (1-X3) or $Ar^3$ in formula (1-X3) at a position "*" in formula (A), and is substituted for at least one hydrogen in the compound represented by formula (1), and among the bonding forms, a form in which the group is bonded with the naphthalene ring in formula (1-X1) or formula (1-X2), the single bond in formula (1-X3) and/or $Ar^3$ in formula (1-X3) is preferred.

Moreover, in the structure represented by formula (A), a position at which the group is bonded with the naphthalene ring in formula (1-X1) or formula (1-X2), the single bond in formula (1-X3) and $Ar^3$ in formula (1-X3), and a position at which the group is substituted for at least one hydrogen in the compound represented by formula (1) may be any position in the structure represented by formula (A), and for example, the group can be bonded thereto at a position of any of two benzene rings in the structure of formula (A), any ring formed by bonding adjacent groups of $R^{21}$ to $R^{28}$ in the structure of formula (A) to each other, or any position in $R^{29}$ in ">N—$R^{29}$" as Y in the structure of formula (A).

Specific examples of the group represented by formula (A) include groups described below. Y and a position "*" in the formulas are defined in the same manner as described above.

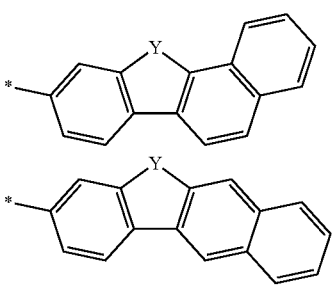

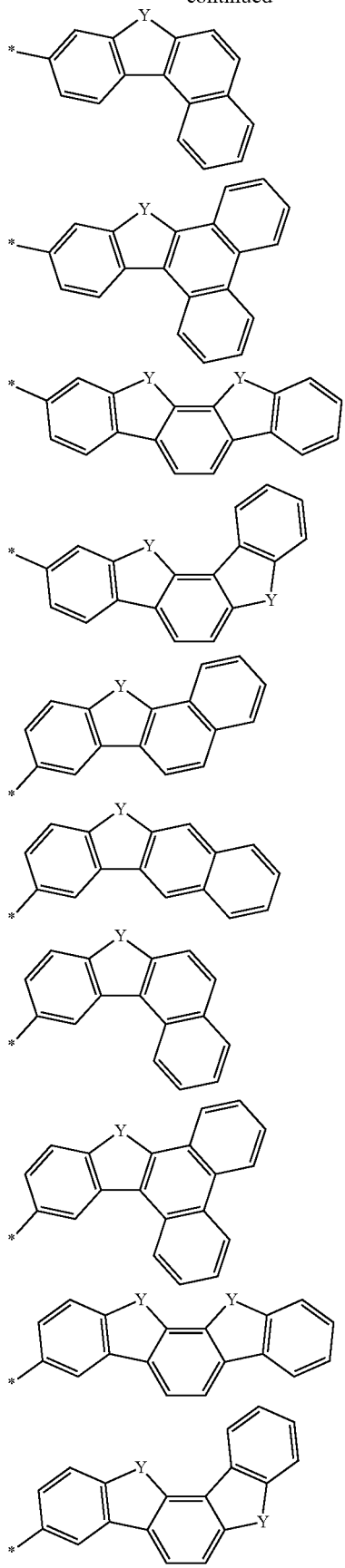
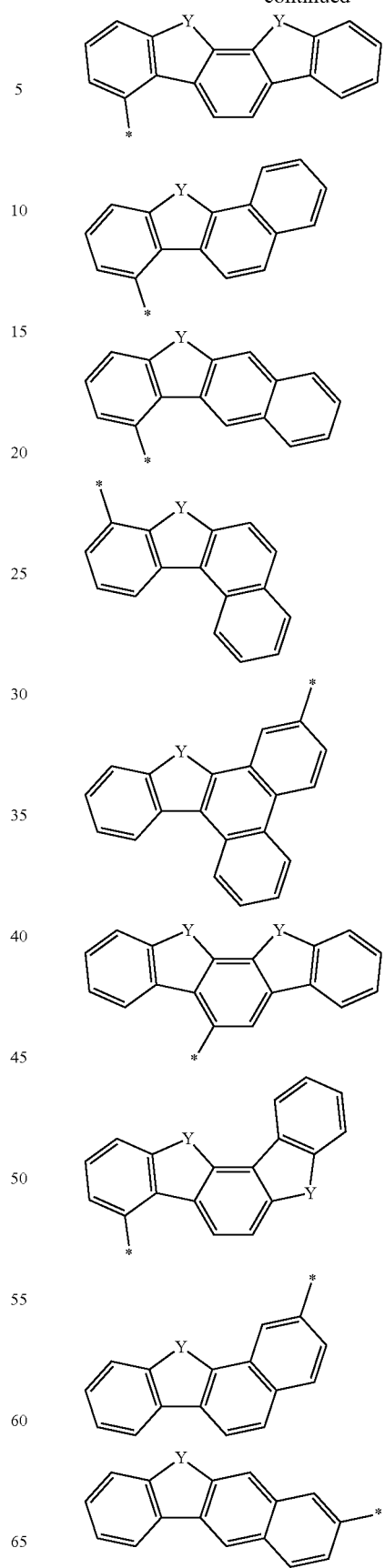

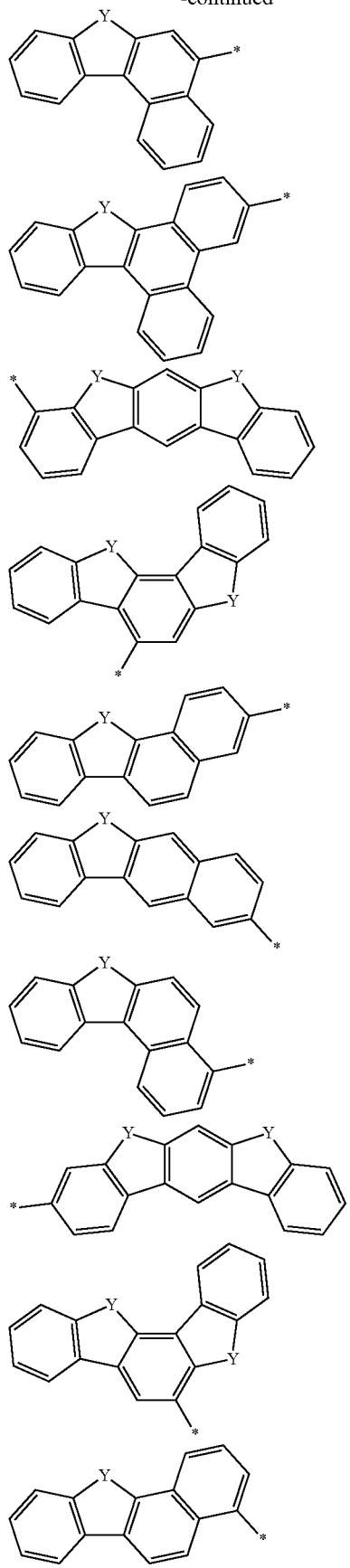
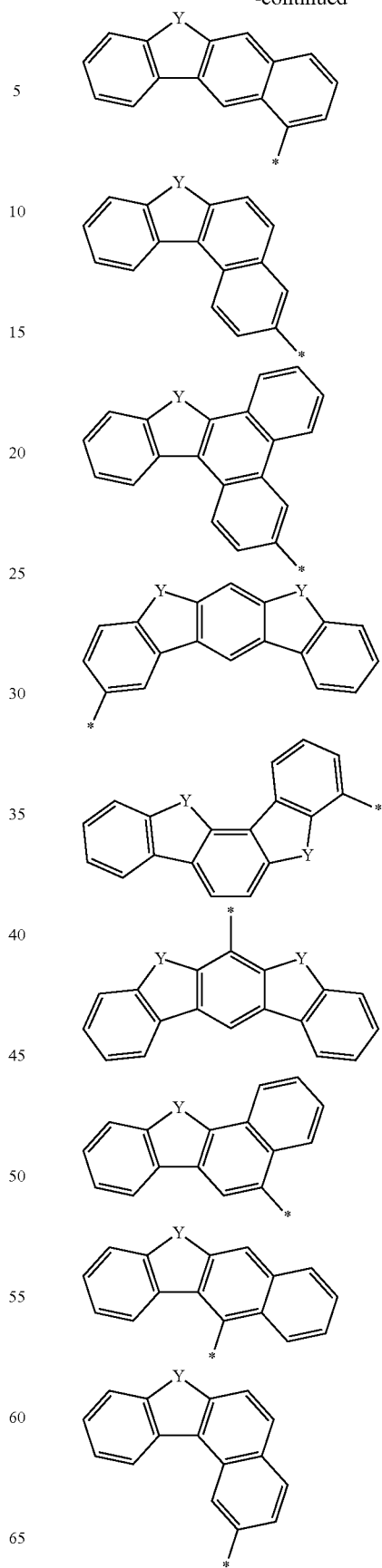

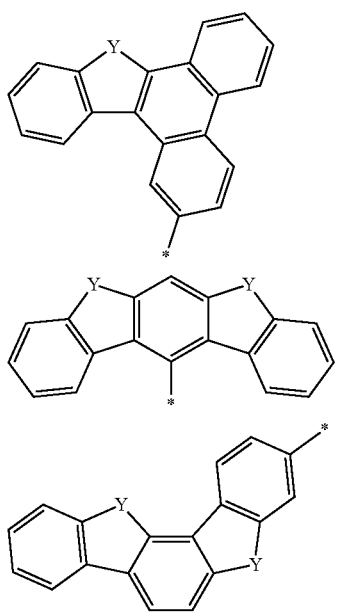
Moreover, a hydrogen in the chemical structure of the anthracene-based compound represented by formula (1) may be wholly or partly deuterium.
Specific examples of the anthracene-based compound include compounds represented by formulas (1-101) to (1-108), (1-111) to (1-119) and (1-121) to (1-127).
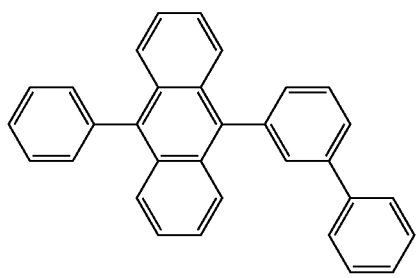
(1-101)
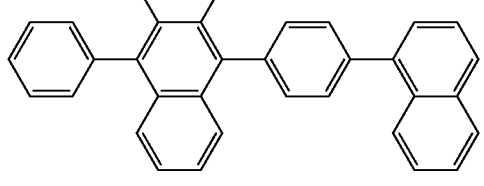
(1-102)
(1-103)
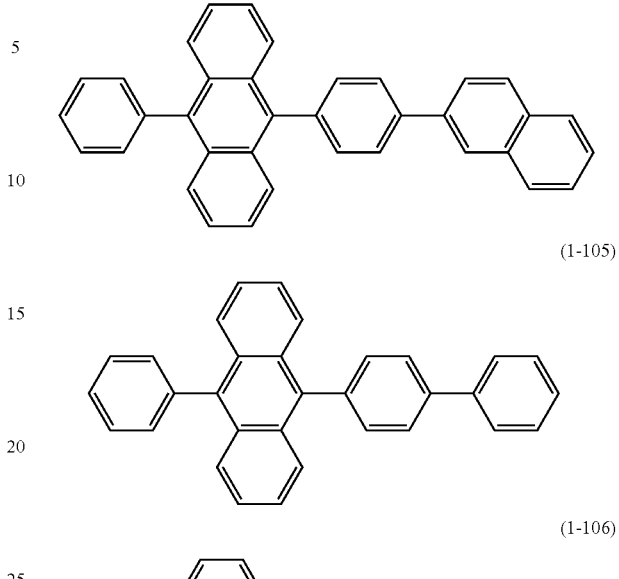
(1-104)
(1-105)
(1-106)
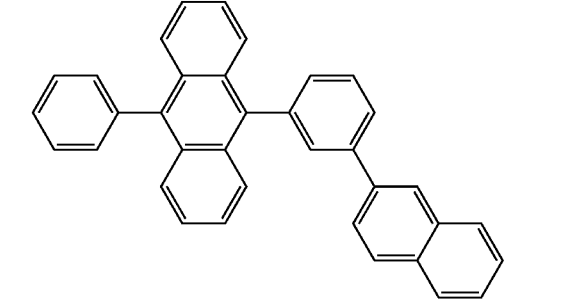
(1-107)
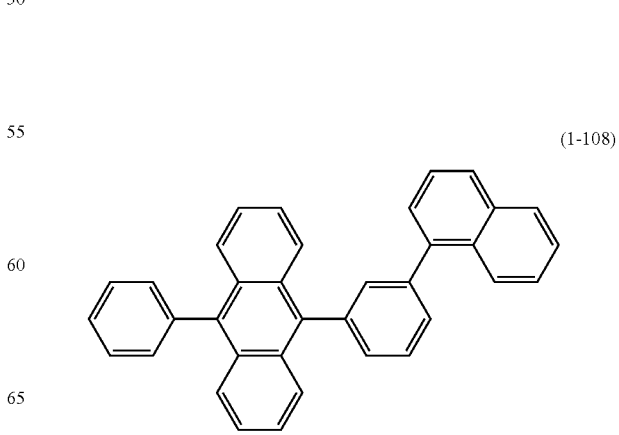
(1-108)

(1-111)
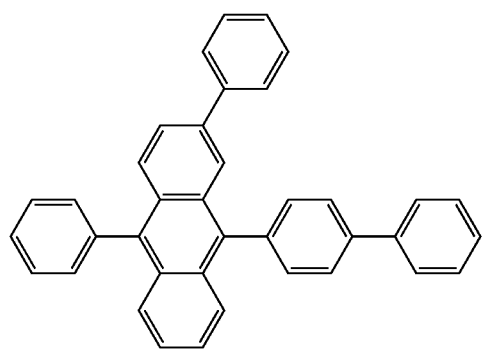
(1-112)
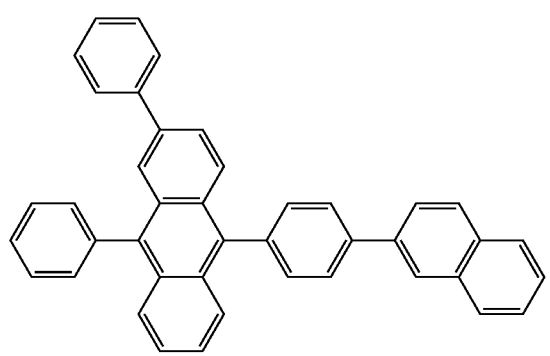
(1-113)
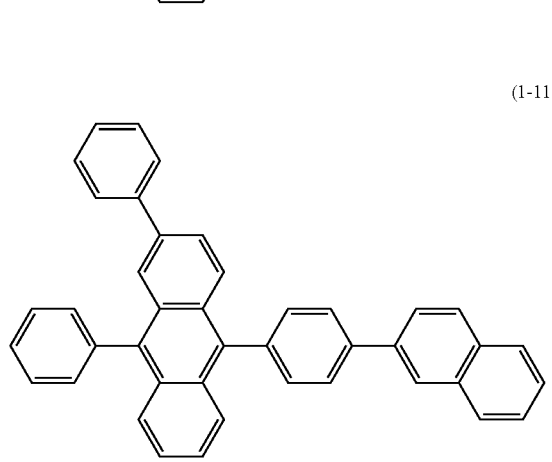
(1-114)
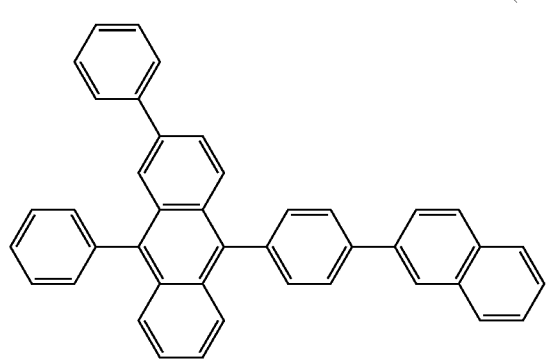
(1-115)
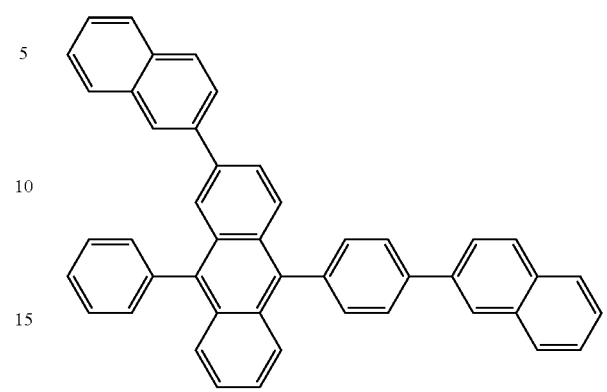
(1-116)
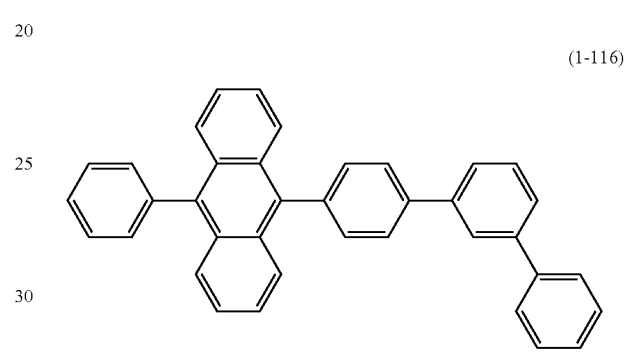
(1-117)
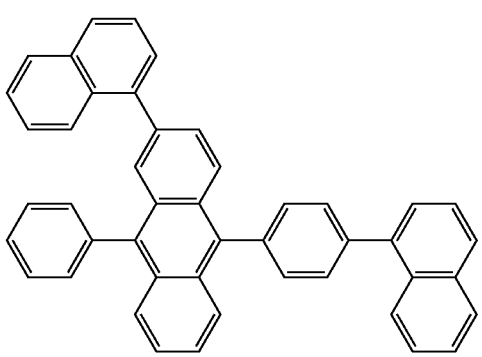
(1-118)
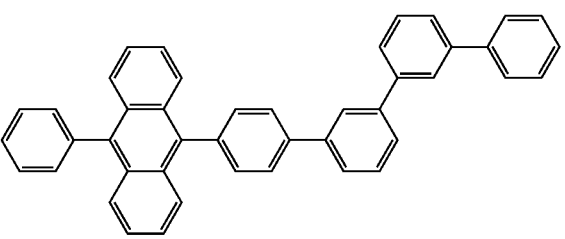

(1-119)
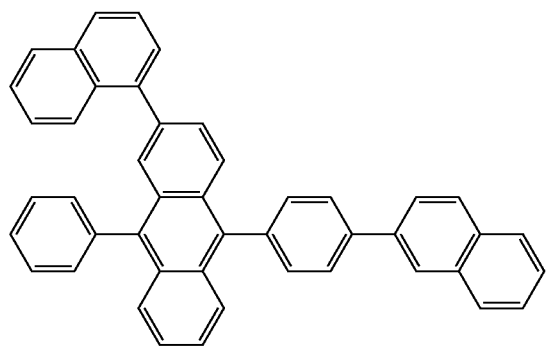

(1-121)
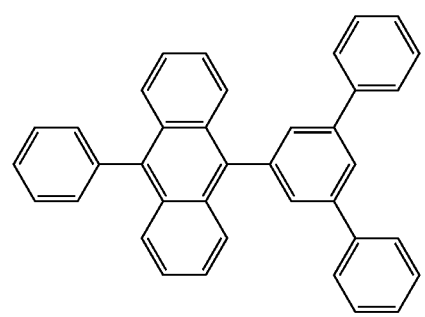

(1-122)
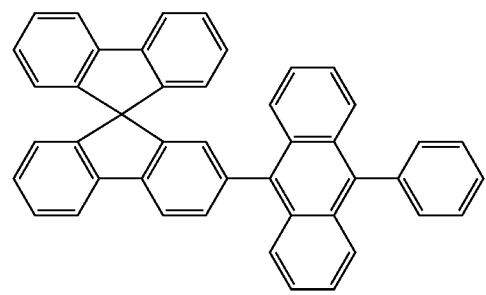

(1-123)
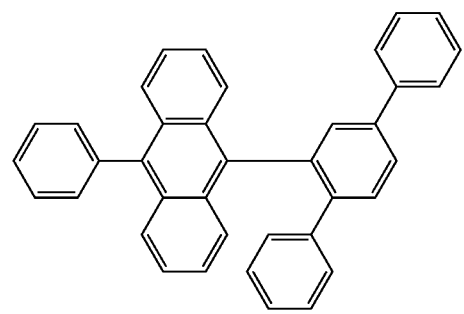

(1-124)
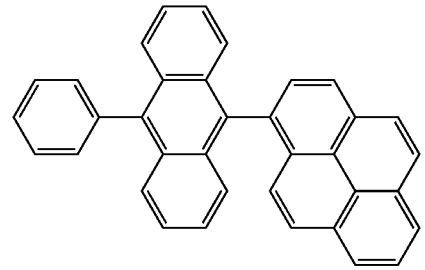

(1-125)
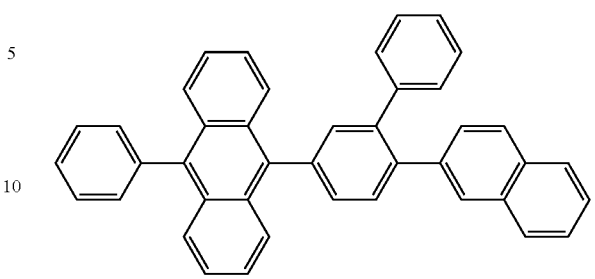

(1-126)

(1-127)
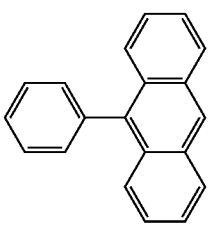

Moreover, other specific examples of the anthracene-based compound include compounds represented by formulas (1-131-Y) to (1-179-Y), compounds represented by formulas (1-180-Y) to (1-182-Y) and a compound represented by formula (1-183-N). Y in each formula may be any of —O—, —S— or >N—R$^{29}$ (R$^{29}$ is defined in the same manner as described above), and R$^{29}$ is phenyl, for example. For a formula number, when Y is O, formula (1-131-Y) is taken as formula (1-131-O), and when Y is —S— or >N—R$^{29}$, formula (1-131-Y) is taken as formula (1-131-S) or formula (1-131-N), for example.

(1-131-Y)
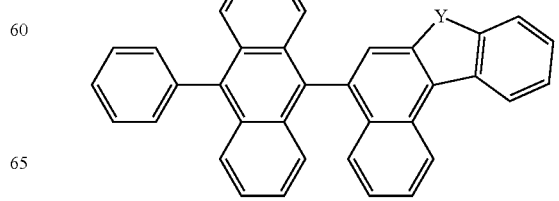

(1-132-Y)
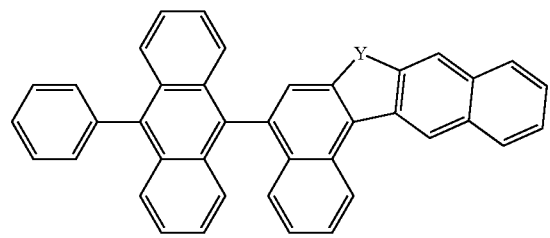
(1-133-Y)
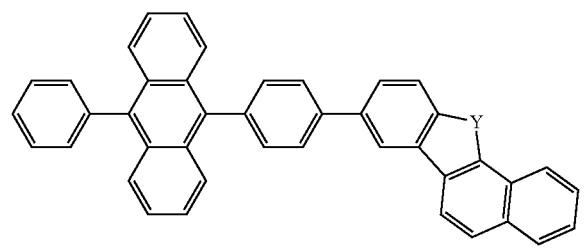
(1-134-Y)
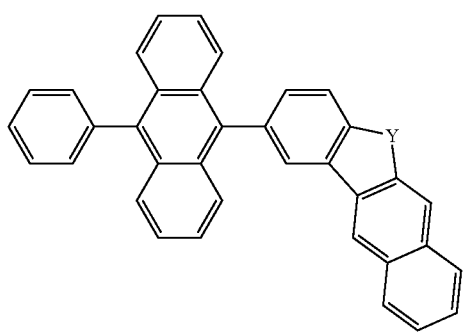
(1-135-Y)
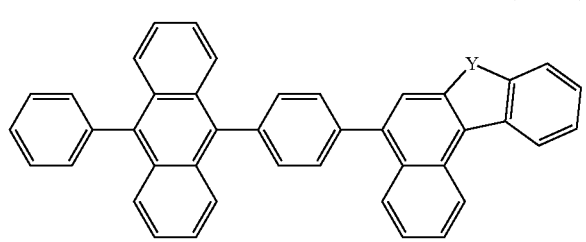
(1-136-Y)
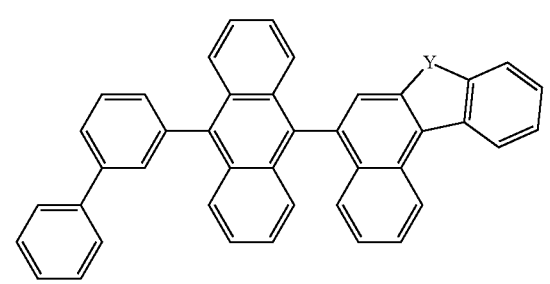
(1-137-Y)
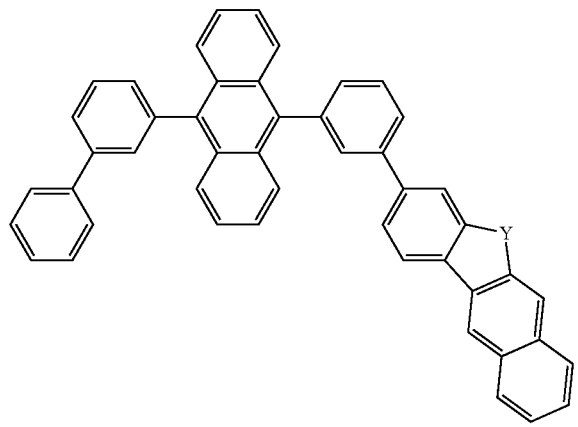
(1-138-Y)
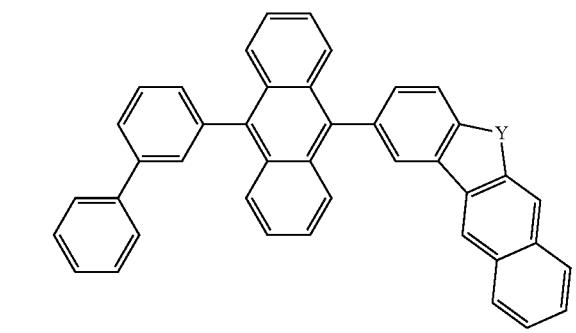
(1-139-Y)
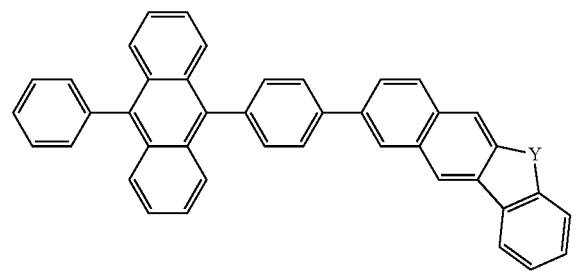
(1-140-Y)
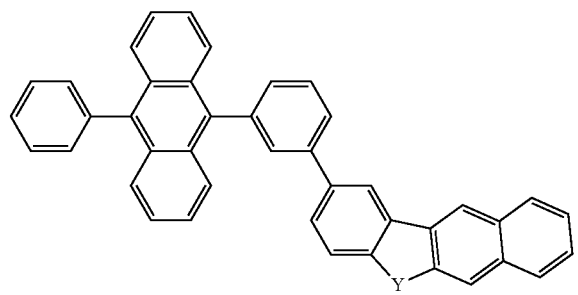

(1-141-Y)
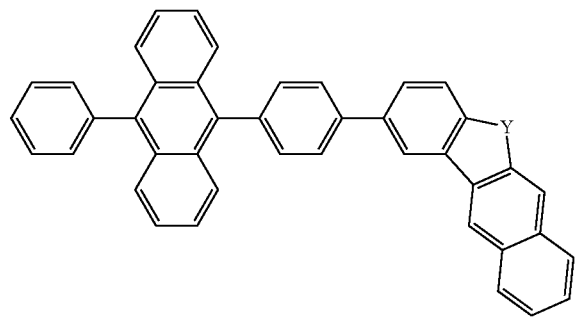
(1-145-Y)
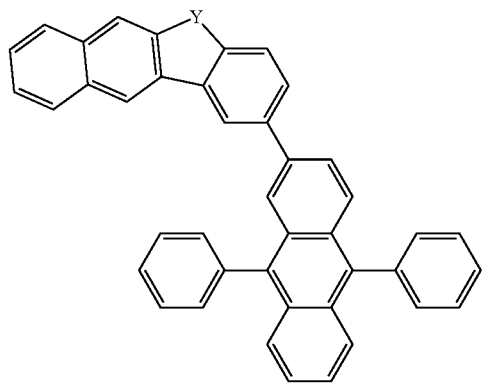
(1-142-Y)
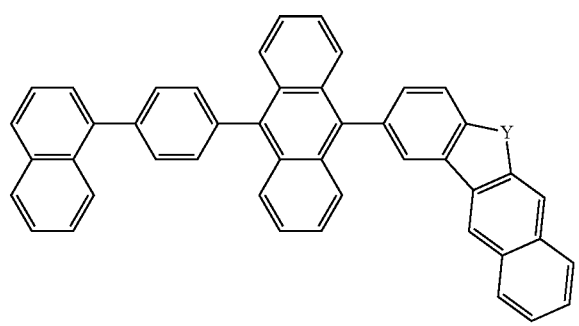
(1-146-Y)
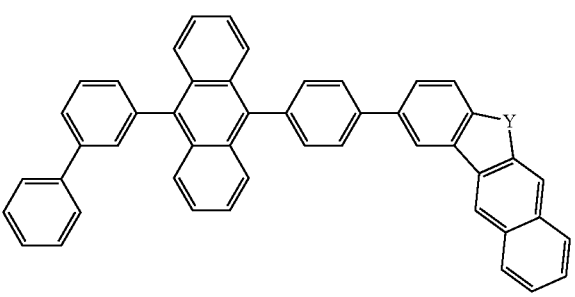
(1-143-Y)
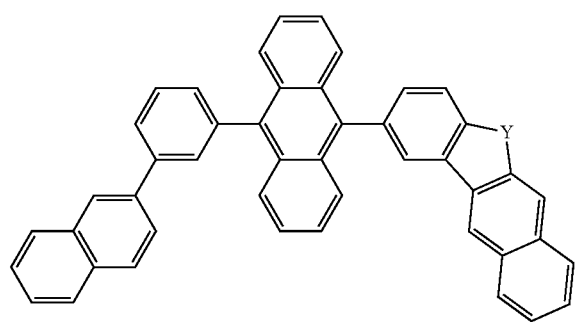
(1-147-Y)
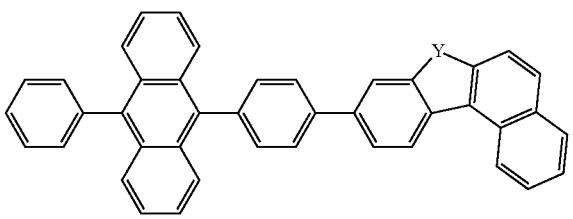
(1-148-Y)
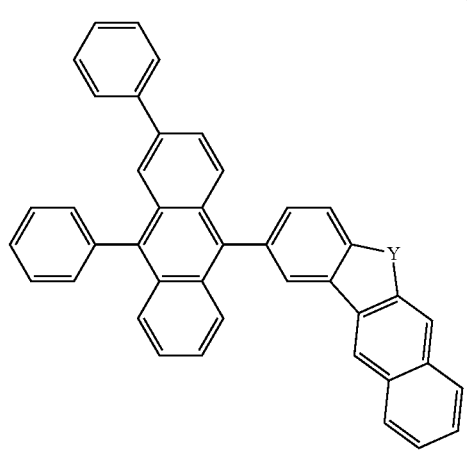
(1-144-Y)
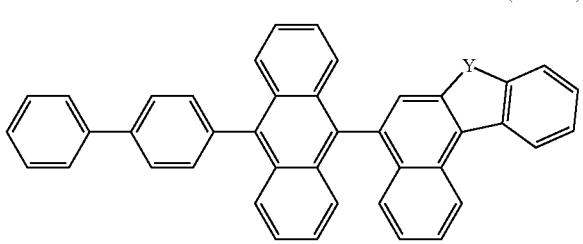

(1-149-Y)
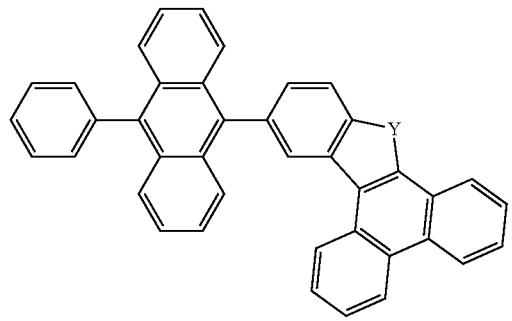
(1-150-Y)
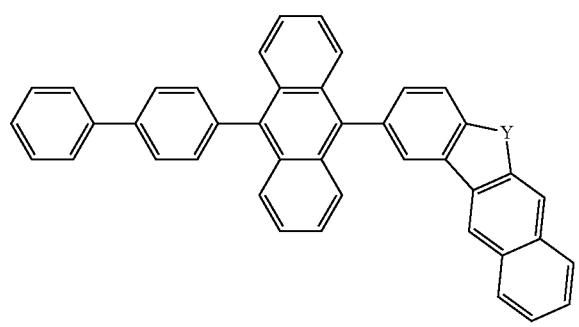
(1-151-Y)
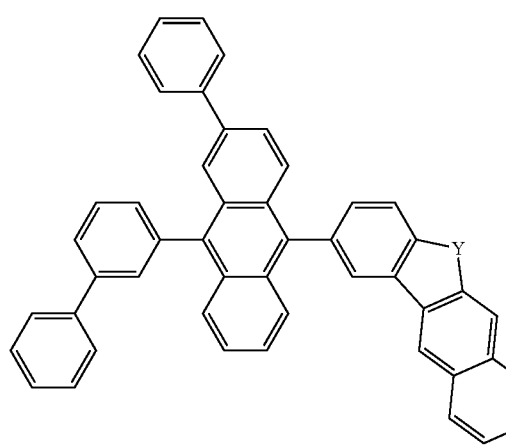
(1-152-Y)
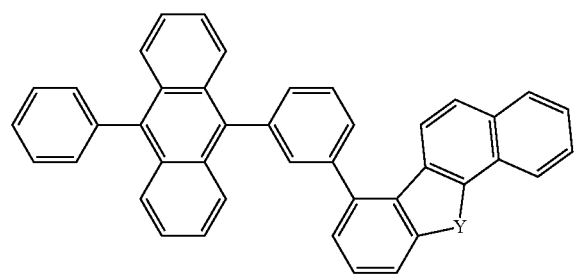
(1-53-Y)
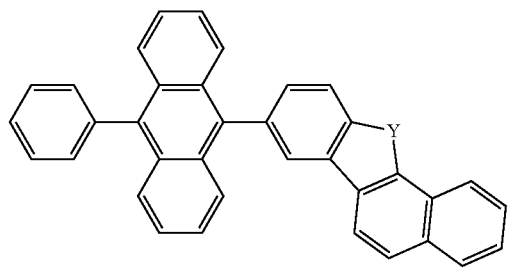
(1-154-Y)
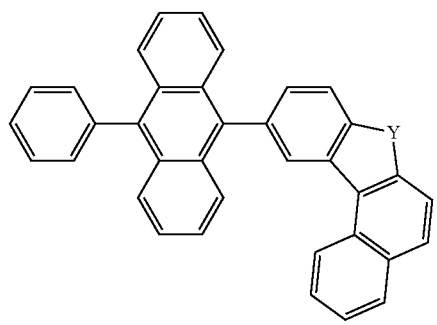
(1-155-Y)
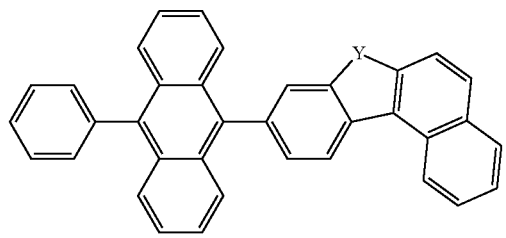
(1-156-Y)
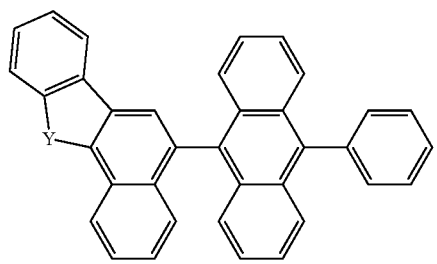
(1-157-Y)
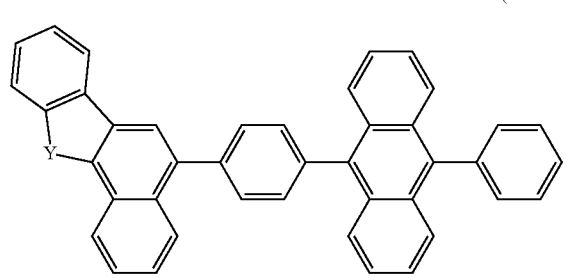

(1-158-Y)
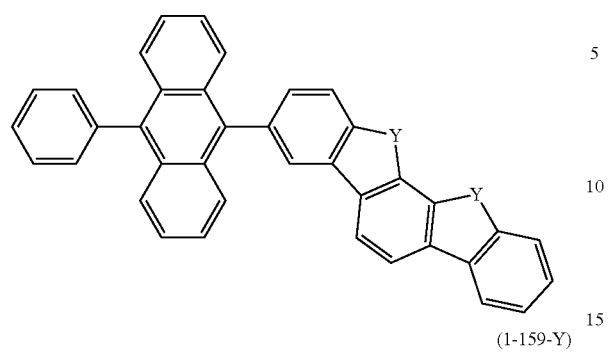
(1-159-Y)
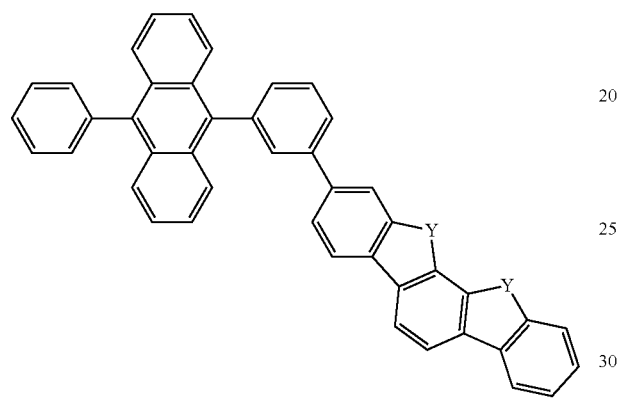
(1-160-Y)
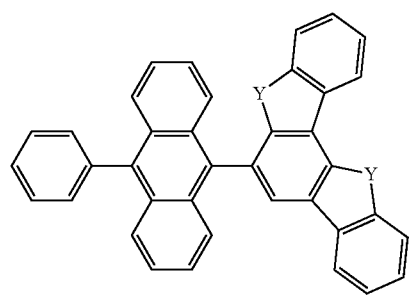
(1-161-Y)
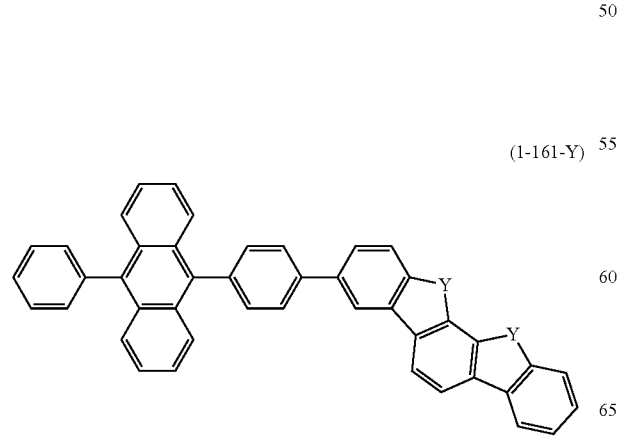
(1-162-Y)
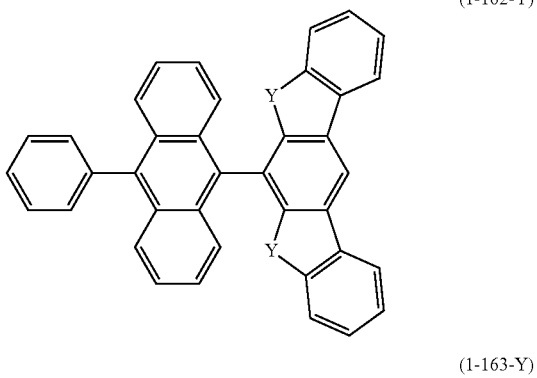
(1-163-Y)
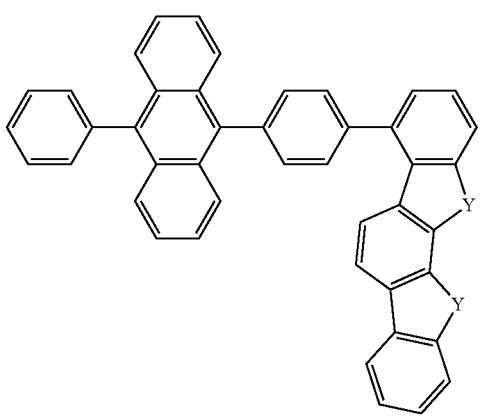
(1-164-Y)
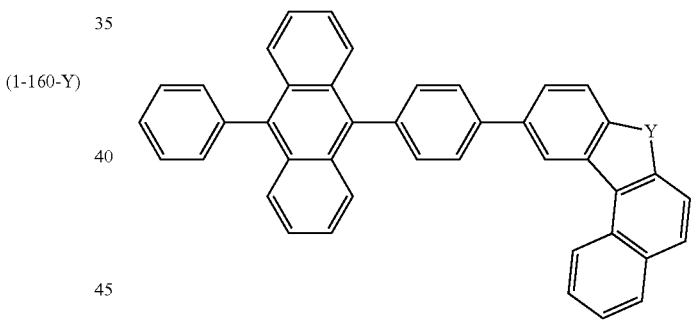
(1-165-Y)
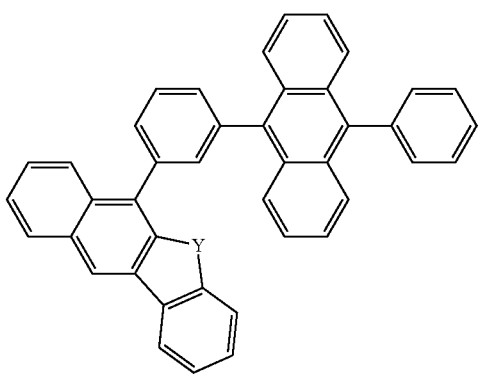

(1-166-Y)
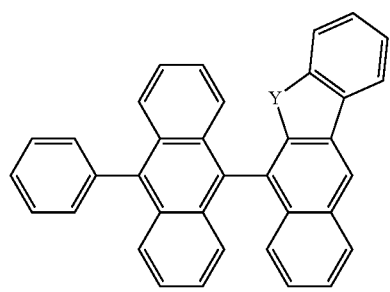
(1-167-Y)
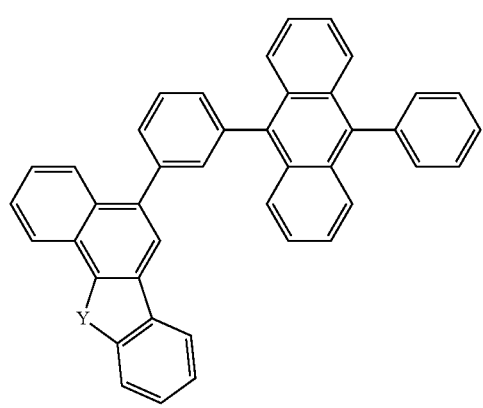
(1-168-Y)
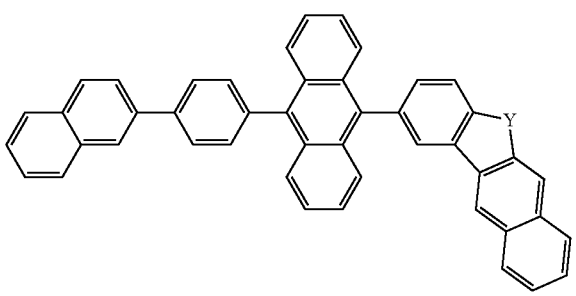
(1-169-Y)
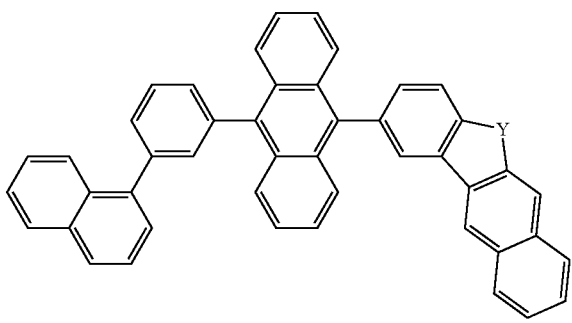
(1-170-Y)
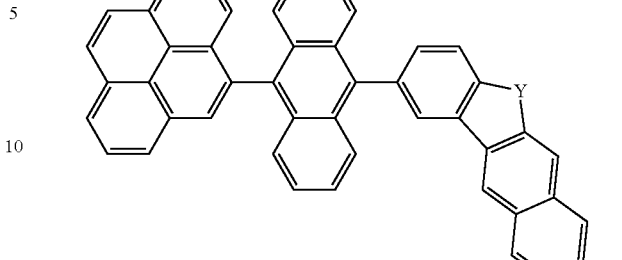
(1-171-Y)
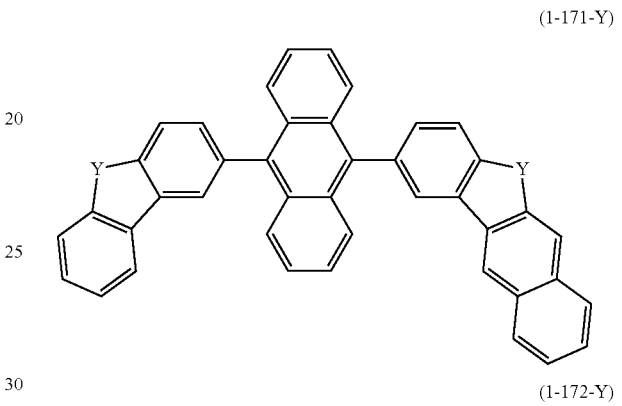
(1-172-Y)
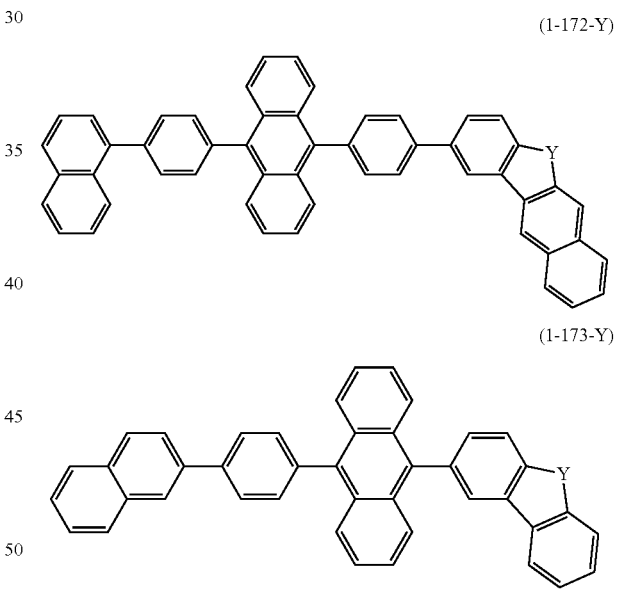
(1-173-Y)
(1-174-Y)
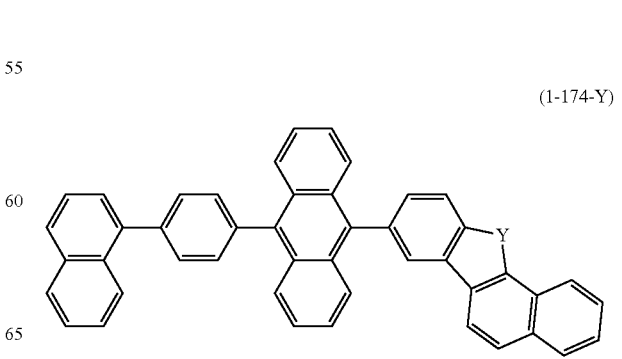

(1-175-Y)
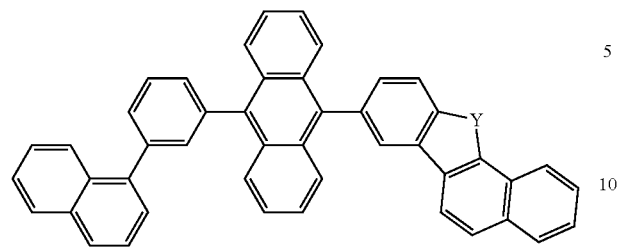
(1-176-Y)
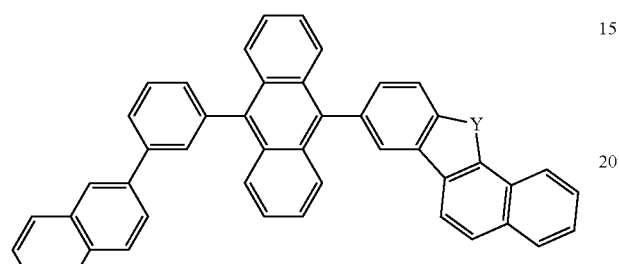
(1-177-Y)
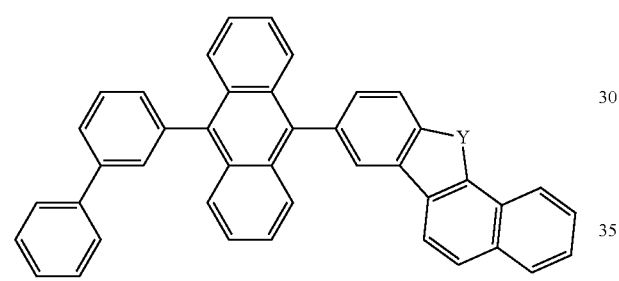
(1-178-Y)
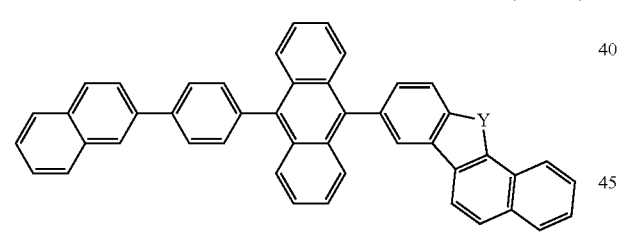
(1-179-Y)
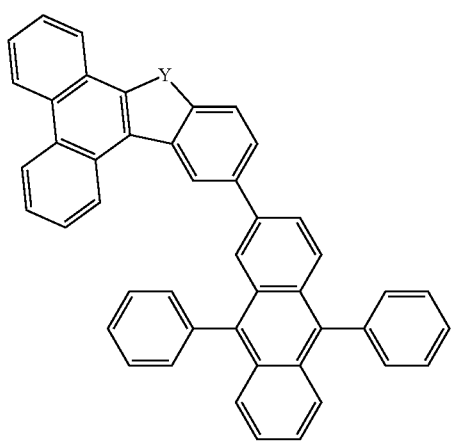
(1-180-Y)
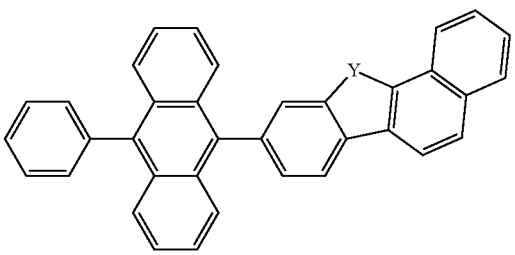
(1-181-Y)
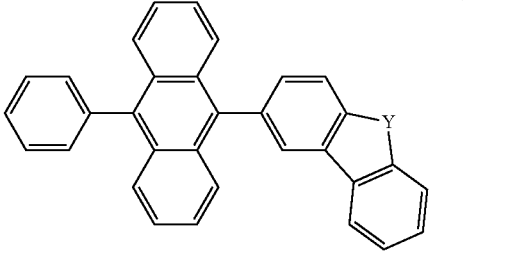
(1-182-Y)
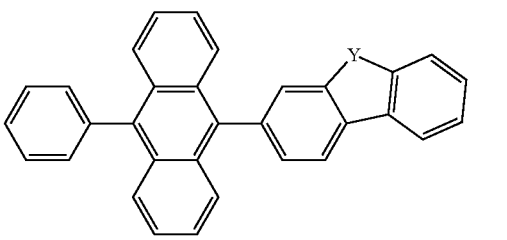
(1-183-N)
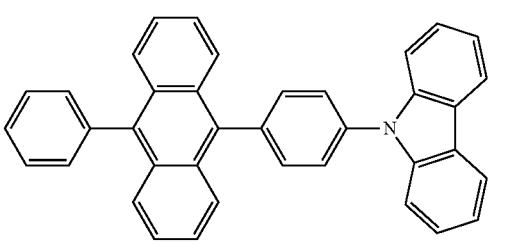
Moreover, specific examples of the anthracene-based compound include compounds represented by formulas (1-191) to (1-222).
(1-191)
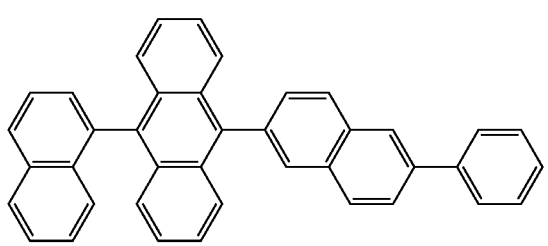

(1-192)
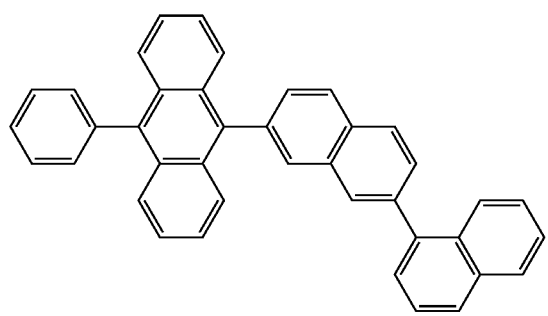
(1-193)
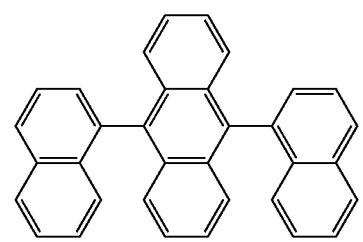
(1-194)
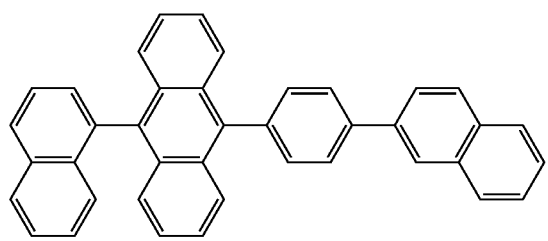
(1-195)
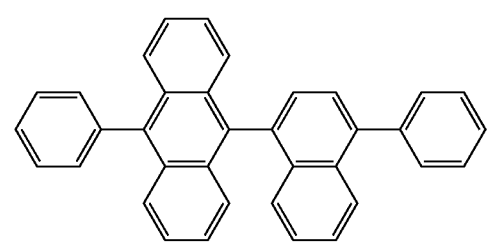
(1-196)
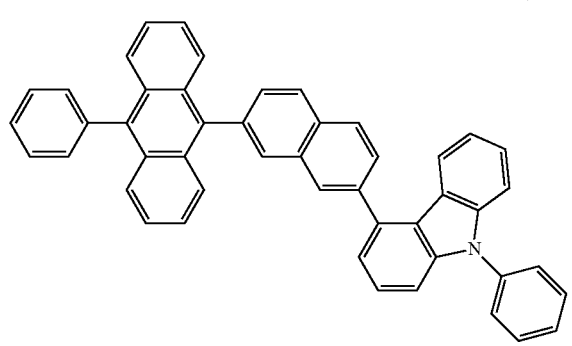
(1-197)
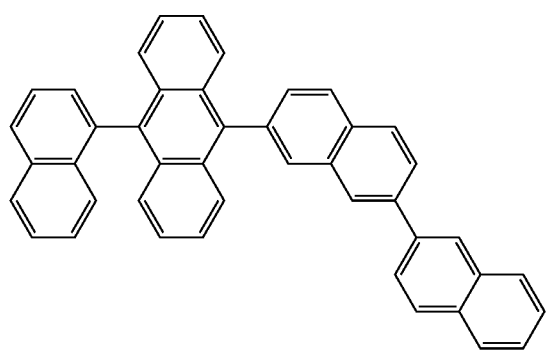
(1-198)
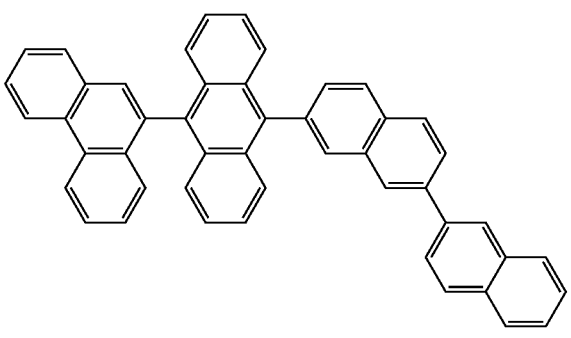
(1-199)
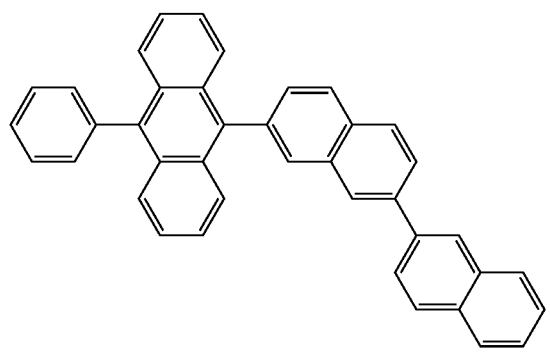
(1-201)
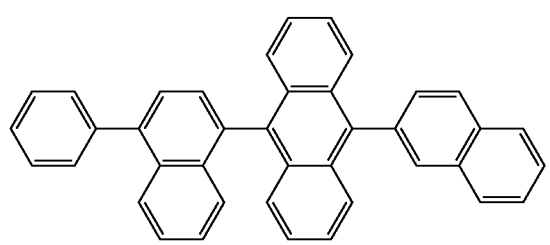

(1-202)
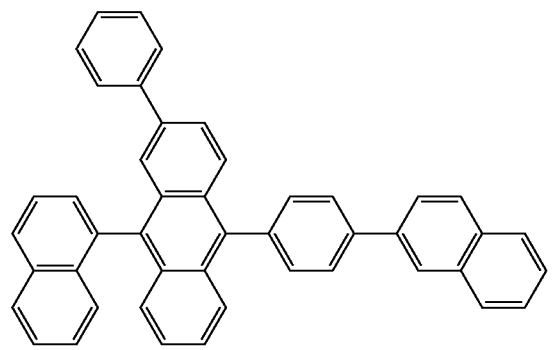
(1-203)
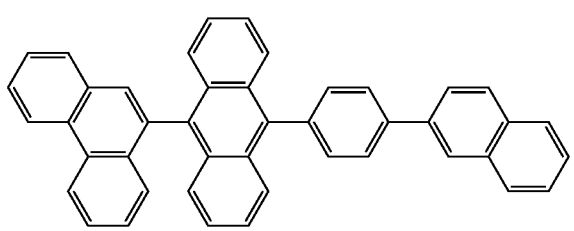
(1-204)
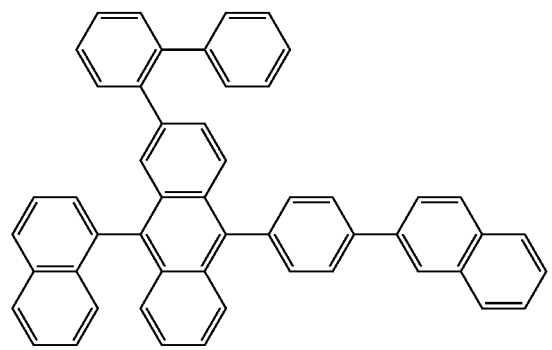
(1-205)
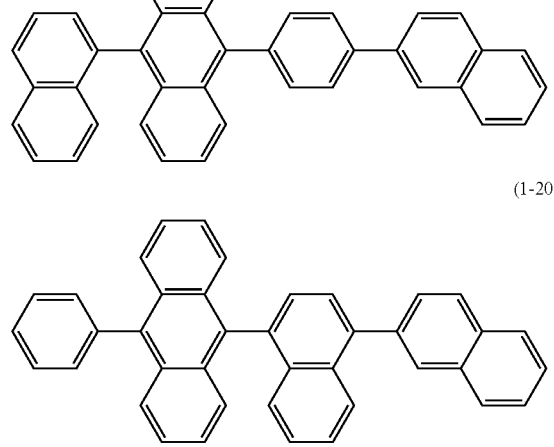
(1-206)
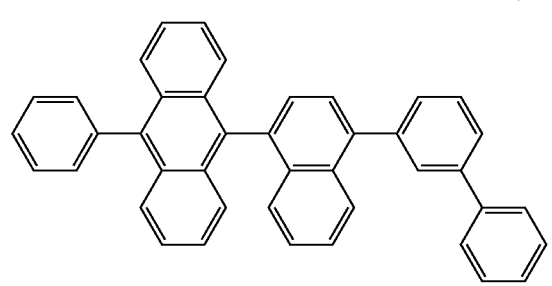
(1-207)
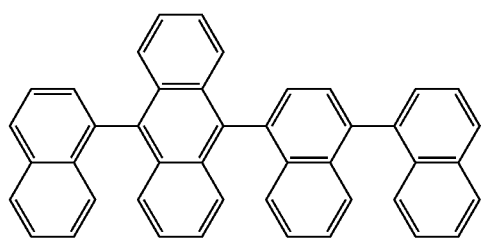
(1-208)
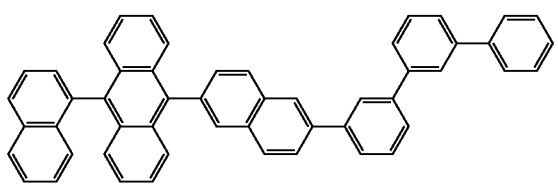
(1-209)
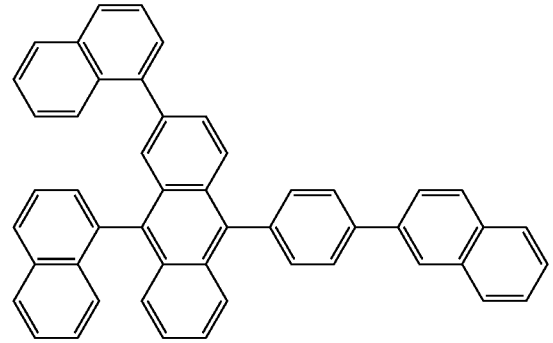
(1-211)
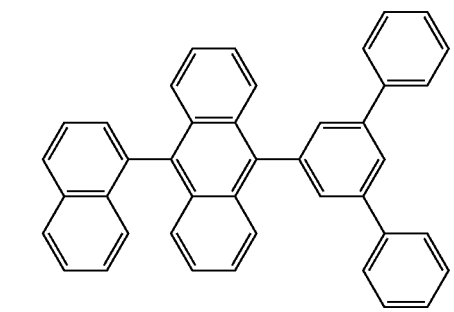
(1-212)
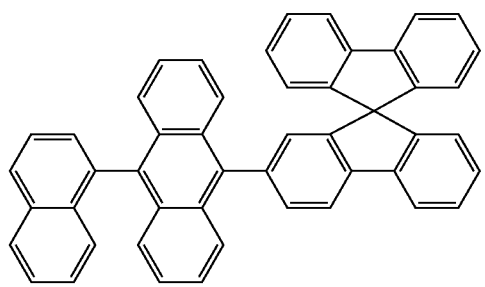

(1-213)
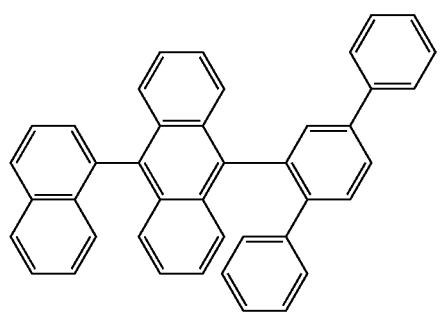
(1-214)
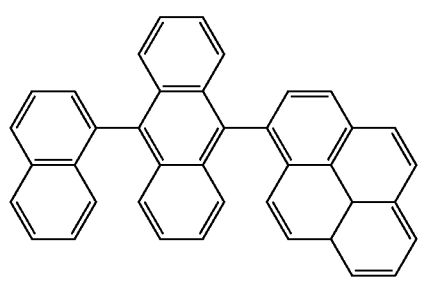
(1-215)
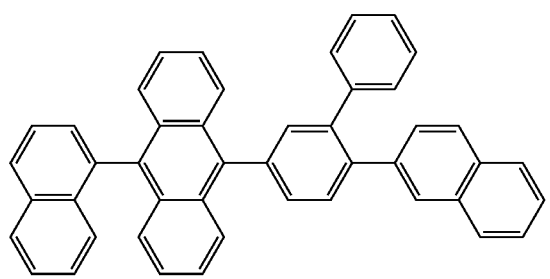
(1-216)
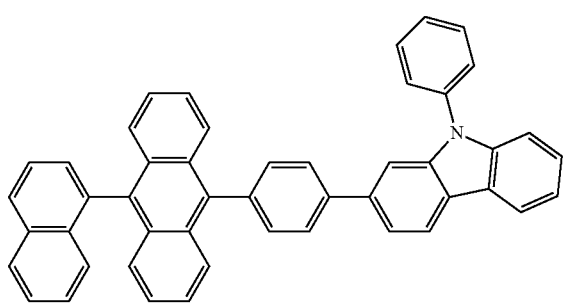
(1-221)
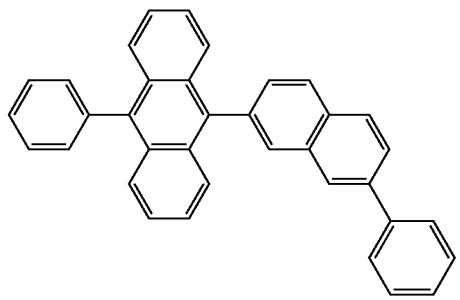
(1-222)
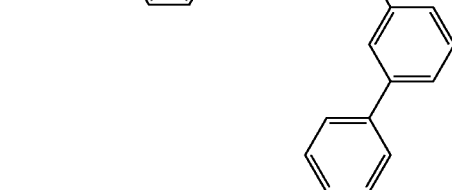
Among the compounds, compounds described below are particularly preferred.
(1-199)
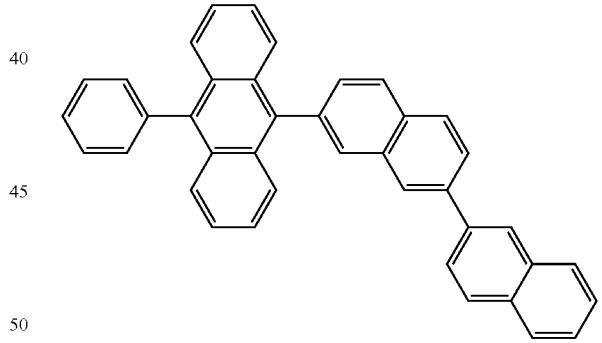
(1-192)
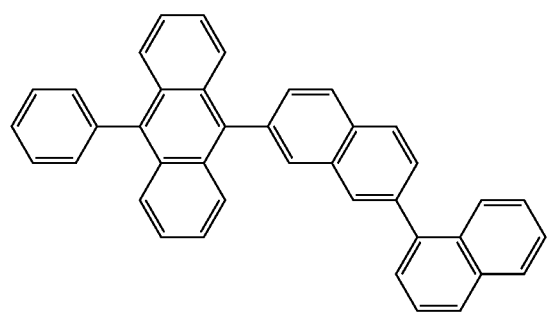

(1-222)

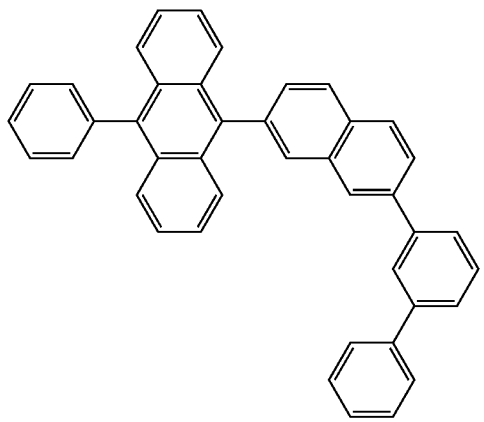

(1-221)

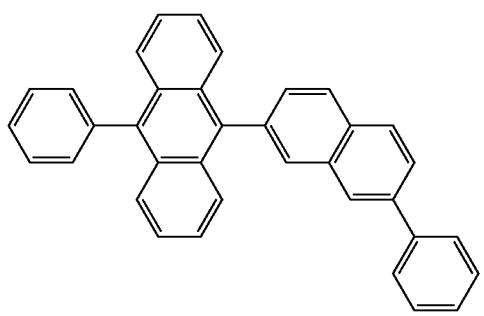

(1-195)

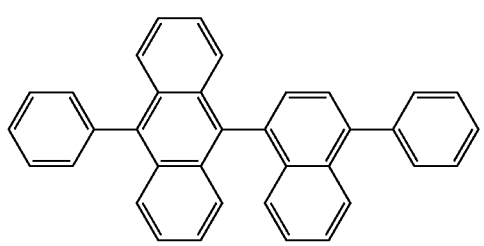

(1-134-O)

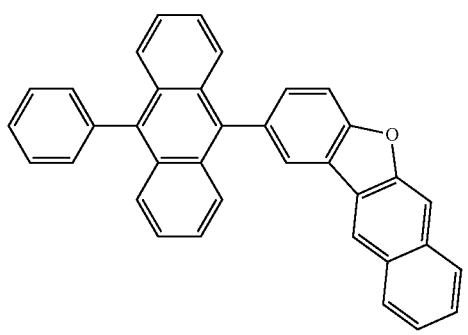

The luminescent layer of the organic electroluminescent device of the invention may include one kind or two or more kinds of the anthracene-based compounds represented by formula (1) as the host material. Moreover, the luminescent layer may include only the anthracene-based compound represented by formula (1) as the host material, and may include other host materials together with the anthracene-based compound represented by formula (1). Specific examples of the host material that can be used together include a pyrene compound, a bisstyryl derivative such as a bisstyryl anthracene derivative and a distyryl benzene derivative, a tetraphenyl butadiene derivative, a cyclopentadiene derivative, a fluorene derivative and a benzofluorene derivative, which have been known so far as a luminous element.

Luminescent Layer Forming Material: A Dopant Material

The dopant material in the luminescent layer of the organic electroluminescent device of the invention is not limited, as long as the dopant material other than the polycyclic aromatic compound represented by formula (2) or the multimer thereof having the plurality of structures represented by formula (2) is applied thereto, and a known compound can be used as the dopant material, and can be selected from various materials according to desired luminescent color. In particular, as the dopant material used in the invention, such a material is used, in which, when the luminescent layer is formed together with the anthracene-based compound represented by formula (1), the color of luminescence is not changed by addition of the polycyclic aromatic compound represented by formula (2) or the multimer thereof having the plurality of structures represented by formula (2).

Specific examples of the dopant material include a fused ring derivative such as phenanthrene, anthracene, tetracene, pentacene, perylene, rubrene and chrysene, a benzooxazol derivative, a benzothiazole derivative, a benzimidazole derivative, a benzotriazole derivatives, an oxazole derivative, an oxadiazole derivative, a thiazole derivative, an imidazole derivative, a thiadiazole derivative, a triazole derivative, a pyrazoline derivative, a stilbene derivative, a thiophene derivative, a tetraphenyl butadiene derivative, a cyclopentadiene derivative, a bisstyryl derivatives such as a bisstyryl anthracene derivative and a distyryl benzene derivative (JP H1-245087 A), a bisstyrylarylene derivative (JP H2-247278 A), a diazaindacene derivative, a furan derivative, a benzofuran derivative, an isobenzofuran derivative such as phenylisobenzofuran, dimesityl isobenzofuran, di(2-methylphenyl)isobenzofuran, di(2-trifluoromethylphenyl)isobenzofuran and phenylisobenzofuran, a dibenzofuran derivative, a coumarin derivative such as a 7-dialkylaminocoumarin derivative, a 7-piperidinocoumarin derivative, a 7-hydroxycoumarin derivative, a 7-methoxycoumarin derivative, a 7-acetoxycoumarin derivative, a 3-benzothiazolylcoumarin derivative, a 3 benzimidazolylcoumarin derivative and a 3-benzoxazolylcoumarin derivative, a dicyanomethylenepyran derivative, a dicyanomethylenethiopyran derivative, a polymethine derivative, a cyanine derivative, an oxobenzoanthracene derivative, a xanthene derivative, a rhodamine derivative, a fluorescein derivative, a pyrylium derivative, a carbostyryl derivative, an acridine derivative, an oxazine derivative, a phenyleneoxide derivative, a quinacridone derivative, a quinazoline derivative, a pyrrolopyridine derivative, a furopyridine derivative, a pyrromethene derivative, a perinon derivative, a pyrrolopyrrole derivative, a squarylium derivative, a violanthrone derivative, a phenazine derivative, an acridone derivative, a deazaflavin derivative, a fluorene derivative and a benzofluorene derivative.

In the invention, as the dopant material, a polycyclic aromatic compound represented by formula (3) or a multimer of a polycyclic aromatic compound having a plurality of structures represented by formula (3), or a compound represented by formula (4) is preferred.

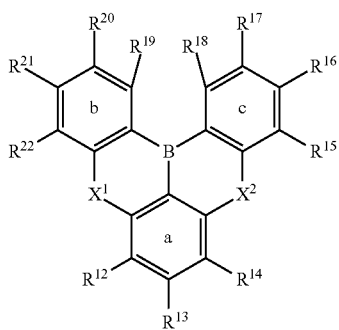

(3)

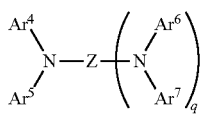

(4)

Polycyclic Aromatic Compound Represented by Formula (3) or a Multimer of the Polycyclic Aromatic Compound Having a Plurality of Structures Represented by Formula (3)

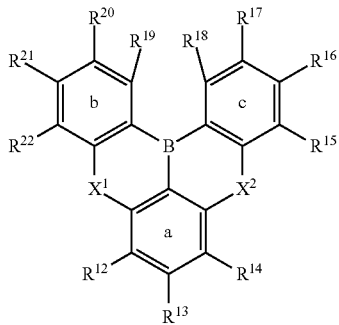

(3)

In formula (3), $R^{12}$ to $R^{22}$ are independently hydrogen, aryl, heteroaryl, diarylamino, diheteroarylamino, arylheteroarylamino, alkyl, cycloalkyl, alkoxy or aryloxy, and at least one hydrogen in the groups may be replaced by aryl, heteroaryl or alkyl. Moreover, adjacent groups of $R^{12}$ to $R^{22}$ may be bonded to each other to form an aryl ring or a heteroaryl ring together with an a ring, a b ring or a c ring, and at least one hydrogen in the ring formed may be replaced by aryl, heteroaryl, diarylamino, diheteroarylamino, arylheteroarylamino, alkyl, alkoxy or aryloxy, and at least one hydrogen in the groups may be replaced by aryl, heteroaryl or alkyl.

$X^1$ and $X^2$ are independently >O, >N—R, >C(—R)$_2$, >S or >Se, in which, at least one of $X^1$ and $X^2$ is >N—R. R of the >N—R is aryl having 6 to 12 carbons which may be subjected to substitution for alkyl having 1 to 6 carbons, heteroaryl having 2 to 15 carbons which may be subjected to substitution for alkyl having 1 to 6 carbons, or alkyl having 1 to 6 carbons, and R of the >C(—R)$_2$ is hydrogen, aryl having 6 to 12 carbons which may be subjected to substitution for alkyl having 1 to 6 carbons, or alkyl having 1 to 6 carbons. Moreover, R of the >N—R and/or R of the >C(—R)$_2$ may be bonded with the a ring, the b ring and/or the c ring by —O—, —S—, —C(—R)$_2$— or a single bond, and R of the —C(—R)$_2$— is alkyl having 1 to 6 carbons.

At least one hydrogen in the compound or the structure represented by formula (3) may be replaced by deuterium, cyano or halogen. Moreover, in the case of a multimer, the multimer is a dimer or trimer having two or three structures represented by formula (3).

In formula (3), adjacent groups of substituents $R^{12}$ to $R^{22}$ of an a ring, a b ring and a c ring may be bonded to each other to form an aryl ring or a heteroaryl ring together with the a ring, the b ring and the c ring, and at least one hydrogen in the ring formed may be replaced by aryl, heteroaryl, diarylamino, diheteroarylamino, arylheteroarylamino, alkyl, cycloalkyl, alkoxy or aryloxy, and at least one hydrogen in the groups may be replaced by aryl, heteroaryl, alkyl or cycloalkyl. Accordingly, in the polycyclic aromatic compound represented by formula (3), as shown in formula (3-1) and formula (3-2), a ring structure constituting the compound is changed by a mutual bonding form of the substituents in the a ring, the b ring and the c ring.

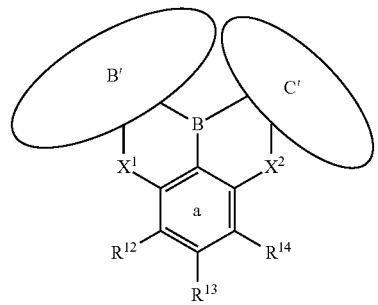

(3-1)

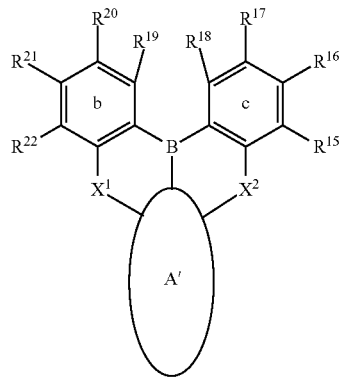

(3-2)

An A' ring and a B' ring and a C' ring in formula (3-1) and formula (3-2) show an aryl ring or a heteroaryl ring in which adjacent groups of substituents $R^{12}$ to $R^{22}$ are bonded to each other to be formed with an a ring, a b ring and a c ring, respectively (also referred to as a fused ring formed by fusing another ring structure to the a ring, the b ring and the c ring). In addition, although not shown in the formula, the polycyclic aromatic compound may be a compound in which all of the a ring, the b ring and the c ring are changed into the A' ring, the B' ring and the C' ring. Moreover, as found from formulas (3-1) to (3-2), for example, $R^{19}$ of the b ring and $R^{18}$ of the c ring, $R^{22}$ of the b ring and $R^{12}$ of the a ring, $R^{15}$ of the c ring and $R^{14}$ of the a ring, and the like do not correspond to the "adjacent groups," and the above-described groups are not bonded to each other. More specifically, the term "adjacent groups" means adjacent groups on the same ring.

The compound represented by formula (3-1) or formula (3-2) is a compound having the A' ring (or the B' ring or the C' ring) formed by fusing a benzene ring, an indole ring, a pyrrole ring, a benzofuran ring, a benzothiophene ring, a cyclohexane ring or an indan ring to a benzene ring being the a ring (or the b ring or the c ring), for example, and the fused ring A' (or the fused ring B' or fused ring C') formed each is a naphthalene ring, a carbazole ring, an indole ring, a dibenzofuran ring, a dibenzothiophene ring, a tetralin ring or a fluorene ring.

$X^1$ and $X^2$ in formula (3) are independently >O, >N—R, >C(—R)$_2$, >S or >Se, in which, at least one of $X^1$ and $X^2$ is >N—R. Both of $X^1$ and $X^2$ are preferably >N—R, or one of $X^1$ and $X^2$ is preferably >O, and the other is preferably >N—R, and both of $X^1$ and $X^2$ are further preferably >N—R. R of the >N—R is aryl which may be subjected to substitution, heteroaryl which may be subjected to substitution, alkyl which may be subjected to substitution, or cycloalkyl which may be subjected to substitution, and R of the >N—R may be bonded with the b ring and/or the c ring by a linking group or a single bond, and as the linking group, —O—, —S— or —C(—R)$_2$— is preferred. In addition, R of the "—C(—R)$_2$—" is hydrogen, alkyl or cycloalkyl.

Here, a specification of "R of the >N—R may be bonded with the a ring, the b ring and/or the c ring by a linking group or a single bond" in formula (3) can be represented by a compound having a ring structure in which X1 or $X^2$ is incorporated into the fused ring B' and the fused ring C' as represented by formula (3-3-1). More specifically, for example, the compound is a compound having the B' ring (or the C' ring) formed by fusing another ring to the benzene ring being the b ring (or the c ring) in formula (3) so as to incorporate $X^1$ (or $X^2$) thereinto. The fused ring B' (or the fused ring C') formed is a phenoxazine ring, a phenothiazine ring or an acridine ring, for example.

Moreover, the above specification can also be represented by a compound having a ring structure in which $X^1$ and/or $X^2$ is incorporated into the fused ring A' as represented by formula (3-3-2) or formula (3-3-3). More specifically, for example, the compound is a compound having the A' ring formed by fusing another ring to the benzene ring being the a ring in formula (3) so as to incorporate $X^1$ (and/or $X^2$) thereinto. The fused A' formed is a phenoxazine ring, a phenothiazine ring or an acridine ring, for example.

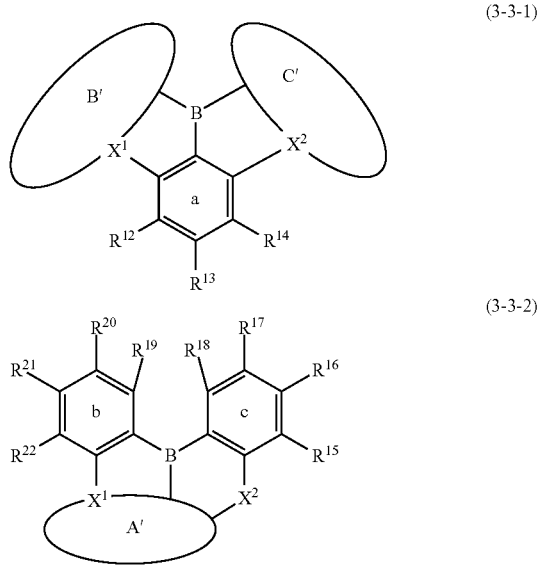

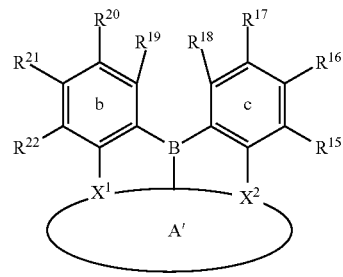

The "aryl ring in which adjacent groups of $R^{12}$ to $R^{22}$ are bonded to each other to be formed with the a ring, the b ring or the c ring" specified in formula (3) is preferably an aryl ring having 9 to 16 carbons, and further preferably an aryl ring having 10 to 12 carbons. Specific examples of such an "aryl ring" include a bicyclic biphenyl ring, a fused bicyclic naphthalene ring, a tricyclic terphenyl ring (m-terphenyl, o-terphenyl, p-terphenyl), a fused tricyclic acenaphthylene ring, fluorene ring, phenalene ring and phenanthrene ring, a fused tetracyclic triphenylene ring, pyrene ring and naphthacene ring, a fused pentacyclic perylene ring and pentacene ring.

Specific examples of the "heteroaryl ring in which adjacent groups of $R^{12}$ to $R^{22}$ are bonded to each other to be formed with the a ring, the b ring or the c ring" specified in formula (3) include a heteroaryl ring having 6 to 30 carbons, and a heteroaryl ring having 6 to 25 carbons is preferred, a heteroaryl ring having 6 to 20 carbons is further preferred, a heteroaryl ring having 6 to 15 carbons is still further preferred, and a heteroaryl ring having 6 to 10 carbons is particularly preferred. Moreover, specific examples of the "heteroaryl ring" include a heterocyclic ring containing, in addition to carbon, 1 to 5 hetero atoms selected from oxygen, sulfur and nitrogen as a ring-forming atom. Specific examples of the "heteroaryl ring" include a benzimidazole ring, a benzooxazole ring, a benzothiazole ring, a 1H-benzotriazol ring, a benzofuran ring, an isobenzofuran ring, a dibenzofuran ring, a benzothiophene ring and a dibenzothiophene ring.

At least one hydrogen in the "aryl ring" or the "heteroaryl ring" may be replaced by, as a first substituent, substituted or unsubstituted "aryl," substituted or unsubstituted "heteroaryl," substituted or unsubstituted "diarylamino," substituted or unsubstituted "diheteroarylamino," substituted or unsubstituted "arylheteroarylamino," substituted or unsubstituted "alkyl," substituted or unsubstituted "cycloalkyl," substituted or unsubstituted "alkoxy," and substituted or unsubstituted "aryloxy," and specific examples of, as the first substituent, aryl of "aryl," "heteroaryl" or "diarylamino," heteroaryl of "diheteroarylamino," aryl and heteroaryl of "arylheteroarylamino" and aryl of "aryloxy" include a monovalent group of the "aryl ring" described above, and specific examples of the "heteroaryl" include a monovalent group of the "heteroaryl ring" described below. More specifically, specific examples of the "heteroaryl ring" include a pyrrole ring, an oxazole ring, an isoxazol ring, a thiazole ring, an isothiazole ring, an imidazole ring, an oxadiazole ring, a thiadiazole ring, a triazole ring, a tetrazole ring, a pyrazole ring, a pyridine ring, a pyrimidine ring, a pyridazine ring, a pyrazine ring, a triazine ring, an indole ring, an isoindole ring, a 1H-indazole ring, a benzimidazole ring, a benzooxazole ring, a benzothiazole ring, a 1H-benzotriazol ring, a quinoline ring, an isoquinoline ring, a cinnoline ring, a quinazoline ring, a quinoxaline ring, a phthalazine ring, a naphthyridine ring, a purine ring, a pteridine ring, a carbazole ring, an acridine ring, a phenoxathiin ring, a phenoxazine ring, a phenothiazine ring, a phenazine ring, an indolizine ring, a furan ring, a benzofuran ring, an isobenzofuran ring, a dibenzofuran ring, a thiophene ring, a benzothiophene ring, a dibenzothiophene ring, a furazan ring and a thianthrene ring.

The "alkyl" as a first substituent in $R^{12}$ to $R^{22}$ in formula (3) may be any of straight-chain alkyl and branched-chain alkyl, and specific examples thereof include straight-chain alkyl having 1 to 24 carbons or branched-chain alkyl having 3 to 24 carbons. Alkyl having 1 to 18 carbons (branched-chain alkyl having 3 to 18 carbons) is preferred, alkyl having 1 to 12 carbons (branched-chain alkyl having 3 to 12 carbons) is further preferred, alkyl having 1 to 6 carbons (branched-chain alkyl having 3 to 6 carbons) is still further preferred, and alkyl having 1 to 4 carbons (branched-chain alkyl having 3 to 4 carbons) is particularly preferred.

Specific examples of the alkyl include methyl, ethyl, n-propyl, isopropyl, n-butyl, isobutyl, s-butyl, t-butyl, n-pentyl, isopentyl, neopentyl, t-pentyl, n-hexyl, 1-methylpentyl, 4-methyl-2-pentyl, 3,3-dimethylbutyl, 2-ethylbutyl, n-heptyl, 1-methylhexyl, n-octyl, t-octyl, 1-methylheptyl, 2-ethylhexyl, 2-propylpentyl, n-nonyl, 2,2-dimethylheptyl, 2,6-dimethyl-4-heptyl, 3,5,5-trimethylhexyl, n-decyl, n-undecyl, 1-methyldecyl, n-dodecyl, n-tridecyl, 1-hexylheptyl, n-tetradecyl, n-pentadecyl, n-hexadecyl, n-heptadecyl, n-octadecyl and n-eicosyl.

Specific examples of the "cycloalkyl" as the first substituent in formula (3) include cycloalkyl having 3 to 24 carbons, cycloalkyl having 3 to 20 carbons, cycloalkyl having 3 to 16 carbons, cycloalkyl having 3 to 14 carbons, cycloalkyl having 5 to 10 carbons, cycloalkyl having 5 to 8 carbons, cycloalkyl having 5 to 6 carbons and cycloalkyl having 5 carbons.

Specific examples of the cycloalkyl include cyclopropyl, cyclobutyl, cyclopentyl, cyclohexyl, cycloheptyl, cyclooctyl, bicyclo[1.0.1]butyl, bicyclo[1.1.1]pentyl, bicyclo[2.0.1]pentyl, bicyclo[1.2.1]hexyl, bicyclo[3.0.1]hexyl, bicyclo[2.2.1]heptyl, bicyclo[2.2.2]octyl, decahydronaphthyl, adamanthyl (particularly 1-adamanthyl), diamantyl and decahydroazulenyl. In addition, specific examples of the cycloalkyl which is subjected to substitution for the second substituent described later particularly include methylcyclopropyl, methylcyclobutyl, methylcyclopentyl, methylcyclohexyl, methylcycloheptyl and methylcyclooctyl.

In addition, specific examples of the "alkoxy" as the first substituent in formula (3) include straight-chain alkoxy having 1 to 24 carbons or branched-chain alkoxy having 3 to 24 carbons. Alkoxy having 1 to 18 carbons (branched-chain alkoxy having 3 to 18 carbons) is preferred, alkoxy having 1 to 12 carbons (branched-chain alkoxy having 3 to 12 carbons) is further preferred, alkoxy having 1 to 6 carbons (branched-chain alkoxy having 3 to 6 carbons) is still further preferred, and alkoxy having 1 to 4 carbons (branched-chain alkoxy having 3 to 4 carbons) is particularly preferred.

Specific examples of the alkoxy include methoxy, ethoxy, propoxy, isopropoxy, butoxy, isobutoxy, s-butoxy, t-butoxy, pentyloxy, hexyloxy, heptyloxy and octyloxy.

In substituted or unsubstituted "aryl," substituted or unsubstituted "heteroaryl," substituted or unsubstituted "diarylamino," substituted or unsubstituted "diheteroarylamino," substituted or unsubstituted "aryiheteroarylamino," substituted or unsubstituted "alkyl," substituted or unsubstituted "cycloalkyl," substituted or unsubstituted "alkoxy," or substituted or unsubstituted "aryloxy" as the first substituent in formula (3), at least one hydrogen therein may be replaced by the second substituent as described as "substituted or unsubstituted." Examples of the second substituent include aryl, heteroaryl, alkyl or cycloalkyl, and specific examples thereof can be referred to the above-described description for the monovalent group of the "aryl ring" and the "heteroaryl ring," and the "alkyl" or the "cycloalkyl" as the first substituent. Moreover, aryl or heteroaryl as the second substituent also includes a group in which, at least one hydrogen therein is replaced by aryl such as phenyl (specific examples include the above-described groups), or alkyl such as methyl (specific examples include the above-described groups). As one example, when the second substituent is a carbazolyl group, a carbazolyl group in which, at least one hydrogen in the 9-position is replaced by aryl such as phenyl or alkyl such as methyl is also included in heteroaryl as the second substituent.

Specific examples of aryl, heteroaryl, aryl of diarylamino, heteroaryl of diheteroarylamino, aryl and heteroaryl of arylheteroarylamino, or aryl of aryloxy in $R^{12}$ to $R^{22}$ in formula (3) include a monovalent group of the "aryl ring" or the "heteroaryl ring" described above. Alkyl, cycloalkyl or alkoxy in formula $R^1$ to $R^{1'}$ can be referred to the description for "alkyl," "cycloalkyl" or "alkoxy" as the first substituent in the above-described description for formula (3). Further, a same rule applies also to aryl, heteroaryl, alkyl or cycloalkyl as a substituent to the above groups. Moreover, a same rule applies also to, when adjacent groups of $R^{11}$ to $R^{22}$ are bonded to each other to form the aryl ring or the heteroaryl ring together with the a ring, the b ring or the c ring, as the substituent to the above groups, heteroaryl, diarylamino, diheteroarylamino, arylheteroarylamino, alkyl, cycloalkyl, alkoxy or aryloxy, and as the further substituent, aryl, heteroaryl, alkyl or cycloalkyl.

R of >N—R in X1 and $X^2$ of formula (3) is aryl, heteroaryl, alkyl or cycloalkyl which may be subjected to substitution for the above-described second substituent, and at least one hydrogen in the aryl, the heteroaryl, the alkyl or the cycloalkyl may be replaced by alkyl or cycloalkyl, for example. Specific examples of the aryl, the heteroaryl, the alkyl or the cycloalkyl include the groups described above. Aryl having 6 to 10 carbons (for example, phenyl, naphthyl or the like), heteroaryl having 2 to 15 carbons (for example, carbazolyl or the like), alkyl having 1 to 4 carbons (for example, methyl, ethyl or the like), and cycloalkyl having 3 to 16 carbons (for example, bicyclooctyl, adamanthyl or the like) are particularly preferred.

R of "—C(—R)$_2$—" being the linking group in formula (3) is hydrogen, alkyl or cycloalkyl, and specific examples of the alkyl or the cycloalkyl include the groups described above. Alkyl having 1 to 4 carbons (for example, methyl, ethyl or the like) is particularly preferred.

Moreover, the multimer of the polycyclic aromatic compound having the plurality of unit structures represented by formula (3) can also be used as the dopant material. The multimer may be a dimer to a trimer. The multimer may have a form having the plurality of unit structures in one compound, and for example, the multimer may have, in addition to a form in which the plurality of unit structures are bonded by the linking group such as a single bond, an alkylene group having 1 to 3 carbons, a phenylene group, a naphthylene group, a form in which arbitrary rings (a ring, b ring or c ring) contained in the unit structure are bonded so as to be shared in the plurality of unit structures, or a form in which arbitrary rings (a ring, b ring or c ring) contained in the unit structure are bonded so as to be fused to each other.

Specific examples of such a multimer include multimer compounds represented by formula (3-4), formula (3-4-1), formulas (3-5-1) to (3-5-4) or formula (3-6). The multimer compound represented by formula (3-4) is, if described in formula (3), a multimer compound having, in one compound, the plurality of unit structures represented by formula (3) so as to share the benzene ring being the a ring. Moreover, the multimer compound represented by formula (3-4-1) is, if described in formula (3), a multimer compound having, in one compound, two unit structures represented by formula (3) so as to share the benzene ring being the a ring. Moreover, the multimer compound represented by formula (3-4-2) is, if described in formula (3), a multimer compound having, in one compound, three unit structures represented by formula (3) so as to share the benzene ring being the a ring. Moreover, the multimer compounds represented by formulas (3-5-1) to (3-5-4) are, if described in formula (3), a multimer compound having, in one compound, the plurality of unit structures represented by formula (3) so as to share the benzene ring being the b ring (or the c ring). Moreover, the multimer compound represented by formula (3-6) is, if described in formula (3), a multimer compound having, in one compound, the plurality of unit structures represented by formula (3) in such a manner that the benzene ring being the b ring (or the a ring, the c ring) having a certain unit structure is fused to the benzene ring being the b ring (or the a ring, the c ring) having a certain unit structure, for example.

(3-4)

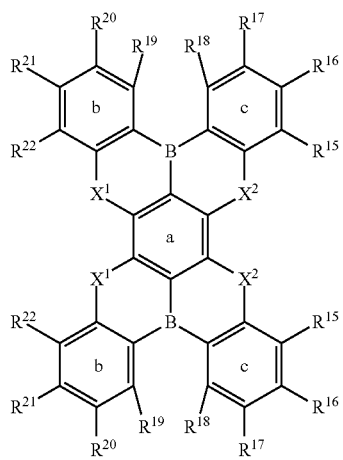

(3-4-1)

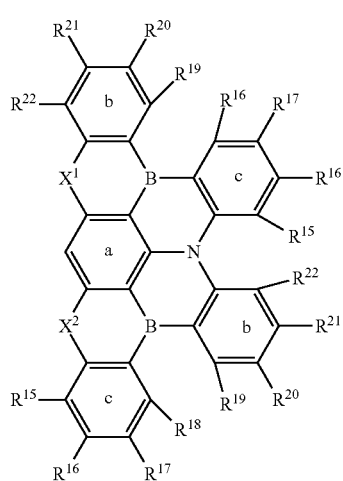

(3-5-1)

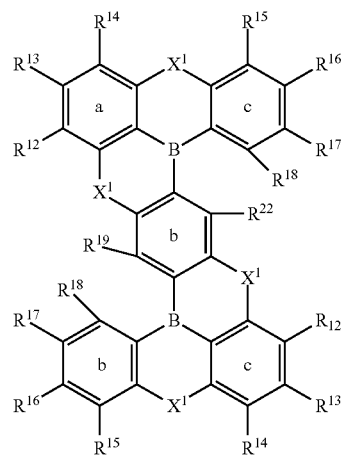

(3-5-2)

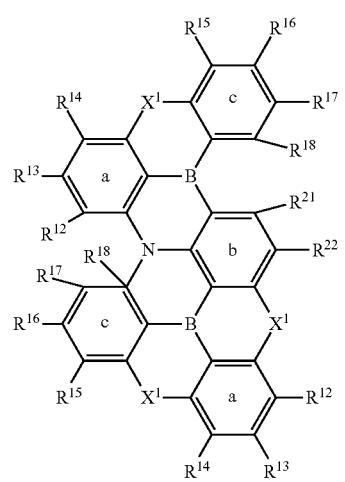

(3-5-3)

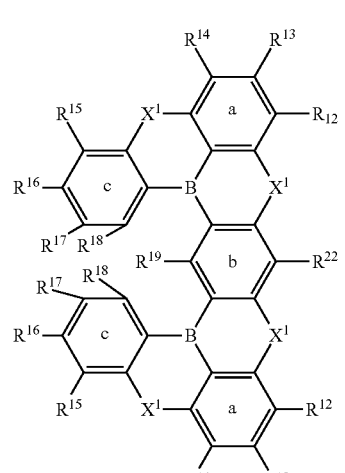

-continued (3-5-4)

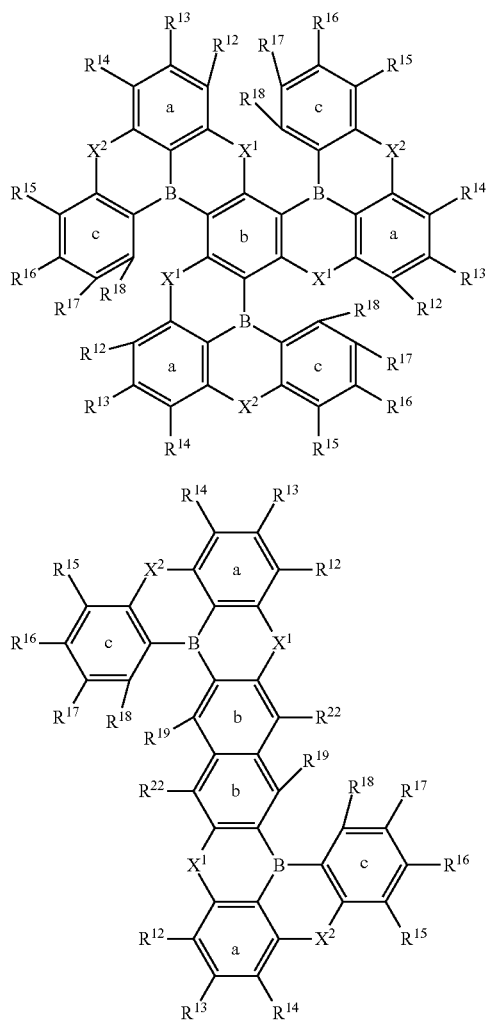

(3-6)

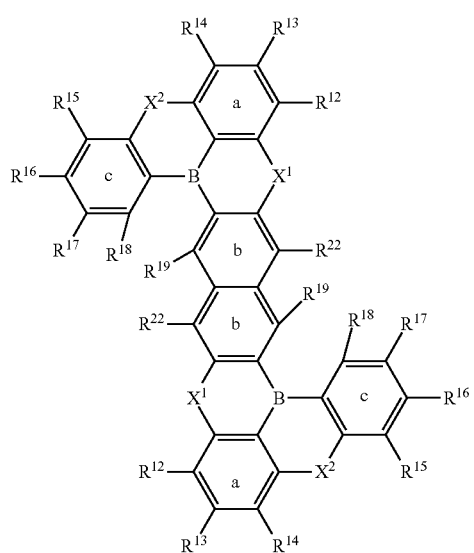

Definitions of $R^{12}$ to $R^{22}$, $X^1$ and $X^2$ in formula (3-4) (3-6) are the same as in formula (3) respectively. (3-6) are the same as in formula (3), respectively.

The multimer compound may be a multimer in which a multimerized form represented by formula (3-4) or formula (3-4-1) is combined with a multimerized form represented by any of formulas (3-5-1) to (3-5-4), or formula (3-6), or a multimer in which a multimerized form represented by any of formulas (3-5-1) to (3-5-4) is combined with a multimerized form represented by formula (3-6), or a multimer in which a multimerized form represented by formula (3-4) or formula (3-4-1), a multimerized form represented by any of formulas (3-5-1) to (3-5-4) and a multimerized form represented by formula (3-6) are combined with each other.

Moreover, a hydrogen in the polycyclic aromatic compound represented by formula (3) and the chemical structure of the multimer thereof may be wholly or partly replaced by halogen, cyano or deuterium. For example, a hydrogen in the a ring, the b ring and the c ring (the a to c rings are an arylamine ring or the heteroaryl ring), the substituents to the a to c rings and R (=aryl, heteroaryl, alkyl and cycloalkyl) when $X^1$ and $X^2$ are >N—R may be replaced by halogen, cyano or deuterium, and above all, specific examples include an aspect in which hydrogen in the arylamine ring or the heteroaryl ring is wholly or partly replaced by halogen, cyano or deuterium. The halogen is fluorine, chlorine, bromine or iodine, preferably fluorine, chlorine or bromine, and further preferably fluorine or chlorine.

Further specific examples of the polycyclic aromatic compound represented by formula (3) include compounds represented by the following structural formulas. In addition, "Me" and "tBu" in the following structural formula represent methyl and tertiary butyl, respectively.

(3-1)

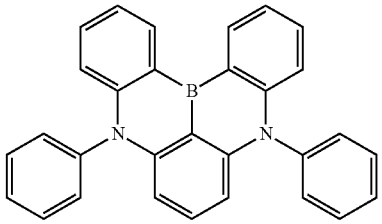

(3-2)

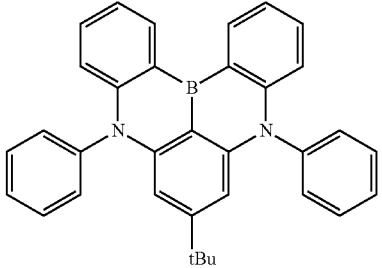

(3-3)

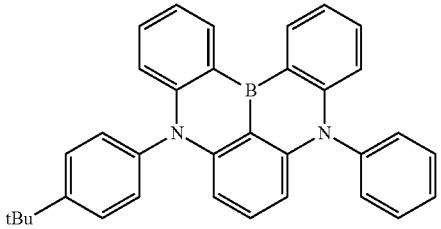

(3-4)

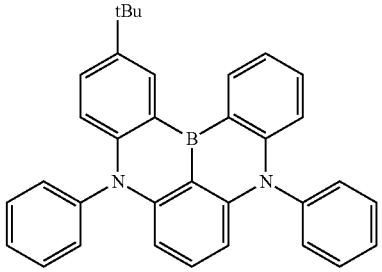

(3-5)

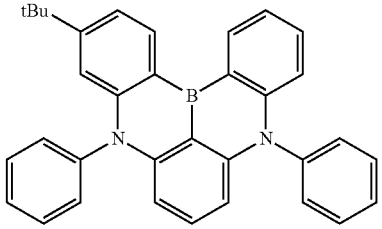

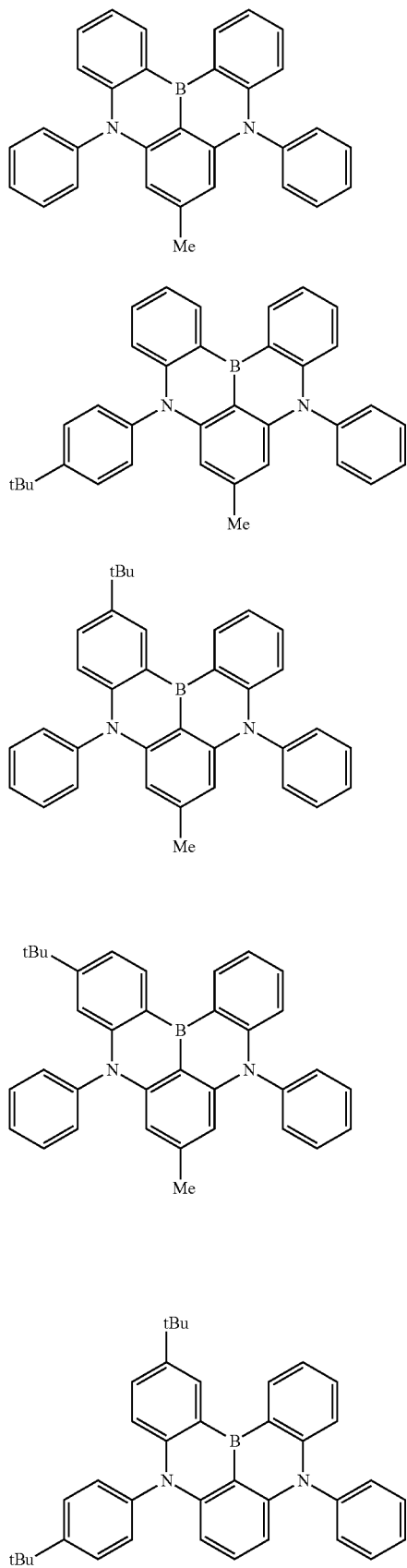
(3-6)
(3-7)
(3-8)
(3-9)
(3-10)
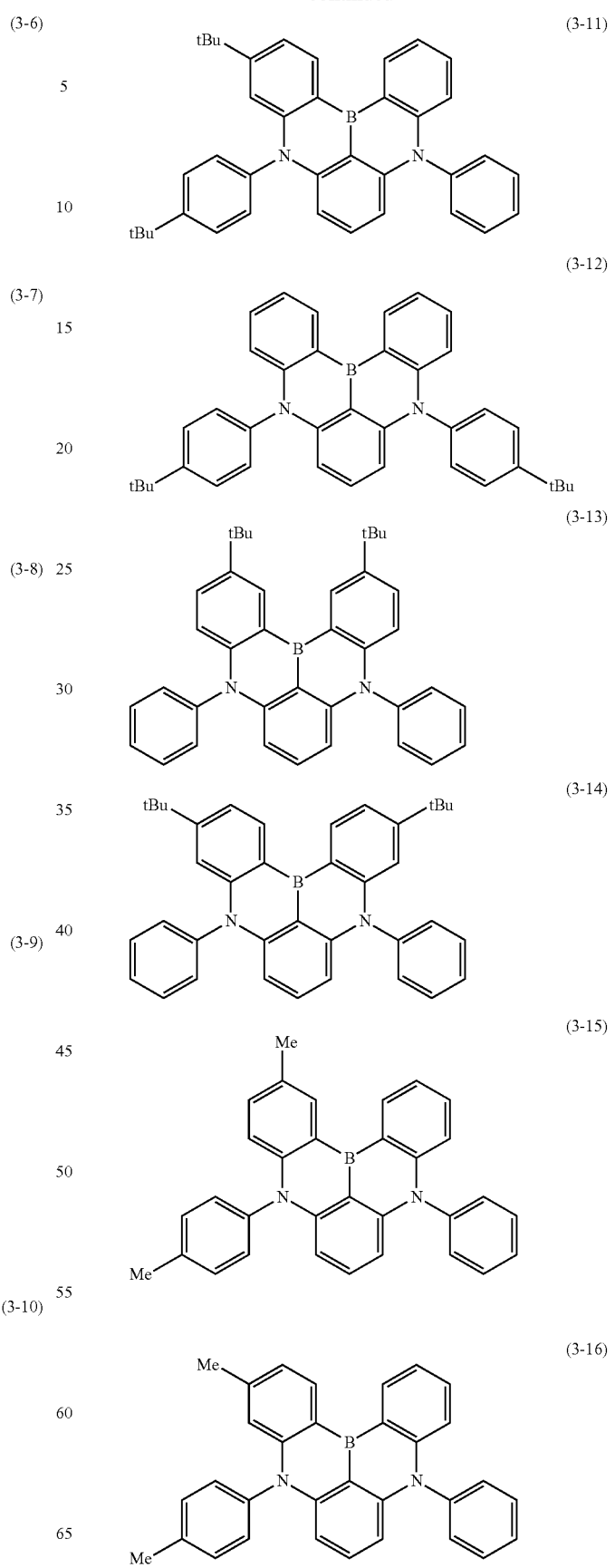
(3-11)
(3-12)
(3-13)
(3-14)
(3-15)
(3-16)

-continued
(3-17)
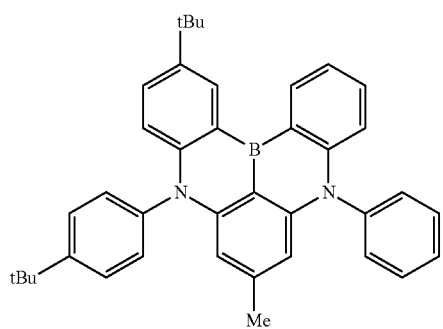
(3-18)
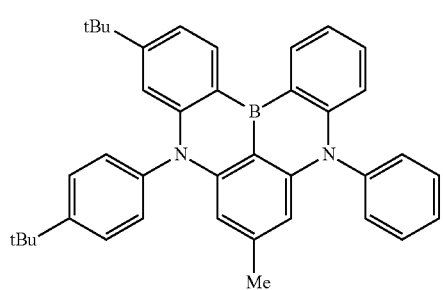
(3-19)
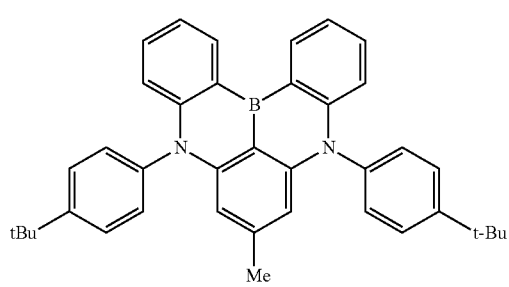
(3-20)
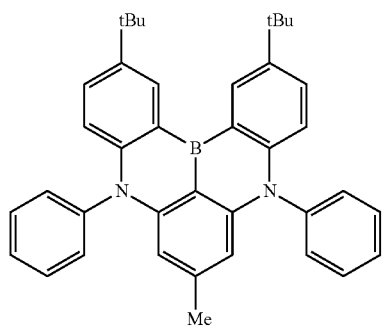
(3-21)
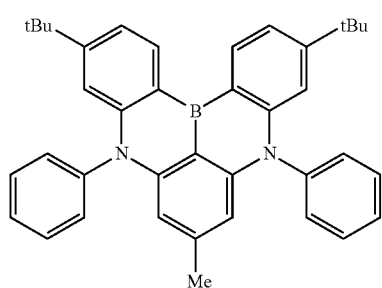
(3-22)
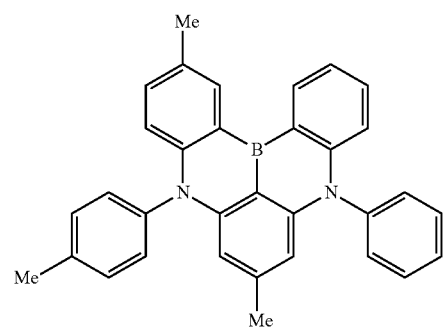
(3-23)
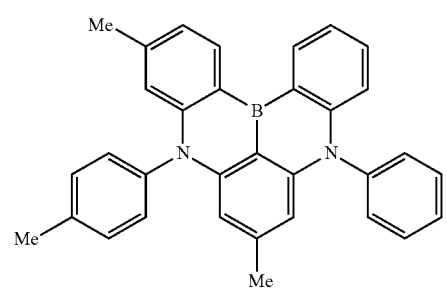
(3-24)
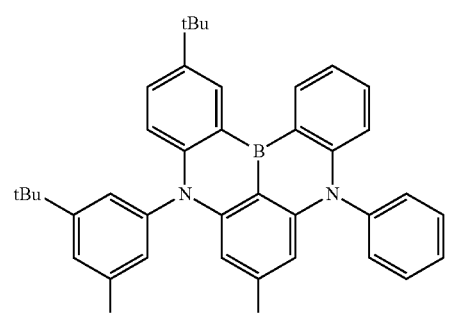
(3-25)
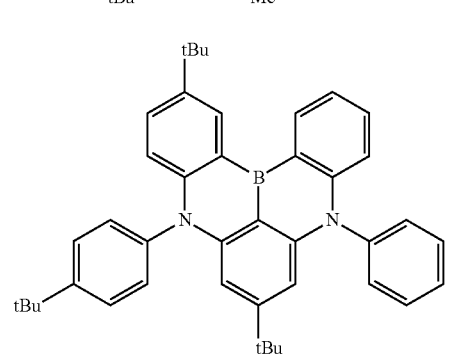
(3-26)
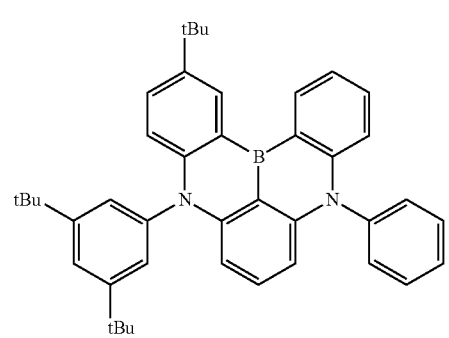

(3-27)
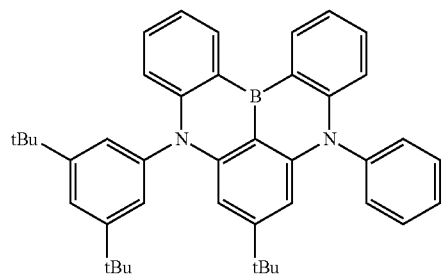
(3-28)
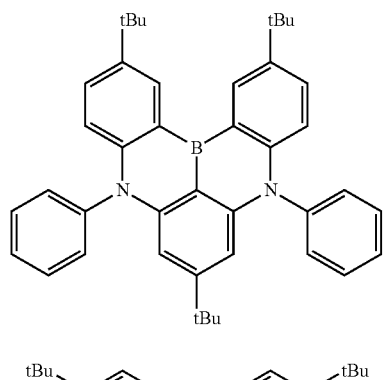
(3-29)
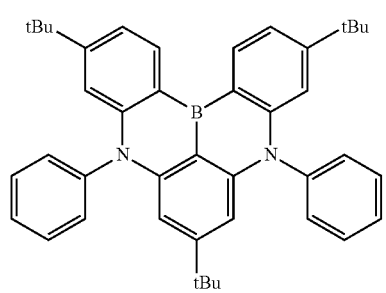
(3-30)
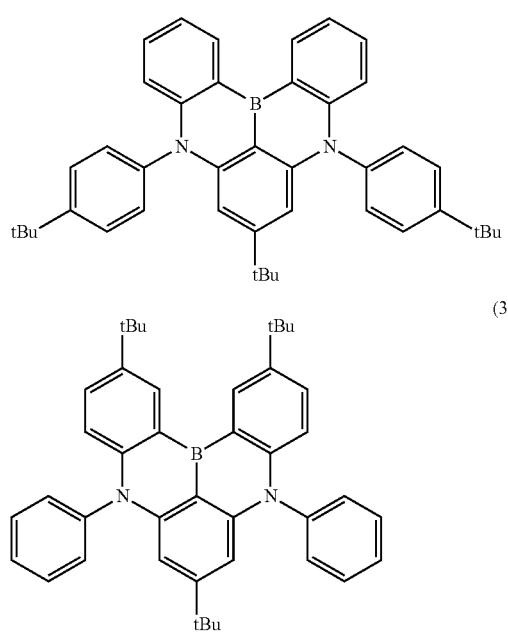
(3-31)
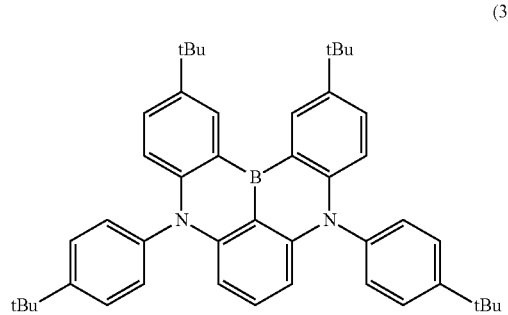
(3-32)
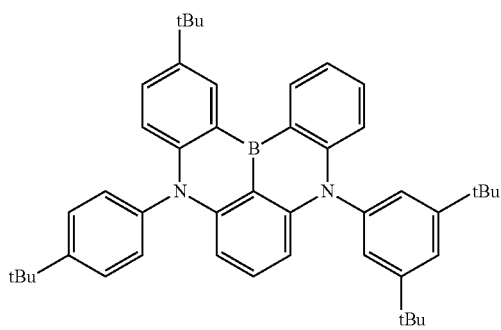
(3-33)
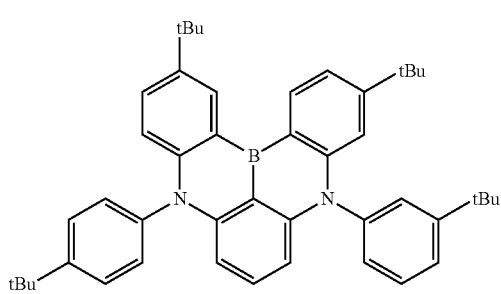
(3-34)
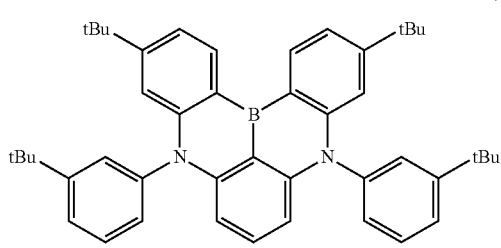
(3-35)
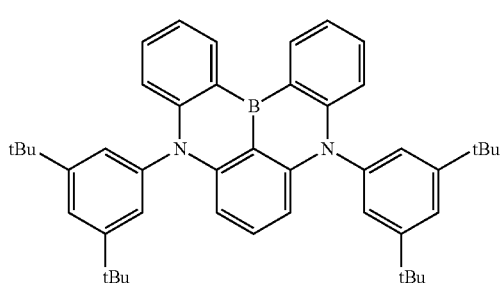
(3-36)
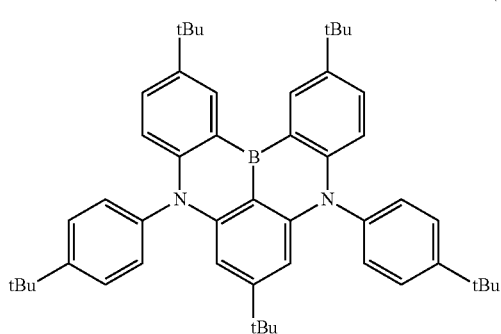

(3-37)
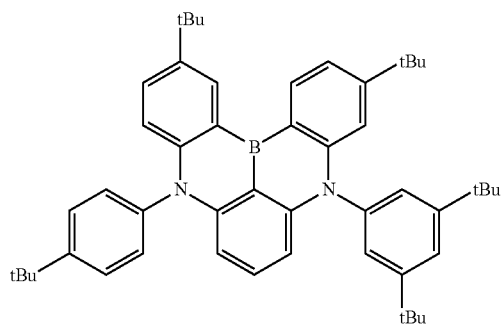
(3-38)
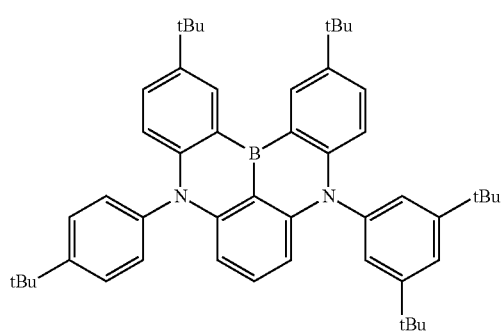
(3-39)
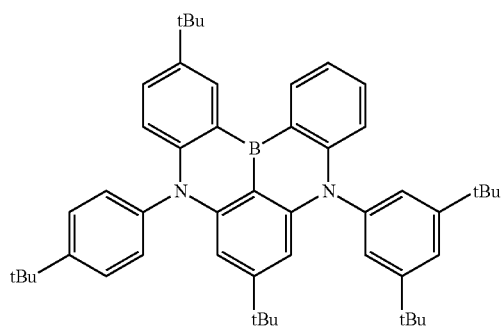
(3-40)
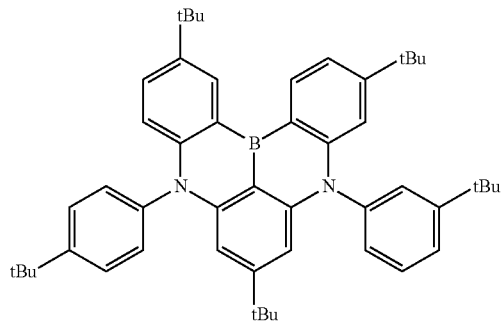
(3-41)
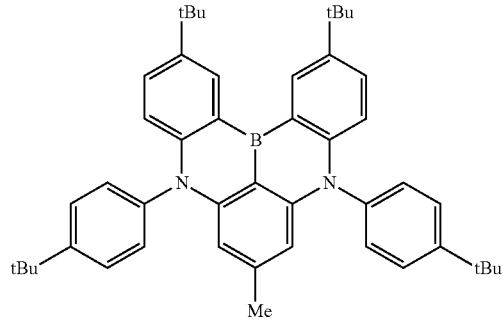
(3-42)
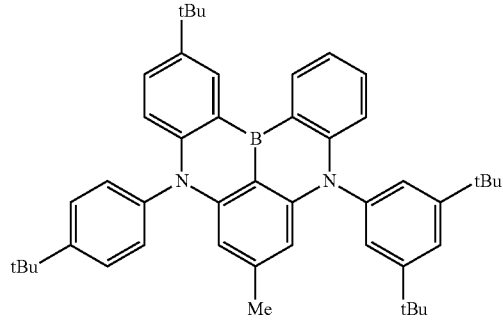
(3-43)
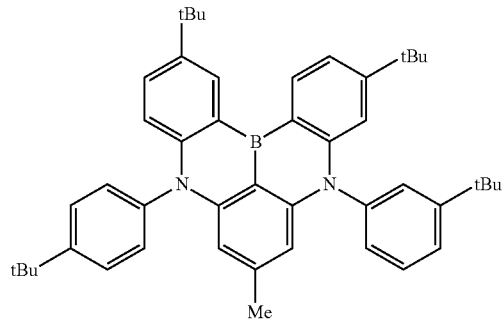
(3-44)
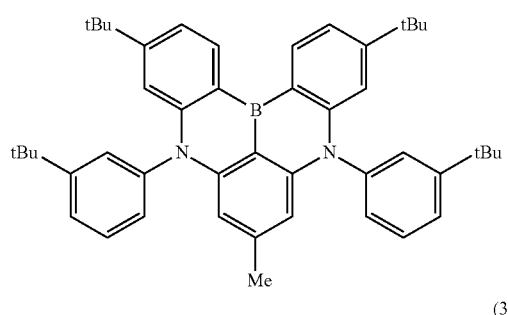
(3-45)
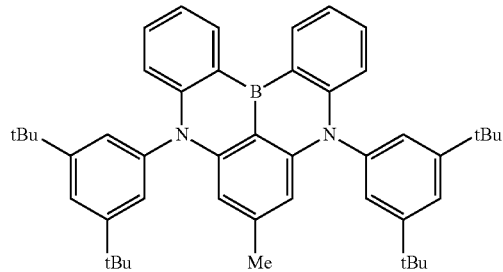

157
-continued
(3-46)
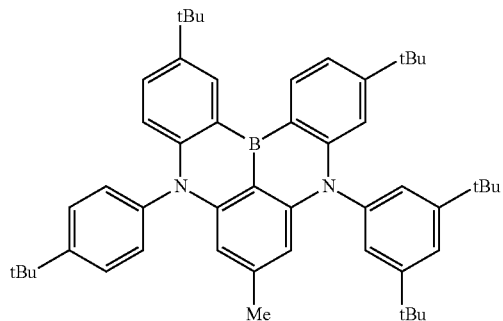
(3-47)
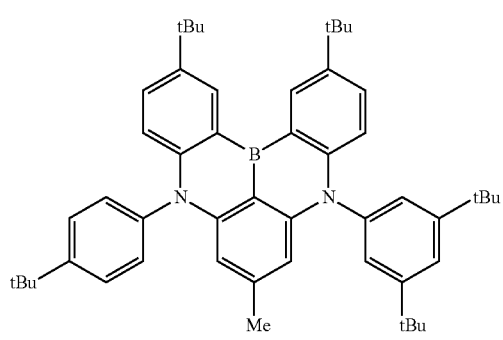
(3-48)
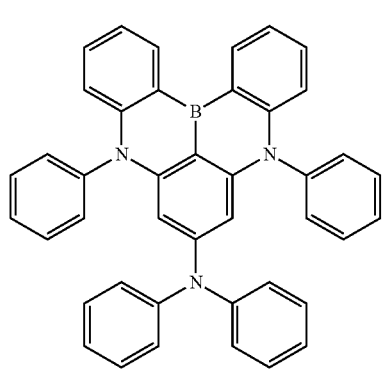
(3-49)
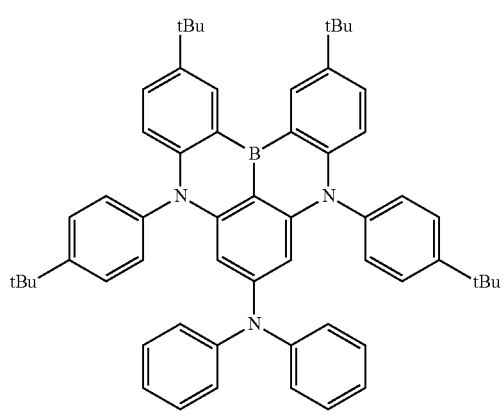
158
-continued
(3-50)
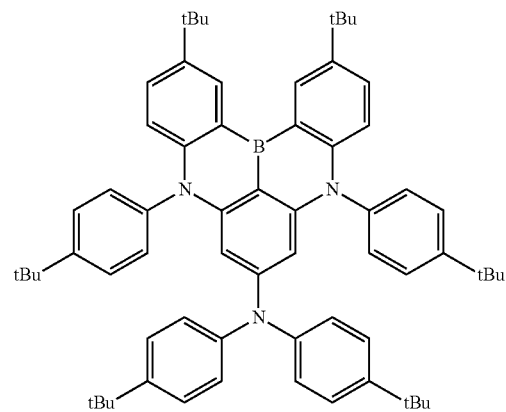
(3-51)
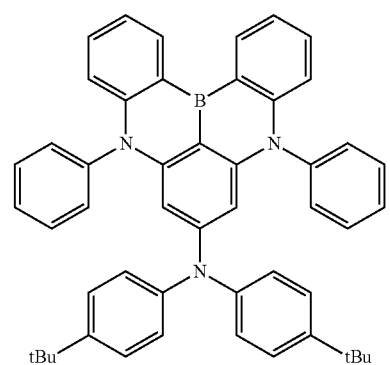
(3-52)
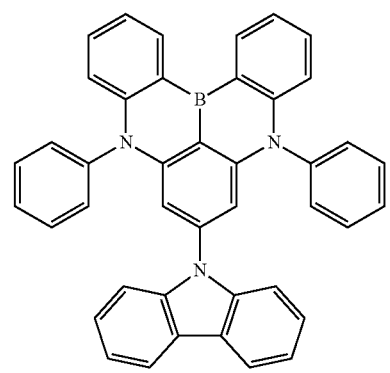
(3-53)
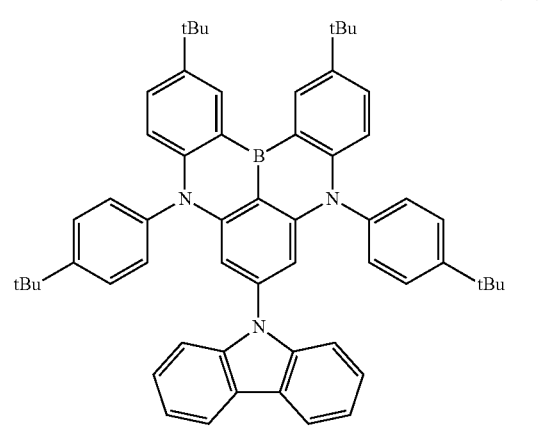

(3-54)
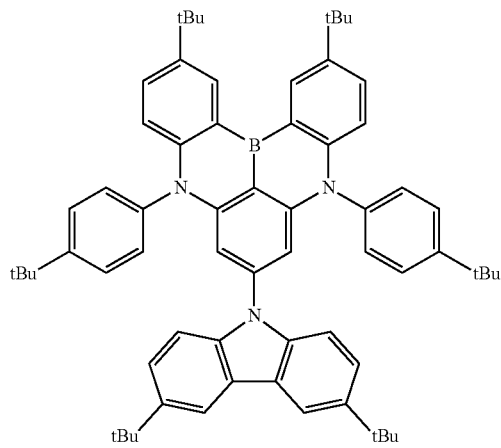
(3-55)
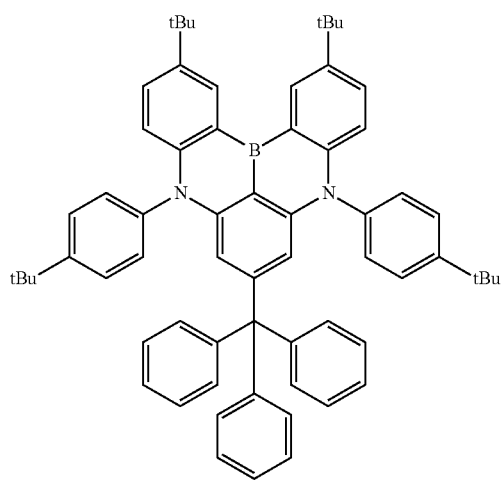
(3-56)
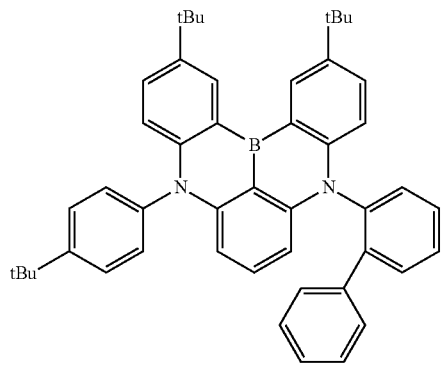
(3-57)
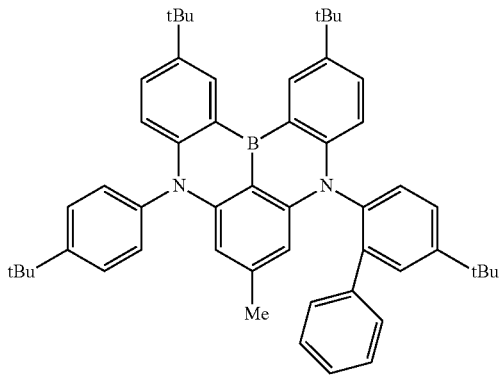
(3-58)
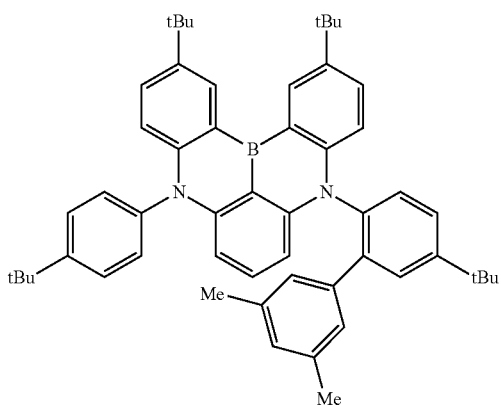
(3-59)
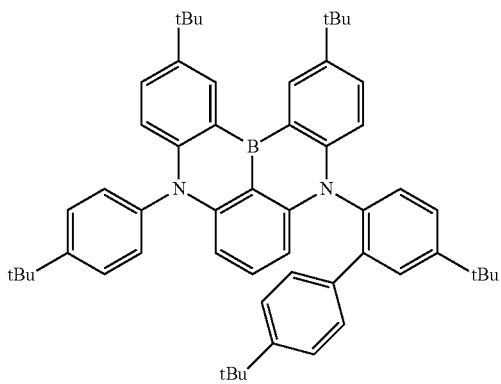
(3-60)
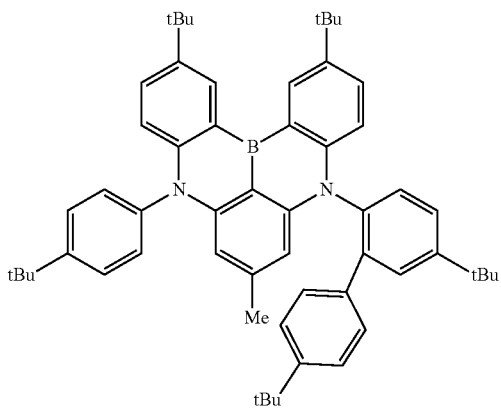

(3-61)
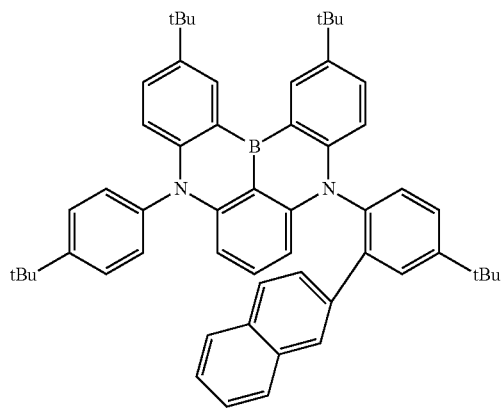
(3-62)
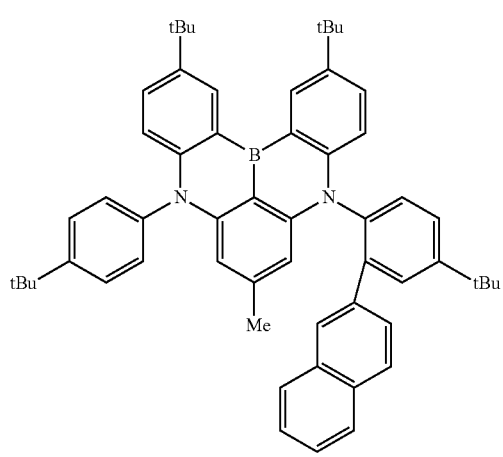
(3-63)
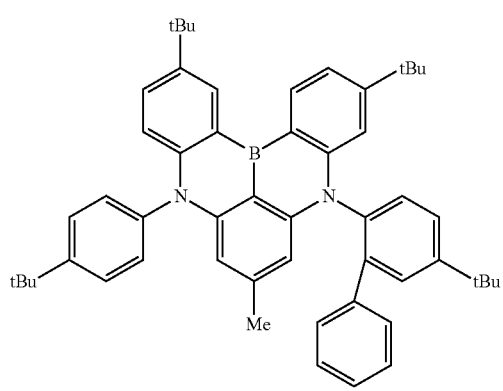
(3-64)
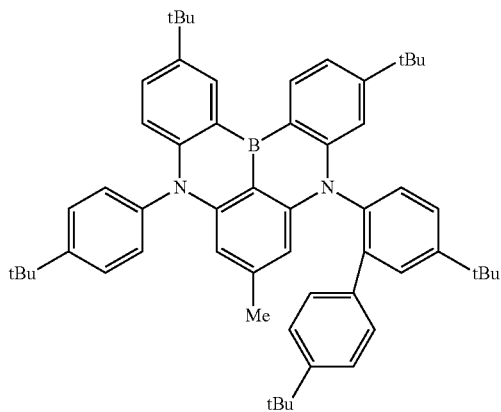
(3-65)
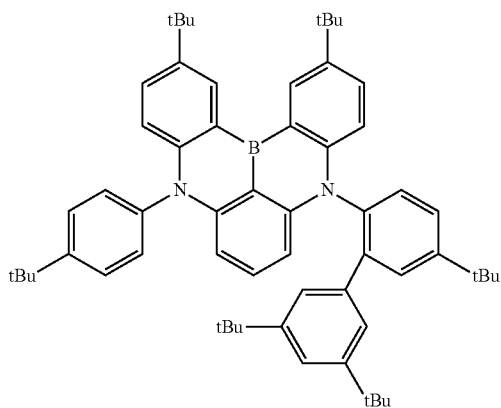
(3-66)
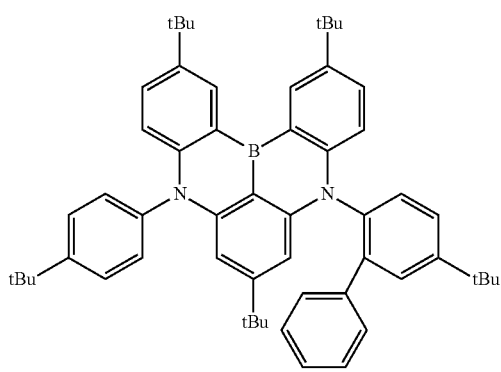
(3-67)
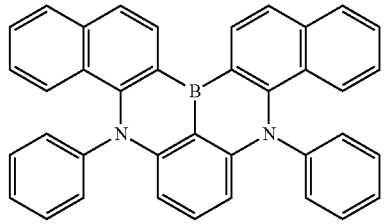

(3-68)
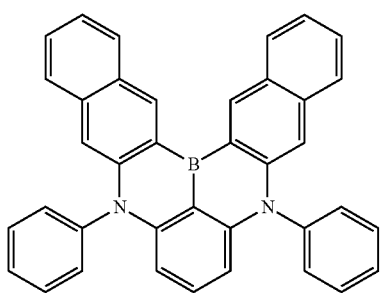
(3-69)
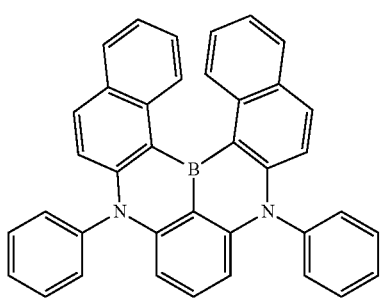
(3-70)
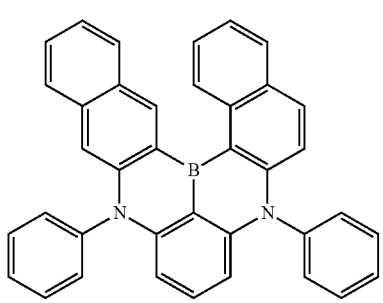
(3-71)
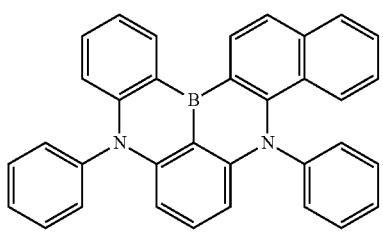
(3-72)
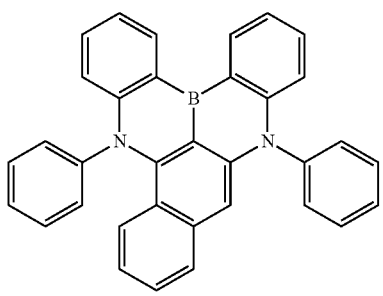
(3-73)
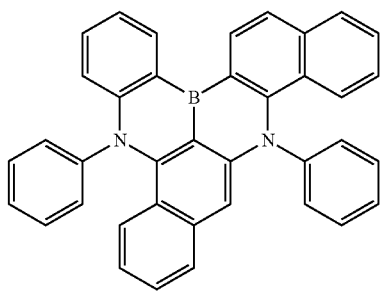
(3-74)
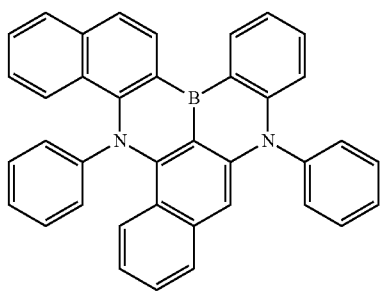
(3-75)
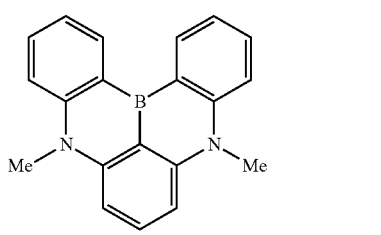
(3-76)
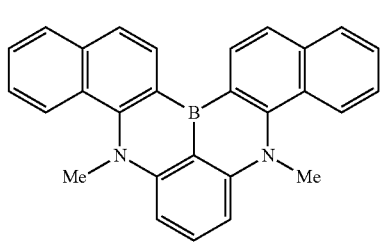
(3-77)
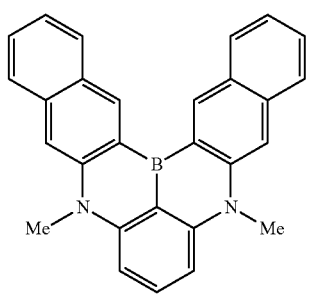

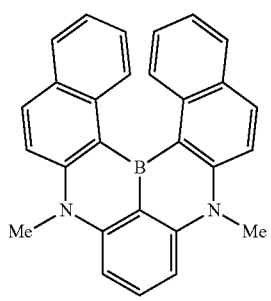
(3-78)
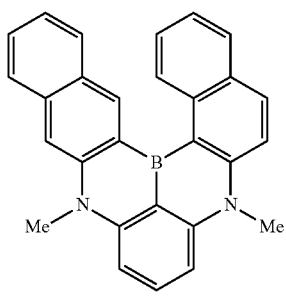
(3-79)
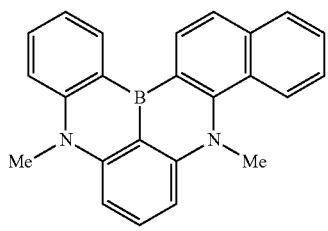
(3-80)
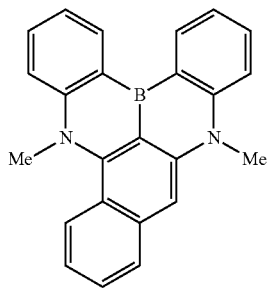
(3-81)
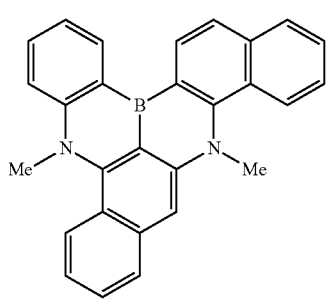
(3-82)
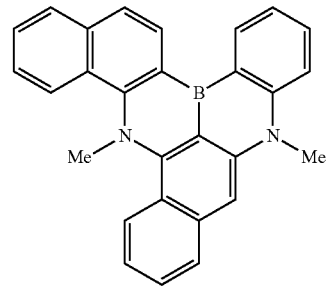
(3-83)
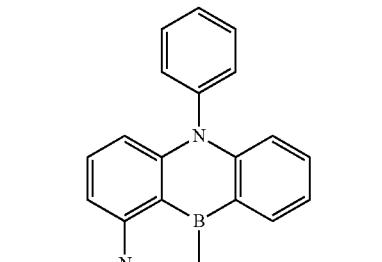
(3-84)
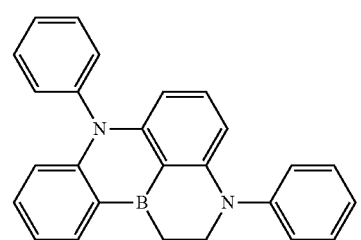
(3-85)
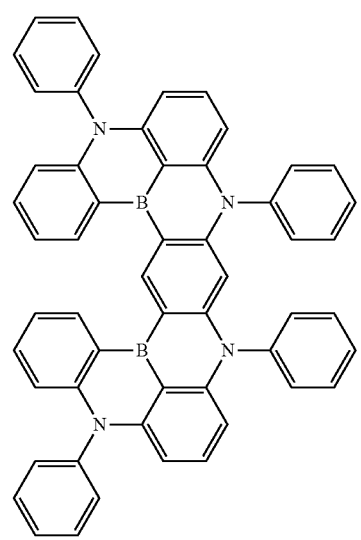

(3-86)
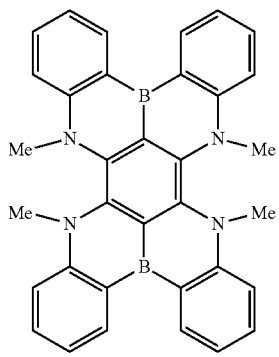
(3-87)
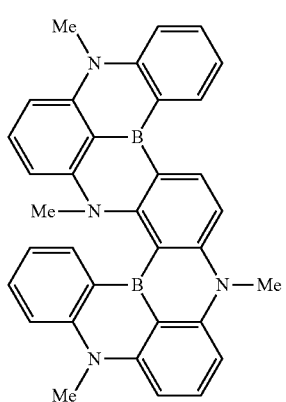
(3-88)
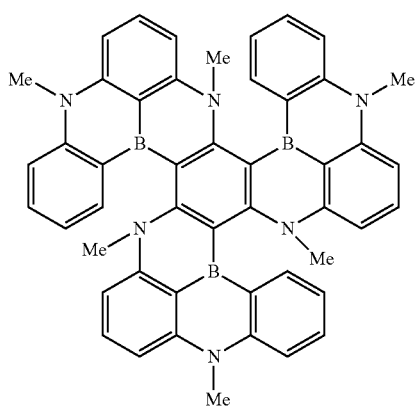
(3-89)
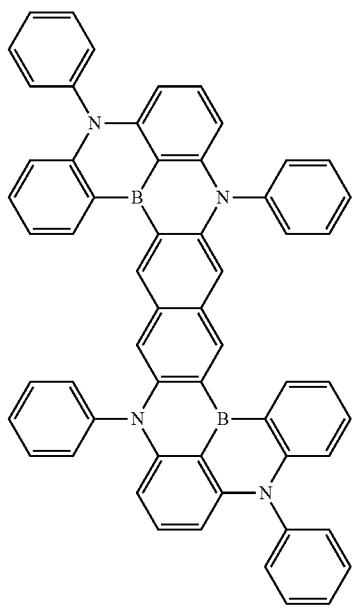
(3-90)
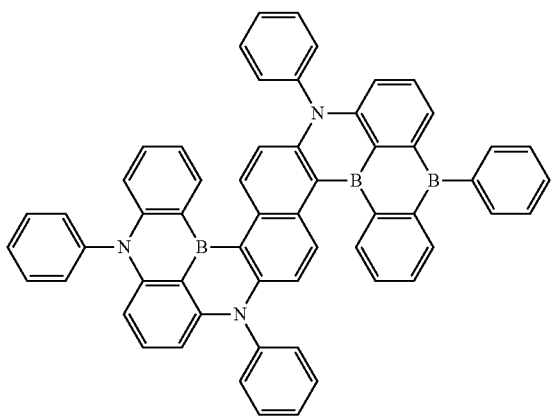
(3-91)
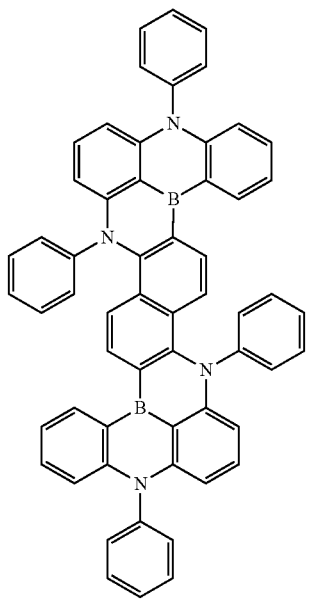

-continued
(3-92)
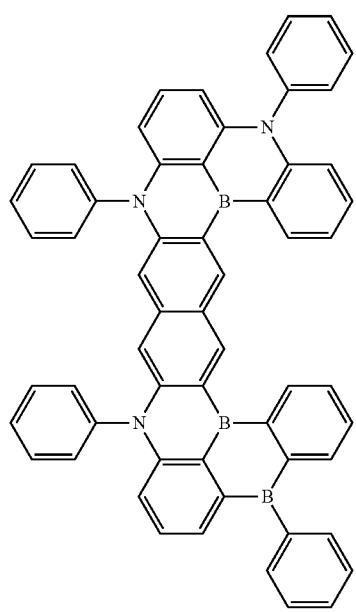
(3-93)
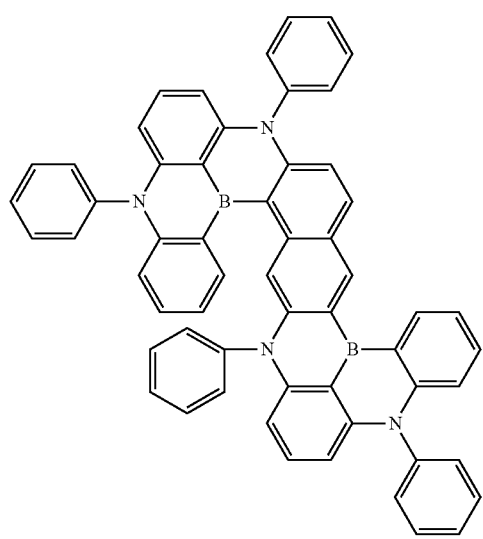
(3-94)
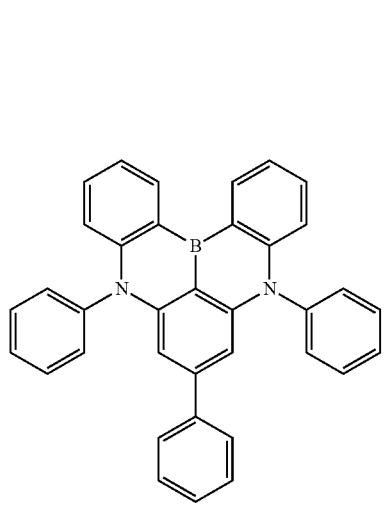
-continued
(3-95)
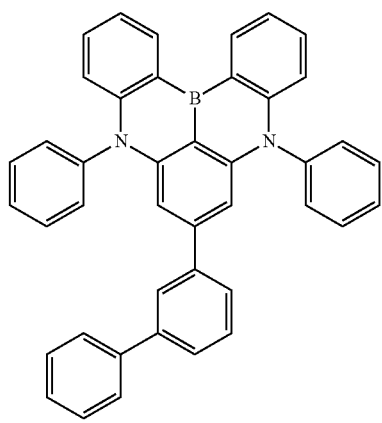
(3-96)
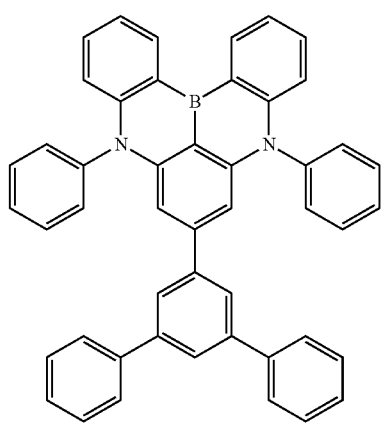
(3-97)
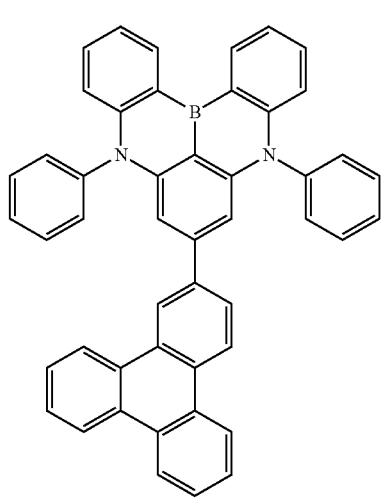

(3-98)
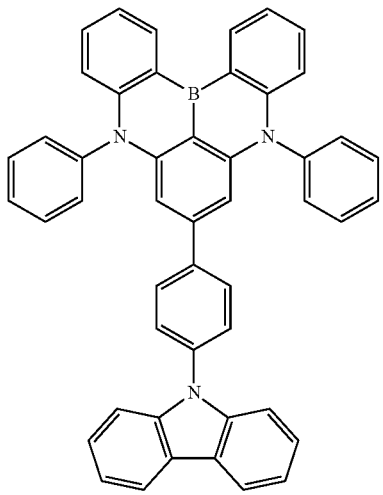
(3-99)
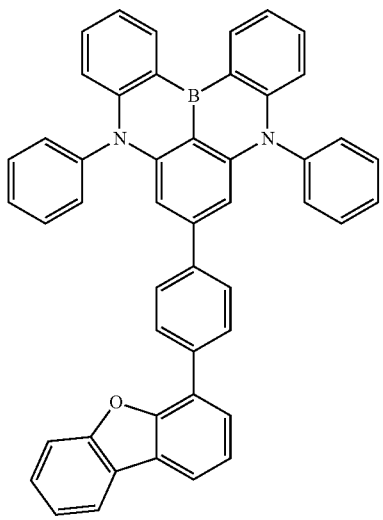
(3-100)
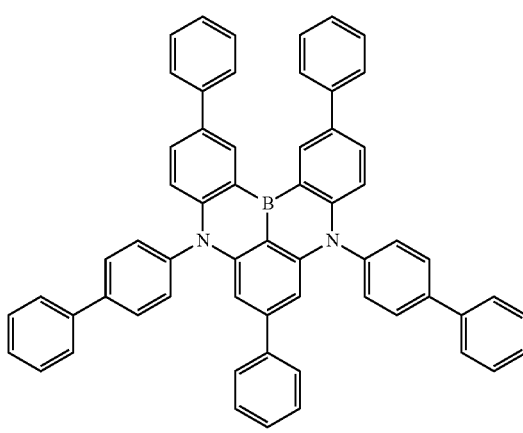
(3-101)
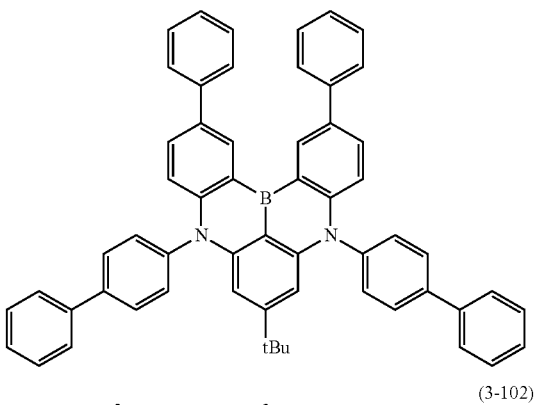
(3-102)
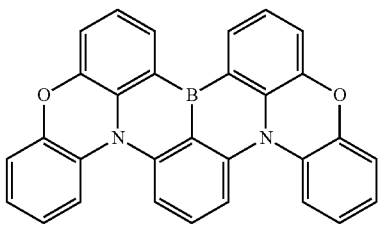
(3-103)
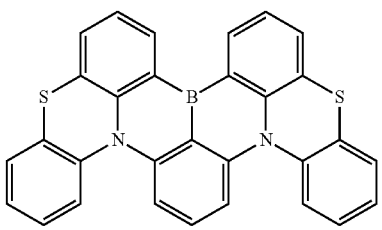
(3-104)
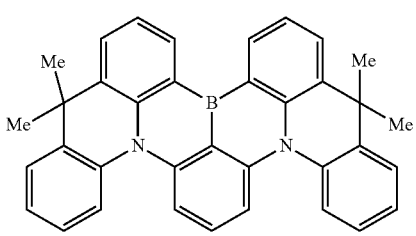
(3-105)
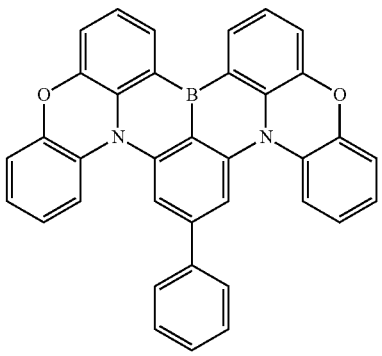

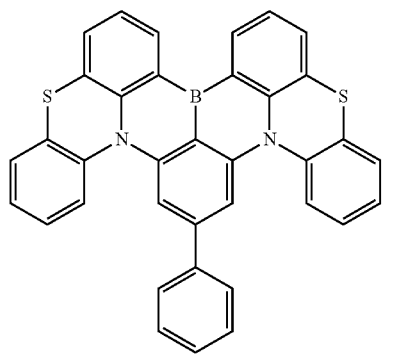
(3-106)
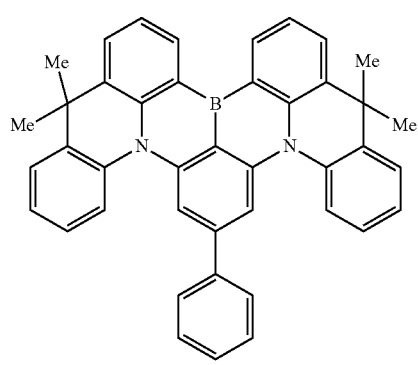
(3-107)
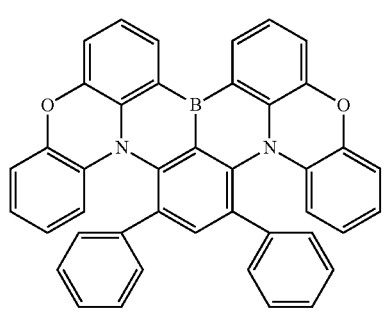
(3-108)
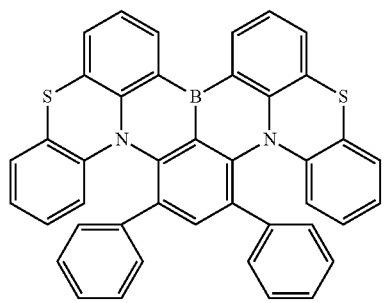
(3-109)
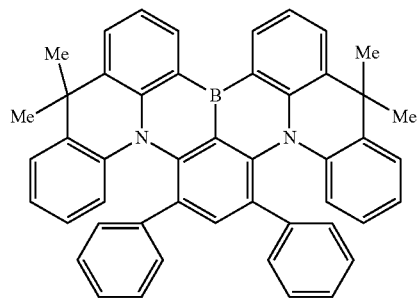
(3-110)
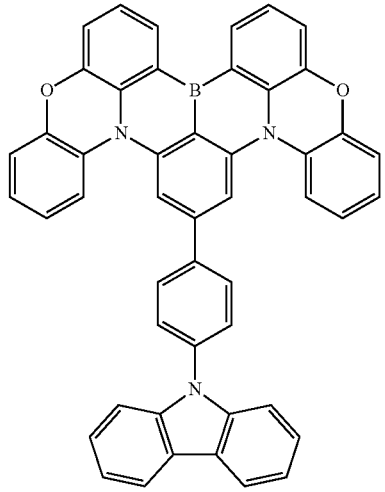
(3-111)
(3-112)
(3-113)

(3-114)
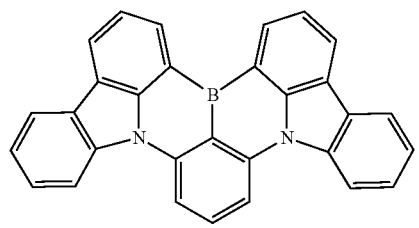
(3-115)
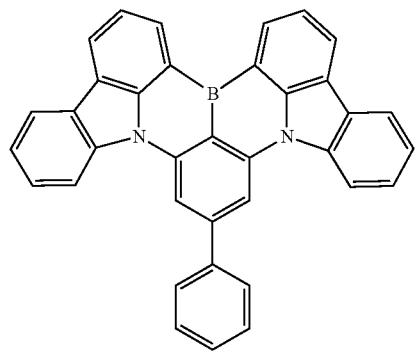
(3-116)
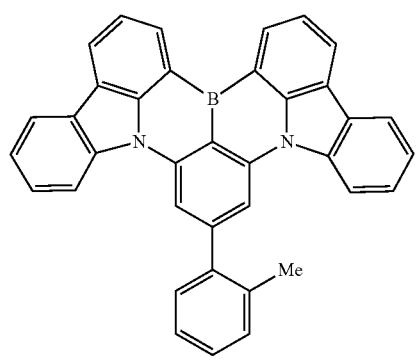
(3-117)
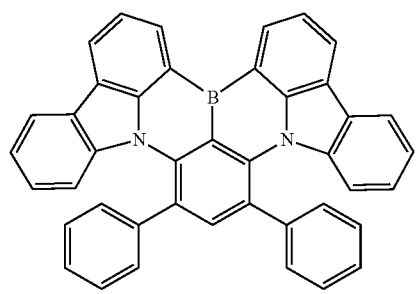
(3-118)
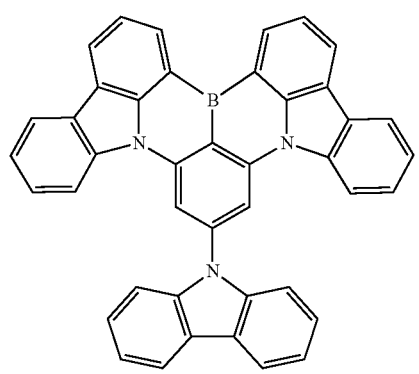
(3-119)
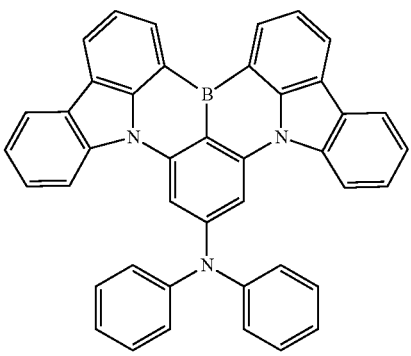
(3-120)
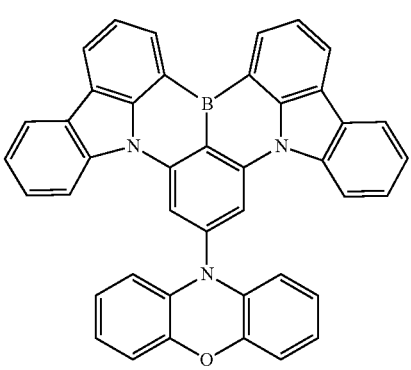
(3-121)
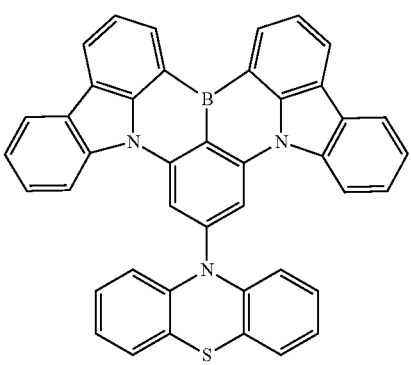
(3-122)
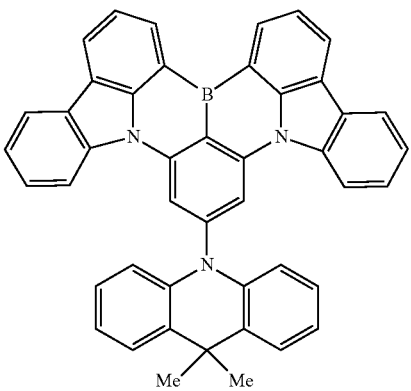

(3-123)
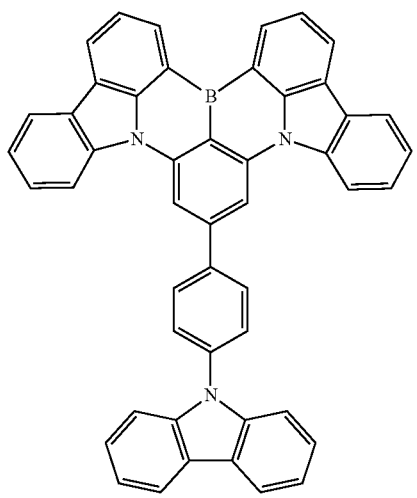
(3-124)
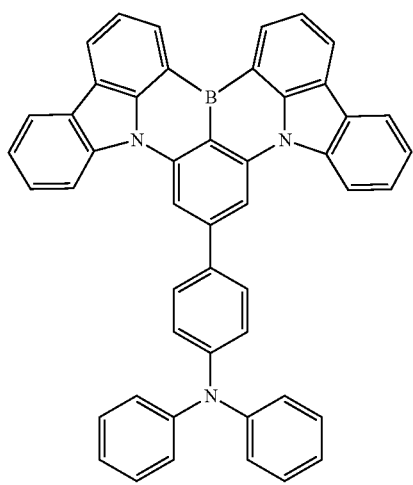
(3-125)
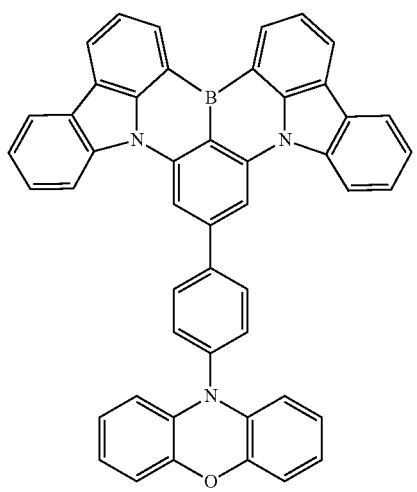
(3-126)
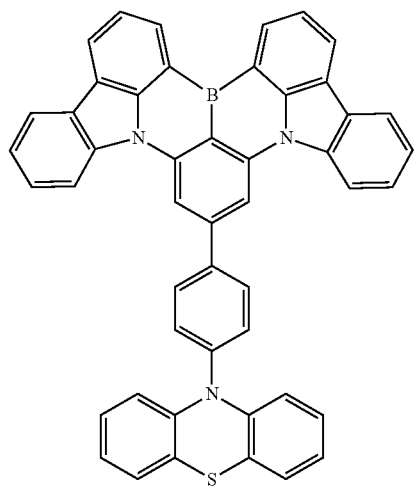
(3-127)
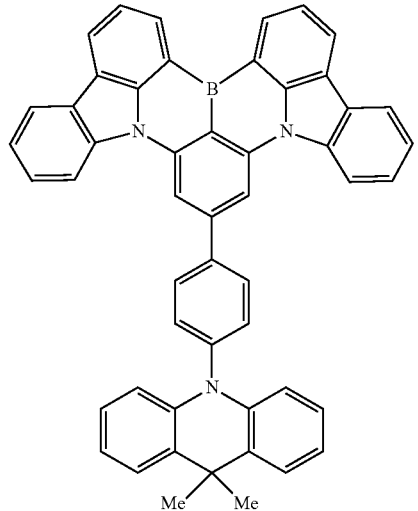
(3-128)
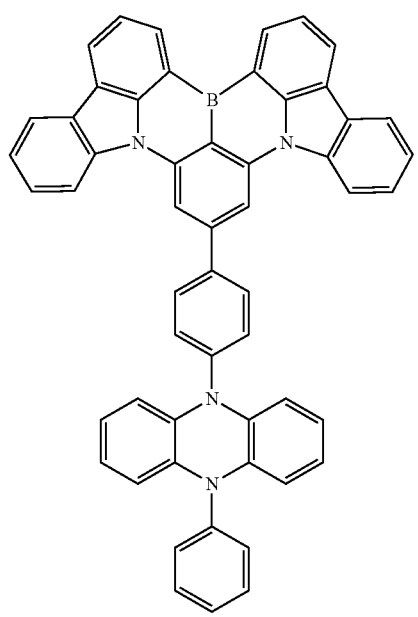

-continued
(3-129)
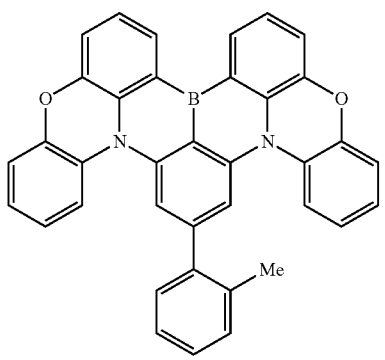
(3-130)
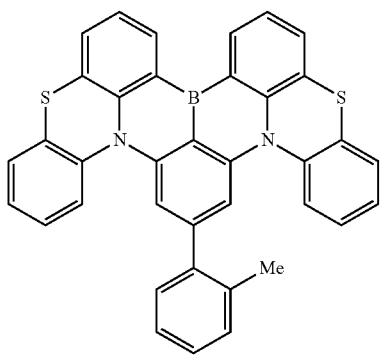
(3-131)
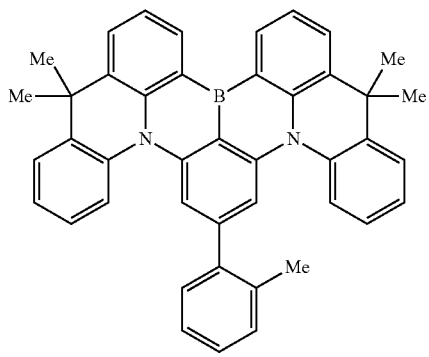
(3-132)
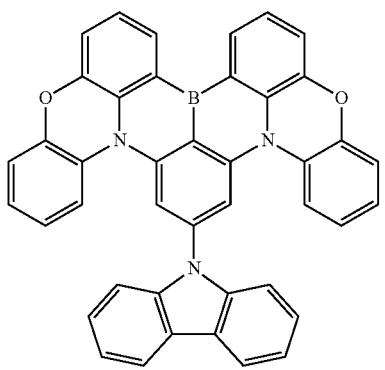
-continued
(3-133)
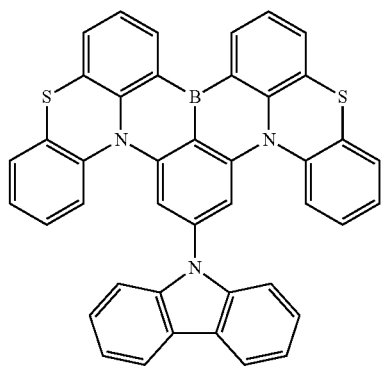
(3-134)
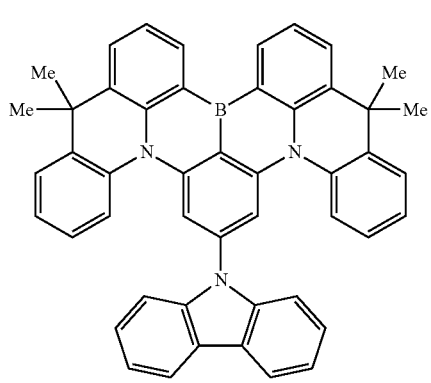
(3-135)
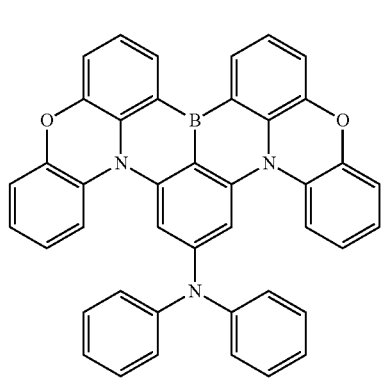
(3-136)
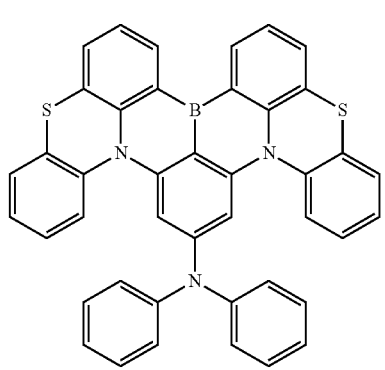

(3-137)
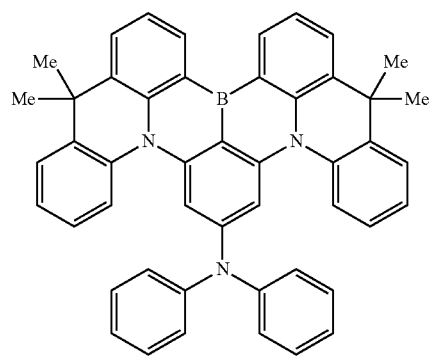
(3-138)
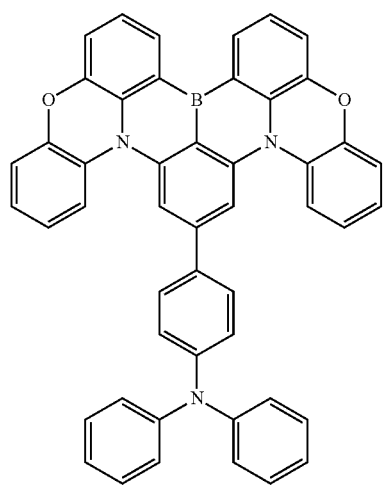
(3-139)
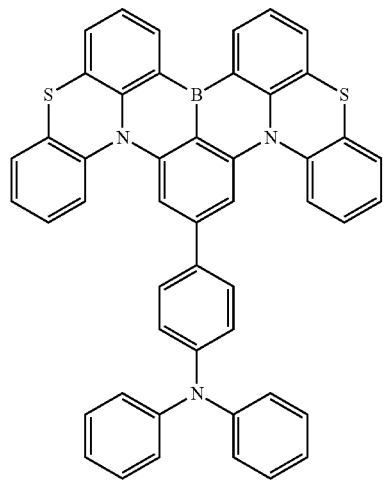
(3-140)
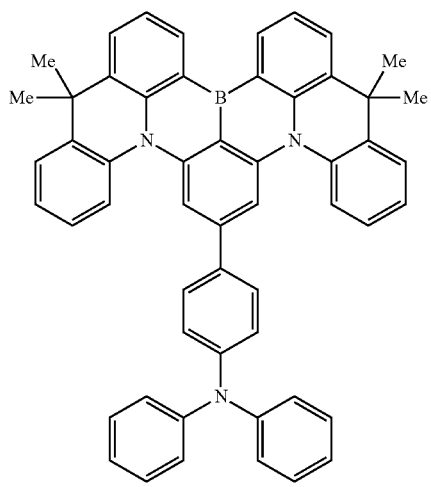
(3-141)
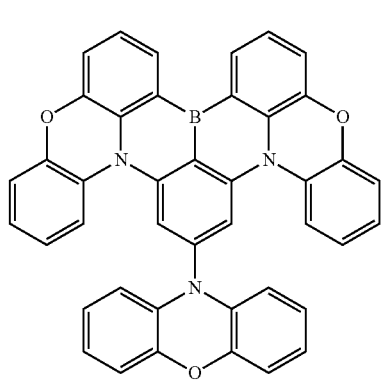
(3-142)
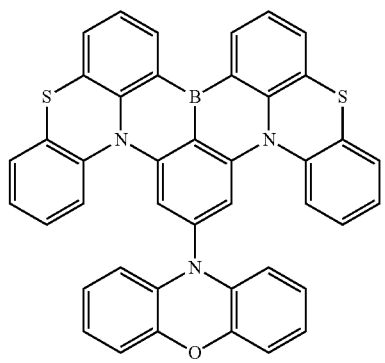
(3-143)
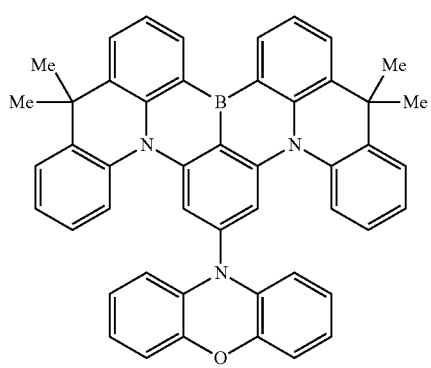

(3-144)
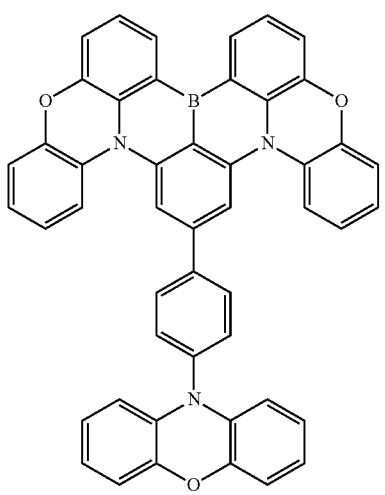
(3-145)
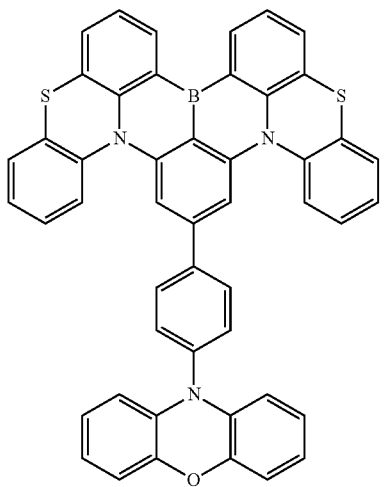
(3-146)
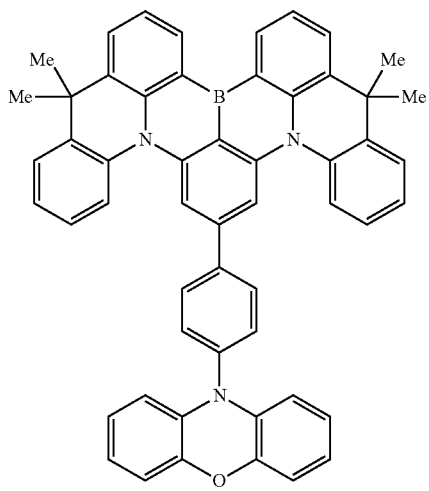
(3-147)
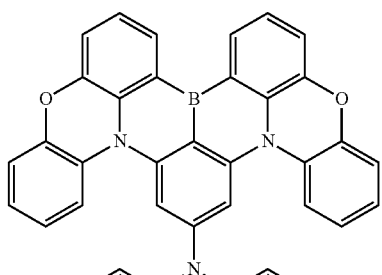
(3-148)
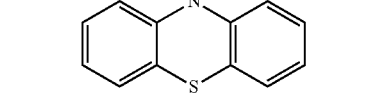
(3-149)
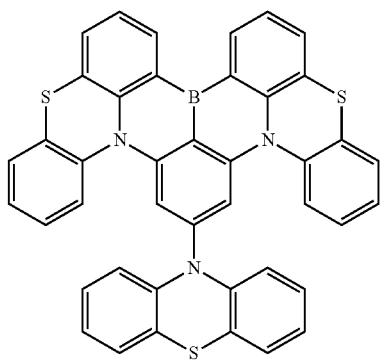
(3-150)
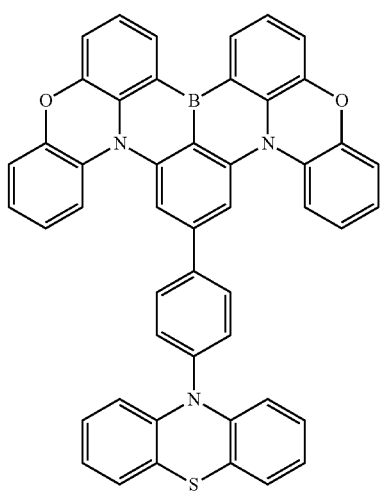

(3-151)
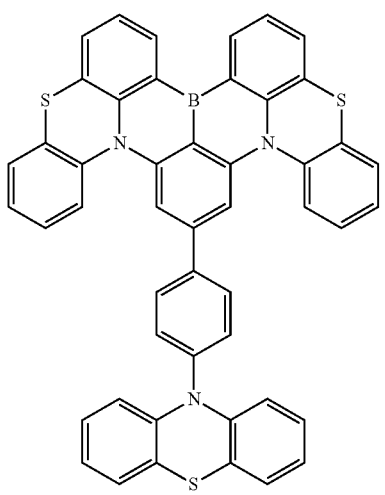
(3-152)
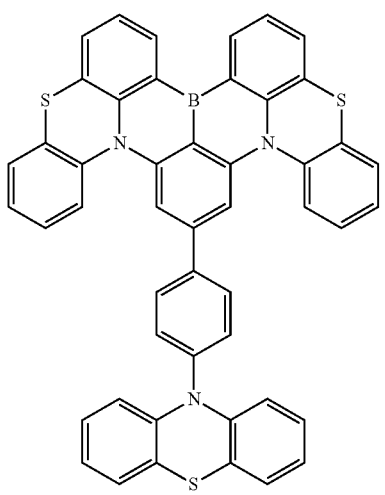
(3-153)
(3-154)
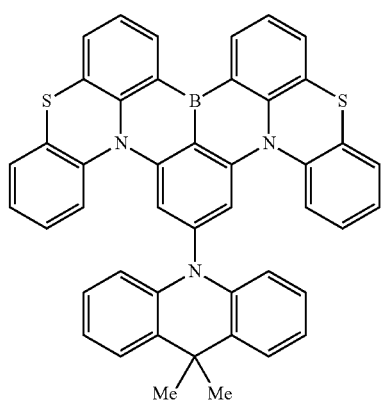
(3-155)
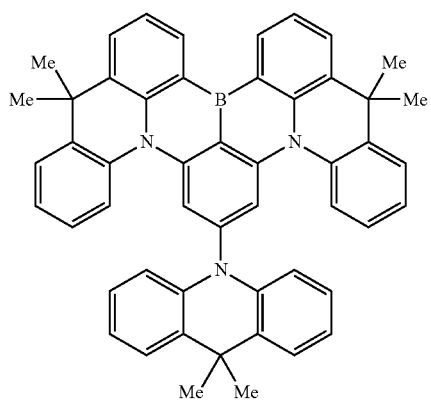
(3-156)
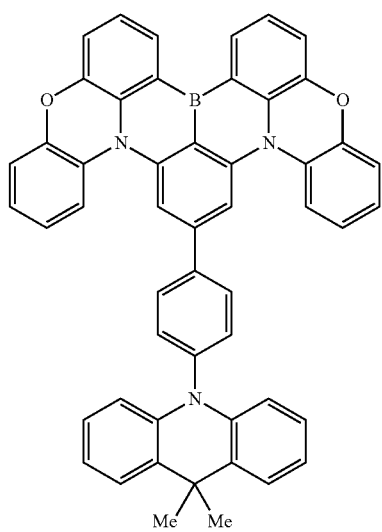
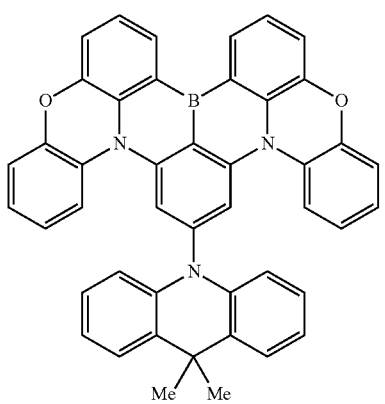

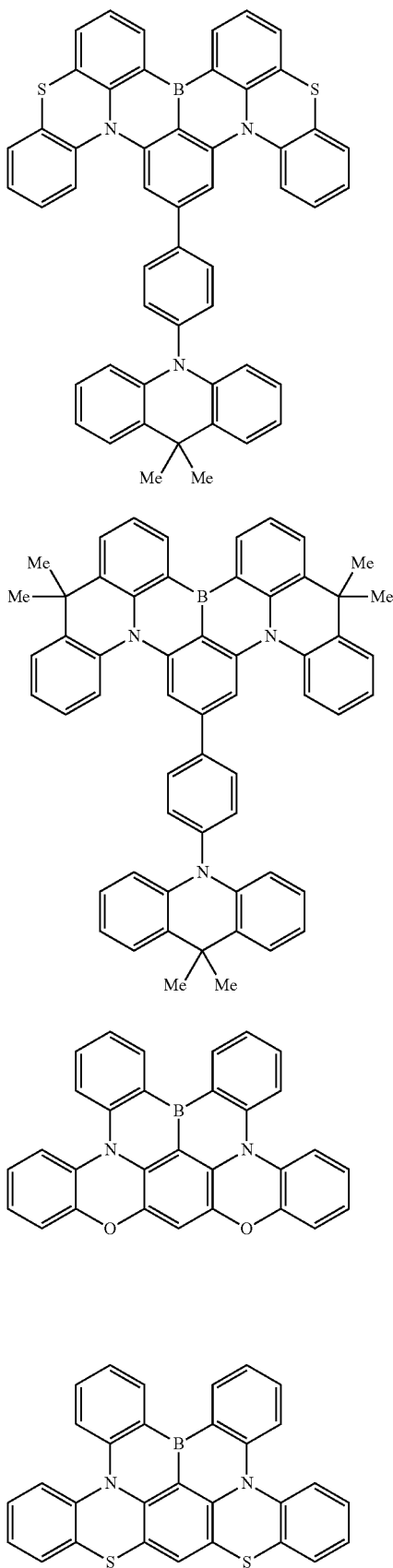
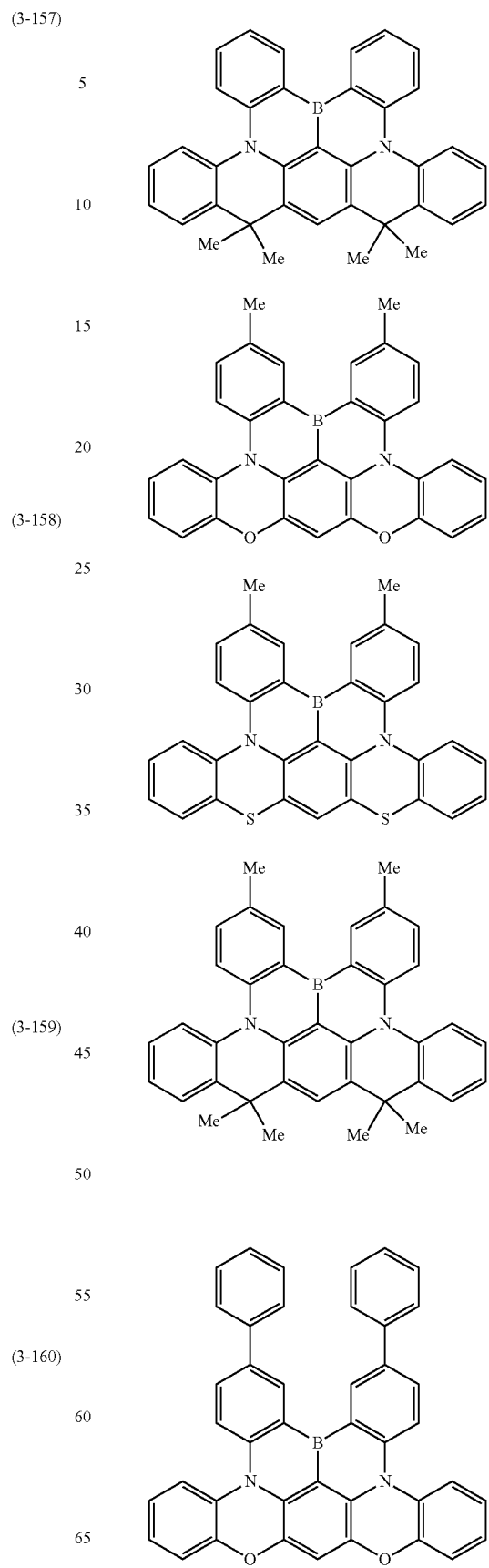

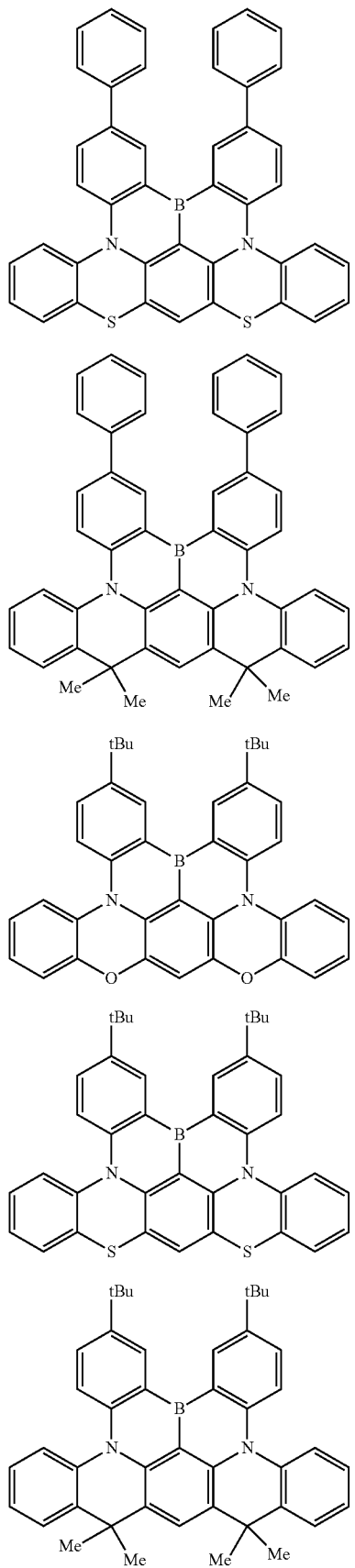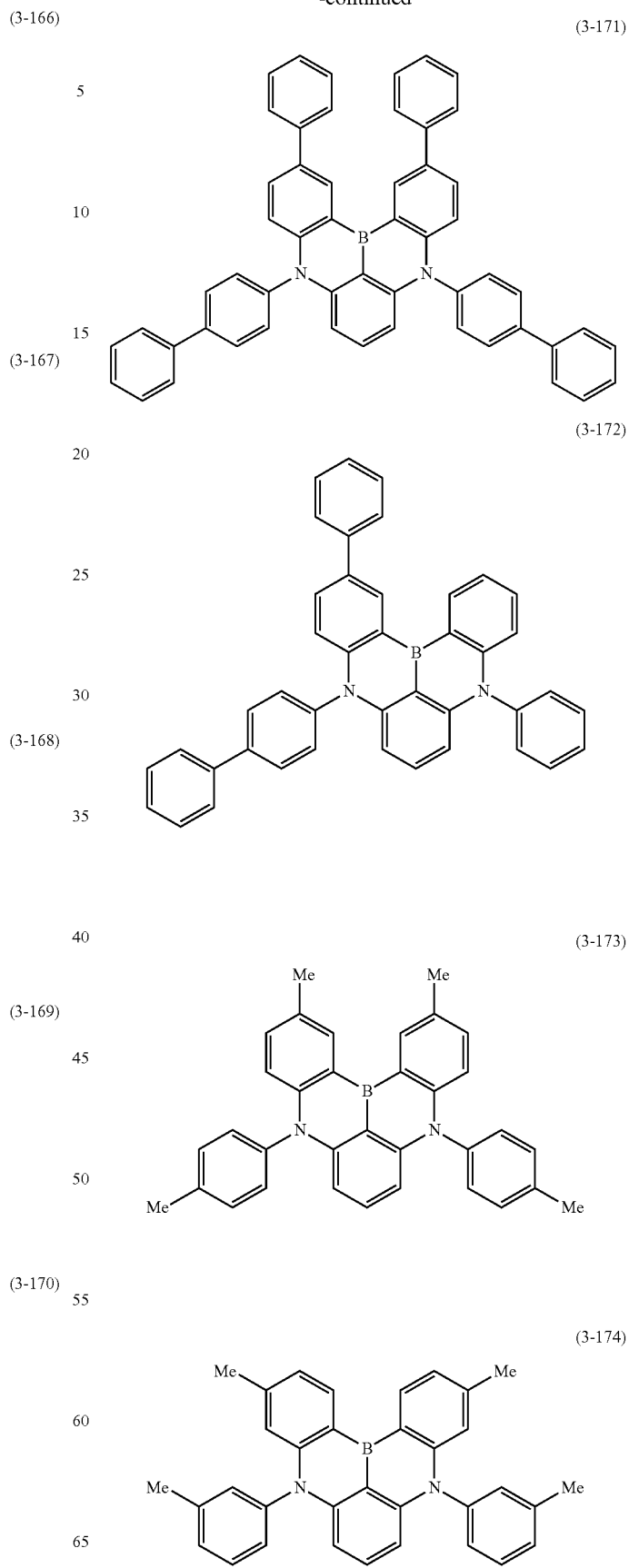

(3-175)
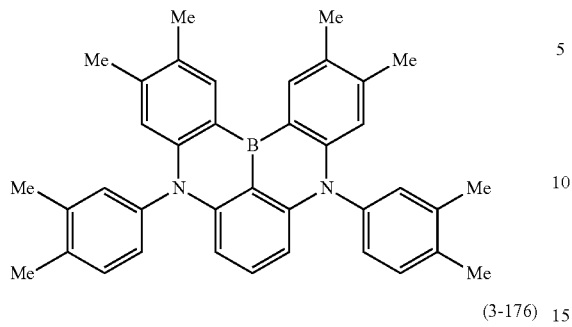
(3-176)
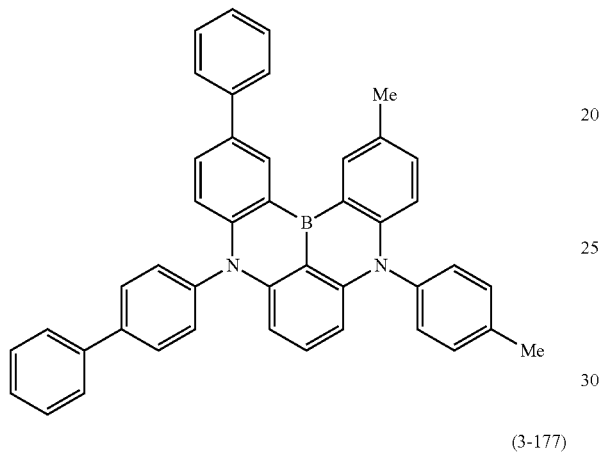
(3-177)
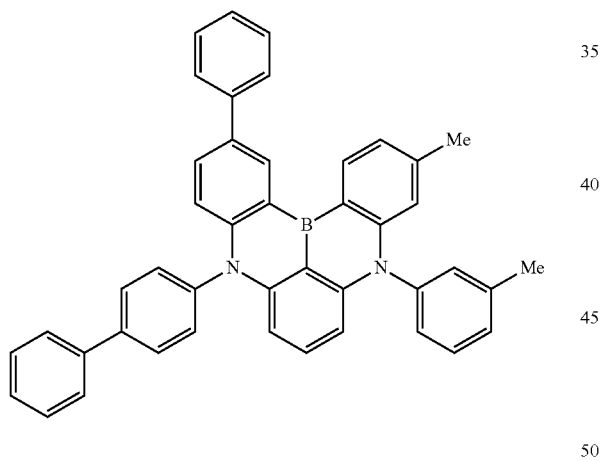
(3-178)
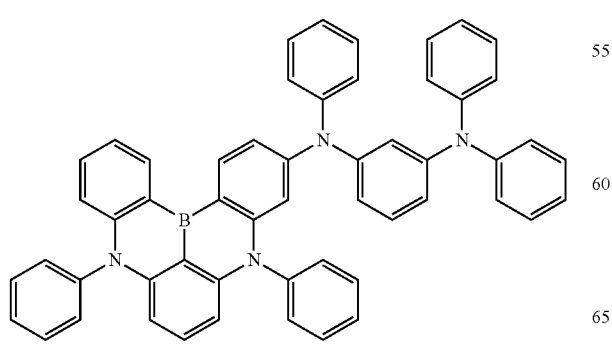
(3-179)
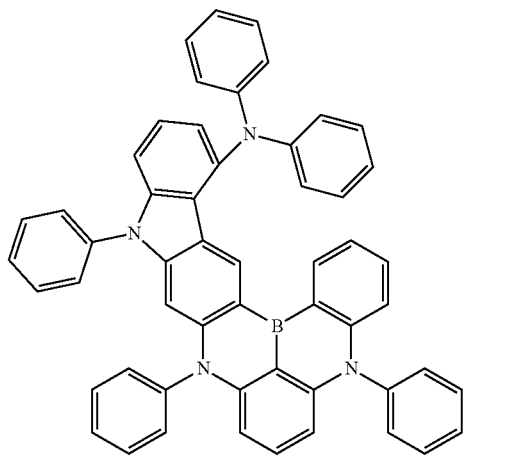
(3-180)
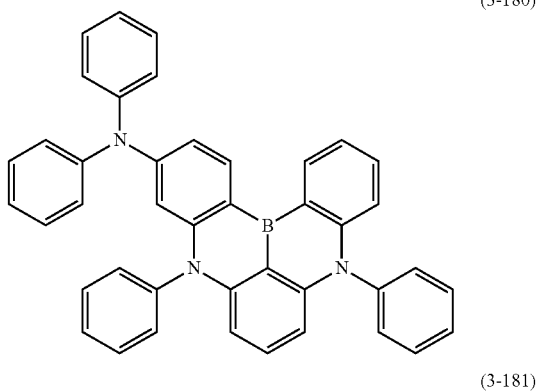
(3-181)
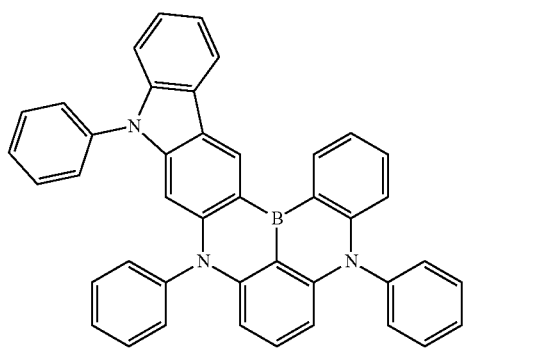
(3-182)
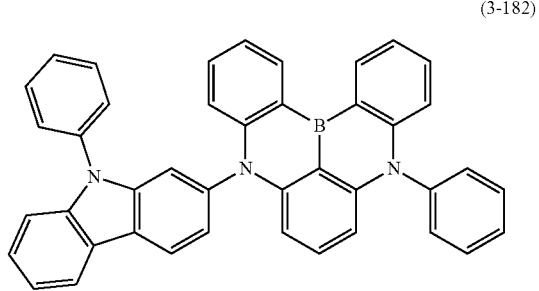

-continued
(3-183)
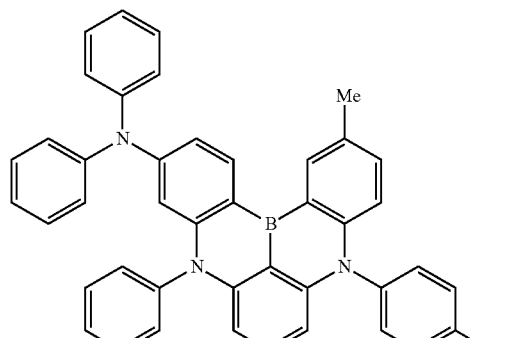
(3-184)
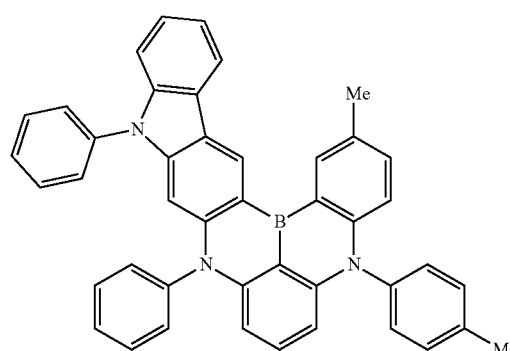
(3-185)
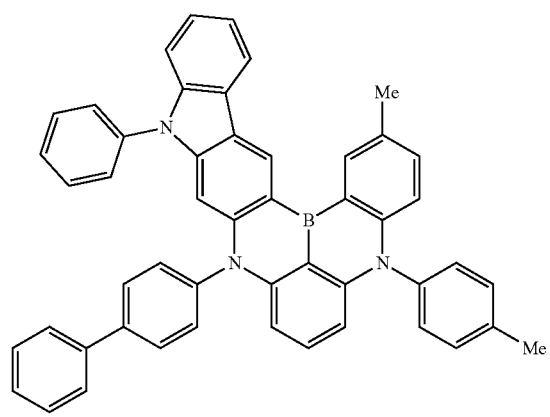
(3-186)
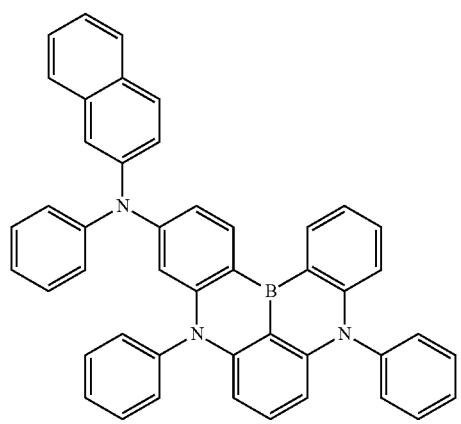
-continued
(3-187)
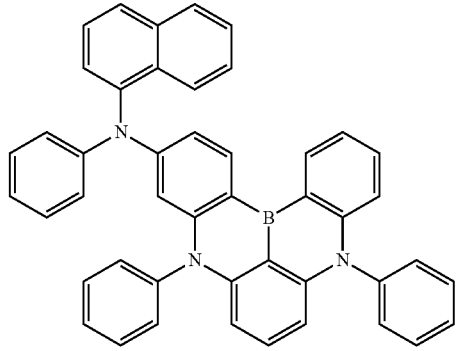
(3-188)
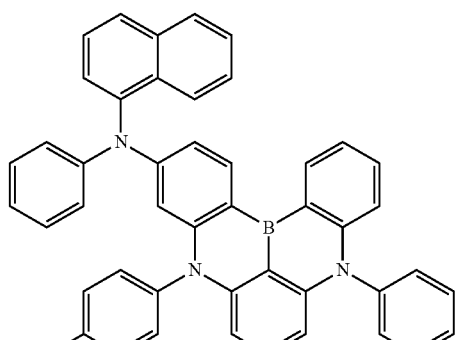
(3-189)
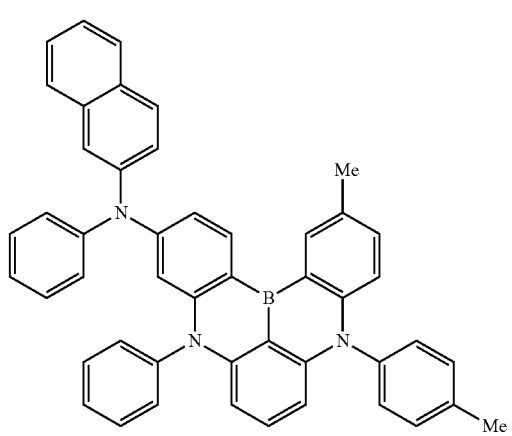
(3-190)
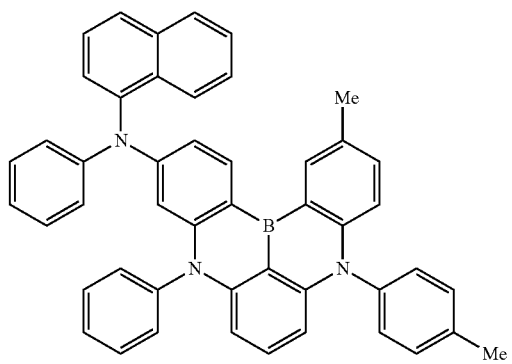

(3-191)
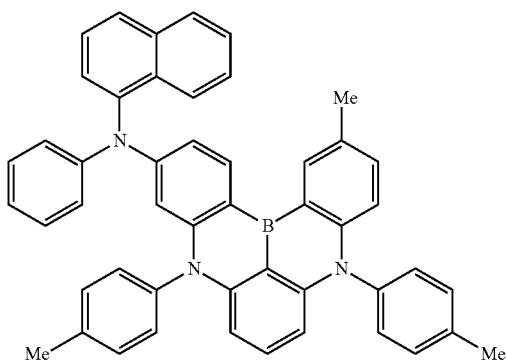
(3-192)
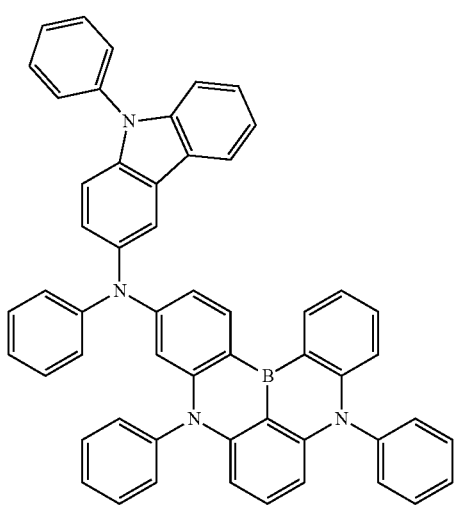
(3-193)
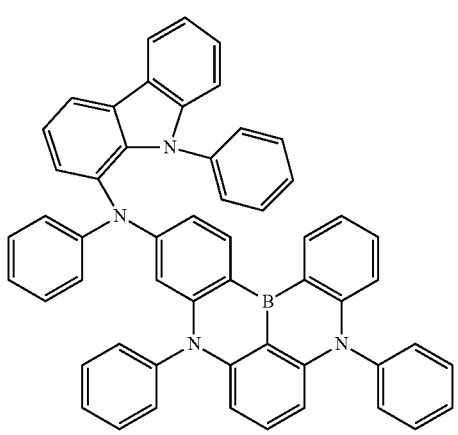
(3-194)
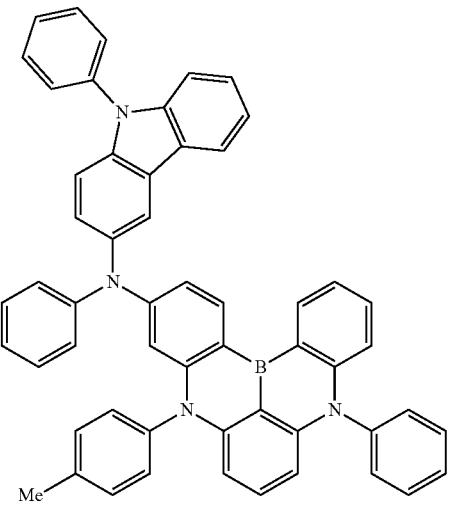
(3-195)
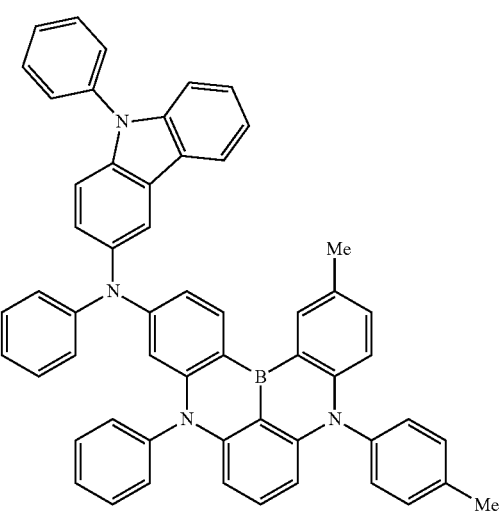
(3-196)
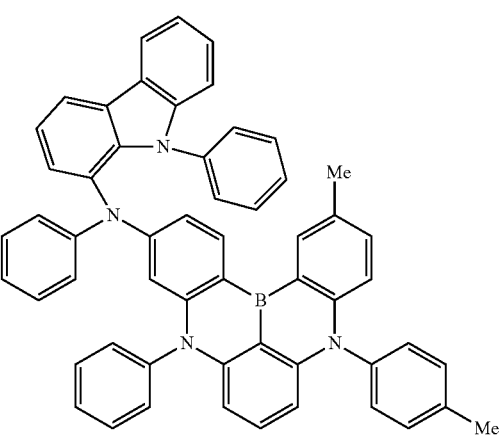

-continued
(3-197)
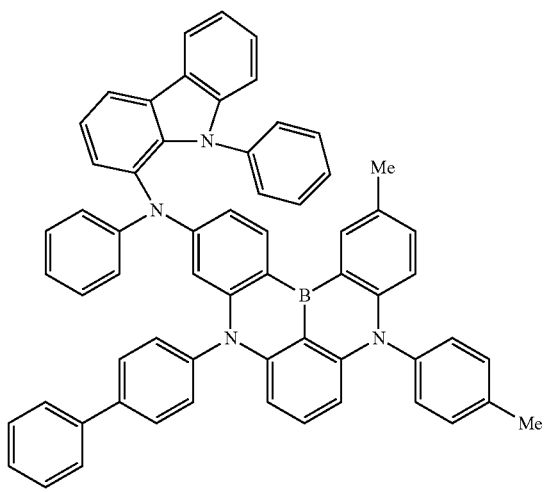
(3-198)
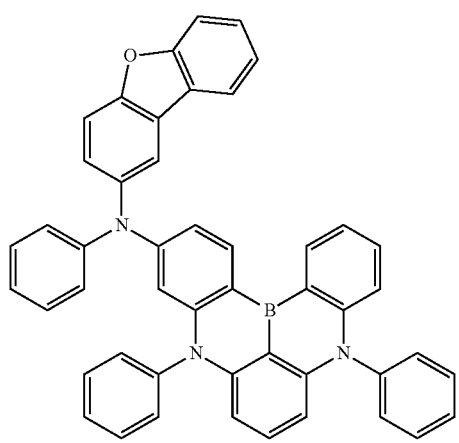
(3-199)
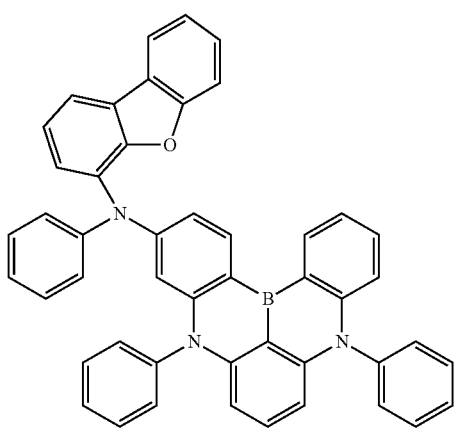
-continued
(3-200)
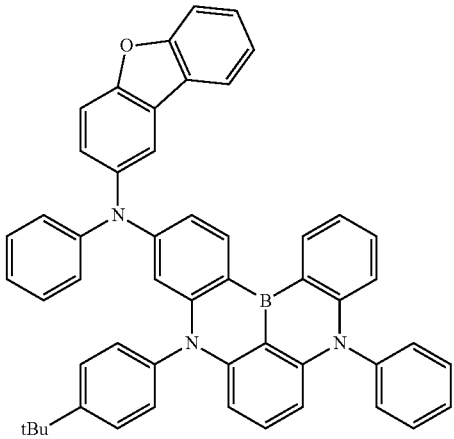
(3-201)
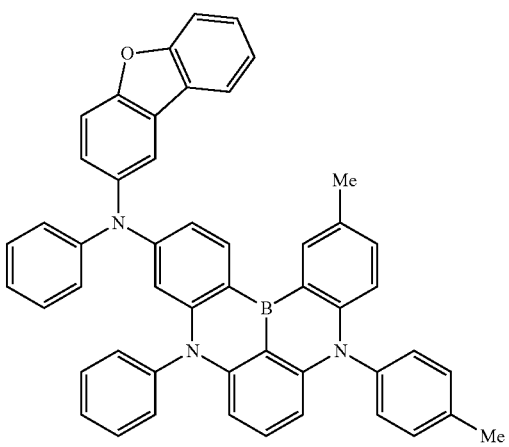
(3-202)
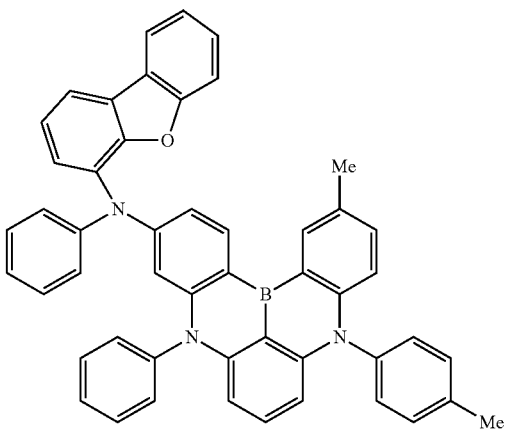

(3-203)
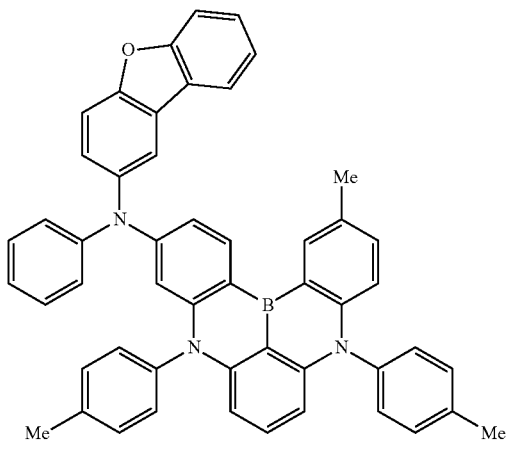
(3-204)
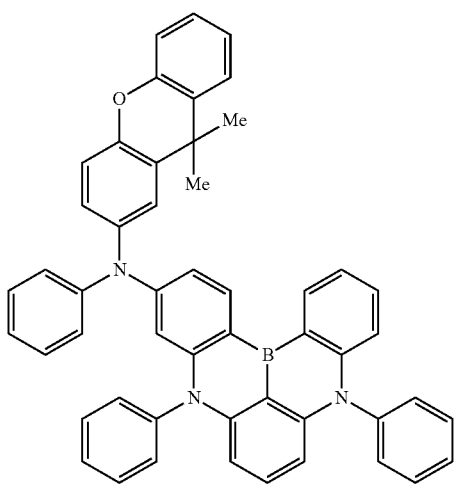
(3-205)
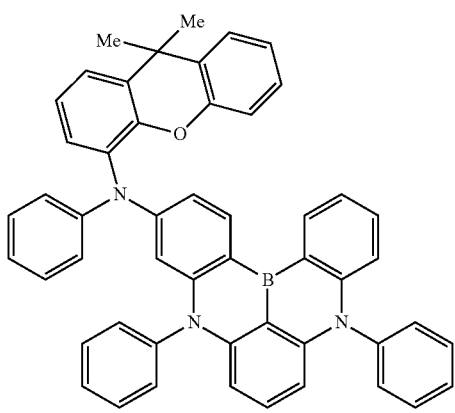
(3-206)
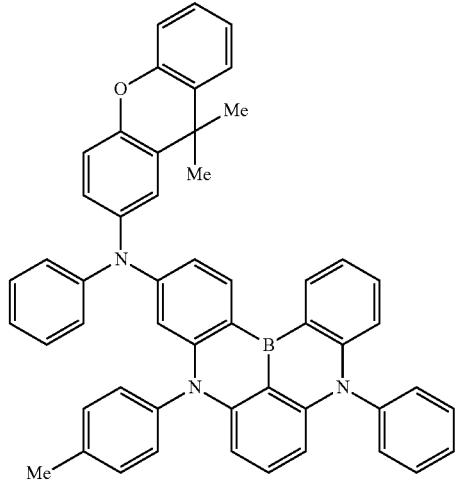
(3-207)
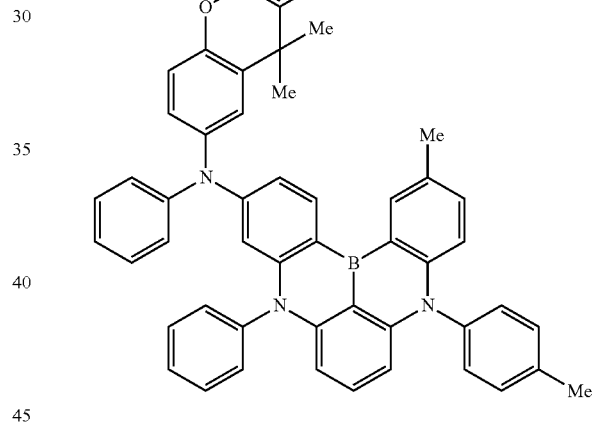
(3-208)
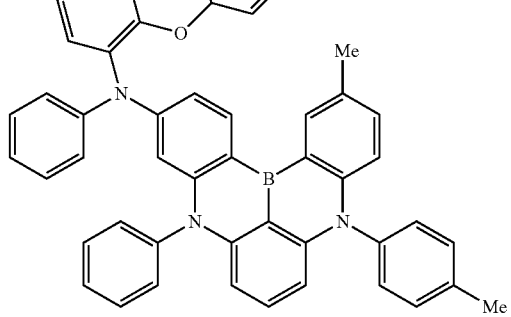

(3-209)
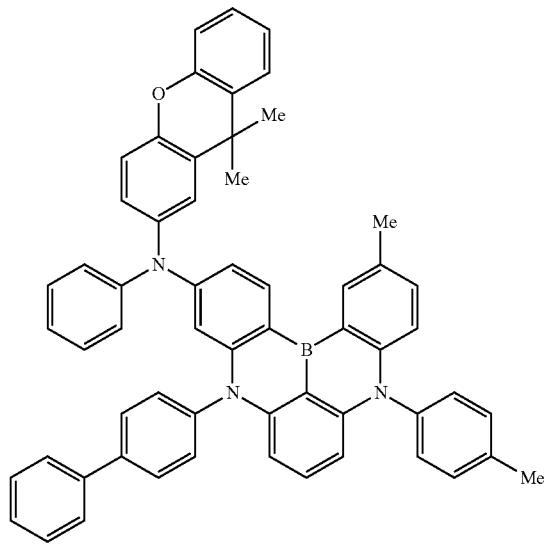
(3-210)
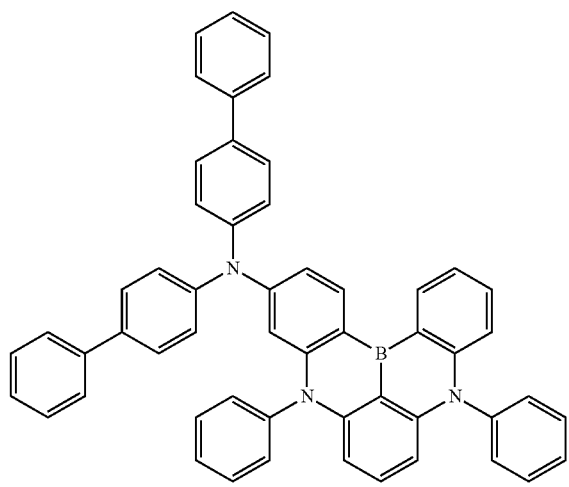
(3-211)
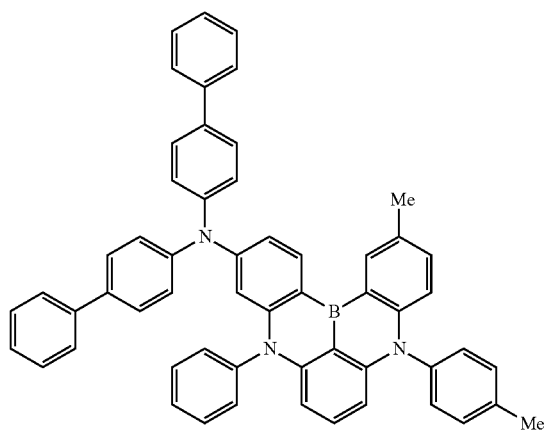
(3-212)
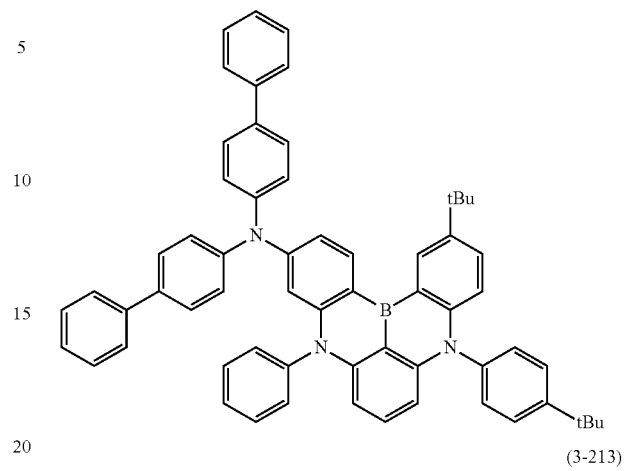
(3-213)
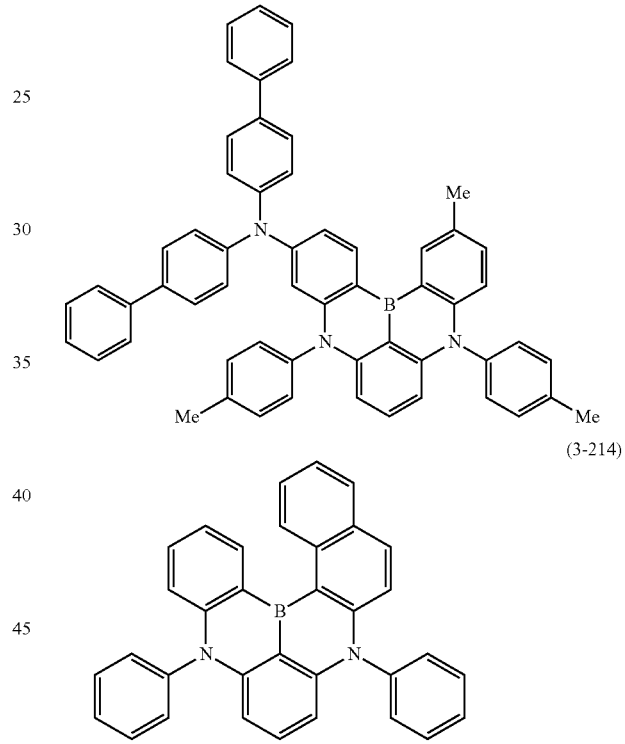
(3-214)
(3-215)
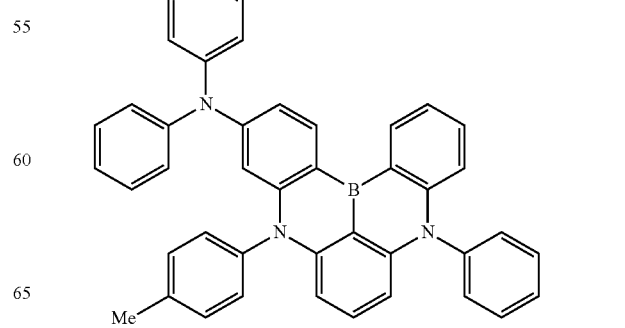

(3-216)
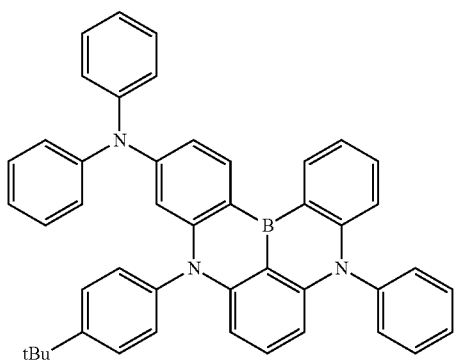
(3-219)
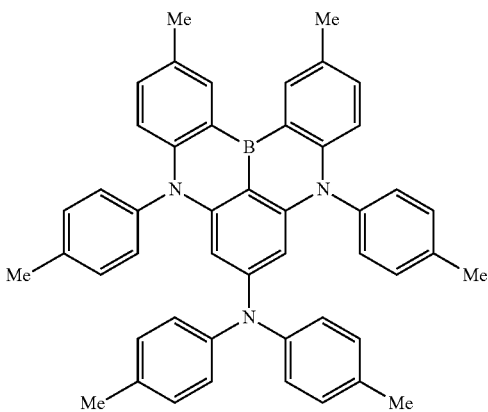
(3-217)
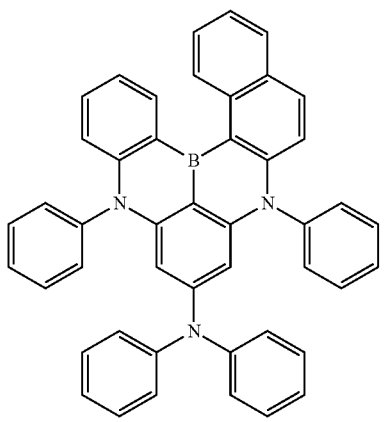
(3-220)
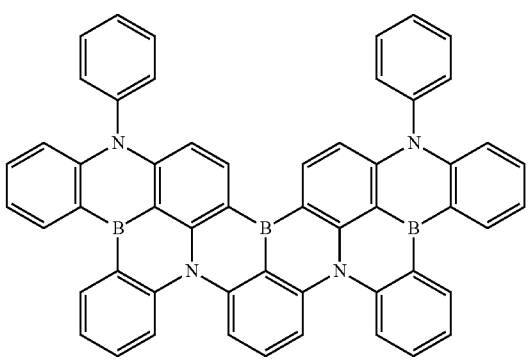
(3-221)
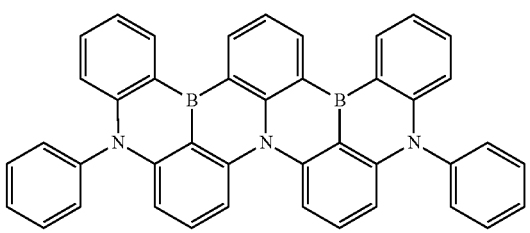
(3-218)
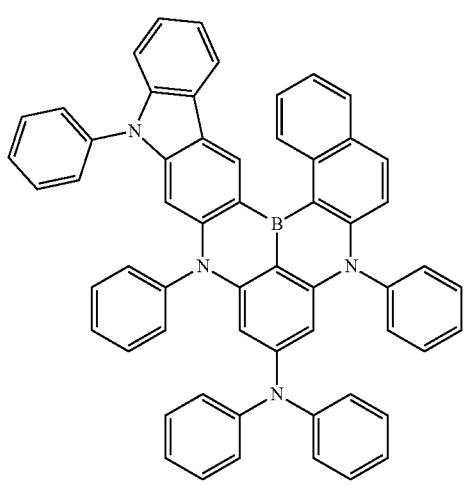
(3-222)
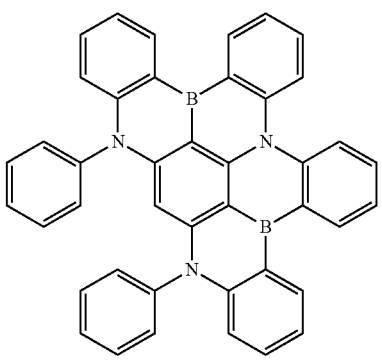

(3-223)
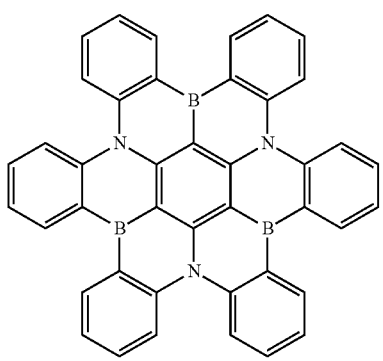
(3-224)
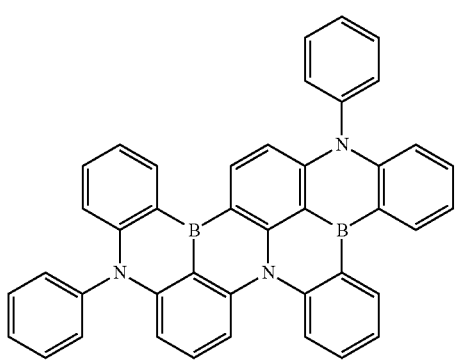
(3-230)
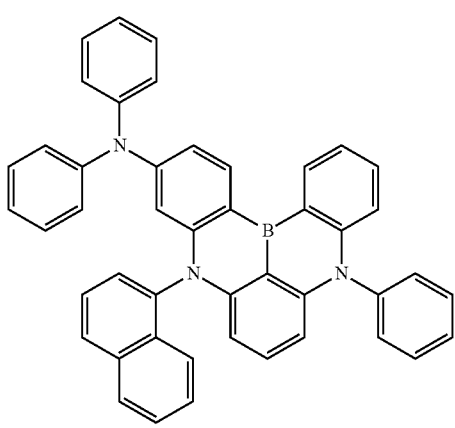
(3-231)
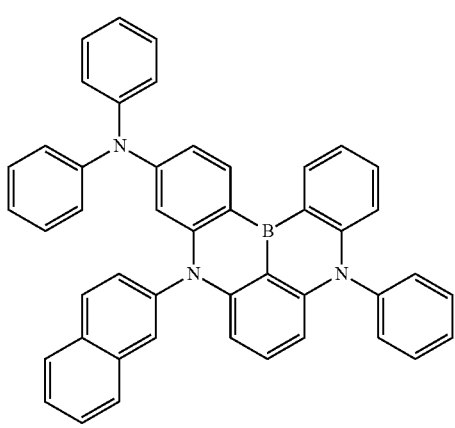
(3-232)
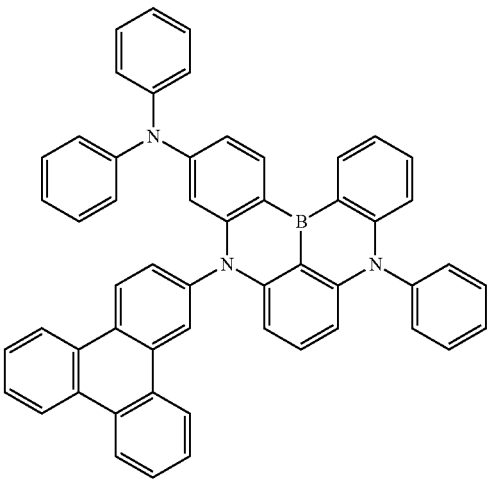
(3-233)
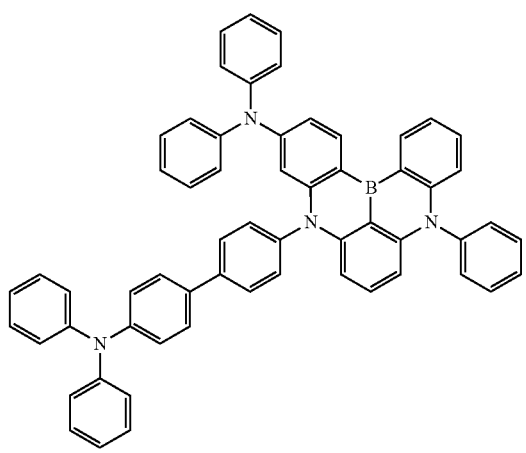
(3-234)
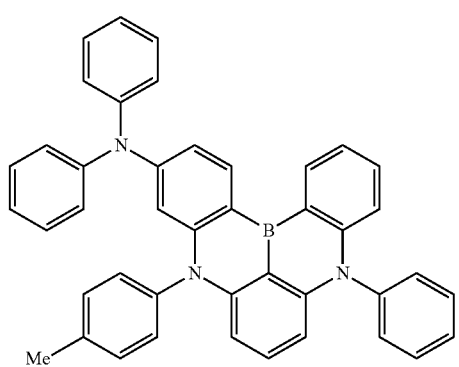

-continued
(3-235)
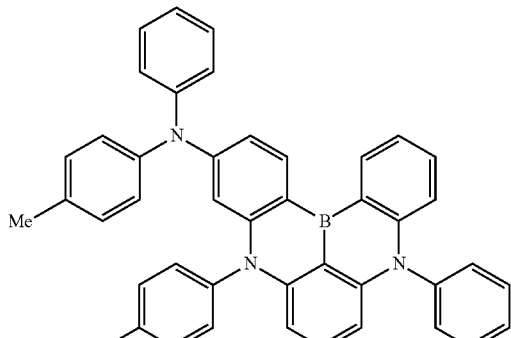
(2-236)
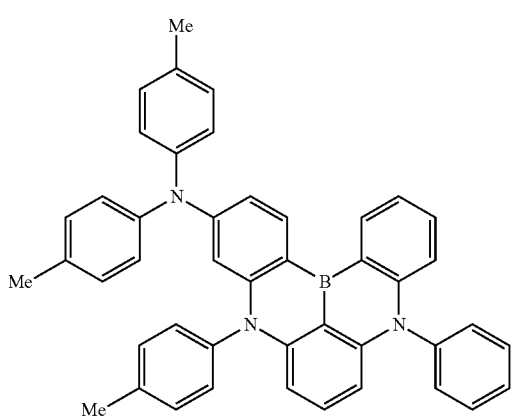
(2-237)
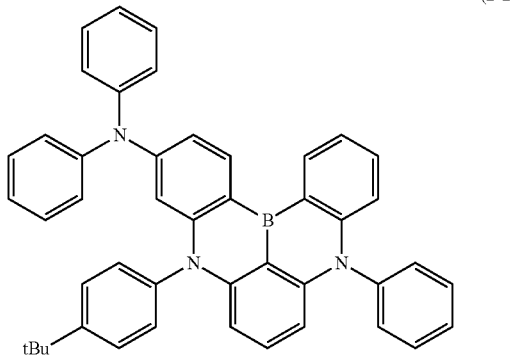
(2-238)
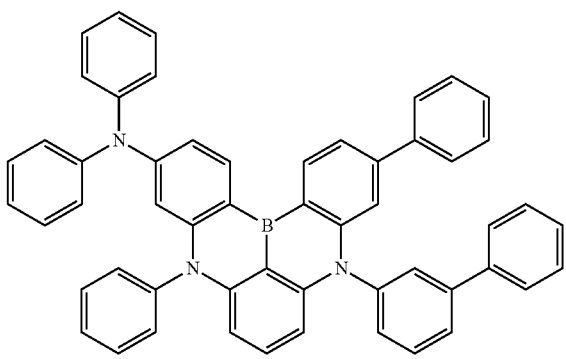
-continued
(2-239)
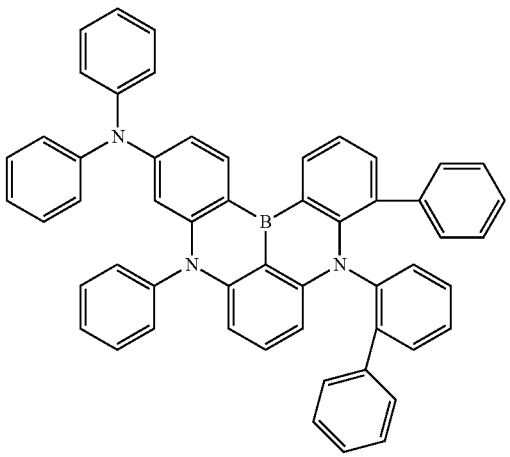
3-240
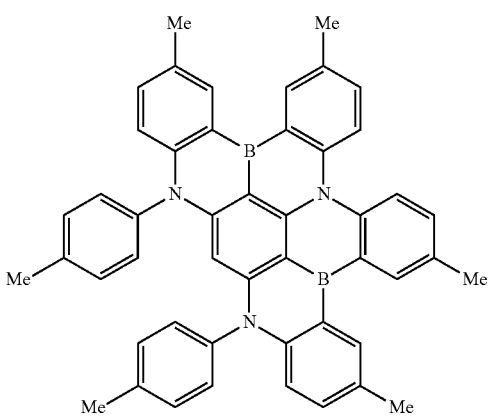
3-250
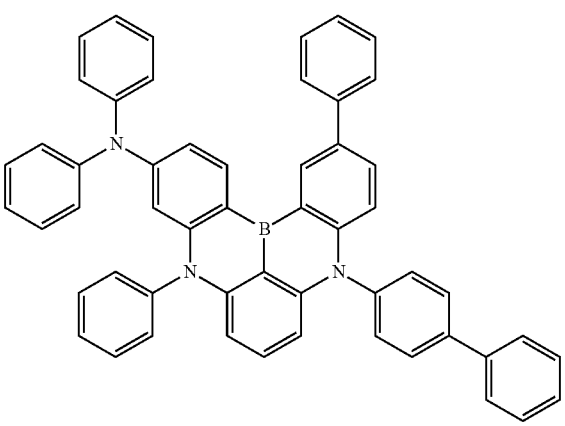

3-251
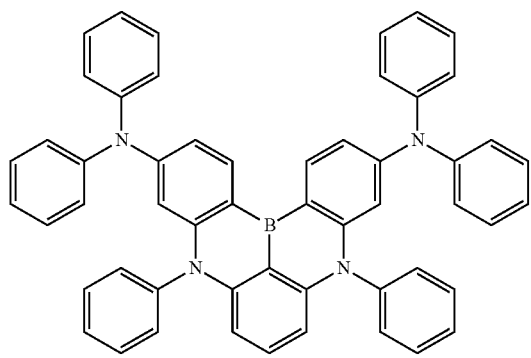
3-252
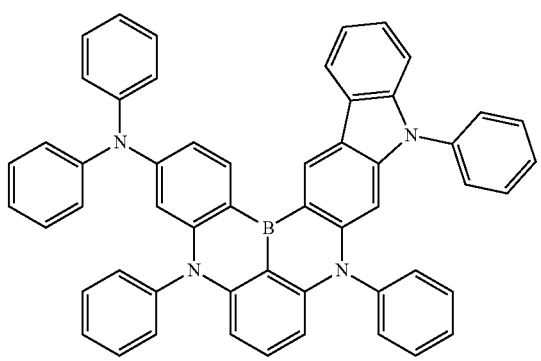
(3-253)
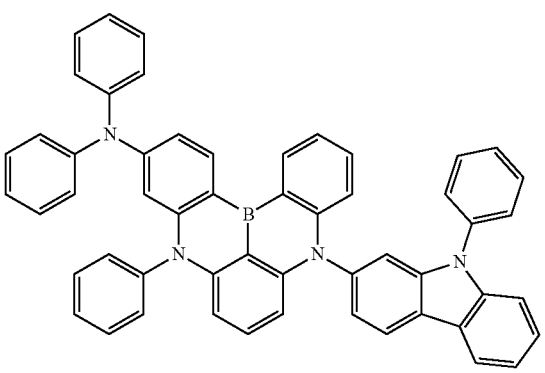
(3-254)
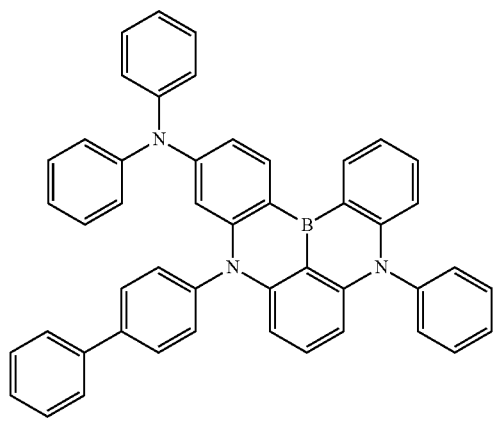
(3-255)
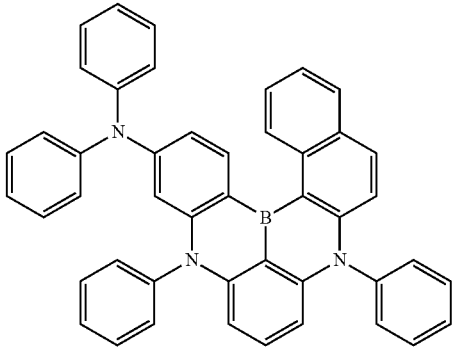
(3-256)
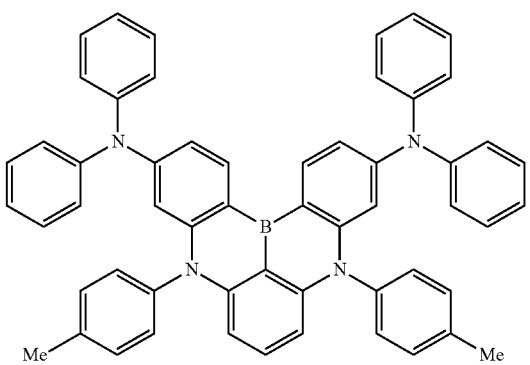
(3-257)
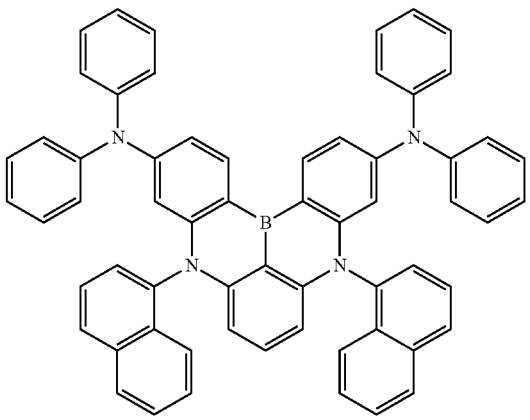

(3-258)
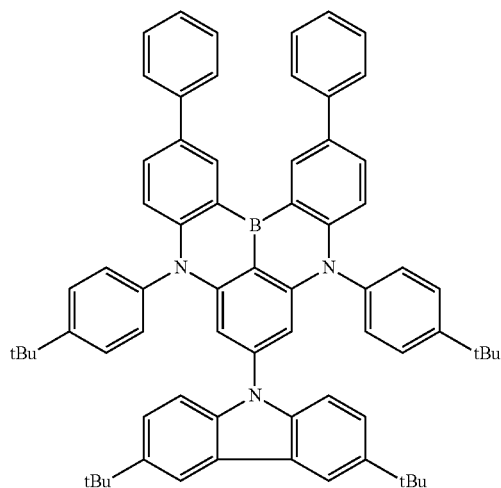
(3-270)
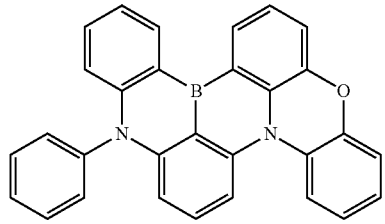
(3-271)
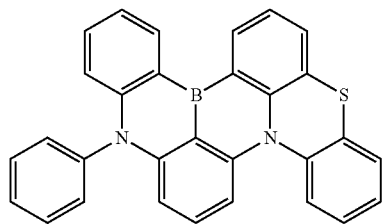
(3-272)
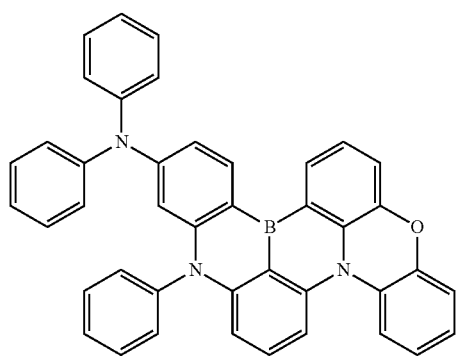
(3-273)
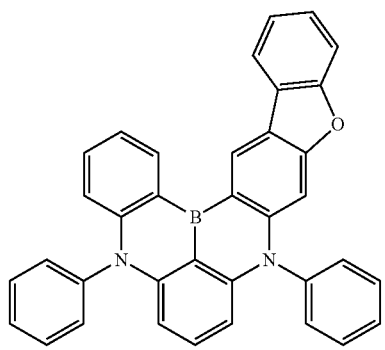
(3-274)
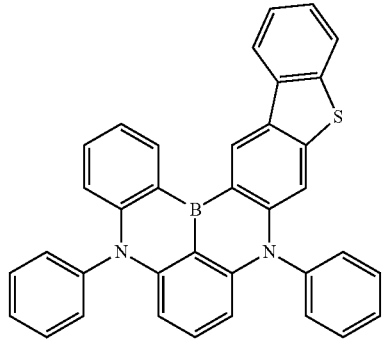
(3-275)
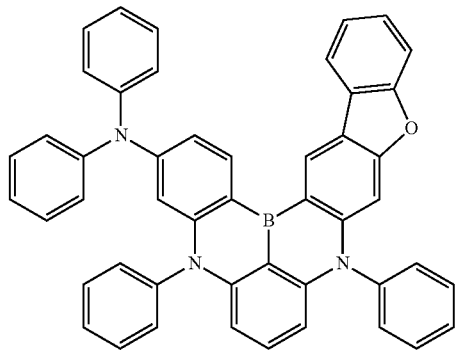
(3-276)
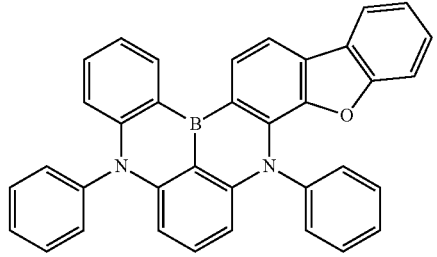
(3-277)
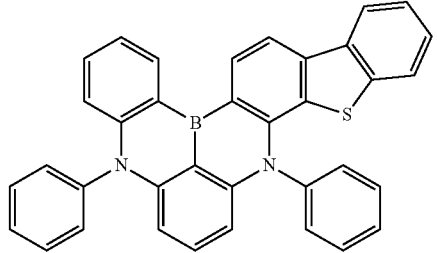

(3-278)
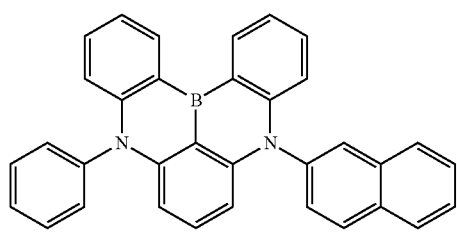
(3-279)
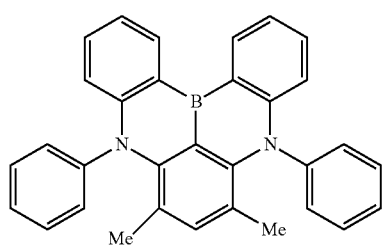
(3-280)
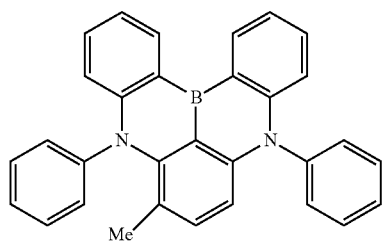
(3-281)
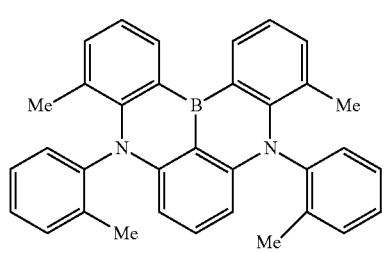
(3-282)
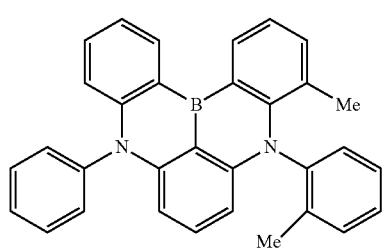
(3-283)
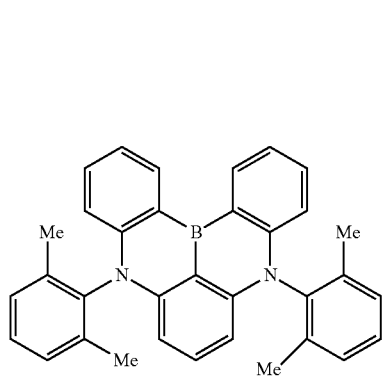
(3-284)
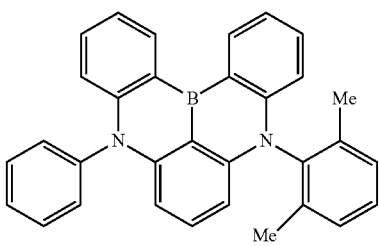
(3-350)
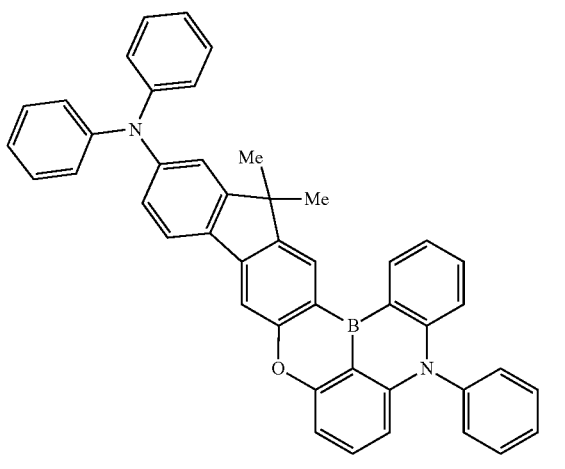
(3-351)
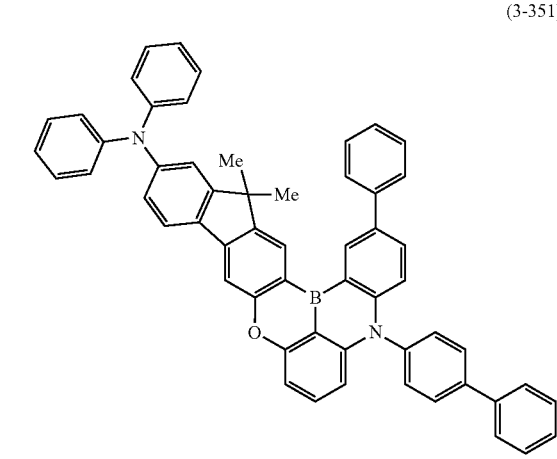
(3-352)
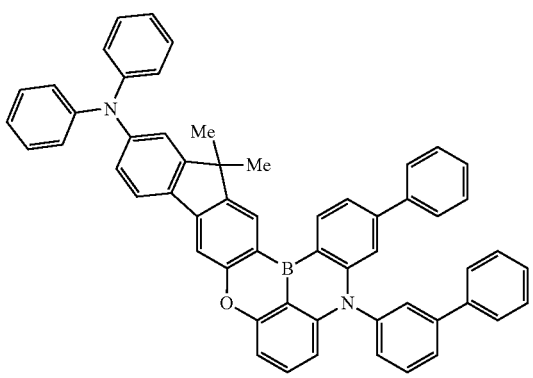

-continued
(3-353)
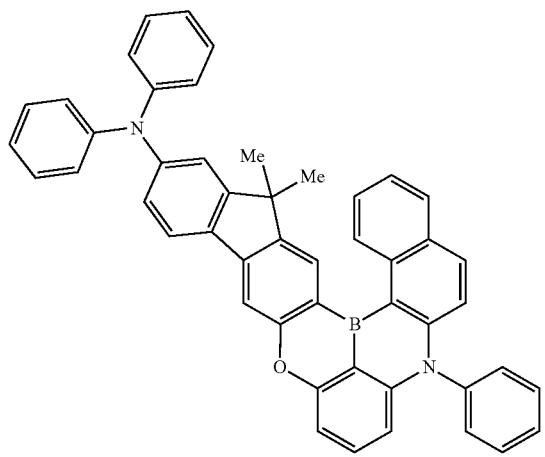
(3-354)
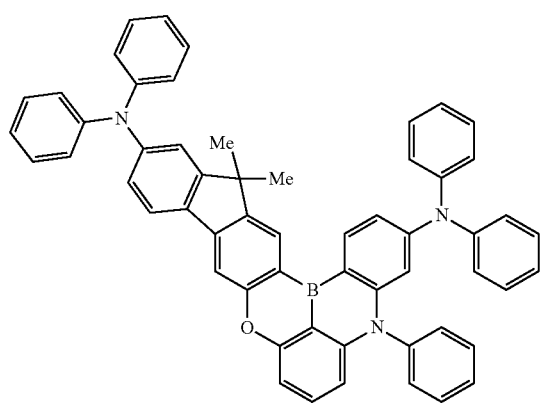
(3-355)
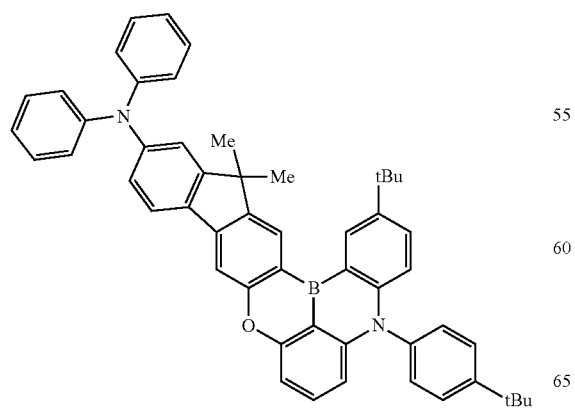
(3-360)
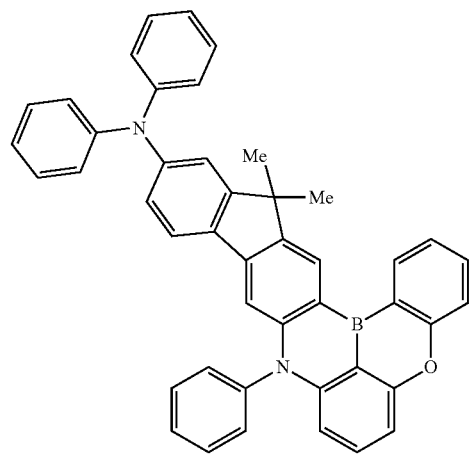
(3-361)
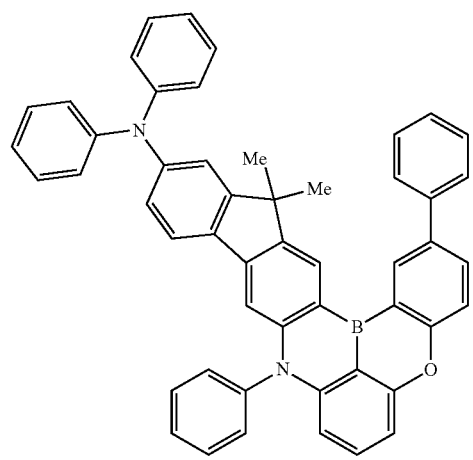
(3-362)
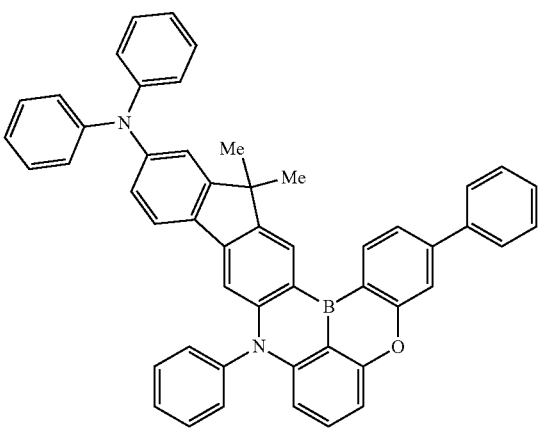

(3-363)
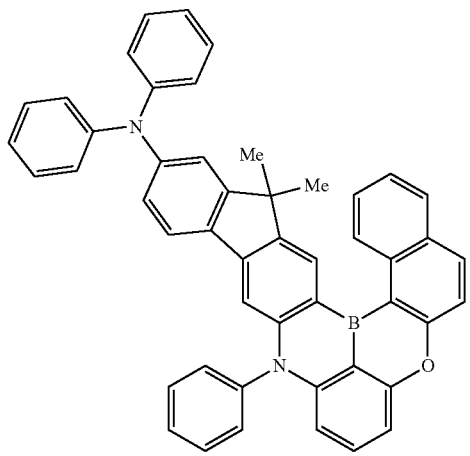
(3-370)
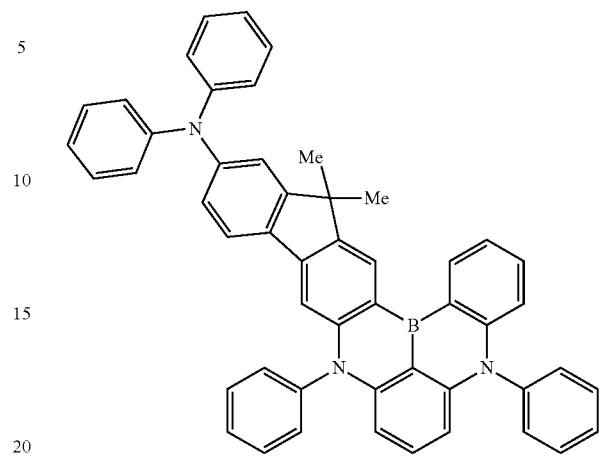
(3-364)
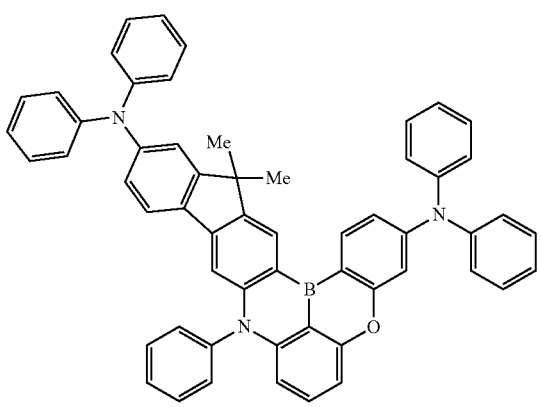
(3-371)
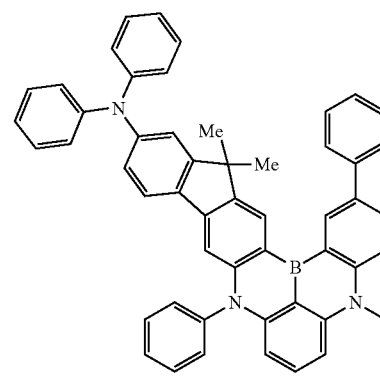
(3-365)
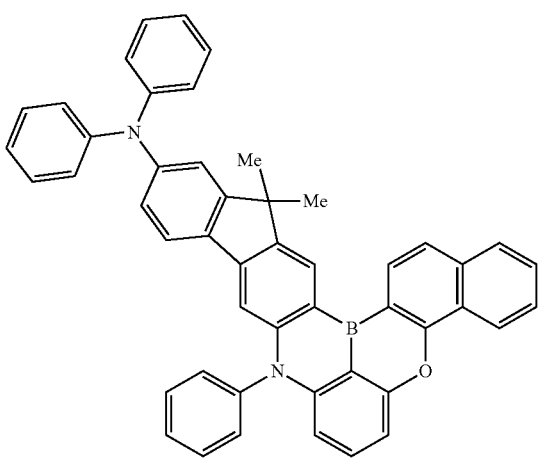
(3-372)
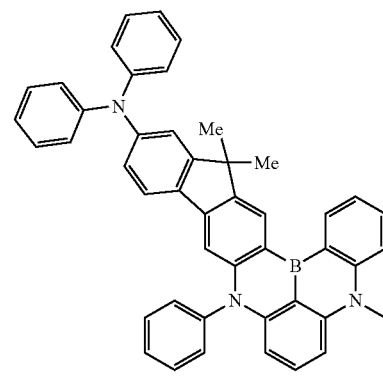

-continued (3-373)

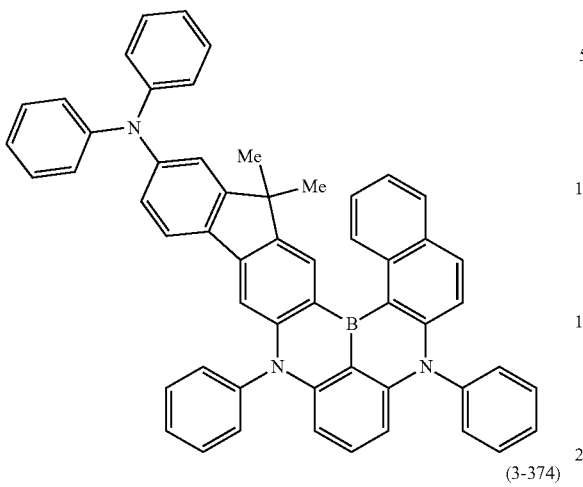

(3-374)

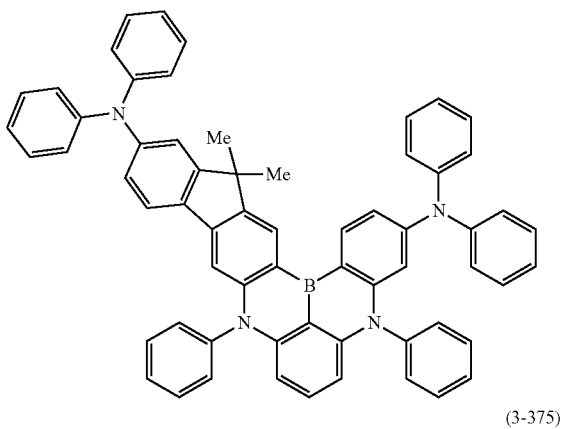

(3-375)

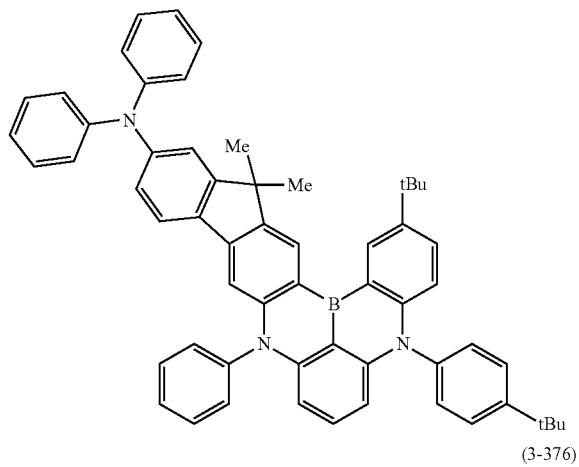

(3-376)

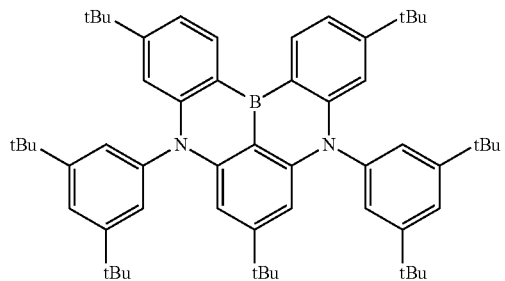

-continued (3-377)

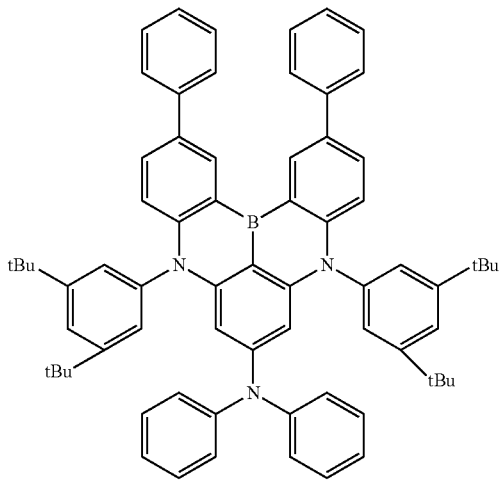

Compound Represented by Formula (4)

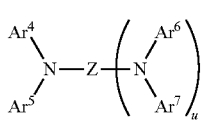

(4)

In formula (4), 2 is a pyrene ring, a benzofluorene ring or a chrysene ring, which may be subjected to substitution, and $Ar^4$, $Ar^5$ $Ar^6$ and $Ar^7$ are independently hydrogen, aryl, heteroaryl, diarylamino, diheteroarylamino, arylheteroarylamino, alkyl, cycloalkyl, alkoxy or aryloxy, and at least one hydrogen in the groups may be replaced by aryl, heteroaryl, alkyl, cycloalkyl, alkoxy, aryloxy or trialkylsilyl. Moreover, adjacent groups of $Ar^4$ to $Ar^7$ are bonded to each other to form a ring, and at least one hydrogen in the ring formed may be replaced by aryl, heteroaryl, diarylamino, diheteroarylamino, arylheteroarylamino, alkyl, alkoxy, aryloxy or trialkylsilyl. Then, u is an integer from 0 to 3, preferably 0 to 2, and further preferably 1. Then, at least one hydrogen in the compound represented by formula (4) may be replaced by halogen, cyano or deuterium.

Specific examples of aryl in $Ar^4$, $Ar^5$, $Ar^6$ and $Ar^7$ in formula (4) include aryl having 6 to 30 carbons, and aryl having 6 to 16 carbons is preferred, aryl having 6 to 12 carbons is further preferred, and aryl having 6 to 10 carbons is particularly preferred.

Specific examples of the aryl include phenyl as monocyclic aryl, biphenylyl as bicyclic aryl, naphthyl as fused bicyclic aryl, terphenylyl (m-terphenylyl, o-terphenylyl, p-terphenylyl) as tricyclic aryl, acenaphthylenyl, fluorenyl, phenalenyl and phenanthrenyl as fused tricyclic aryl, triphenylenyl, pyrenyl and naphthacenyl as fused tetracyclic aryl, and perylenyl and pentacenyl as fused pentacyclic aryl.

Specific examples of the heteroaryl in $Ar^4$, $Ar^5$, $Ar^6$ and $Ar^7$ in formula (4) include heteroaryl having 2 to 30 carbons or heteroaryl having 2 to 25 carbons is preferred, heteroaryl having 2 to 20 carbons is further preferred, heteroaryl having 2 to 15 carbons is still further preferred, and heteroaryl having 2 to 10 carbons is particularly preferred. Moreover, specific examples of the heteroaryl include a heterocyclic ring containing, in addition to carbon, 1 to 5 hetero atoms selected from oxygen, sulfur and nitrogen as a ring-forming atom.

Specific examples of the heteroaryl include pyrrolyl, oxazolyl, isoxazolyl, thiazolyl, isothiazolyl, imidazolyl, oxadiazolyl, thiadiazolyl, triazoryl, tetrazoryl, pyrazolyl, pyridyl, pyrimidinyl, pyridazinyl, pyrazinyl, thoriadinyl, indolyl, isoindolyl, 1H-indazolyl, benzimidazolyl, benzoxazolyl, benzothiazolyl, 1H-benzotriazoryl, quinolyl, isoquinolyl, cinnolyl, quinazolyl, quinoxalinyl, phthalazinyl, naphthyridinyl, purinyl, pteridinyl, carbazolyl, acridinyl, phenoxathiinyl, phenoxazinyl, phenothiazinyl, phenazinyl, indrizinyl, furyl, benzofuranyl, isobenzofuranyl, dibenzofuranyl, thienyl, benzo[b]thienyl, dibenzothienyl, furazanyl, oxadiazolyl, thianthrenyl, naphthobenzofuranyl and naphthobenzothienyl.

Diarylamino, diheteroarylamino and arylheteroarylamino in $Ar^4$, $Ar^5$, $Ar^6$ and $Ar^7$ in formula (4) each are a group in which an amino group is replaced by two aryl groups, two heteroaryl groups, and one aryl group and one heteroaryl group, respectively, and for the aryl and the heteroaryl herein, the above-mentioned description can be quoted.

The alkyl as $Ar^4$, $Ar^5$, $Ar^6$ and $Ar^7$ in formula (4) may be any of straight-chain alkyl and branched-chain alkyl, and specific examples thereof include straight-chain alkyl having 1 to 24 carbons or branched-chain alkyl having 3 to 24 carbons. Alkyl having 1 to 18 carbons (branched-chain alkyl having 3 to 18 carbons) is preferred, alkyl having 1 to 12 carbons (branched-chain alkyl having 3 to 12 carbons) is further preferred, alkyl having 1 to 6 carbons (branched-chain alkyl having 3 to 6 carbons) is still further preferred, and alkyl having 1 to 4 carbons (branched-chain alkyl having 3 to 4 carbons) is particularly preferred.

Specific examples of the alkyl include methyl, ethyl, n-propyl, isopropyl, n-butyl, isobutyl, s-butyl, t-butyl, n-pentyl, isopentyl, neopentyl, t-pentyl, n-hexyl, 1-methylpentyl, 4-methyl-2-pentyl, 3,3-dimethylbutyl, 2-ethylbutyl, n-heptyl, 1-methylhexyl, n-octyl, t-octyl, 1-methylheptyl, 2-ethylhexyl, 2-propylpentyl, n-nonyl, 2,2-dimethylheptyl, 2,6-dimethyl-4-heptyl, 3,5,5-trimethylhexyl, n-decyl, n-undecyl, 1-methyldecyl, n-dodecyl, n-tridecyl, 1-hexylheptyl, n-tetradecyl, n-pentadecyl, n-hexadecyl, n-heptadecyl, n-octadecyl and n-eicosyl.

The cycloalkyl in $Ar^4$, $Ar^5$, $Ar^6$ and $Ar^7$ in formula (4) may be any of cycloalkyl formed of one ring, cycloalkyl formed of a plurality of rings, cycloalkyl containing a nonconjugated double bond in the ring, and cycloalkyl containing a branched chain outside the ring, and is cycloalkyl having 3 to 14 carbons, for example. Cycloalkyl having 5 to 10 carbons is preferred, and cycloalkyl having 6 to 10 carbons is further preferred.

Specific examples of the cycloalkyl include cyclopropyl, cyclobutyl, cyclopentyl, cyclohexyl, cycloheptyl, cyclooctyl, bicyclo[2.2.1]heptyl, bicyclo[2.2.2]octyl, decahydronaphthyl and adamanthyl (particularly, 1-adamanthyl).

Specific examples of the alkoxy in $Ar^4$, $Ar^5$, $Ar^6$ and $Ar^7$ in formula (4) include straight-chain alkoxy having 1 to 24 carbons or branched-chain alkoxy having 3 to 24 carbons. Alkoxy having 1 to 18 carbons (branched-chain alkoxy having 3 to 18 carbons) is preferred, alkoxy having 1 to 12 carbons (branched-chain alkoxy having 3 to 12 carbons) is further preferred, alkoxy having 1 to 6 carbons (branched-chain alkoxy having 3 to 6 carbons) is still further preferred, and alkoxy having 1 to 4 carbons (branched-chain alkoxy having 3 to 4 carbons) is particularly preferred.

Specific examples of the alkoxy include methoxy, ethoxy, propoxy, isopropoxy, butoxy, isobutoxy, s-butoxy, t-butoxy, pentyloxy, hexyloxy, heptyloxy and octyloxy.

The aryloxy in $Ar^4$, $Ar^5$, $Ar^6$ and $Ar^7$ in formula (4) is a group in which hydrogen of a hydroxyl group is replaced by aryl, and also for the aryl herein, the above-mentioned description can also be quoted.

At least one hydrogen in each substituent described above in formula (4) may be replaced by aryl, heteroaryl, alkyl, cycloalkyl, alkoxy, aryloxy or trialkylsilyl. As the aryl, the heteroaryl, the alkyl, the cycloalkyl, the alkoxy and the aryloxy, the above-mentioned descriptions can be quoted, respectively.

Specific examples of the trialkylsilyl include a structure in which three hydrogens in a silyl group are independently replaced by alkyl, and specific examples of the alkyl include a group described in a column of alkyl as $R^1$ to $R^6$. Alkyl by which hydrogen is preferably replaced is alkyl having 1 to 4 carbons, and specific examples thereof include methyl, ethyl, propyl, i-propyl, butyl, sec-butyl, t-butyl and cyclobutyl.

Specific examples of the trialkylsilyl include trimethylsilyl, triethylsilyl, tripropylsilyl, triisopropylsilyl, tributylsilyl, trisec-butylsilyl, trit-butylsilyl, ethyldimethylsilyl, propyldimethylsilyl, i-propyldimethylsilyl, butyldimethylsilyl, sec-butyldimethylsilyl, t-butyldimethylsilyl, methyldiethylsilyl, propyldiethylsilyl, i-propyldiethylsilyl, butyldiethylsilyl, sec-butyldiethylsilyl, t-butyldiethylsilyl, methyldipropylsilyl, ethyldipropylsilyl, butyldipropylsilyl, sec-butyldipropylsilyl, t-butyldipropylsilyl, methyldiisopropylsilyl, methyldiisopropylsilyl, butyldiisopropylsilyl, sec-butyldiisopropylsilyl and t-butyldiisopropylsilyl.

Adjacent groups of $Ar^4$ to $Ar^7$ in formula (4) may be bonded to each other to form a ring, and at least one hydrogen in the ring formed may be replaced by aryl, heteroaryl, diarylamino, diheteroarylamino, arylheteroarylamino, alkyl, alkoxy, aryloxy or trialkylsilyl. For a further substituent, the above-mentioned description can be quoted.

Specific examples of the ring formed by bonding adjacent groups of $Ar^4$ to $Ar^7$ in formula (4) to each other include a pyrrole ring, an imidazole ring, an indole ring, an isoindole ring, a 1H-indazole ring, a carbazole ring, a carboline ring, a phenoxazine ring, a pyrroline ring, a pyrrolidine ring, an imidazoline ring, a pyrazolidine ring, a pyrazoline ring, a piperidine ring, a piperazine ring, an indoline ring, an isoindoline ring and a morpholine ring.

The compound represented by formula (4) is preferably a compound represented by formulas (4-A) to (4-C).

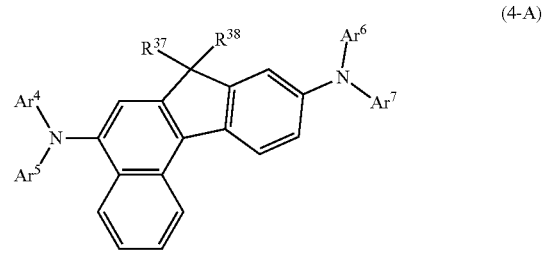

(4-A)

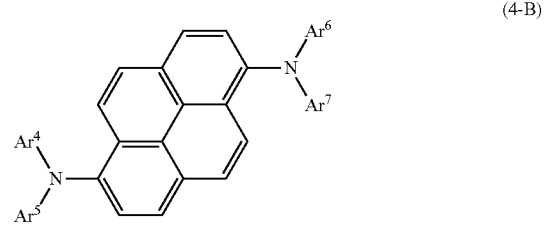

(4-B)

(4-C)

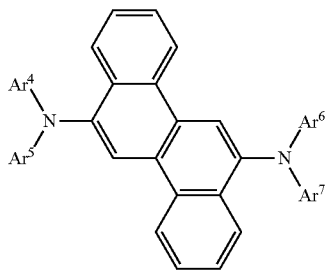

In formulas (4-A) to (4-C), $Ar^4$, $Ar^5$, $Ar^6$ and $Ar^7$ are independently aryl having 6 to 30 carbons, heteroaryl having 5 to 30 carbons, and at least one hydrogen in the groups may be replaced by aryl having 6 to 10 carbons, heteroaryl having 5 to 12 carbons, alkyl having 1 to 6 carbons, cycloalkyl having 3 to 10 carbons, alkoxy having 1 to 6 carbons, aryloxy having 6 to 10 carbons or trialkylsilyl having 3 to 12 carbons. $Ar^4$, $Ar^5$, $Ar^6$ and $Ar^7$ are preferably independently aryl having 6 to 10 carbons or heteroaryl having 5 to 12 carbons, and at least one hydrogen in the groups may be replaced by aryl having 6 to 10 carbons, heteroaryl having 5 to 12 carbons, alkyl having 1 to 6 carbons, cycloalkyl having 3 to 6 carbons or trialkylsilyl having 3 to 12 carbons. $Ar^4$, $Ar^5$, $Ar^6$ and $Ar^7$ are preferably independently phenyl, naphthyl or a group represented by formula (4-X), and at least one hydrogen in the groups may be replaced by phenyl, naphthyl, methyl, isopropyl, tertiary butyl or trimethylsilyl.

(4-X)

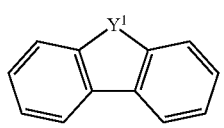

In formula (4-X), $Y^1$ is —O—, —S— or >N—$R^{39}$, and $R^{39}$ is hydrogen or phenyl. Formula (4-X) is bonded to a nitrogen atom in formulas (4-A) to (4-C) at any position in the structure.

In formulas (4-A) to (4-C), adjacent groups of $Ar^4$ to $Ar^7$ may be bonded to each other to form a ring. As an example of the ring to be formed, the above-mentioned description for formula (4) can be quoted.

In formula (4-A), $R^{37}$ and $R^{38}$ are independently hydrogen, aryl having 6 to 30 carbons, heteroaryl having 5 to 30 carbons, alkyl having 1 to 10 carbons, cycloalkyl having 3 to 12 carbons or trialkylsilyl having 3 to 12 carbons, and at least one hydrogen in the groups may be replaced by aryl having 6 to 10 carbons, heteroaryl having 5 to 12 carbons, alkyl having 1 to 6 carbons, cycloalkyl having 3 to 10 carbons or trialkylsilyl having 3 to 12 carbons. $R^{37}$ and $R^{3a}$ are preferably independently hydrogen, aryl having 6 to 10 carbons, heteroaryl having 5 to 12 carbons, alkyl having 1 to 6 carbons, cycloalkyl having 3 to 6 carbons or trialkylsilyl having 3 to 6 carbons, and at least one hydrogen in the groups may be replaced by aryl having 6 to 10 carbons, heteroaryl having 5 to 12 carbons, alkyl having 1 to 6 carbons, cycloalkyl having 3 to 6 carbons or trialkylsilyl having 3 to 6 carbons. $R^{37}$ and $R^{38}$ are preferably independently methyl, phenyl which may be subjected to substitution for methyl, naphthyl or biphenyl, and further preferably phenyl.

$R^{37}$ and $R^{38}$ may be bonded to each other to form a ring. Specific examples of the ring formed by bonding $R^{37}$ and $R^{38}$ to each other include a fluorene ring and a benzofluorene ring.

At least one hydrogen in the compounds represented by formulas (4-A) to (4-C) may be replaced by halogen, cyano or deuterium.

As an example of each substituent in formulas (4-A) to (4-C), the above-mentioned description for formula (4) can be quoted.

Specific examples of the compound represented by formula (4-A) include the following compounds described in JP 2008-291006 A.

(1'-1)

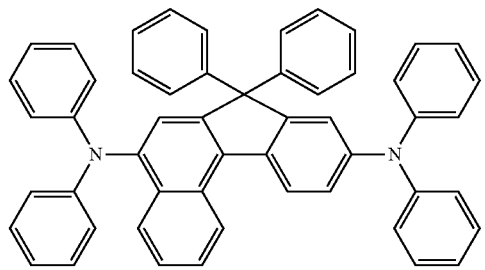

(1'-2)

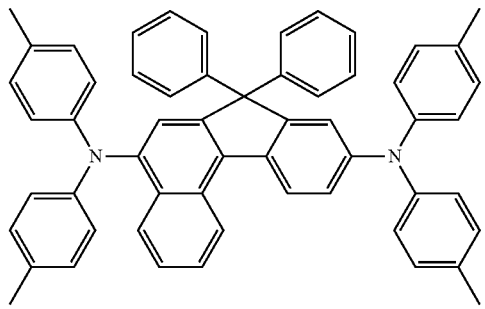

(1'-3)

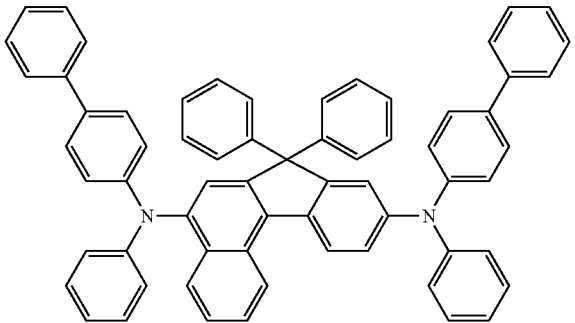

(1'-4)

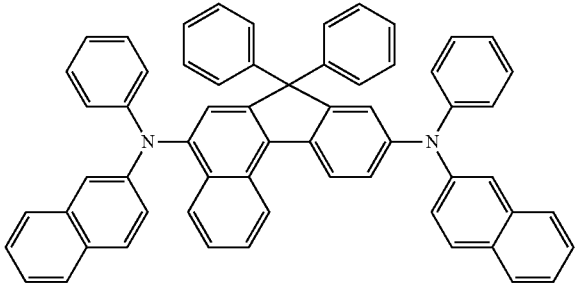

(1'-5)
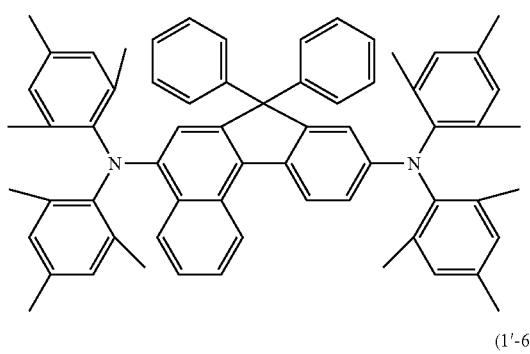
(1'-6)
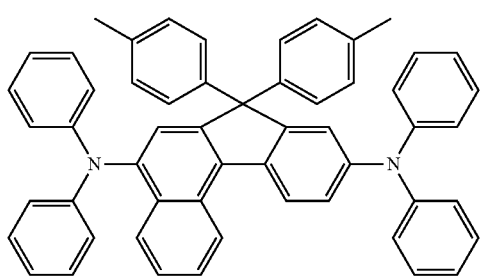
(1'-7)
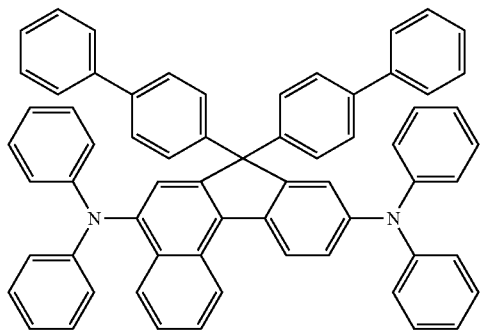
(1'-8)
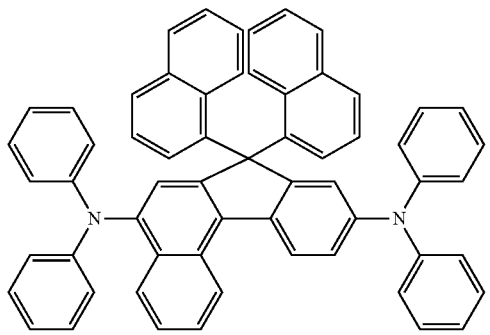
(1'-9)
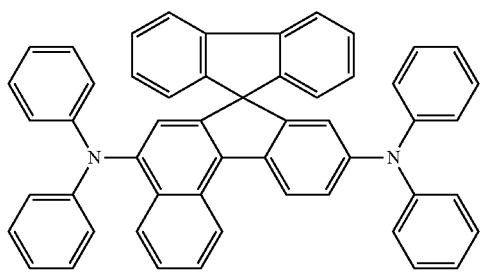
(1'-10)
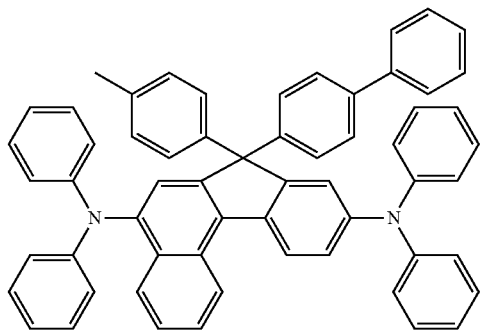
(1'-11)
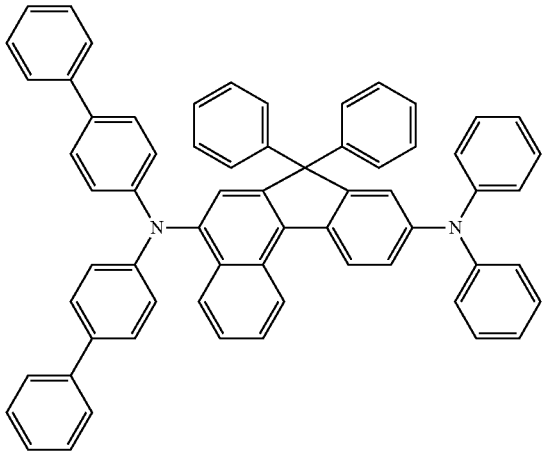
(1'-12)
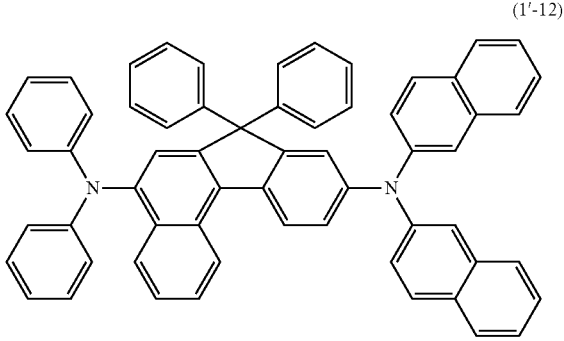
(1'-13)
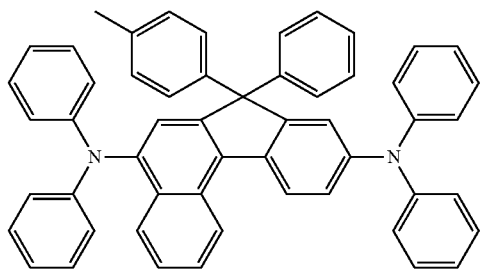

(1'-14)
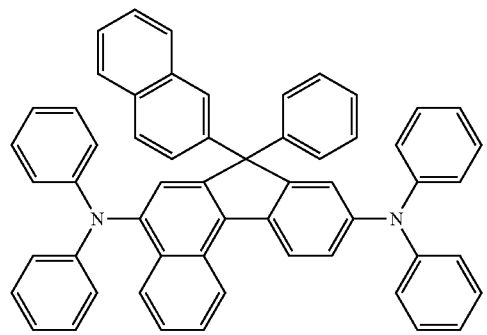
D-3
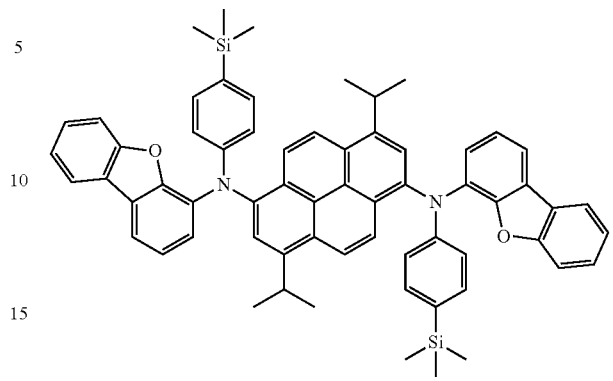
(1'-15)
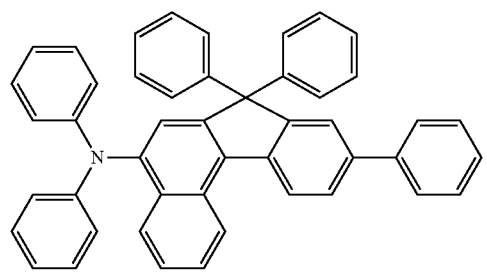
D-4
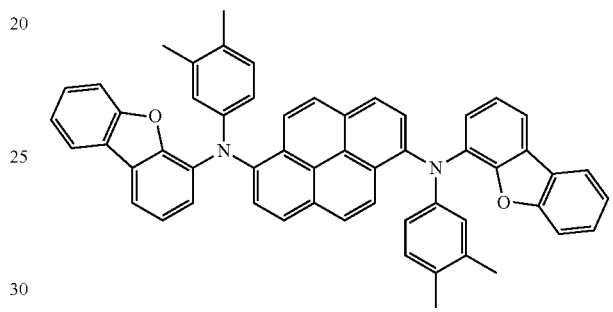
(1'-16)
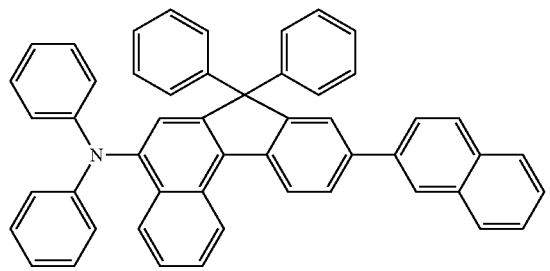
D-5
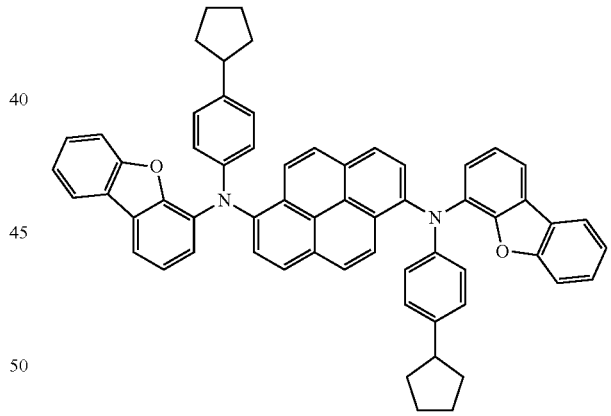
Specific examples of the compound represented by formula (4-B) include the following compounds described in JP 2013-080961 A.
D-1
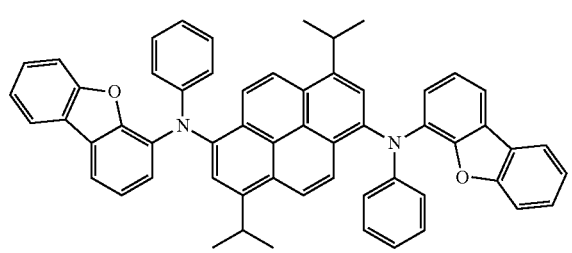
D-29
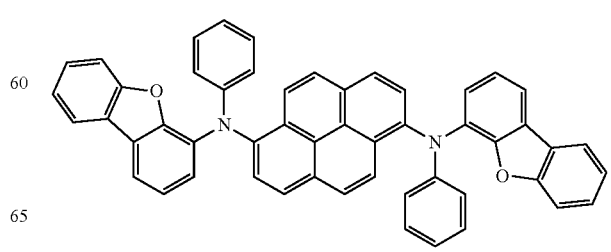

D-30
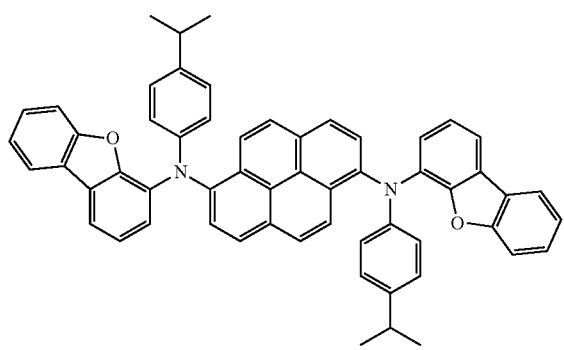
D-31
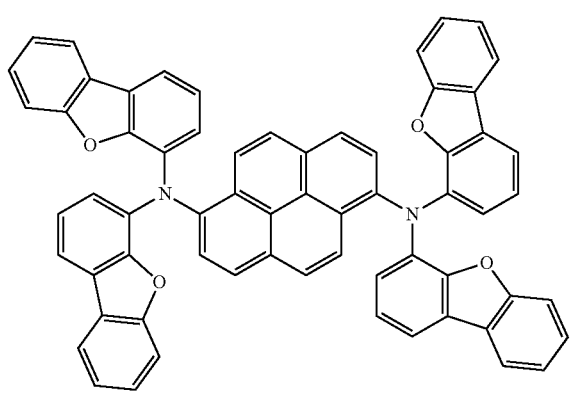
D-32
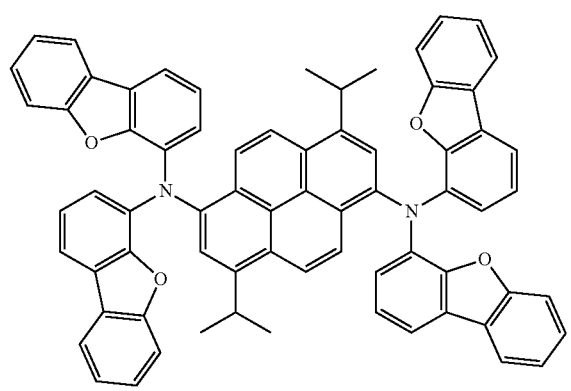
D33
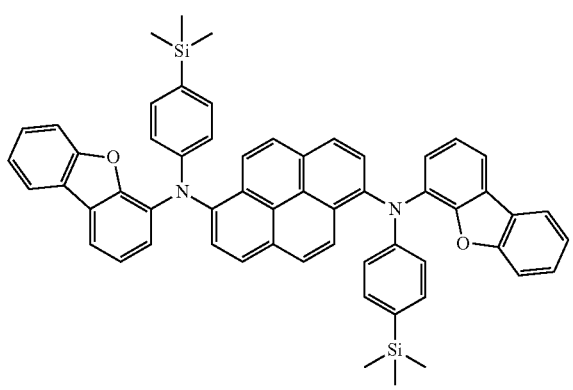
D-34
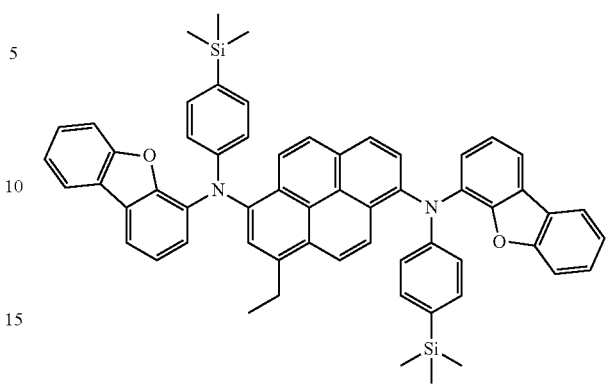
D-35
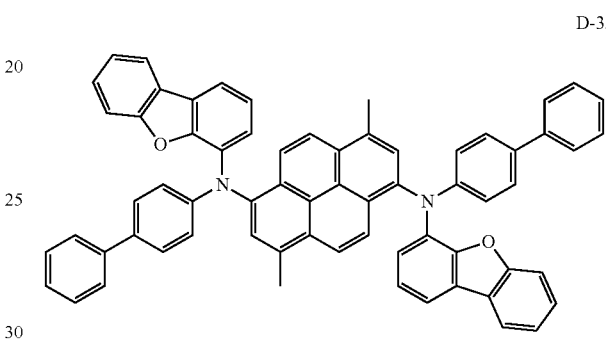
D-36
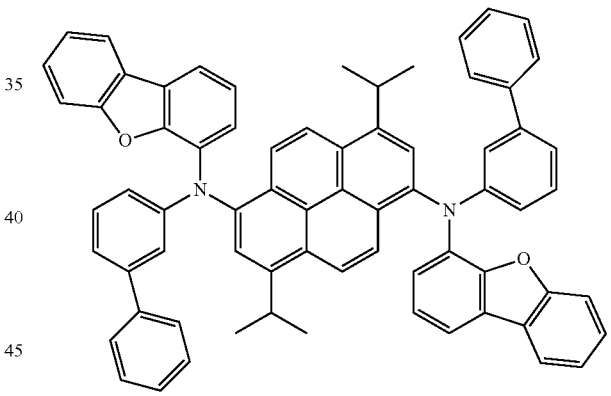
D-51
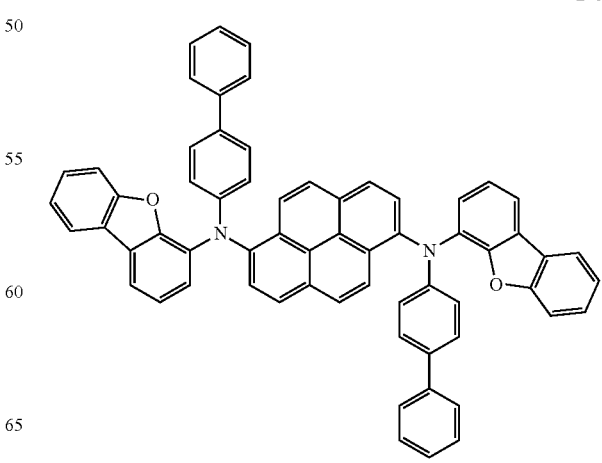

D-52
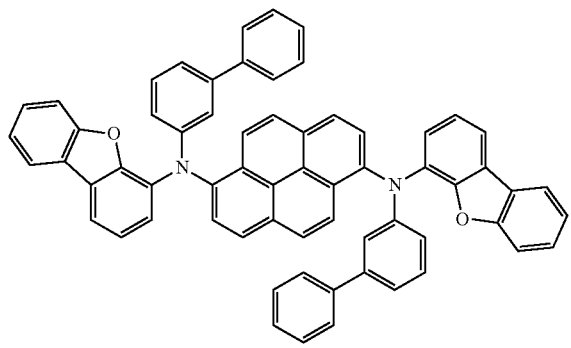
D-53
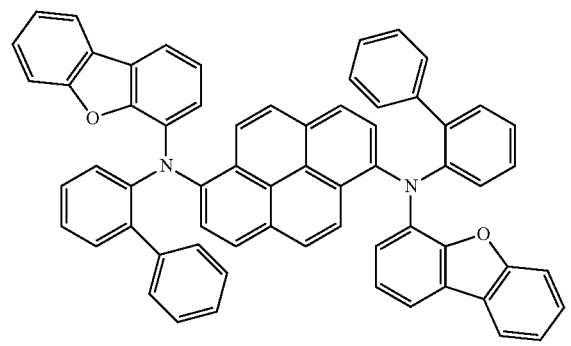
D-54
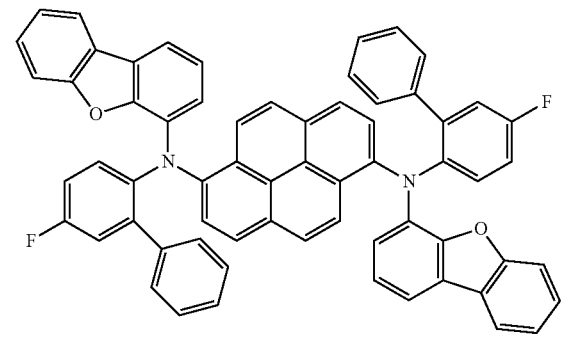
D-57
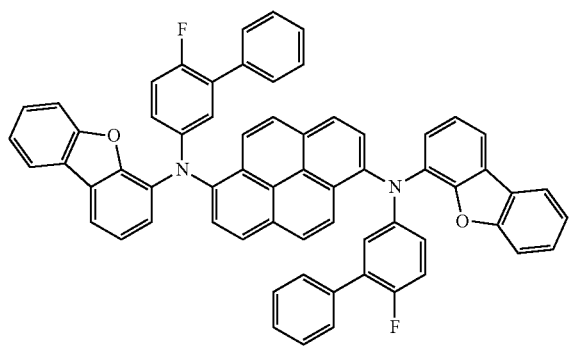
D-58
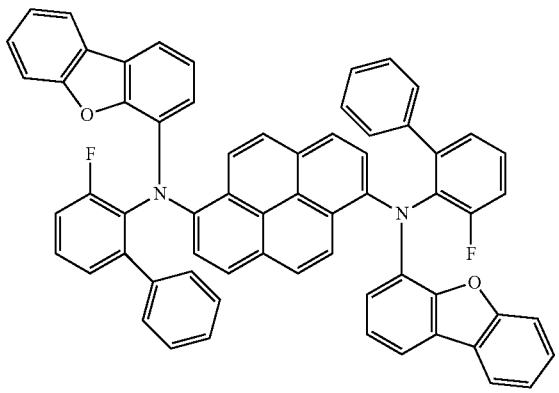
D-61
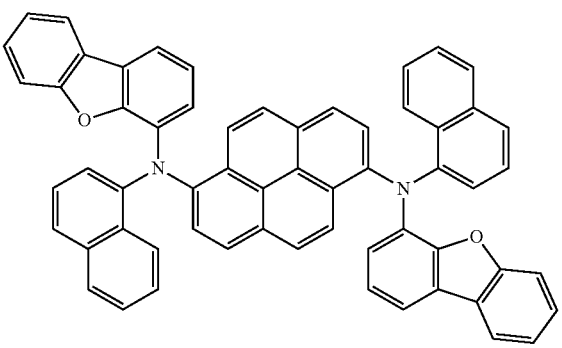
D-64
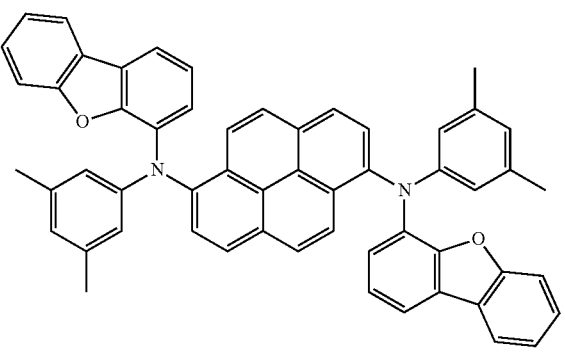
D-65
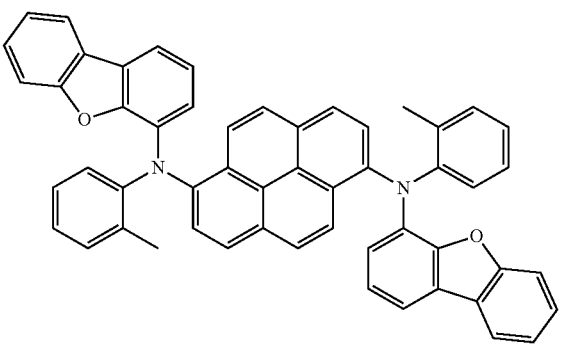

D-84
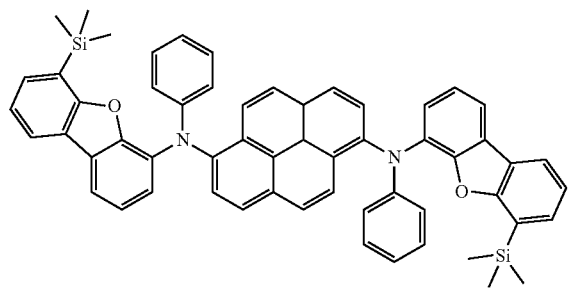
D-85
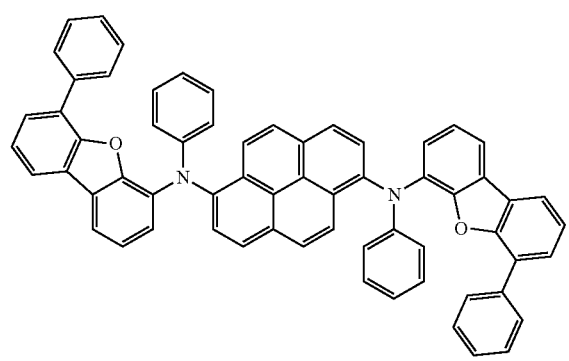
Specific examples of the compound represented by formula (4-C) include the following compounds described in WO 2009/008356 A and JP 2005-302667 A.
(A)-51
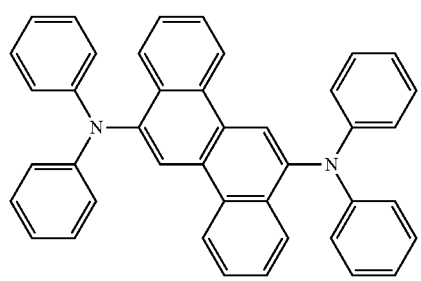
(A)-52
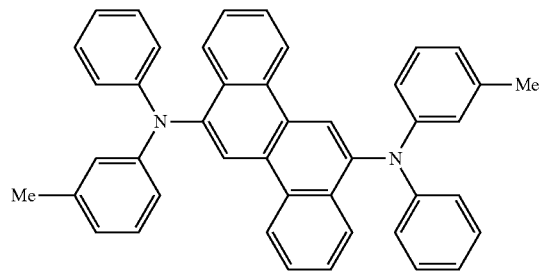
(A)-53
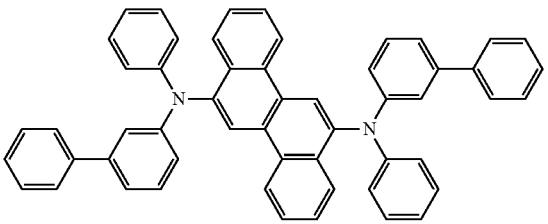
(A)-54
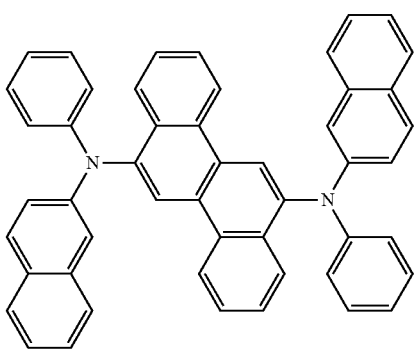
(A)-55
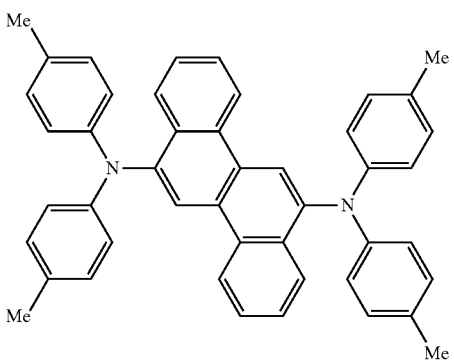
(A)-56
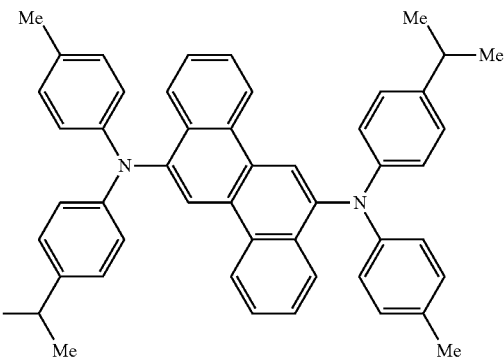

(A)-2
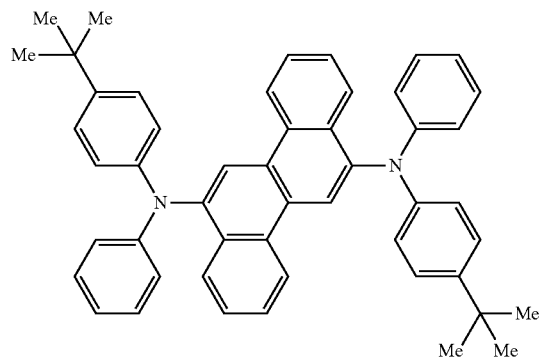
The dopant material is preferably a compound having any of structures described below.
(3-41)
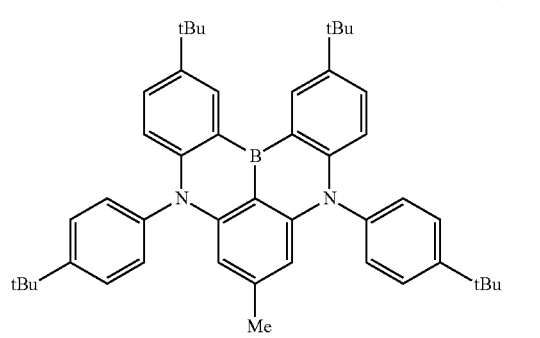
(3-31)
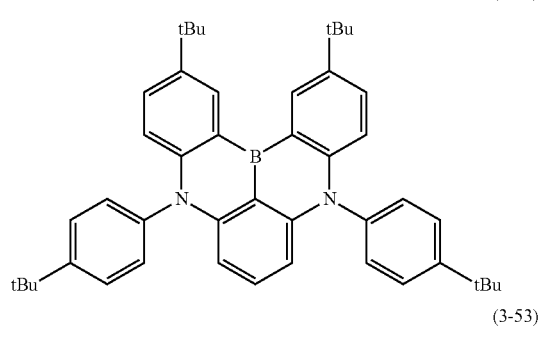
(3-53)
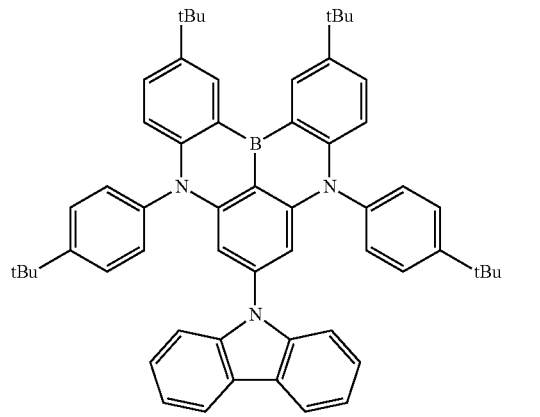
(3-37)
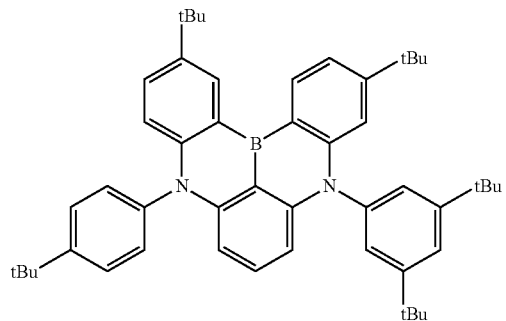
(3-46)
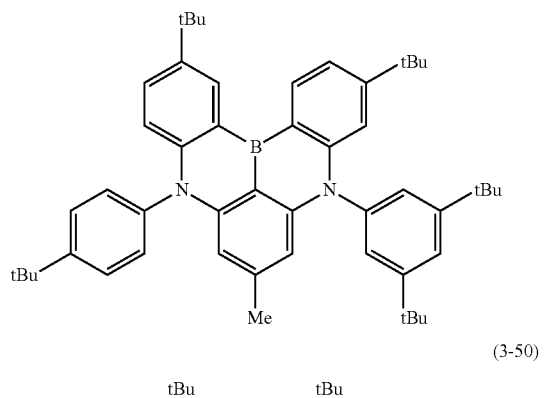
(3-50)
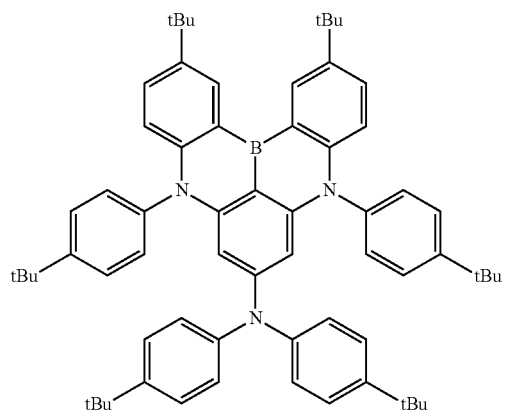
(3-49)
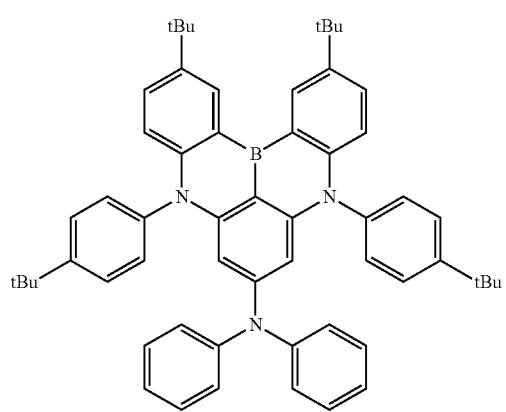

(3-A-1)
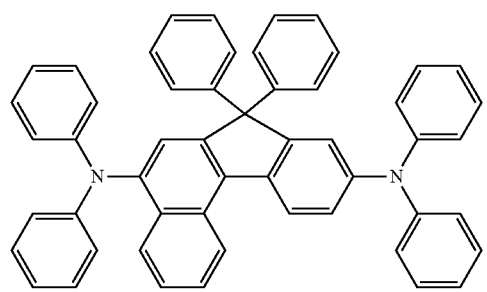
(3-A-2)
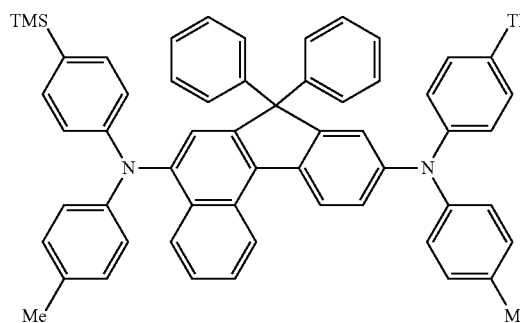
(3-A-3)
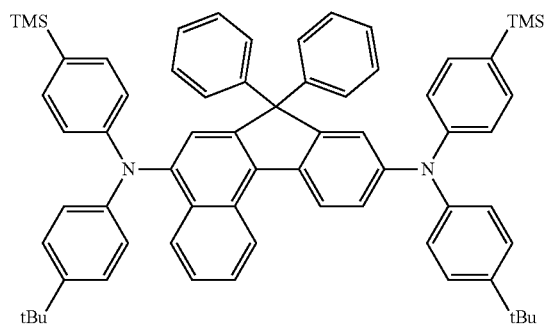
(3-A-4)
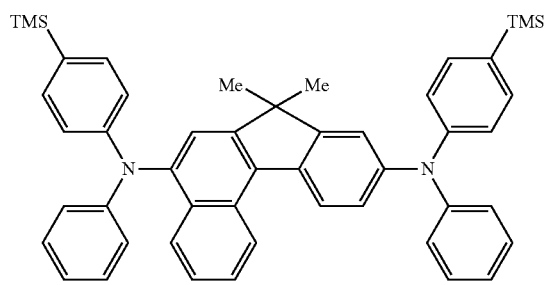
(3-A-5)
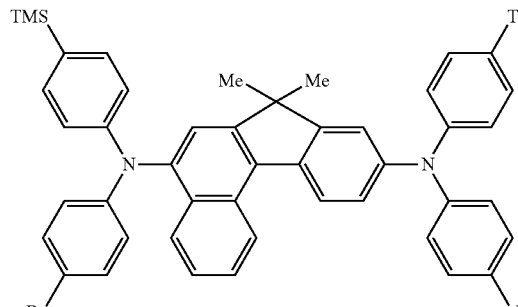
(3-B-1)
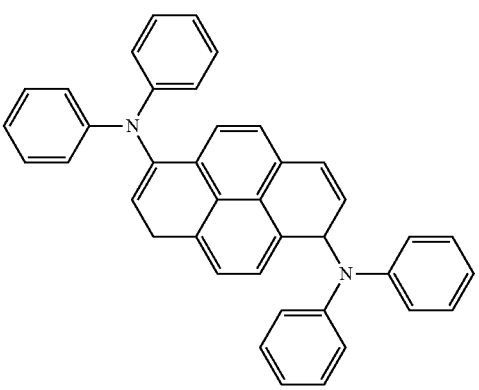
(3-B-2)
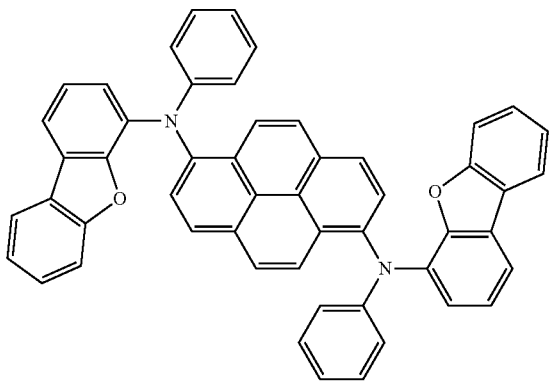
(3-B-3)
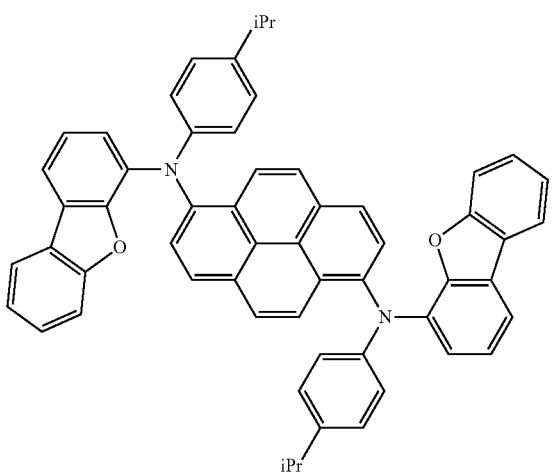

-continued (3-B-4)

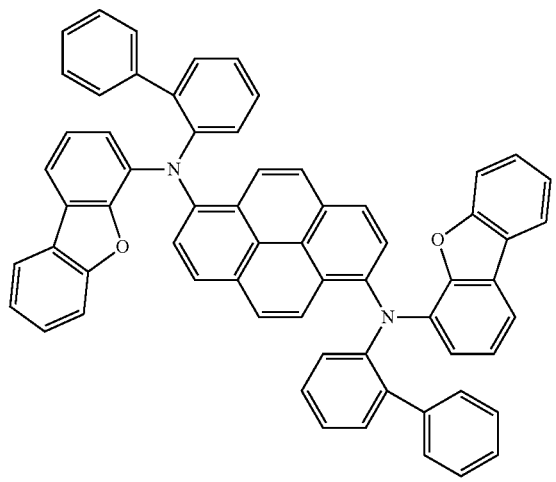

(3-C-1)

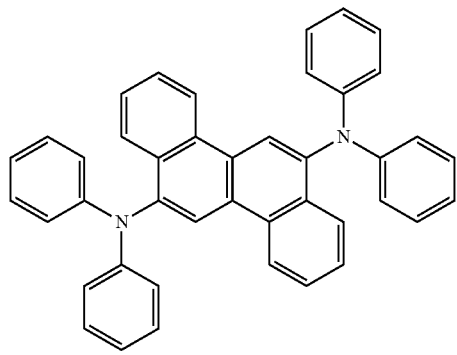

(3-C-2)

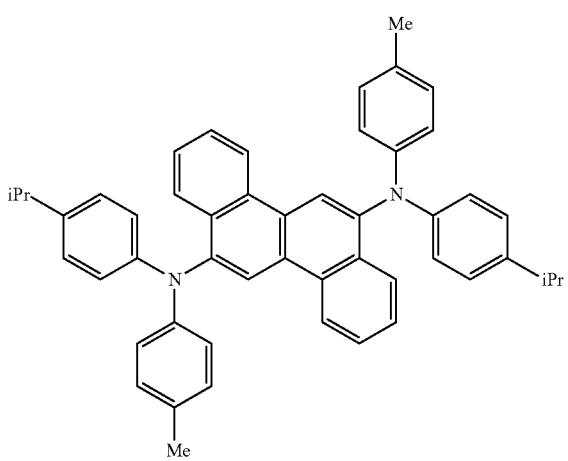

-continued (3-C-3)

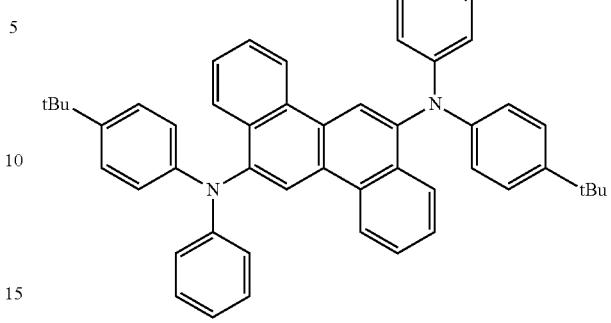

In the structural formulas, "Me" represents methyl, "iPr" represents isopropyl, "tBu" represents tertiary butyl, and "TMS" represents trimethylsilyl.

Structure of an Organic Electroluminescent Device

The FIGURE shows a schematic cross-sectional view of an organic electroluminescent device. Organic EL device 100 shown in the FIGURE has substrate 101, anode 102 provided on substrate 101, hole injection layer 103 provided on anode 102, hole transport layer 104 provided on hole injection layer 103, luminescent layer 105 provided on hole transport layer 104, electron transport layer 106 provided on luminescent layer 105, electron injection layer 107 provided on electron transport layer 106 and cathode 108 provided on electron injection layer 107.

In addition, with reversing preparation order, organic EL device 100 may be formed into a configuration having substrate 101, cathode 108 provided on substrate 101, electron injection layer 107 provided on cathode 108, electron transport layer 106 provided on electron injection layer 107, luminescent layer 105 provided on electron transport layer 106, hole transport layer 104 provided on luminescent layer 105, hole injection layer 103 provided on hole transport layer 104 and anode 102 provided on hole injection layer 103, for example.

All of the respective layers are not necessarily required, and a minimum constitutional unit may be formed into a configuration formed of anode 102, luminescent layer 105 and cathode 108, and hole injection layer 103, hole transport layer 104, electron transport layer 106 and electron injection layer 107 are an arbitrarily provided layer. Moreover, each layer described above may be formed of a single layer, or may be formed of a plurality of layers.

A form of the layers constituting the organic EL device may be, in addition to the constitutional form of "substrate/anode/hole injection layer/hole transport layer/luminescent layer/electron transport layer/electron injection layer/cathode" described above, in a constitutional form such as "substrate/anode/hole transport layer/luminescent layer/electron transport layer/electron injection layer/cathode," "substrate/anode/hole injection layer/luminescent layer/electron transport layer/electron injection layer/cathode," "substrate/anode/hole injection layer/hole transport layer/luminescent layer/electron injection layer/cathode," "substrate/anode/hole injection layer/hole transport layer/luminescent layer/electron transport layer/cathode," "substrate/anode/luminescent layer/electron transport layer/electron injection layer/cathode," "substrate/anode/hole transport layer/luminescent layer/electron injection layer/cathode," "substrate/anode/hole transport layer/luminescent layer/ electron transport layer/cathode," "substrate/anode/hole injection layer/luminescent layer/electron injection layer/cathode," "substrate/anode/hole injection layer/luminescent layer/electron transport layer/cathode," "substrate/anode/luminescent layer/electron transport layer/cathode" and "substrate/anode/luminescent layer/electron injection layer/cathode."

Luminescent Layer in an Organic Electroluminescent Device

Luminescent layer 105 is a layer which produces luminescence by allowing holes injected from anode 102 to recombine with electrons injected from cathode 108, between electrodes to which an electric field is applied. A material forming luminescent layer 105 only needs be a compound (luminescent compound) which produces luminescence by being excited by recombination between the holes and the electrons, and is preferably a compound that can forms a stable thin film shape, and exhibits strong luminescence (fluorescence) efficiency in a solid state. The luminescent layer of the organic electroluminescent device of the invention includes the anthracene-based compound represented by formula (1) as the host material, the dopant material, and at least one of the polycyclic aromatic compound represented by formula (2) or the multimer thereof having the plurality of structures represented by formula (2).

The luminescent layer may be formed of a single layer or a plurality of layers, and each layer is formed of a luminescent layer material (the host material and the dopant material). The host material and the dopant material may be in one kind, or in combination of a plurality of kinds, respectively. The dopant material may be wholly contained in the host material, or may be partly contained therein. As a doping method, the layer can be formed by vapor codeposition with the host material, or the dopant material is previously mixed with the host material, and then the resulting mixture may be simultaneously deposited.

A use amount of the host material is preferably about 50 to about 99.999%, further preferably about 80 to about 99.95%, and still further preferably about 90 to about 99.9%, based on the total of the luminescent layer material.

A use amount of the dopant material is different depending on a kind of the dopant material, and may be determined according to characteristics of the dopant material. A measure of the use amount of the dopant material is preferably about 0.001 to about 50%, further preferably about 0.05 to about 20%, and still further preferably about 0.1 to about 10%, based on the total of the luminescent layer material. If the amount is within the above-described range, such an amount is preferred in view of capability of preventing a concentration quenching phenomenon, for example.

Substrate in an Organic Electroluminescent Device

Substrate 101 is a support for organic EL device 100, and quartz, glass, metal, plastics or the like is ordinarily used. Substrate 101 is formed in a plate form, a film form or a sheet form according to the purpose, and a glass plate, a metal plate, metallic foil, a plastic film, a plastic sheet or the like is used, for example. Above all, a glass plate and a plate made of a transparent synthetic resin such as polyester, polymethacrylate, polycarbonate or polysulfone are preferred. If the glass substrate is used, soda lime glass, alkali-free glass or the like is used, and a thickness should be at a level enough to maintain mechanical strength, and therefore may be about 0.2 millimeter or more, for example. An upper limit of the thickness is about 2 millimeters or less, and preferably about 1 millimeter or less, for example. As a material of glass, alkali-free glass is preferred because a smaller amount of eluted ions from the glass is better, but soda lime glass on which barrier coating such as $SiO_2$ is applied is also commercially available, and therefore such soda lime glass can be used. Moreover, in order to improve gas barrier properties, a dense gas barrier film such as a silicon oxide film may be provided on at least one side of substrate 101, and particularly when a synthetic resin plate, film or sheet having low gas barrier properties is used as substrate 101, the gas barrier film is preferably provided.

Anode in an Organic Electroluminescent Device

Anode 102 plays a role of injecting the holes into luminescent layer 105. In addition, when hole injection layer 103 and/or hole transport layer 104 is provided between anode 102 and luminescent layer 105, the holes are to be injected into luminescent layer 105 through the above layers.

Specific examples of the material forming anode 102 include an inorganic compound and an organic compound. Specific examples of the inorganic compound include metal (such as aluminum, gold, silver, nickel, palladium and chromium), metal oxide (such as oxide of indium, oxide of tin, indium-tin oxide (ITO) and indium-zinc oxide (IZO)), metal halide (such as copper iodide), copper sulfide, carbon black, ITO glass and NESA glass. Specific examples of the organic compound include polythiophene such as poly(3-methylthiophene), and an electroconductive polymer such as polypyrrole and polyaniline. In addition thereto, the material can be appropriately selected and used from materials used as the anode of the organic EL device.

Resistance of a transparent electrode is not limited, as long as a current sufficient for luminescence of the luminescent device can be supplied, but low resistance is desirable from a viewpoint of power consumption of the luminescent device. For example, an ITO substrate having resistance of about 300 $\Omega$/sq. or less can function as a device electrode, but a substrate having resistance of about 10 $\Omega$/sq. can be supplied at present, and therefore a low-resistance material, for example, a material having resistance of about 100 to 5 $\Omega$/sq., and preferably a material having resistance of about 50 to about 5 $\Omega$/sq. is particularly preferably used. A thickness of ITO can be arbitrarily selected according to a resistance value, but a thickness between about 50 to about 300 nanometers is ordinarily used in many cases.

Hole Injection Layer and a Hole Transport Layer in an Organic Electroluminescent Device Hole injection layer 103 plays a role of efficiently injecting the holes moved from anode 102 into luminescent layer 105 or hole transport layer 104. Hole transport layer 104 plays a role of efficiently transport the holes injected from anode 102 or the holes injected from anode 102 through hole injection layer 103 to luminescent layer 105. Hole injection layer 103 and hole transport layer 104 are formed by lamination and mixing one kind or two or more kinds of hole injection/transport materials, or a mixture of the hole injection/transport materials and a polymer binding agent. Moreover, the layer may be formed by adding inorganic salt such as iron(III) chloride to the hole injection/transport material.

A hole injection/transportable material is required to efficiently inject/transport the holes from a positive electrode between the electrodes to which an electric field is applied, and desirably has high hole injection efficiency to efficiently transport injected holes. Accordingly, a material having low ionization potential, large hole mobility and excellent stability, and hard to generate impurities to be a trap during production and use is preferred.

As the material for forming hole injection layer 103 and hole transport layer 104, an arbitrary compound can be selected and used from a compound which has been commonly used so far as a charge transport material of holes, and a publicly-known compound used for the hole injection layer and the hole transport layer of a p-type semiconductor and the organic EL device. Specific examples thereof include a carbazole derivative (such as N-phenylcarbazole, polyvinylcarbazole), a biscarbazole derivative (such as bis (N-aryl carbazole or bis(N-alkylcarbazole), a triarylamine derivative (such as a polymer having aromatic tertiary amino in a main chain or a side chain, 1,1-bis(4-di-p-tolylaminophenyl)cyclohexane, N,N'-diphenyl-N,N'-di(3-methylphenyl)-4,4'-diaminobiphenyl, N,N'-diphenyl-N,N'-dinaphthyl-4,4'-diaminobiphenyl, N,N'-diphenyl-N,N'-di(3-methylphenyl-4,4'-diphenyl-1,1'-diamine, N,N'-dinaphthyl-N,N'-diphenyl-4,4'-diphenyl-1,1'-diamine, N4,N4'-diphenyl-N4,N4'-bis(9-phenyl-9H-carbazole-3-yl-[1,1'-biphenyl]-4,4'-diamine, N4,N4,N4',N4'-tetra[1,1'-biphenyl]-4-yl-[1,1'-biphenyl]-4,4'-diamine, a triphenylamine derivative such as 4,4',4"-tris(3-methylphenyl(phenyl)amino)triphenylamine and a starburstamine derivative), a stilbene derivative, a phthalocyanine derivative (such as non-metal and copper phthalocyanine), a pyrazoline derivative, a hydrazone-based compound, a benzofuran derivative or a thiophene derivative, an oxadiazole derivative, a quinoxaline derivative (such as 1,4,5,8,9,12-hexaazatriphenylene-2,3,6,7,10,11-hexacarbonitrile), a heterocyclic compound (such as a porphyrin derivative) and polysilane. As a polymer-based compound, polycarbonate having the monomer in a side chain, a styrene derivative, polyvinyl carbazole and polysilane and the like are preferred, but the compound is not limited, as long as the compound can form a thin film required for preparing the luminescent device, and can have the holes injected from the anode and transport the holes.

Moreover, conductivity of an organic semiconductor is known to be significantly influenced by the doping. Such an organic semiconductor matrix material is composed of a compound having good electron donating properties or a compound having good electron accepting properties. A strong electron acceptor such as tetracyano quinone dimethane (TCNQ) or 2,3,5,6-tetrafluorotetracyano-1,4-benzoquinonedimethane (F4TCNQ) is known for doping of an electron donating material (for example, refer to literature "M. Pfeiffer, A. Beyer, T. Fritz, KLeo, Appl. Phys. Lett., 73 (22), 3202-3204 (1998)" and literature "J. Blochwitz, M. Pheiffer, T. Fritz, KLeo, Appl. Phys. Lett., 73 (6), 729-731 (1998)"). The above compounds generate so-called holes by an electron transfer process in an electron donating base material (hole transport material). Conductivity of the base material is fairly significantly changed by the number and mobility of the holes. As a matrix material having hole transport characteristics, for example, a benzidine derivative (such as TPD) or a starburstamine derivative (such as TDATA), or specific metal phthalocyanine (particularly, such as zinc phthalocyanine (ZnPc)) is known (JP 2005-167175 A).

Electron Injection Layer and an Electron Transport Layer in an Organic Electroluminescent Device Electron injection layer 107 plays a role of efficiently injecting electrons moved from cathode 108 into luminescent layer 105 or electron transport layer 106. Electron transport layer 106 plays a role of efficiently transport the electrons injected from cathode 108 or the electrons injected from cathode 108 through electron injection layer 107 to luminescent layer 105. Electron injection layer 107 and electron transport layer 106 are formed by lamination and mixing one kind or two or more kinds of electron injection/transport materials, or a mixture of the electron injection/transport materials and a polymer binding agent.

An electron injection/transport layer means a layer that manages injection of the electrons from the cathode and transportation of the electrons, and desirably has high electron injection efficiency and efficiently transports the electrons injected. Accordingly, a material having large electron affinity, large electron mobility and excellent stability, and hard to generate impurities to be a trap during production and use is preferred. However, in consideration of a transport balance between the holes and the electrons, when the material mainly plays a role of being able to efficiently inhibit the holes from the anode from flowing to a cathode side without recombination, even if the material has a comparatively low electron transport capability, the material has an effect on improving luminescent efficiency as high as a material having high electron transport capability. Accordingly, the electron injection/transport layer in the present embodiment may also include a function of a layer that can efficiently inhibit movement of the holes.

A material (electron transport material) that forms electron transport layer 106 or electron injection layer 107 can be selected and used from a compound which has been commonly used so far as an electron transfer compound in a photoconductive material, and a publicly-known compound used for a hole injection layer and a hole transport layer of an organic EL device.

A material used for the electron transport layer or the electron injection layer preferably contains at least one kind selected from a compound formed of an aromatic ring or a complex aromatic ring composed of one or more atoms selected from carbon, hydrogen, oxygen, sulfur, silicon and phosphorus, a pyrrole derivative and a fused ring derivative thereof and a metal complex having electron accepting nitrogen. Specific examples thereof include a fused ring-based aromatic ring derivative such as naphthalene and anthracene, a styryl-based aromatic ring derivative typified by 4,4'-bis(diphenylethenyl)biphenyl, a perinon derivative, a coumarin derivative, a naphthalimide derivative, a quinone derivative such as anthraquinone and diphenoquinone, a phosphine oxide derivative, a carbazole derivative and an indole derivative. Specific examples of the metal complex having electron accepting nitrogen include a hydroxy azole complex such as a hydroxyphenyl oxazole complex, an azomethine complex, a tropolone metal complex, a flavonol metal complex and a benzoquinoline metal complex. The above materials may be used alone, or in combination of a different material.

Specific examples of other electron transport compounds include a borane derivative, a pyridine derivative, a naphthalene derivative, a fluoranthene derivative, a BO-based derivative, an anthracene derivative, a benzofluorene derivative, a phenanthroline derivative, a perinone derivative, a coumarin derivative, a naphthalimide derivative, an anthraquinone derivative, a diphenoquinone derivative, a diphenylquinone derivative, a perylene derivative, an oxadiazole derivative (such as 1,3-bis[(4-t-butylphenyl)1,3,4-oxadiazolyl]phenylene), a thiophene derivative, a triazole derivative (such as N-naphthyl-2,5-diphenyl-1,3,4-triazole), a thiadiazole derivative, a metal complex of an oxime derivative, a quinolinol metal complex, a quinoxaline derivative, a polymer of a quinoxaline derivative, a benzazole compound, a gallium complex, a pyrazol derivative, a perfluorophenylene derivative, a triazine derivative, a pyrazine derivative, a benzoquinoline derivative (such as 2,2'-bis(benzo[h]quinolin-2-yl)-9,9'-spirobifluorene), an imidazopyridine derivative, a borane derivative, a benzimidazole derivative (such as tris(N-phenylbenzimidazole-2-yl)benzene), a benzooxazol derivative, a thiazole derivative, a benzothiazole derivative, a quinoline derivative, an oligo pyridine derivative such as terpyridine, a bipyridine derivative, a terpyridine derivative (such as 1,3-bis(4'-(2,2':6',2''-terpyridinyl))benzene), a naphthyridine derivative (such as bis(1-naphthyl)-4-(1,8-naphthyridine-2-yl)phenyl phosphine oxide), an aldazine derivative, a pyrimidine derivative, a carbazole derivative, an indole derivative, a phosphorus oxide derivative, a bis-styryl derivative, a silole derivative and an azo phosphorus derivative.

Moreover, a metal complex having electron accepting nitrogen can also be used, and specific examples thereof include a quinolinol-based metal complex, a hydroxyazole complex such as a hydroxyphenyloxazole complex, an azomethine complex, a tropolone metal complex, a flavonol metal complex and a benzoquinoline metal complex.

The above materials may be used alone, or in combination of a different material.

Among the above-mentioned materials, a borane derivative, a pyridine derivative, a fluoranthene derivative, a BO-based derivative, an anthracene derivative, a benzofluorene derivative, a phosphine oxide derivative, a pyrimidine derivative, a carbazole derivative, a triazine derivative, a benzimidazole derivative, a phenanthroline derivative and a quinolinol metal complex are preferred.

Borane Derivative

The borane derivative is a compound represented by formula (ETM-1), for example, and is disclosed in detail in JP 2007-27587 A.

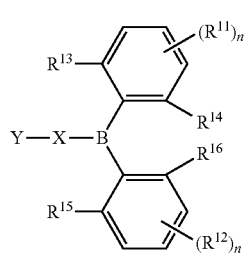
(ETM-1)

In formula (ETM-1), $R^{11}$ and $R^{12}$ are independently at least one of hydrogen, alkyl, cycloalkyl, aryl which may be subjected to substitution, silyl which is subjected to substitution, a nitrogen-containing heterocyclic ring which may be subjected to substitution, or cyano, and $R^{13}$ to $R^{16}$ are independently alkyl which may be subjected to substitution, cycloalkyl which may be subjected to substitution or aryl which may be subjected to substitution, and X is arylene which may be subjected to substitution, and Y is aryl having 16 or less carbons which may be subjected to substitution, boryl which is subjected to substitution, or carbazolyl which may be subjected to substitution, and n is independently an integer from 0 to 3. Moreover, specific examples of the substituent in the case of "which may be subjected to substitution" or "which is subjected to substitution" include aryl, heteroaryl, alkyl or cycloalkyl.

Among the compounds represented by formula (ETM-1), a compound represented by (ETM-1-2) and a compound represented by formula (ETM-1-1) are preferred.

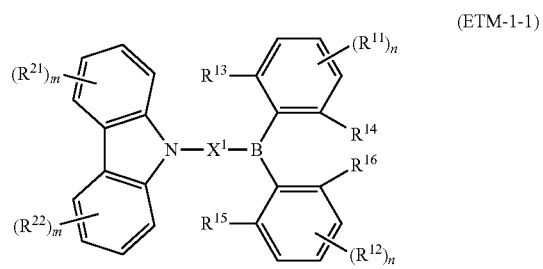
(ETM-1-1)

In formula (ETM-1-1), $R^{11}$ and $R^{12}$ are independently at least one of hydrogen, alkyl, cycloalkyl, aryl which may be subjected to substitution, silyl which is subjected to substitution, a nitrogen-containing heterocyclic ring which may be subjected to substitution or cyano, and $R^{13}$ to $R^{16}$ are independently alkyl which may be subjected to substitution, cycloalkyl which may be subjected to substitution or aryl which may be subjected to substitution, and $R^{21}$ and $R^{22}$ are independently at least one of hydrogen, alkyl, cycloalkyl, aryl which may be subjected to substitution, silyl which is subjected to substitution, a nitrogen-containing heterocyclic ring which may be subjected to substitution or cyano, and $X^1$ is arylene having 20 or less carbons which may be subjected to substitution, and n is independently an integer from 0 to 3, and m is independently an integer from 0 to 4. Moreover, specific examples of the substituent in the case of "which may be subjected to substitution" or "which is subjected to substitution" include aryl, heteroaryl, alkyl or cycloalkyl.

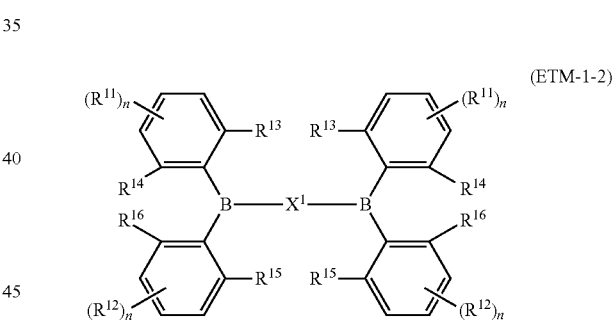
(ETM-1-2)

In formula (ETM-1-2), $R^{11}$ and $R^{12}$ are independently at least one of hydrogen, alkyl, cycloalkyl, aryl which may be subjected to substitution, silyl which is subjected to substitution, a nitrogen-containing heterocyclic ring which may be subjected to substitution or cyano, and $R^{13}$ to $R^{16}$ are independently alkyl which may be subjected to substitution, cycloalkyl which may be subjected to substitution or aryl which may be subjected to substitution, and $X^1$ is arylene having 20 or less carbons which may be subjected to substitution, and n is independently an integer from 0 to 3. Moreover, specific examples of the substituent in the case of "which may be subjected to substitution" or "which is subjected to substitution" include aryl, heteroaryl, alkyl or cycloalkyl.

Specific examples of $X^1$ include divalent groups represented by formulas (X-1) to (X-9).

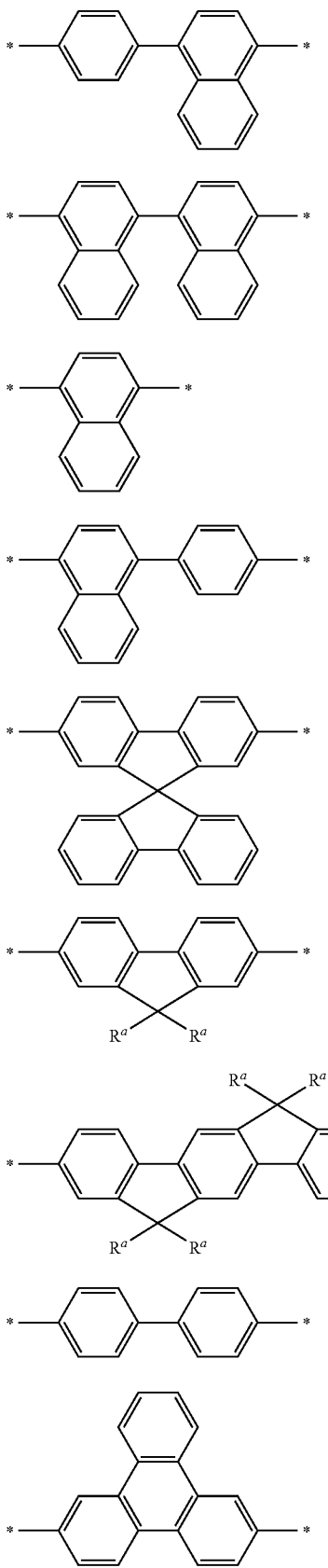

(X-1)
(X-2)
(X-3)
(X-4)
(X-5)
(X-6)
(X-7)
(X-8)
(X-9)

wherein, in each formula, $R^a$ is independently alkyl cycloalkyl or phenyl which may be subjected to substitution, and a position "*" represents a bonding position.

Specific examples of the borane derivative include compounds described below.

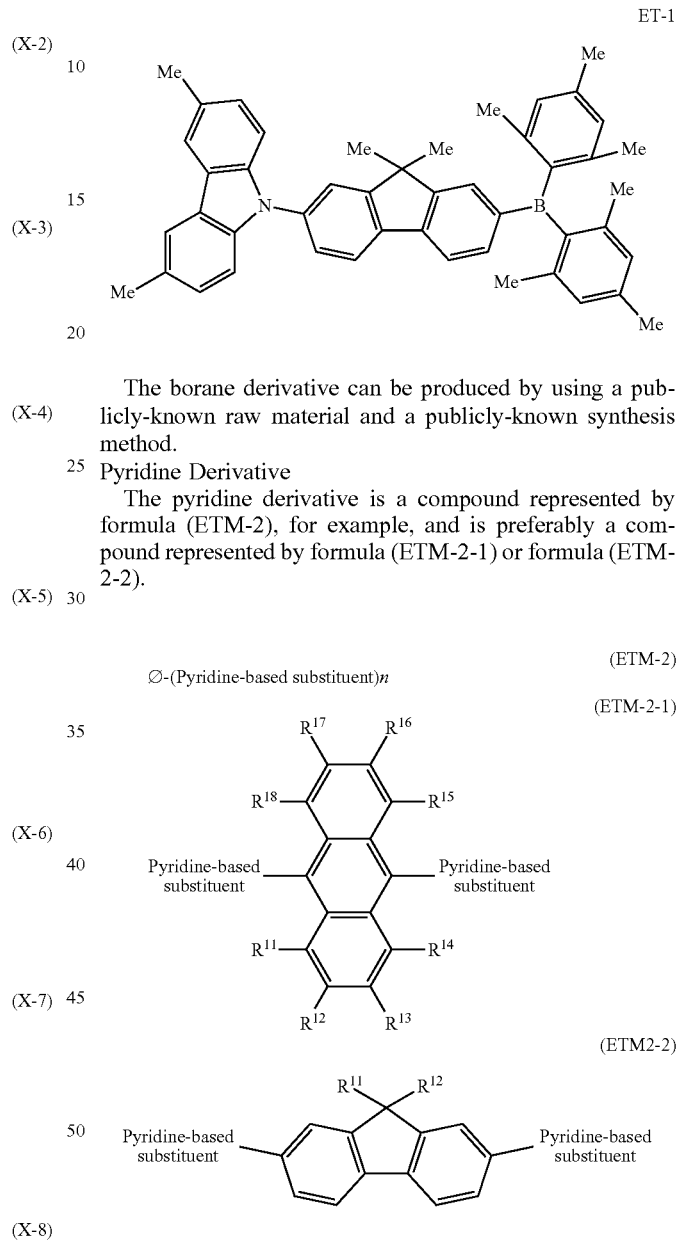

The borane derivative can be produced by using a publicly-known raw material and a publicly-known synthesis method.

Pyridine Derivative

The pyridine derivative is a compound represented by formula (ETM-2), for example, and is preferably a compound represented by formula (ETM-2-1) or formula (ETM-2-2).

Then, φ is an n-valent aryl ring (preferably, an n-valent benzene ring, naphthalene ring, anthracene ring, fluorene ring, benzofluorene ring, phenalene ring, phenanthrene ring or triphenylene ring), and n is an integer from 1 to 4.

In formula (ETM-2-1), $R^{11}$ to $R^{18}$ are independently hydrogen, alkyl (preferably alkyl having 1 to 24 carbons), cycloalkyl (preferably cycloalkyl having 3 to 12 carbons) or aryl (preferably aryl having 6 to 30 carbons).

In formula (ETM-2-2), $R^{11}$ and $R^{12}$ are independently hydrogen, alkyl (preferably alkyl having 1 to 24 carbons), cycloalkyl (preferably cycloalkyl having 3 to 12 carbons), or aryl (preferably aryl having 6 to 30 carbons), and $R^1$ and $R^{12}$ may be bonded to each other to form a ring.

In each formula, the "pyridine-based substituents" is represented by any of formulas (Py-1) to (Py-15), and the pyridine-based substituent may be independently subjected substitution for alkyl having 1 to 4 carbons or cycloalkyl having 5 to 10 carbons. Moreover, the pyridine-based substituent may be bonded to p, an anthracene ring or a fluorene ring in each formula through a phenylene group or a naphthylene group.

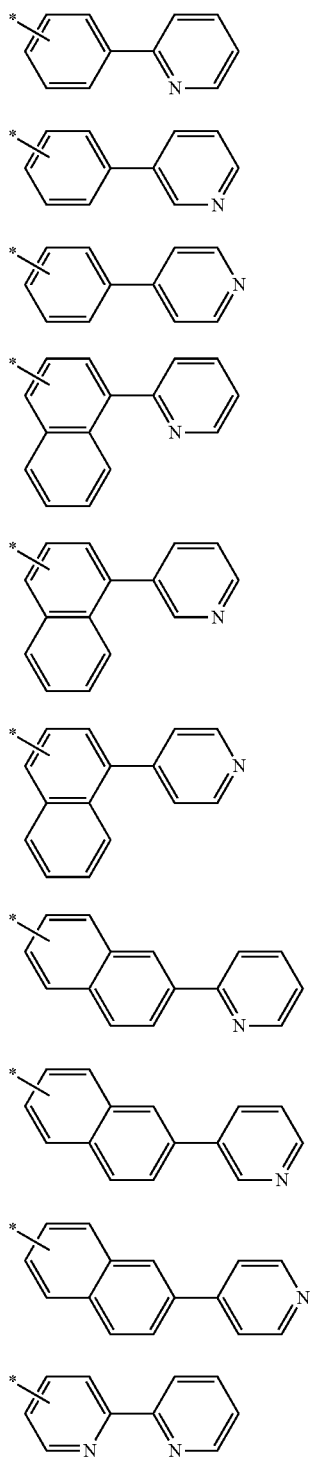

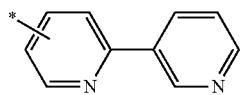
(Py-11)

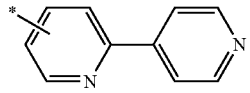
(Py-12)

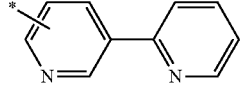
(Py-13)

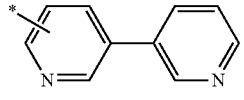
(Py-14)

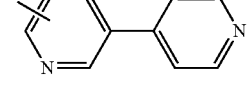
(Py-15)

The pyridine-based substituents is represented by any of formulas (Py-1) to (Py-15), and is preferably represented by any of formulas (Py-21) to (Py-44) among the formulas (a position "*" in the formula represents a bonding position).

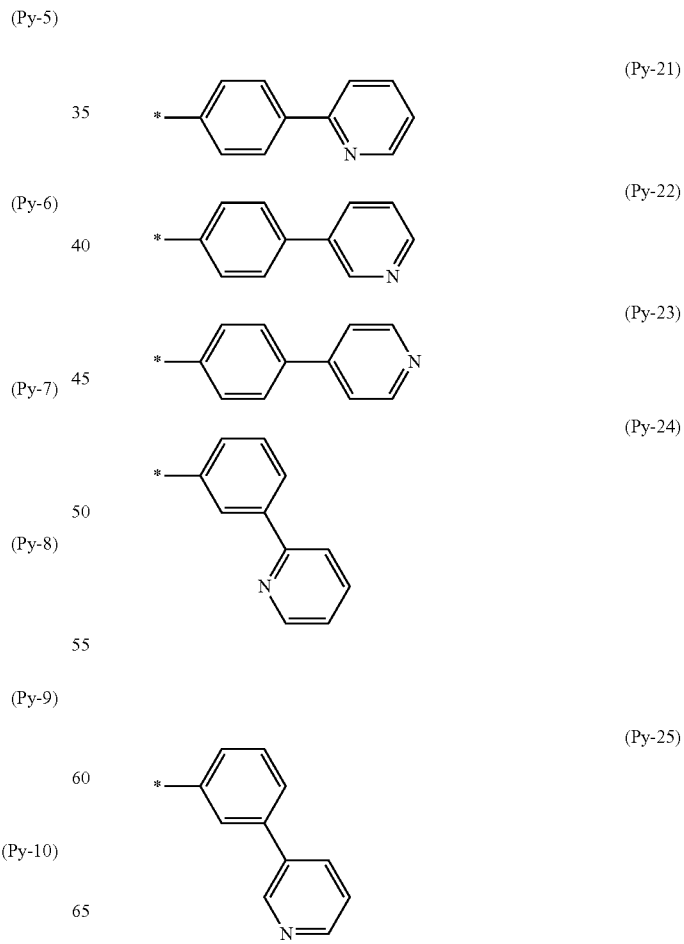

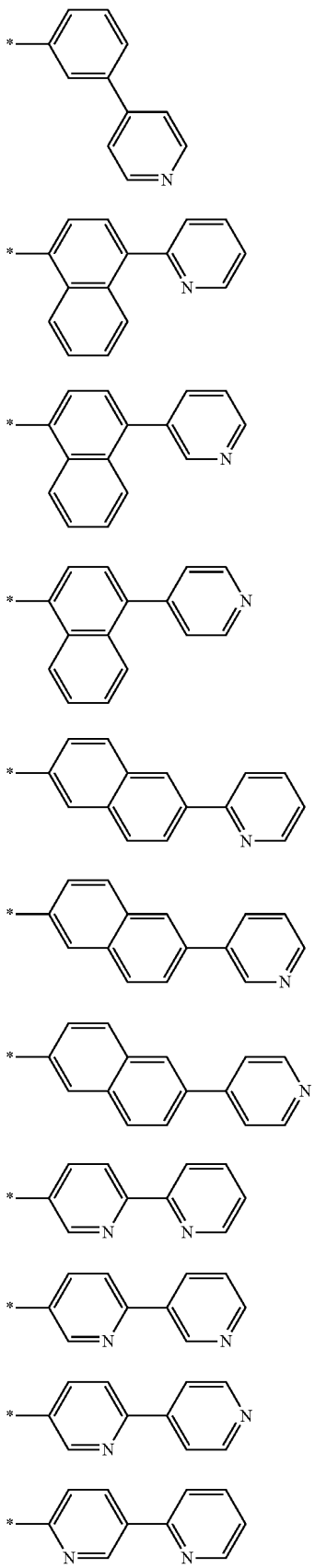
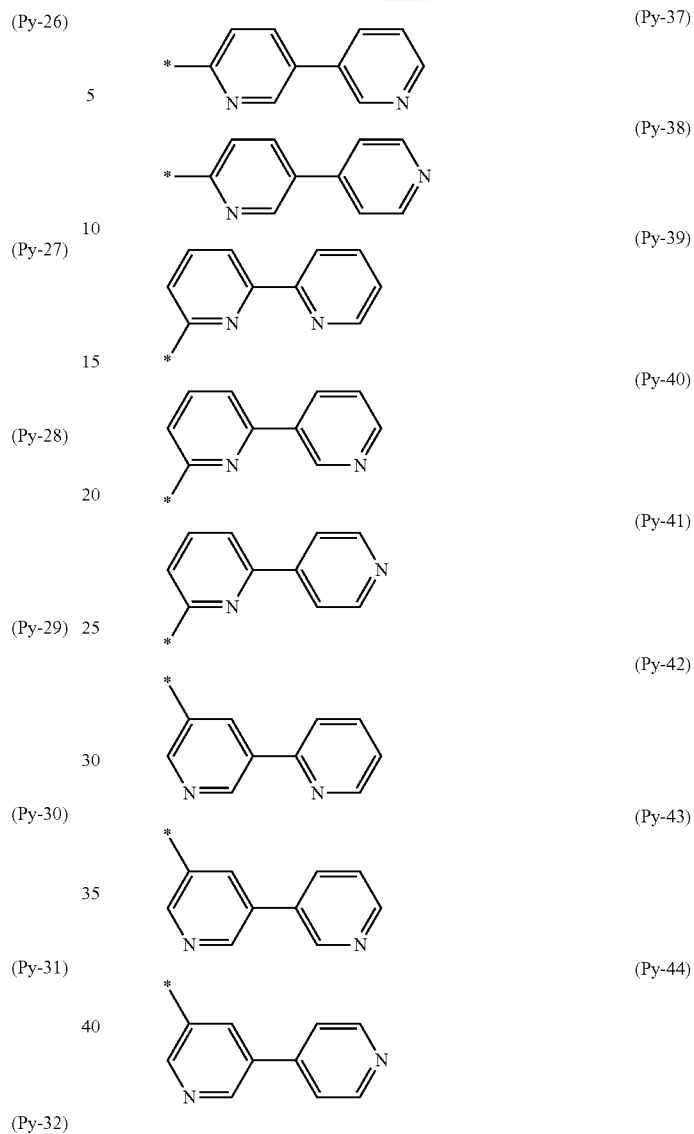

At least one hydrogen in each pyridine derivative may be replaced by deuterium, and one of two "pyridine-based substituents" in formula (ETM-2-1) and formula (ETM-2-2) may be subjected to substitution for aryl.

The "alkyl" in $R^{11}$ to $R^{18}$ may be any of straight-chain alkyl and branched-chain alkyl, and specific examples thereof include straight-chain alkyl having 1 to 24 carbons or branched-chain alkyl having 3 to 24 carbons. Preferred "alkyl" is alkyl having 1 to 18 carbons (branched-chain alkyl having 3 to 18 carbons). Further preferred "alkyl" is alkyl having 1 to 12 carbons (branched-chain alkyl having 3 to 12 carbons). Still further preferred "alkyl" is alkyl having 1 to 6 carbons (branched-chain alkyl having 3 to 6 carbons). Particularly preferred "alkyl" is alkyl having 1 to 4 carbons (branched-chain alkyl having 3 to 4 carbons).

Specific examples of the "alkyl" include methyl, ethyl, n-propyl, isopropyl, n-butyl, isobutyl, s-butyl, t-butyl, n-pentyl, isopentyl, neopentyl, t-pentyl, n-hexyl, 1-methylpentyl, 4-methyl-2-pentyl, 3,3-dimethylbutyl, 2-ethylbutyl, n-heptyl, 1-methylhexyl, n-octyl, t-octyl, 1-methylheptyl, 2-ethylhexyl, 2-propylpentyl, n-nonyl, 2,2-dimethylheptyl, 2,6-dimethyl-4-heptyl, 3,5,5-trimethylhexyl, n-decyl, n-undecyl, 1-methyldecyl, n-dodecyl, n-tridecyl, 1-hexylheptyl, n-tetradecyl, n-pentadecyl, n-hexadecyl, n-heptadecyl, n-octadecyl and n-eicosyl.

As the alkyl having 1 to 4 carbons by which a pyridine-based substituent is replaced, the above-mentioned description for the alkyl can be quoted.

Specific examples of the "cycloalkyl" in $R^{11}$ to $R^{18}$ include cycloalkyl having 3 to 12 carbons. Preferred "cycloalkyl" is cycloalkyl having 3 to 10 carbons. Further preferred "cycloalkyl" is cycloalkyl having 3 to 8 carbons. Still further preferred "cycloalkyl" is cycloalkyl having 3 to 6 carbons. Specific examples of the "cycloalkyl" include cyclopropyl, cyclobutyl, cyclopentyl, cyclohexyl, methyl cyclopentyl, cycloheptyl, methylcyclohexyl, cyclooctyl or dimethylcyclohexyl.

As the cycloalkyl having 5 to 10 carbons by which a pyridine-based substituent is replaced, the above-mentioned description for the cycloalkyl can be quoted.

The "aryl" in $R^{11}$ to $R^{18}$ is preferably aryl having 6 to 30 carbons, further preferably aryl having 6 to 18 carbons, still further preferably aryl having 6 to 14 carbons, and particularly preferably aryl having 6 to 12 carbons.

Specific examples of the "aryl having 6 to 30 carbons" include phenyl as monocyclic aryl, (1-,2-)naphthyl as fused bicyclic aryl, acenaphthylene(1-,3-,4-,5-)yl, fluorene-(1-, 2-, 3-, 4-, 9-)yl, phenalene(1-,2-)yl, and (1-,2-,3-,4-,9-)phenanthryl as fused tricyclic aryl, triphenylene(1-,2-)yl, pyrene(1-,2-,4-)yl, and naphthacene(1-,2-,5-)yl as fused tetracyclic aryl, perylene(1-,2-,3-)yl and pentacene(1-,2-,5-,6-)yl as fused pentacyclic aryl.

Preferred examples of the "aryl having 6 to 30 carbons" include phenyl, naphthyl, phenanthryl, chrysenyl or triphenylenyl, and further preferred examples thereof include phenyl, 1-naphthyl, 2-naphthyl or phenanthryl, and particularly preferred examples thereof include phenyl, 1-naphthyl or 2-naphthyl.

$R^{11}$ and $R^{12}$ in formula (ETM-2-2) may be bonded to each other to form a ring, and as a result, cyclobutane, cyclopentane, cyclopentene, cyclopentadiene, cyclohexane, fluorene, indene or the like may be spiro-bonded to a 5-membered ring of a fluorene skeleton.

Specific examples of the pyridine derivative include compounds described below.

ET-2

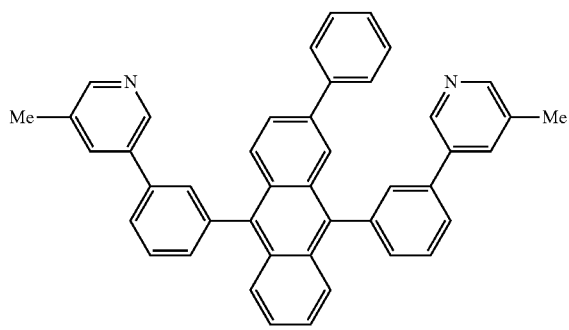

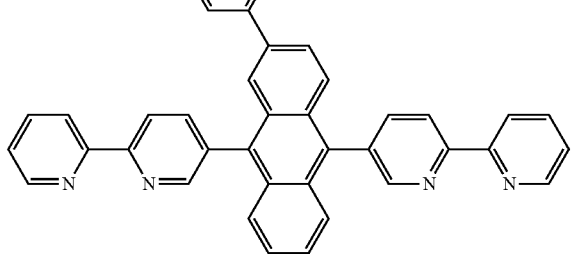

ET-3

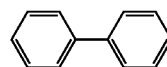

ET-6

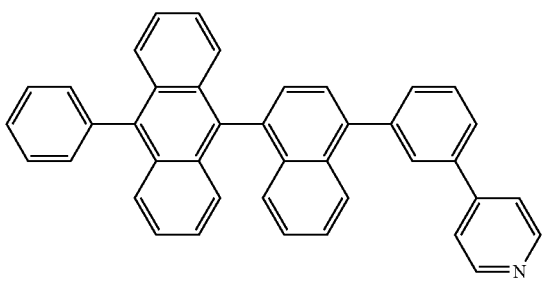

ET-7

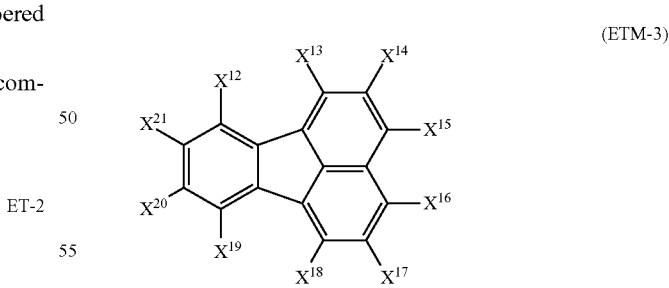

The pyridine derivative can be produced by using a publicly-known raw material and a publicly-known synthesis method.

Fluoranthene Derivative

The fluoranthene derivative is a compound represented by formula (ETM-3), for example, and is disclosed in detail in WO 2010/134352 A.

(ETM-3)

$X^{12}$ $X^{13}$ $X^{14}$
$X^{21}$ $X^{15}$
$X^{20}$ $X^{16}$
$X^{19}$ $X^{18}$ $X^{17}$

In formula (ETM-3), $X^{12}$ to $X^{21}$ represent hydrogen, halogen, straight-chain, branched-chain or cyclic alkyl, straight-chain, branched-chain or cyclic alkoxy, substituted or unsubstituted aryl or substituted or unsubstituted heteroaryl. Here, specific examples of a substituent in the case of being subjected to substitution include aryl, heteroaryl, alkyl or cycloalkyl.

Specific examples of the fluoranthene derivative include compounds described below.

(ETM-3-1)

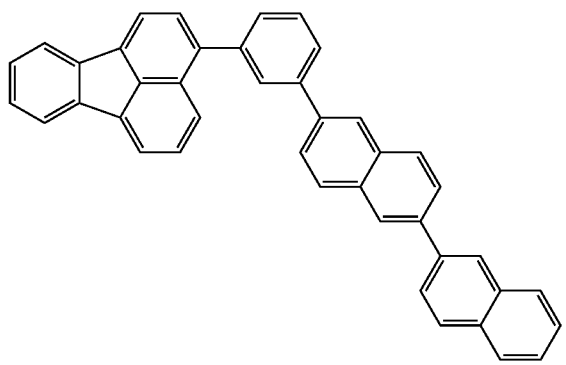

(ETM-3-2)

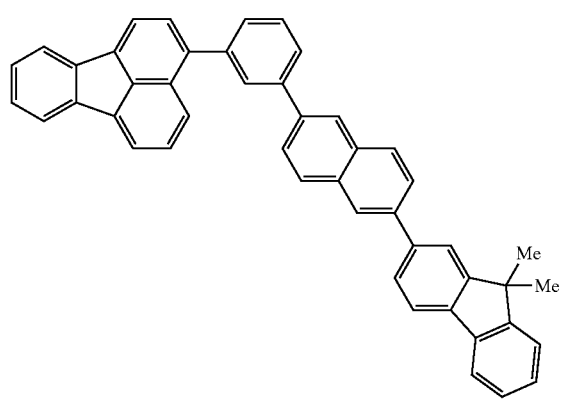

(ETM-3-3)

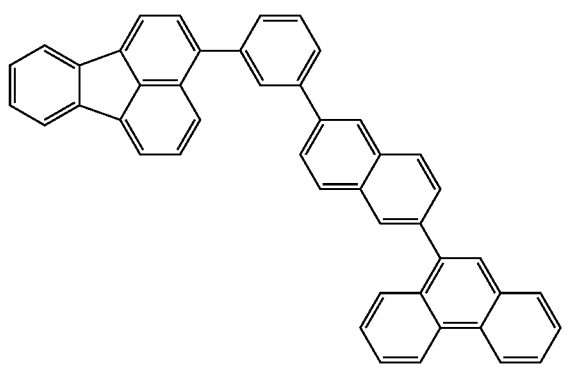

BO-Based Derivative

The BO-based derivative is a polycyclic aromatic compound represented by formula (ETM-4) or a multimer of a polycyclic aromatic compound having a plurality of structures represented by formula (ETM-4), for example.

(ETM-4)

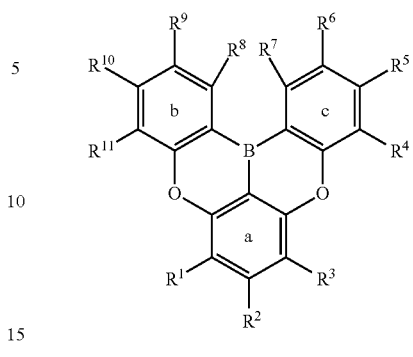

$R^1$ to $R^{11}$ are independently hydrogen, aryl, heteroaryl, diarylamino, diheteroarylamino, arylheteroarylamino, alkyl, cycloalkyl, alkoxy or aryloxy, and at least one hydrogen in the groups may be replaced by aryl, heteroaryl, alkyl or cycloalkyl.

Moreover, adjacent groups of $R^1$ to $R^{11}$ may be bonded to form an aryl ring or a heteroaryl ring together with an a ring, a b ring or a c ring, and at least one hydrogen in the ring formed may be replaced by aryl, heteroaryl, diarylamino, diheteroarylamino, arylheteroarylamino, alkyl, cycloalkyl, alkoxy or aryloxy, and at least one hydrogen in the groups may be replaced by aryl, heteroaryl, alkyl or cycloalkyl.

Moreover, at least one hydrogen in the compound or the structure represented by formula (ETM-4) may be replaced by halogen or deuterium.

For description of a substituent or a form of ring formation in formula (ETM-4), the above-mentioned description for the polycyclic aromatic compound represented by formula (1) can be quoted.

Specific examples of the BO-based derivative include compounds described below.

ET-5

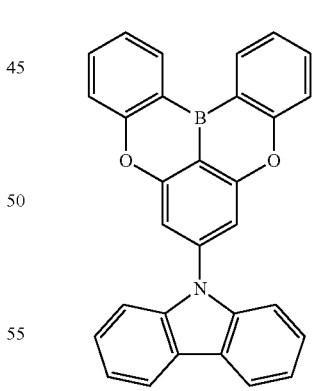

The BO-based derivative can be produced by using a publicly-known raw material and a publicly-known synthesis method.

Anthracene Derivative

One of the anthracene derivatives is a compound represented by formula (ETM-5-1), for example.

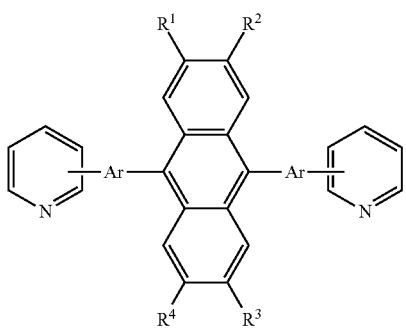

(ETM-5-1)

Ar is independently divalent benzene or naphthalene, and $R^1$ to $R^4$ are independently hydrogen, alkyl having 1 to 6 carbons, cycloalkyl having 3 to 6 carbons or aryl having 6 to 20 carbons.

Ar can be independently appropriately selected from divalent benzene or naphthalene, and two Ar's may be different from or identical to each other, but is preferably identical to each other from a viewpoint of ease of synthesis of the anthracene derivative. Ar is bonded to pyridine to form a "site formed of Ar and pyridine," and the site is bonded to anthracene as a group represented by any of formulas (Py-1) to (Py-12). A position "*" in the following formulas represents a bonding position.

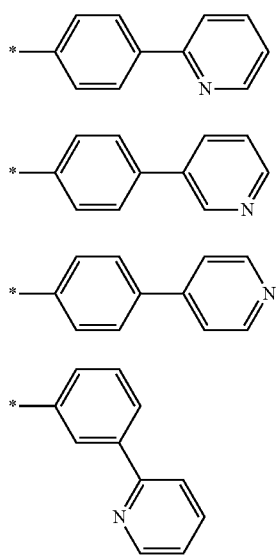

(Py-1)

(Py-2)

(Py-3)

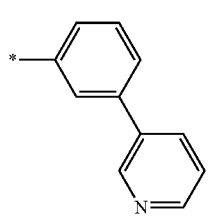

(Py-4)

(Py-5)

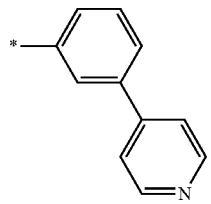

(Py-6)

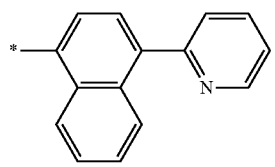

(Py-7)

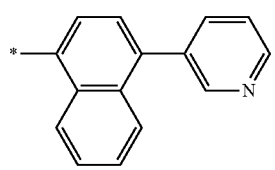

(Py-8)

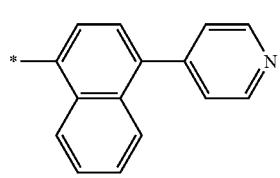

(Py-9)

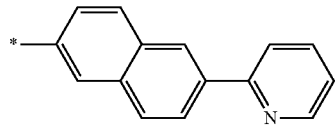

(Py-10)

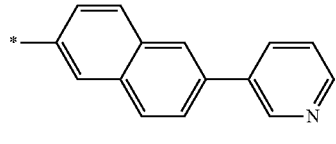

(Py-11)

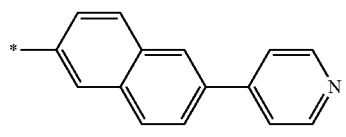

(Py-12)

Among the above groups, a group represented by any of formulas (Py-1) to (Py-6) is preferred, and a group represented by any of formulas (Py-1) to (Py-9) is further preferred. In two "sites formed of Ar and pyridine" bonded to anthracene, the structure may be identical to or different from each other, but is preferably identical to each other from a viewpoint of ease of synthesis of the anthracene derivative. However, from a viewpoint of device characteristics, the structures of two "sites formed of Ar and pyridine" are preferably identical to or different from each other.

Alkyl having 1 to 6 carbons in $R^1$ to $R^4$ may be any of straight-chain alkyl and branched-chain alkyl. More specifically, straight-chain alkyl having 1 to 6 carbons or branched-chain alkyl having 3 to 6 carbons is preferred. Alkyl having 1 to 4 carbons (branched-chain alkyl having 3 to 4 carbons) is further preferred. Specific examples thereof include methyl, ethyl, n-propyl, isopropyl, n-butyl, isobutyl, s-butyl, t-butyl, n-pentyl, isopentyl, neopentyl, t-pentyl, n-hexyl, 1-methylpentyl, 4-methyl-2-pentyl, 3,3-dimethylbutyl or 2-ethylbutyl, and methyl, ethyl, n-propyl, isopropyl, n-butyl, isobutyl, s-butyl or t-butyl is preferred, and methyl, ethyl or t-butyl is further preferred.

Specific examples of the cycloalkyl having 3 to 6 carbons in $R^1$ to $R^4$ include cyclopropyl, cyclobutyl, cyclopentyl, cyclohexyl, methylcyclopentyl, cycloheptyl, methylcyclohexyl, cyclooctyl or dimethylcyclohexyl.

As the aryl having 6 to 20 carbons in $R^1$ to $R^4$, aryl having 6 to 16 carbons is preferred, aryl having 6 to 12 carbons is further preferred, and aryl having 6 to 10 carbons is particularly preferred.

Specific examples of the "aryl having 6 to 20 carbons" include phenyl, (o-,m-,p-)tolyl, (2,3-, 2,4-, 2,5-, 2,6-, 3,4-, 3,5-)xylyl, mesityl(2,4,6-trimethylphenyl) and (o-,m-,p-)cumenyl as monocyclic aryl, (2-,3-,4-)biphenylyl as bicyclic aryl, (1-,2-)naphthyl as fused bicyclic aryl, terphenylyl (m-terphenyl-2'-yl, m-terphenyl-4'-yl, m-terphenyl-5'-yl, o-terphenyl-3'-yl, o-terphenyl-4'-yl, p-terphenyl-2'-yl, m-terphenyl-2-yl, m-terphenyl-3-yl, m-terphenyl-4-yl, o-terphenyl-2-yl, o-terphenyl-3-yl, o-terphenyl-4-yl, p-terphenyl-2-yl, p-terphenyl-3-yl, and p-terphenyl-4-yl) as tricyclic aryl, anthracene-(1-,2-,9-)yl, acenaphthylene(1-,3-,4-,5-)yl, fluorene-(1-,2-,3-,4-,9-)yl, phenalene (1-,2-)yl, and (1-,2-,3-,4-,9-)phenanthryl as fused tricyclic aryl, triphenylene(1-,2-)yl, pyrene(1-,2-,4-)yl, and tetracene (1-,2-,5-)yl as fused tetracyclic aryl, and perylene-(1-,2-,3-)yl as fused pentacyclic aryl.

As the "aryl having 6 to 20 carbons," phenyl, biphenylyl, terphenylyl or naphthyl is preferred, phenyl, biphenylyl, 1-naphthyl, 2-naphthyl or m-terphenyl-5'-yl is further preferred, phenyl, biphenylyl, 1-naphthyl or 2-naphthyl is still further preferred, and phenyl is most preferred.

One of the anthracene derivatives is a compound represented by formula (ETM-5-2), for example.

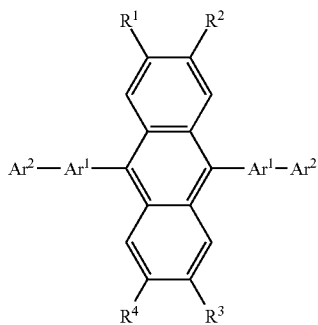

(ETM-5-2)

$Ar^1$ is independently a single bond, divalent benzene, naphthalene, anthracene, fluorene or phenalene.

$Ar^2$ is independently aryl having 6 to 20 carbons, and the same description as the "aryl having 6 to 20 carbons" in formula (ETM-5-1) can be quoted. Aryl having 6 to 16 carbons is preferred, aryl having 6 to 12 carbons is further preferred, and aryl having 6 to 10 carbons is particularly preferred. Specific examples thereof include phenyl, biphenylyl, naphthyl, terphenylyl, anthracenyl, acenaphthylenyl, fluorenyl, phenalenyl, phenanthryl, triphenylenyl, pyrenyl, tetracenyl and perylenyl.

$R^1$ to $R^4$ are independently hydrogen, alkyl having 1 to 6 carbons, cycloalkyl having 3 to 6 carbons or aryl having 6 to 20 carbons, and the description in formula (ETM-5-1) can be quoted.

Specific examples of the above anthracene derivatives include compounds described below.

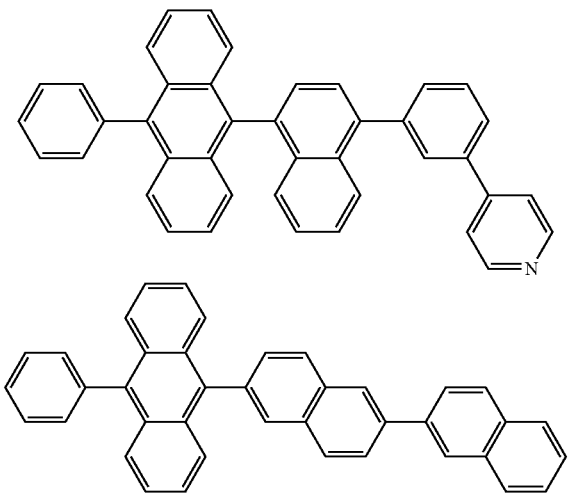

ET-7

The above anthracene derivatives can be produced by using a publicly-known raw material and a publicly-known synthesis method.

Benzofluorene Derivative

The benzofluorene derivative is a compound represented by formula (ETM-6), for example.

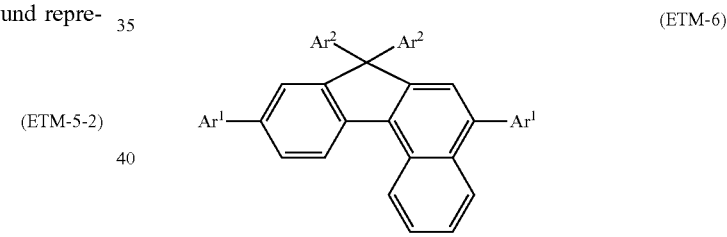

(ETM-6)

$Ar^1$ is independently aryl having 6 to 20 carbons, and the same description as the "aryl having 6 to 20 carbons" in formula (ETM-5-1) can be quoted. Aryl having 6 to 16 carbons is preferred, aryl having 6 to 12 carbons is further preferred, and aryl having 6 to 10 carbons is particularly preferred. Specific examples thereof include phenyl, biphenylyl, naphthyl, terphenylyl, anthracenyl, acenaphthylenyl, fluorenyl, phenalenyl, phenanthryl, triphenylenyl, pyrenyl, tetracenyl and perylenyl.

$Ar^2$ is independently hydrogen, alkyl (preferably alkyl having 1 to 24 carbons), cycloalkyl (preferably cycloalkyl having 3 to 12 carbons), or aryl (preferably aryl having 6 to 30 carbons), and two $Ar^2$'s may be bonded to form a ring.

The "alkyl" in $Ar^2$ may be any of straight-chain alkyl and branched-chain alkyl, and specific examples thereof include straight-chain alkyl having 1 to 24 carbons or branched-chain alkyl having 3 to 24 carbons. Preferred "alkyl" is alkyl having 1 to 18 carbons (branched-chain alkyl having 3 to 18 carbons). Further preferred "alkyl" is alkyl having 1 to 12 carbons (branched-chain alkyl having 3 to 12 carbons). Still further preferred "alkyl" is alkyl having 1 to 6 carbons (branched-chain alkyl having 3 to 6 carbons). Particularly preferred "alkyl" is alkyl having 1 to 4 carbons (branched-chain alkyl having 3 to 4 carbons). Specific examples of the "alkyl" include methyl, ethyl, n-propyl, isopropyl, n-butyl, isobutyl, s-butyl, t-butyl, n-pentyl, isopentyl, neopentyl, t-pentyl, n-hexyl, 1-methylpentyl, 4-methyl-2-pentyl, 3,3-dimethylbutyl, 2-ethylbutyl, n-heptyl and 1-methylhexyl.

Specific examples of the "cycloalkyl" in $Ar^2$ include cycloalkyl having 3 to 12 carbons. Preferred "cycloalkyl" is cycloalkyl having 3 to 10 carbons. Further preferred "cycloalkyl" is cycloalkyl having 3 to 8 carbons. Still further preferred "cycloalkyl" is cycloalkyl having 3 to 6 carbons. Specific examples of the "cycloalkyl" include cyclopropyl, cyclobutyl, cyclopentyl, cyclohexyl, methyl cyclopentyl, cycloheptyl, methylcyclohexyl, cyclooctyl or dimethylcyclohexyl.

As the "aryl" in $Ar^2$, aryl having 6 to 30 carbons is preferred, aryl having 6 to 18 carbons is further preferred, aryl having 6 to 14 carbons is still further preferred, and aryl having 6 to 12 carbons is particularly preferred.

Specific examples of the "aryl having 6 to 30 carbons" include phenyl, naphthyl, acenaphthylenyl, fluorenyl, phenalenyl, phenanthryl, triphenylenyl, pyrenyl, naphthacenyl, perylenyl and pentacenyl.

Two $Ar^2$'s may be bonded to form a ring, and as a result, cyclobutane, cyclopentane, cyclopentene, cyclopentadiene, cyclohexane, fluorene, indene or the like may be spiro-bonded to a 5-membered ring of a fluorene skeleton.

Specific examples of the benzofluorene derivative include compounds described below.

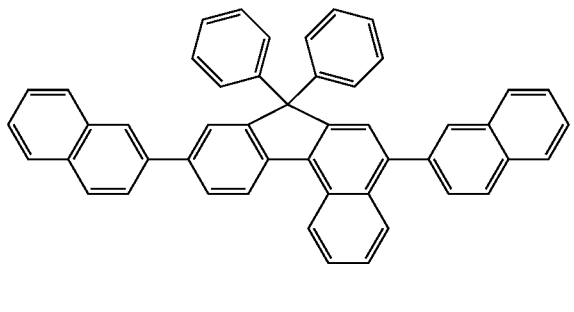

The benzofluorene derivative can be produced by using a publicly-known raw material and a publicly-known synthesis method.

Phosphine Oxide Derivative

The phosphine oxide derivative is a compound represented by formula (ETM-7-1), for example. The detail is also described in WO 2013/079217 A.

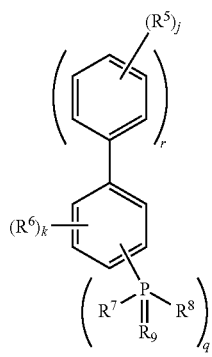

(ETM-7-1)

$R^5$ is substituted or unsubstituted, alkyl having 1 to 20 carbons, cycloalkyl having 3 to 20 carbons, aryl having 6 to 20 carbons or heteroaryl having 5 to 20 carbons, $R^6$ is CN, substituted or unsubstituted, alkyl having 1 to 20 carbons, cycloalkyl having 3 to 20 carbons, heteroalkyl having 1 to 20 carbons, aryl having 6 to 20 carbons, heteroaryl having 5 to 20 carbons, alkoxy having 1 to 20 carbons or aryloxy having 5 to 20 carbons, $R^7$ and $R^8$ are independently substituted or unsubstituted, aryl having 6 to 20 carbons or heteroaryl having 5 to 20 carbons, and R9 is oxygen or sulfur, and j is 0 or 1, k is 0 or 1, r is an integer from 0 to 4, and q is an integer from 1 to 3.

Here, specific examples of the substituent in the case of being subjected to substitution include aryl, heteroaryl, alkyl or cycloalkyl.

The phosphine oxide derivative may be a compound represented by formula (ETM-7-2), for example.

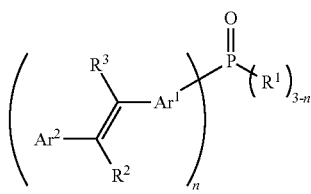

(ETM-7-2)

$R^1$ to $R^3$ may be identical to or different from each other, and is selected from hydrogen, alkyl, cycloalkyl, aralkyl, alkenyl, cycloalkenyl, alkynyl, alkoxy, alkylthio, cycloalkylthio, aryl ether, aryl thioether, aryl, a heterocyclic group, halogen, cyano, aldehyde, carbonyl, carboxyl, amino, nitro, silyl and a fused ring formed between an adjacent substituent and one of $R^1$ to $R^3$.

$Ar^1$ may be identical to or different from each other, and is allylene or heteroallylene. $Ar^2$ may be identical to or different from each other, and is aryl or heteroaryl, in which, at least one of $Ar^1$ and $Ar^2$ has a substituent, or forms a fused ring between an adjacent substituent and one of $Ar^1$ and $Ar^2$. Then, n is an integer from 0 to 3, and when n is 0, an unsaturated structure part does not exist, and when n is 3, $R^1$ does not exist.

Among the above substituents, the alkyl represents a saturated aliphatic hydrocarbon group such as methyl, ethyl, propyl and butyl, which may be unsubstituted or substituted. The substituent in the case of being subjected to substitution is not particularly limited, and specific examples thereof include alkyl, aryl and a heterocycle group, and the above point is common also in the following description. Moreover, the number of carbons of the alkyl is not particularly limited, and is ordinarily in the range of 1 to 20 in view of ease of availability or cost.

Moreover, the cycloalkyl represents a saturated alicyclic hydrocarbon group such as cyclopropyl, cyclohexyl, norbornyl and adamanthyl, which may be unsubstituted or substituted. The number of carbons in an alkyl part is not particularly limited, and is ordinarily in the range of 3 to 20.

Moreover, the aralkyl represents an aromatic hydrocarbon group through aliphatic hydrocarbon such as benzyl and phenylethyl, for example, and both of the aliphatic hydrocarbon and the aromatic hydrocarbon may be unsubstituted or substituted. The number of carbons on an aliphatic part is not particularly limited, and is ordinarily in the range of 1 to 20.

Moreover, the alkenyl represents an unsaturated aliphatic hydrocarbon group containing a double bond such, as vinyl, allyl and butadienyl, for example, which may be unsubstituted or substituted. The number of carbons in the alkenyl is not particularly limited, and is ordinarily in the range of 2 to 20.

Moreover, the cycloalkenyl represents an unsaturated alicyclic hydrocarbon group containing a double bond, such as cyclopentenyl, cyclopentadienyl and cyclohexene, for example, which may be unsubstituted or substituted.

Moreover, the alkynyl represents an unsaturated aliphatic hydrocarbon group containing a triple bond, such as acetylenyl, for example, which may be unsubstituted or substituted. The number of carbons in the alkynyl is not particularly limited, and is ordinarily in the range of 2 to 20.

Moreover, the alkoxy represents an aliphatic hydrocarbon group through an ether bond, such as methoxy, for example, which may be unsubstituted or substituted. The number of carbons in the alkoxy is not particularly limited, and is ordinarily in the range of 1 to 20.

Moreover, the alkylthio is a group in which an oxygen atom of an ether bond in the alkoxy is replaced by a sulfur atom.

Moreover, the cycloalkylthio is a group in which an oxygen atom of an ether bond in the cycloalkoxy is replaced by a sulfur atom.

Moreover, the aryl ether represents an aromatic hydrocarbon group through an ether bond such as phenoxy, for example, which may be unsubstituted or substituted. The number of carbons in the aryl ether is not particularly limited, and is ordinarily in the range of 6 to 40.

Moreover, the aryl thioether is a group in which an oxygen atom of an ether bond in the aryl ether is replaced by a sulfur atom.

Moreover, the aryl represents an aromatic hydrocarbon group such as phenyl, naphthyl, biphenyl, phenanthryl, terphenyl and pyrenyl, for example. The aryl may be unsubstituted or substituted. The number of carbons in the aryl is not particularly limited, and is ordinarily in the range of 6 to 40.

Moreover, the heterocycle group represents a cyclic structure group having an atom other than carbon, such as furanyl, thiophenyl, oxazolyl, pyridyl, quinolinyl and carbazolyl, for example, which may be unsubstituted or substituted. The number of carbons in the heterocycle group is not particularly limited, and is ordinarily in the range of 2 to 30.

The halogen represents fluorine, chlorine, bromine and iodine.

The aldehyde, the carbonyl and the amino can also include a group replaced by aliphatic hydrocarbon, alicyclic hydrocarbon, aromatic hydrocarbon, a heterocyclic ring or the like.

Moreover, the aliphatic hydrocarbon, the alicyclic hydrocarbon, the aromatic hydrocarbon and the heterocyclic ring may be unsubstituted or substituted.

The silyl represents a silicon compound group such as trimethylsilyl, for example, which may be unsubstituted or substituted. The number of carbons in the silyl is not particularly limited, and is ordinarily in the range of 3 to 20. Moreover, the number of silicon is ordinarily 1 to 6.

The fused ring formed between the adjacent substituent and one of substituents is a conjugated or unconjugated fused ring formed between $Ar^1$ and $R^2$, $Ar^1$ and $R^3$, $Ar^2$ and $R^2$, $Ar^2$ and $R^3$, $R^2$ and $R^3$, $Ar^1$ and $Ar^2$ and the like, for example. Here, when n is 1, two $R^1$'s may form a conjugated or unconjugated fused ring. The above fused rings may contain nitrogen, oxygen and sulfur atoms in an endocyclic structure, and may be fused to another ring.

Specific examples of the phosphine oxide derivative include compounds described below, for example.

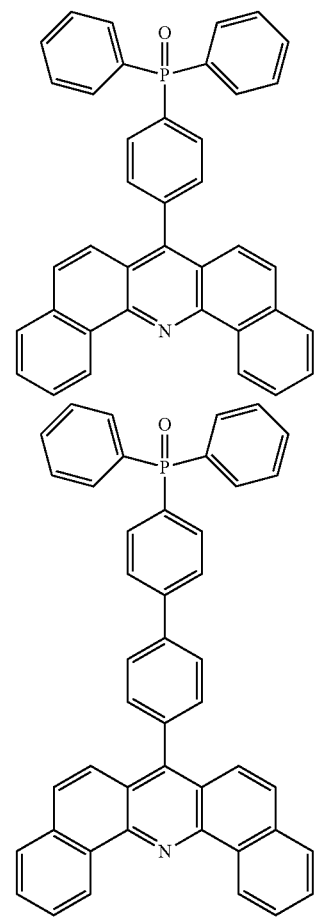

The phosphine oxide derivative can be produced by using a publicly-known raw material and a publicly-known synthesis method.

Pyrimidine Derivative

The pyrimidine derivative is a compound represented by formula (ETM-8), for example, and is preferably a compound represented by formula (ETM-8-1). The detail is described also in WO 2011/021689 A.

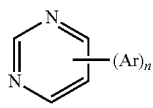
(ETM-8)

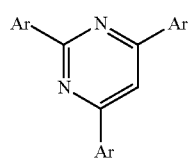
(ETM-8-1)

Ar is independently aryl which may be subjected to substitution, or heteroaryl which may be subjected to substitution. Then, n is an integer from 1 to 4, is preferably an integer from 1 to 3, and is further preferably 2 or 3.

Specific examples of the "aryl" of the "aryl which may be subjected to substitution" include aryl having 6 to 30 carbons, and aryl having 6 to 24 carbons is preferred, aryl having 6 to 20 carbons is further preferred, and aryl having 6 to 12 carbons is still further preferred.

Specific examples of the "aryl" include phenyl as monocyclic aryl, (2-,3-,4-)biphenylyl as bicyclic aryl, (1-,2-)naphthyl as fused bicyclic aryl, terphenylyl(m-terphenyl-2'-yl, m-terphenyl-4'-yl, m-terphenyl-5'-yl, o-terphenyl-3'-yl, o-terphenyl-4'-yl, p-terphenyl-2'-yl, m-terphenyl-2-yl, m-terphenyl-3-yl, m-terphenyl-4-yl, o-terphenyl-2-yl, o-terphenyl-3-yl, o-terphenyl-4-yl, p-terphenyl-2-yl, p-terphenyl-3-yl, and p-terphenyl-4-yl) as tricyclic aryl, acenaphthylene(1-,3-,4-,5-)yl, fluorene-(1-,2-,3-,4-,9-)yl, phenalene-(1-,2-)yl, and (1-,2-,3-,4-,9-)phenanthryl as fused tricyclic aryl, quaterphenylyl(5'-phenyl-m-terphenyl-2-yl, 5'-phenyl-m-terphenyl-3-yl, 5'-phenyl-m-terphenyl-4-yl, and m-quaterphenylyl) as tetracyclic aryl, triphenylene (1-,2-)yl, pyrene(1-,2-,4-)yl, naphthacene-(1-,2-,5-)yl as fused tetracyclic aryl, and perylene(1-, 2-, 3-)yl and pentacene(1-, 2-, 5-, 6-)yl as fused pantacyclic aryl.

Specific examples of the "heteroaryl" of the "heteroaryl which may be subjected to substitution" include heteroaryl having 2 to 30 carbons or heteroaryl having 2 to 25 carbons is preferred, heteroaryl having 2 to 20 carbons is further preferred, heteroaryl having 2 to 15 carbons is still further preferred, and heteroaryl having 2 to 10 carbons is particularly preferred. Moreover, specific examples of the heteroaryl include a heterocyclic ring containing, in addition to carbon, 1 to 5 hetero atoms selected from oxygen, sulfur and nitrogen as a ring-forming atom.

Specific examples of the heteroaryl include furyl, thienyl, pyrrolyl, oxazolyl, isoxazolyl, thiazolyl, isothiazolyl, imidazolyl, pyrazolyl, oxadiazolyl, furazanyl, thiadiazolyl, triazoryl, tetrazolyl, pyridyl, pyrimidinyl, pyridazinyl, pyrazinyl, thoriadinyl, benzofuranyl, isobenzofuranyl, benzo[b]thienyl, indolyl, isoindolyl, 1H-indazolyl, benzimidazolyl, benzoxazolyl, benzothiazolyl, 1H-benzotriazoryl, quinolyl, isoquinolyl, cinnolyl, quinazolyl, quinoxalinyl, phthalazinyl, naphthyridinyl, purinyl, pteridinyl, carbazolyl, acridinyl, phenoxazinyl, phenothiazinyl, phenazinyl, phenoxathiinyl, thianthrenyl and indrizinyl.

Moreover, the aryl and the heteroaryl may be replaced, and may be replaced by the aryl and the heteroaryl, for example, respectively.

Specific examples of the pyrimidine derivative include compounds described below.

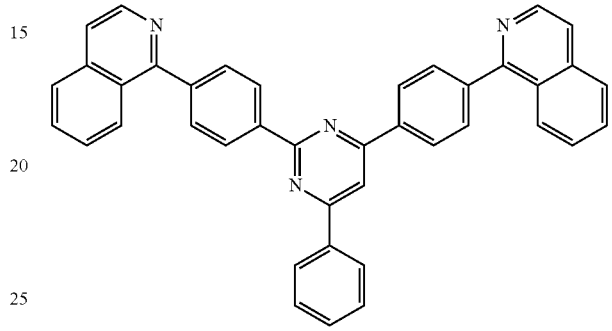

The pyrimidine derivative can be produced by using a publicly-known raw material and a publicly-known synthesis method.

Carbazole Derivative

The carbazole derivative is a compound represented by formula (ETM-9), or a multimer formed by bonding a plurality of compounds by a single bond or the like, for example. The detail is described in US 2014/0197386 A.

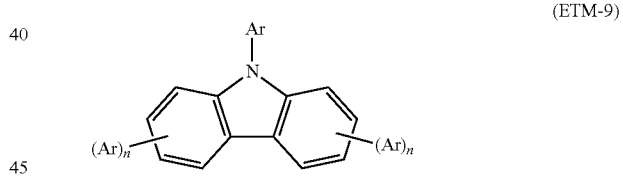
(ETM-9)

Ar is independently aryl which may be subjected to substitution, or heteroaryl which may be subjected to substitution. Then, n is independently an integer from 0 to 4, is preferably an integer from 0 to 3, and is further preferably 0 or 1.

Specific examples of the "aryl" of the "aryl which may be subjected to substitution" include aryl having 6 to 30 carbons, and aryl having 6 to 24 carbons is preferred, aryl having 6 to 20 carbons is further preferred, and aryl having 6 to 12 carbons is still further preferred.

Specific examples of the "aryl" include phenyl as monocyclic aryl, (2-, 3-, 4-)biphenylyl as bicyclic aryl, (1-, 2-)naphthyl as fused bicyclic aryl, terphenylyl(m-terphenyl-2'-yl, m-terphenyl-4'-yl, m-terphenyl-5'-yl, o-terphenyl-3'-yl, o-terphenyl-4'-yl, p-terphenyl-2'-yl, m-terphenyl-2-yl, m-terphenyl-3-yl, m-terphenyl-4-yl, o-terphenyl-2-yl, o-terphenyl-3-yl, o-terphenyl-4-yl, p-terphenyl-2-yl, p-terphenyl-3-yl, p-terphenyl-4-yl), which are tricyclic aryl, acenaphthylene(1-,3-,4-,5-)yl, fluorene-(1-,2-,3-,4-,9-)yl, phenalene-(1-,2-)yl, and (1-,2-,3-,4-,9-)phenanthryl as fused tricyclic aryl, quaterphenylyl(5'-phenyl-m-terphenyl-2-yl, 5'-phenyl-m-terphenyl-3-yl, 5'-phenyl-m-terphenyl-4 yl, and m-quaterphenylyl) as tetracyclic aryl, triphenylene (1-, 2-)yl, pyrene(1-, 2-, 4-)yl, and naphthacene-(1-,2-,5-)yl as fused tetracyclic aryl, and perylene(1-,2-,3-)yl and pentacene(1-,2-,5-,6-)yl as fused pentacyclic aryl.

Specific examples of the "heteroaryl" of the "heteroaryl which may be subjected to substitution" include heteroaryl having 2 to 30 carbons or heteroaryl having 2 to 25 carbons is preferred, heteroaryl having 2 to 20 carbons is further preferred, heteroaryl having 2 to 15 carbons is still further preferred, and heteroaryl having 2 to 10 carbons is particularly preferred. Moreover, specific examples of the heteroaryl include a heterocyclic ring containing, in addition to carbon, 1 to 5 hetero atoms selected from oxygen, sulfur and nitrogen as a ring-forming atom.

Specific examples of the heteroaryl include furyl, thienyl, pyrrolyl, oxazolyl, isoxazolyl, thiazolyl, isothiazolyl, imidazolyl, pyrazolyl, oxadiazolyl, furazanyl, thiadiazolyl, triazoryl, tetrazolyl, pyridyl, pyrimidinyl, pyridazinyl, pyrazinyl, thoriadinyl, benzofuranyl, isobenzofuranyl, benzo[b]thienyl, indolyl, isoindolyl, 1H-indazolyl, benzimidazolyl, benzoxazolyl, benzothiazolyl, 1H-benzotriazoryl, quinolyl, isoquinolyl, cinnolyl, quinazolyl, quinoxalinyl, phthalazinyl, naphthyridinyl, purinyl, pteridinyl, carbazolyl, acridinyl, phenoxazinyl, phenothiazinyl, phenazinyl, phenoxathiinyl, thianthrenyl and indrizinyl.

Moreover, the aryl and the heteroaryl may be replaced, and may be replaced by the aryl and the heteroaryl, for example, respectively.

The carbazole derivative may be the multimer formed by bonding the plurality of compounds represented by formula (ETM-9) by a single bond or the like. In the above case, the compounds may be bonded by, in addition to the single bond, an aryl ring (preferably a polyvalent benzene ring, a naphthalene ring, an anthracene ring, a fluorene ring, a benzofluorene ring, a phenalene ring, a phenanthrene ring or a triphenylene ring).

Specific examples of the carbazole derivative include compounds described below.

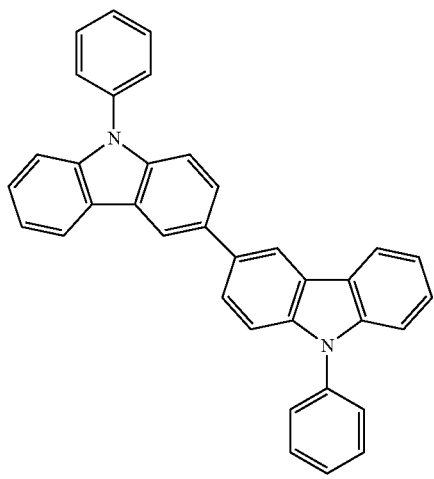

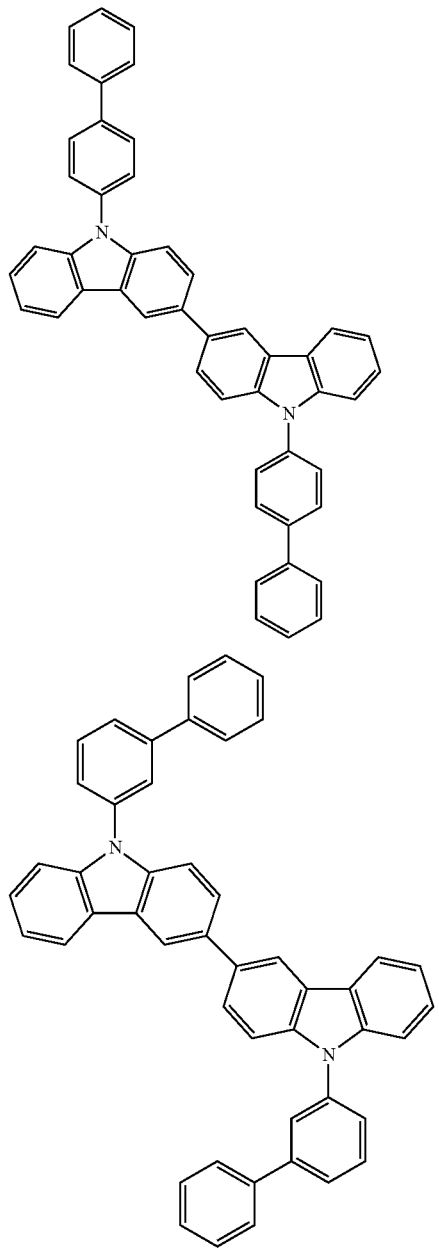

The carbazole derivative can be produced by using a publicly-known raw material and a publicly-known synthesis method.

Triazine Derivative

The triazine derivative is a compound represented by formula (ETM-10), for example, and is preferably a compound represented by formula (ETM-10-1). The detail is described in US 2011/0156013 A.

(ETM-10)

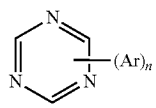

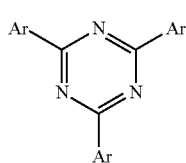

(ETM-10-1)

Ar is independently aryl which may be subjected to substitution, or heteroaryl which may be subjected to substitution. Then, n is an integer from 1 to 3, and is preferably 2 or 3.

Specific examples of the "aryl" of the "aryl which may be subjected to substitution" include aryl having 6 to 30 carbons, and aryl having 6 to 24 carbons is preferred, aryl having 6 to 20 carbons is further preferred, and aryl having 6 to 12 carbons is still further preferred.

Specific examples of the "aryl" include phenyl as monocyclic aryl, (2-,3-,4-)biphenylyl as bicyclic aryl, (1-,2-)naphthyl as fused bicyclic aryl, terphenylyl(m-terphenyl-2'-yl, m-terphenyl-4'-yl, m-terphenyl-5'-yl, o-terphenyl-3'-yl, o-terphenyl-4'-yl, p-terphenyl-2'-yl, m-terphenyl-2-yl, m-terphenyl-3-yl, m-terphenyl-4-yl, o-terphenyl-2-yl, o-terphenyl-3-yl, o-terphenyl-4-yl, p-terphenyl-2-yl, p-terphenyl-3-yl, p-terphenyl-4-yl), which are tricyclic aryl, acenaphthylene-(1-,3-,4-, -)yl, fluorene-(1-,2-,3-,4-,9-)yl, phenalene-(1-,2-)yl, and (1-,2-,3-,4-,9-)phenanthryl as fused tricyclic aryl, quaterphenylyl(5'-phenyl-m-terphenyl-2-yl, 5'-phenyl-m-terphenyl-3-yl, 5'-phenyl-m-terphenyl-4 yl, m-quaterphenylyl), which are tetracyclic aryl, triphenylene-(1-,2-)yl, pyrene-(1-,2-,4-)yl, naphthacene-(1-,2-,5-)yl, which are fused tetracyclic aryl, and perylene-(1-,2-,3-)yl and pentacene-(1-,2-,5-,6-)yl as fused pantacyclic aryl.

Specific examples of the "heteroaryl" of the "heteroaryl which may be subjected to substitution" include heteroaryl having 2 to 30 carbons or heteroaryl having 2 to 25 carbons is preferred, heteroaryl having 2 to 20 carbons is further preferred, heteroaryl having 2 to 15 carbons is still further preferred, and heteroaryl having 2 to 10 carbons is particularly preferred. Moreover, specific examples of the heteroaryl include a heterocyclic ring containing, in addition to carbon, 1 to 5 hetero atoms selected from oxygen, sulfur and nitrogen as a ring-forming atom.

Specific examples of the heteroaryl include furyl, thienyl, pyrrolyl, oxazolyl, isoxazolyl, thiazolyl, isothiazolyl, imidazolyl, pyrazolyl, oxadiazolyl, furazanyl, thiadiazolyl, triazoryl, tetrazolyl, pyridyl, pyrimidinyl, pyridazinyl, pyrazinyl, thoriadinyl, benzofuranyl, isobenzofuranyl, benzo[b]thienyl, indolyl, isoindolyl, 1H-indazolyl, benzimidazolyl, benzoxazolyl, benzothiazolyl, 1H-benzotriazoryl, quinolyl, isoquinolyl, cinnolyl, quinazolyl, quinoxalinyl, phthalazinyl, naphthyridinyl, purinyl, pteridinyl, carbazolyl, acridinyl, phenoxazinyl, phenothiazinyl, phenazinyl, phenoxathiinyl, thianthrenyl and indrizinyl.

Moreover, the aryl and the heteroaryl may be replaced, and may be replaced by the aryl and the heteroaryl, for example, respectively.

Specific examples of the triazine derivative include compounds described below.

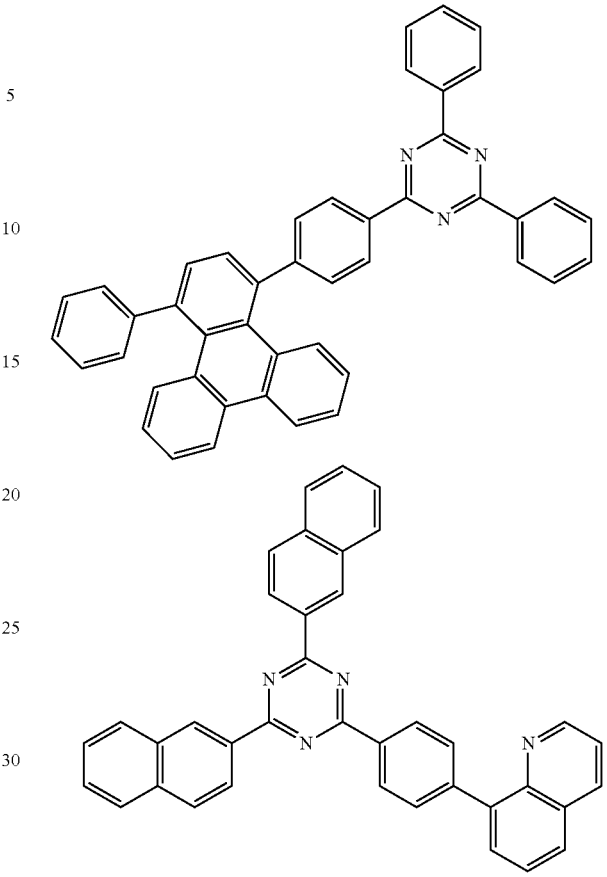

The triazine derivative can be produced by using a publicly-known raw material and a publicly-known synthesis method.

Bensimidazole Derivative

The benzimidazole derivative is a compound represented by formula (ETM-11), for example.

ϕ-(benzimidazole-based substituent)n　　　(ETM-11)

Then, q is an n-valent aryl ring (preferably an n-valent benzene ring, naphthalene ring, anthracene ring, fluorene ring, benzofluorene ring, phenalene ring, phenanthrene ring or triphenylene ring), and n is an integer from 1 to 4, and a "benzimidazole-based substituent" is a substituent in which a pyridyl group in the "pyridine-based substituent" in formula (ETM-2), formula (ETM-2-1) and formula (ETM-2-2) is replaced by a benzimidazole group, and at least one hydrogen in the benzimidazole derivative may be replaced by deuterium.

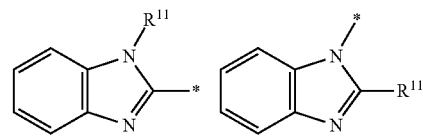

Benzimidazole group $R^{11}$ in the benzimidazole group is hydrogen, alkyl having 1 to 24 carbons, cycloalkyl having 3 to 12 carbons or aryl having 6 to 30 carbons, and the description for $R^{11}$ in formula (ETM-2-1) and formula (ETM-2-2) can be quoted. Moreover, a position "*" in the formulas represents a bonding position.

Then, φ is preferably an anthracene ring or a fluorene ring, and for the structure in the above case, the description in formula (ETM-2-1) or formula (ETM-2-2) can be quoted, and for $R^{11}$ to $R^{18}$ in each formula, the description in formula (ETM-2-1) or formula (ETM-2-2) can be quoted. Moreover, in formula (ETM-2-1) or formula (ETM-2-2), described in a form in which the two pyridine-based substituents are bonded, and when the substituent is replaced by the benzimidazole-based substituent, both of the pyridine-based substituents may be replaced by the benzimidazole-based substituent (namely, n=2), or one of the pyridine-based substituents may be replaced by the benzimidazole-based substituent, and the other of the pyridine-based substituents may be replaced by $R^{11}$ to $R^{18}$ (namely, n=1). Further, for example, at least one of $R^{11}$ to $R^{18}$ in formula (ETM-2-1) may be replaced by the benzimidazole-based substituent, and the "pyridine-based substituent" may be replaced by $R^{11}$ to $R^{18}$.

Specific examples of the benzimidazole derivative include 1-phenyl-2-(4-(10-phenylanthracen-9-yl)phenyl)-1H-benzo[d]imidazole, 2-(4-(10-(naphthalene-2-yl)anthracene-9-yl)phenyl)-1-phenyl-1H-benzo[d]imidazole, 2-(3-(10-(naphthalene-2-yl)anthracene-9-yl)phenyl)-1-phenyl-1H-benzo[d]imidazole, 5-(10-(naphthalene-2-yl)anthracene-9-yl)-1,2-diphenyl-1H-benzo[d]imidazole, 1-(4-(10-(naphthalene-2-yl)anthracene-9-yl)phenyl)-2-phenyl-1H-benzo[d]imidazole, 2-(4-(9,10-di(naphthalene-2-yl)anthracene-2-yl)phenyl-1-phenyl-11H-benzo[d]imidazole, 1-(4-(9,10-di(naphthalene-2-yl)anthracene-2-yl)phenyl-2-phenyl-1H-benzo[d]imidazole and 5-(9,10-di(naphthalene-2-yl)anthracene-2-yl-1,2-diphenyl-1H-benzo[d]imidazole.

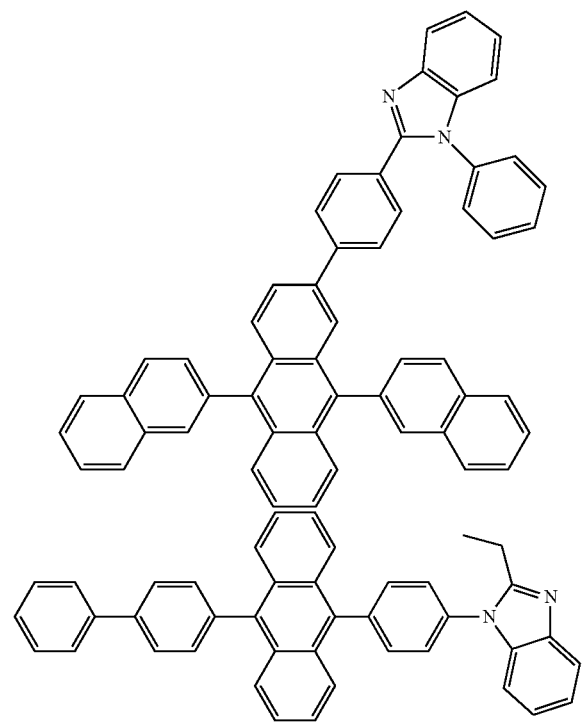

The benzimidazole derivative can be produced by using a publicly-known raw material and a publicly-known synthesis method.

Phenanthroline Derivative

The phenanthroline derivative is a compound represented by formula (ETM-12) or formula (ETM-12-1), for example. The detail is described in WO 2006/021982 A.

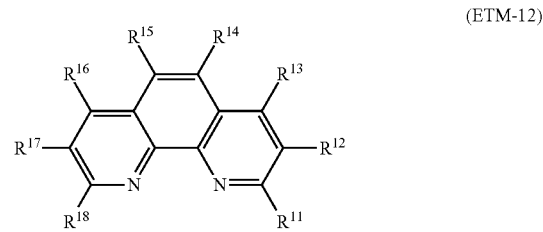

(ETM-12)

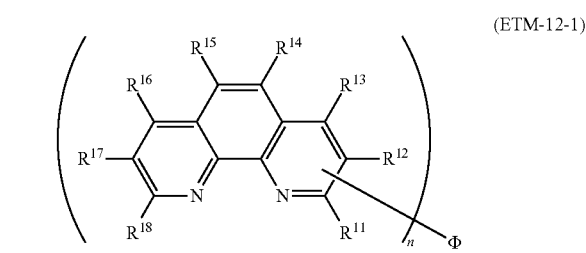

(ETM-12-1)

Then, φ is an n-valent aryl ring (preferably, an n-valent benzene ring, naphthalene ring, anthracene ring, fluorene ring, benzofluorene ring, phenalene ring, phenanthrene ring or triphenylene ring), and n is an integer from 1 to 4.

$R^{11}$ to $R^{18}$ in each formula are independently hydrogen, alkyl (preferably alkyl having 1 to 24 carbons), cycloalkyl (preferably cycloalkyl having 3 to 12 carbons) or aryl (preferably aryl having 6 to 30 carbons). In formula (ETM-12-1), any one of $R^{11}$ to $R^{18}$ is bonded to c being an aryl ring.

At least one hydrogen in each phenanthroline derivative may be replaced by deuterium.

As the alkyl, the cycloalkyl and the aryl in $R^{11}$ to $R^{18}$, the description for $R^{11}$ to $R^{18}$ in formula (ETM-2) can be quoted. Moreover, specific examples of 9 include the following structural formula in addition to the above examples. In addition, R in the structural formulas described below is independently hydrogen, methyl, ethyl, isopropyl, cyclohexyl, phenyl, 1-naphthyl, 2-naphthyl, biphenylyl or terphenylyl, and a position "*" represents a bonding position.

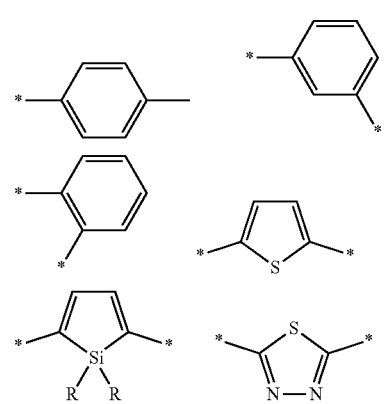

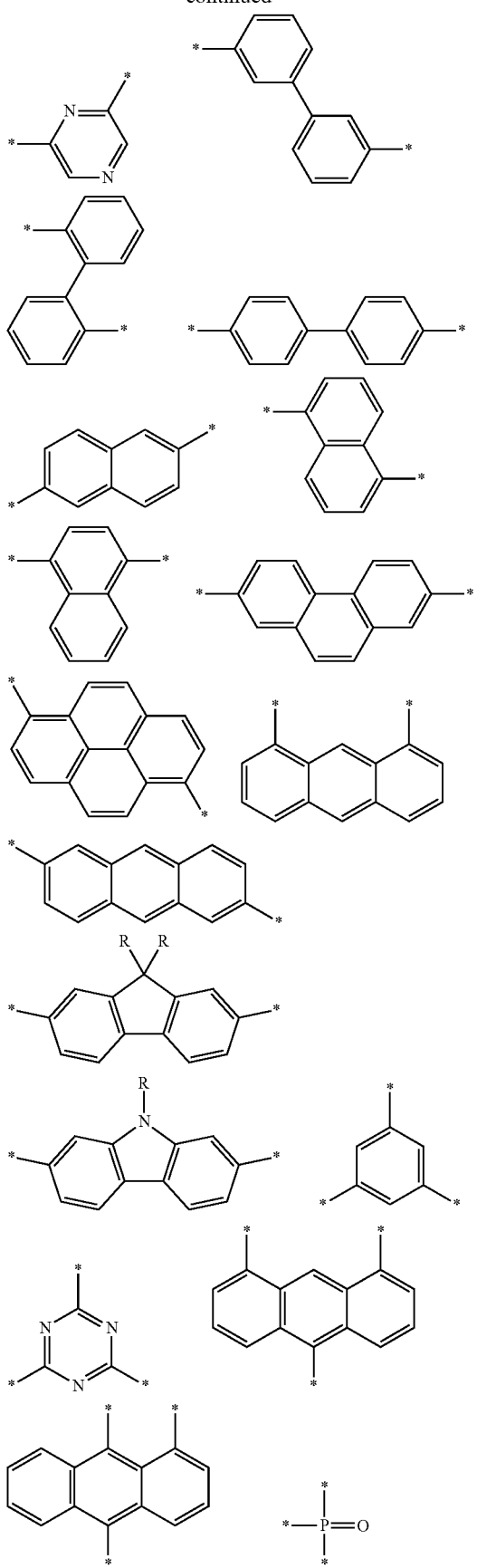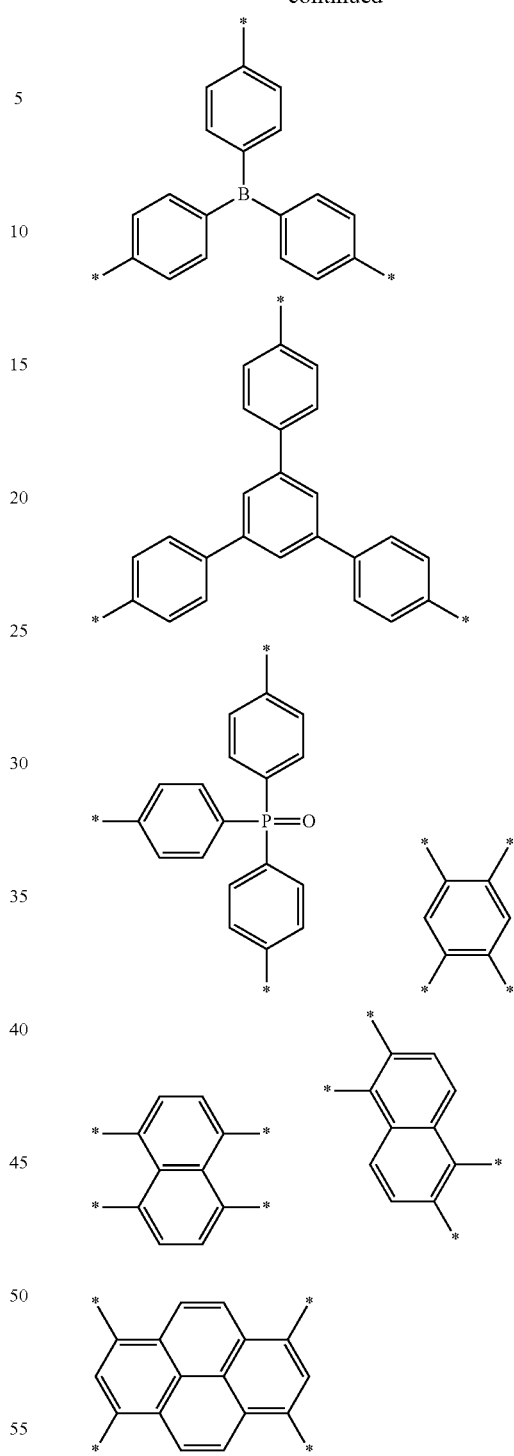

Specific examples of the phenanthroline derivative include 4,7-diphenyl-1,10-phenanthroline, 2,9-dimethyl-4,7-diphenyl-1,10-phenanthroline, 9,10-di(1,10-phenanthroline-2-yl)anthracene, 2,6-di(1,10-phenanthroline-5-yl)pyridine, 1,3,5-tri(1,10-phenanthroline-5-yl)benzene, 9,9'-difluoro-bis(1,10-phenanthroline-5-yl, bathocuproine, 1,3-bis(2-phenyl-1,10-phenanthroline-9-yl)benzene, and a compound represented by the following structural formula.

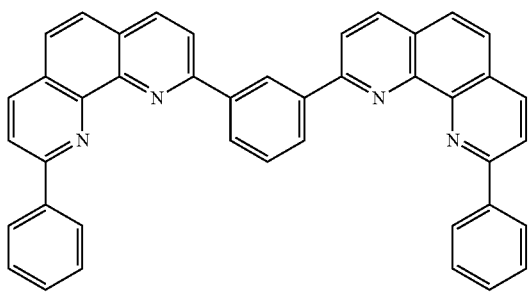 [SMILES: c1ccc(-c2ccc3ccc4ccc(-c5cccc(-c6ccc7ccc8ccc(-c9ccccc9)nc8c7n6)c5)nc4c3n2)cc1]

The phenanthroline derivative can be produced by using a publicly-known raw material and a publicly-known synthesis method.

Quinolinol Metal Complex

The quinolinol metal complex is a compound represented by formula (ETM-13), for example.

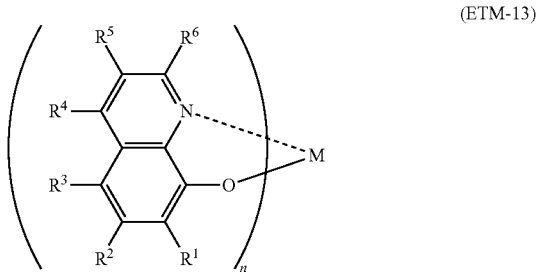

(ETM-13)

In the formula, $R^1$ to $R^4$ are independently hydrogen, fluorine, alkyl, cycloalkyl, aralkyl, alkenyl, cyano, alkoxy or aryl, and M is Li, Al, Ga, Be or Zn, and n is an integer from 1 to 3.

Specific examples of the quinolinol metal complex include 8-quinolinol lithium, tris(8-quinolate)aluminum, tris(4-methyl-8-quinolate)aluminum, tris(5-methyl-8-quinolate)aluminum, tris(3,4-dimethyl-8-quinolate)aluminum, tris(4,5-dimethyl-8-quinolate)aluminum, tris(4,6-dimethyl-8-quinolate)aluminum, bis(2-methyl-8-quinolate(phenolate) aluminum, bis(2-methyl-8-quinolate(2-methylphenolate) aluminum, bis(2-methyl-8-quinolate(3-methylphenolate) aluminum, bis(2-methyl-8-quinolate(4-methylphenolate) aluminum, bis(2-methyl-8-quinolate(2-phenylphenolate) aluminum, bis(2-methyl-8-quinolate(3-phenylphenolate) aluminum, bis(2-methyl-8-quinolate(4-phenylphenolate) aluminum, bis(2-methyl-8-quinolate(2,3-dimethylphenolate)aluminum, bis(2-methyl-8-quinolate(2,6-dimethylphenolate)aluminum, bis(2-methyl-8-quinolate(3,4-dimethylphenolate)aluminum, bis(2-methyl-8-quinolate(3,5-dimethylphenolate)aluminum, bis(2-methyl-8-quinolate(3,5-di-t-butylphenolate)aluminum, bis(2-methyl-8-quinolate(2,6-diphenylphenolate)aluminum, bis(2-methyl-8-quinolate(2,4,6-triphenylphenolate)aluminum, bis(2-methyl-8-quinolate(2,4,6-trimethylphenolate)aluminum, bis(2-methyl-8-quinolate(2,4,5,6-tetramethylphenolate)aluminum, bis(2-methyl-8-quinolate(1-naphtholate)aluminum, bis(2-methyl-8-quinolate(2-naphtholate)aluminum, bis(2,4-dimethyl-8-quinolate(2-phenylphenolate)aluminum, bis(2,4-dimethyl-8-quinolate(3-phenylphenolate)aluminum, bis(2,4-dimethyl-8-quinolate(4-phenylphenolate)aluminum, bis(2,4-dimethyl-8-quinolate(3,5-dimethylphenolate)aluminum, bis(2,4-dimethyl-8-quinolate(3,5-di-t-butylphenolate) aluminum, bis(2-methyl-8-quinolate)aluminum-µ-oxo-bis (2-methyl-8-quinolate)aluminum, bis(2,4-dimethyl-8-quinolate)aluminum-p-oxo-bis(2,4-dimethyl-8-quinolate) aluminum, bis(2-methyl-4-ethyl-8-quinolate)aluminum-µ-oxo-bis(2-methyl-4-ethyl-8-quinolate)aluminum, bis(2-methyl-4-methoxy-8-quinolate)aluminum-µ-oxo-bis(2-methyl-4-methoxy-8-quinolate)aluminum, bis(2-methyl-5-cyano-8-quinolate)aluminum-µ-oxo-bis(2-methyl-5-cyano-8-quinolate)aluminum, bis(2-methyl-5-trifluoromethyl-8-quinolate)aluminum-µ-oxo-bis(2-methyl-5-trifluoromethyl-8-quinolate)aluminum and bis(10-hydroxybenzo[h]quinoline)beryllium.

The quinolinol metal complex can be produced by using a publicly-known raw material and a publicly-known synthesis method.

Thiazole Derivative and a Benzothiazole Derivative

The thiazole derivative is a compound represented by formula (ETM-14-1), for example.

φ-(thiazole-based substituent)n          (ETM-14-1)

The benzothiazole derivative is a compound represented by formula (ETM-14-2), for example.

φ-(benzothiazole-based substituent)n          (ETM-14-2)

Then, φ in each formula is an n-valent aryl ring (preferably an n-valent benzene ring, naphthalene ring, anthracene ring, fluorene ring, benzofluorene ring, phenalene ring, phenanthrene ring or triphenylene ring), and n is an integer from 1 to 4, and the "thiazole-based substituent" or the "benzothiazole-based substituent" are a substituent in which the pyridyl group in the "pyridine-based substituent" in formula (ETM-2), formula (ETM-2-1) and formula (ETM-2-2) is replaced by a thiazole group or a benzothiazole group described below (a position "*" in the formulas represents a bonding position.), and at least one hydrogen in the thiazole derivative and the benzothiazole derivative may be replaced by deuterium.

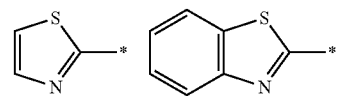

Thiazole group     Benzothiazole group

Then, φ is preferably an anthracene ring or a fluorene ring, and for the structure in the above case, the description in formula (ETM-2-1) or formula (ETM-2-2) can be quoted, and for $R^{11}$ to $R^{18}$ in each formula, the description in formula (ETM-2-1) or formula (ETM-2-2) can be quoted. Moreover, in formula (ETM-2-1) or formula (ETM-2-2), described in a form in which the two pyridine-based substituents are bonded, and when the substituent is replaced by the thiazole-based substituent (or benzothiazole-based substituent), both of the pyridine-based substituents may be replaced by the thiazole-based substituent (or benzothiazole-based substituent) (namely, n=2), or one of the pyridine-based substituents may be replaced by the thiazole-based substituent (or benzothiazole-based substituent), and the other of the pyridine-based substituents may be replaced by $R^{11}$ to $R^{18}$ (namely, n=1). Further, for example, at least one of $R^{11}$ to $R^{18}$ in formula (ETM-2-1) may be replaced by the thiazole-based substituent (or benzothiazole-based substituent), and the "pyridine-based substituent" may be replaced by $R^{11}$ to $R^{18}$.

The above thiazole derivative or benzothiazole derivative can be produced by using a publicly-known raw material and a publicly-known synthesis method.

Reducing Substance

The electron transport layer or the electron injection layer further includes a substance that can reduce a material forming the electron transport layer or the electron injection layer. Various substances are used as the reducing substance if the substance has predetermined reducing properties. For example, at least one selected from the group of alkali metal, alkaline earth metal, rare earth metal, an oxide of alkali metal, a halide of alkali metal, an oxide of alkaline earth metal, a halide of alkaline earth metal, an oxide of rare earth metal, a halide of rare earth metal, an organic complex of alkali metal, an organic complex of alkaline earth metal and an organic complex of rare earth metal can be preferably used.

Specific examples of the preferred reducing substance include alkali metal such as Na (work function: 2.36 eV), K (work function: 2.28 eV), Rb (work function: 2.16 eV) or Cs (work function 1.95 eV), and alkaline earth metal such as Ca (work function: 2.9 eV), Sr (work function: 2.0 to 2.5 eV) or Ba (work function: 2.52 eV), and a substance having a work function of about 2.9 eV or less is particularly preferred. Among the above substances, as the reducing substance, alkali metal of K, Rb or Cs is preferred, Rb or Cs is further preferred, and Cs is most preferred. The above alkali metals have particularly high reduction capability, and improvement in luminance and extension of a service life in the organic EL device can be achieved by adding a relatively small amount thereof to the material forming the electron transport layer or the electron injection layer. Moreover, as the reducing substance having a work function of about 2.9 eV or less, a combination of two or more kinds of alkali metals is preferred, and a combination including Cs, for example, a combination of Cs and Na, Cs and K, Cs and Rb, or Cs and Na and K is particularly preferred. The reduction capability can be efficiently exhibited by containing Cs, and improvement in luminance and extension of a service life in the organic EL device can be achieved by adding Cs to the material forming the electron transport layer or the electron injection layer.

Cathode in an Organic Electroluminescent Device

Cathode 108 plays a role of injecting electrons into luminescent layer 105 through electron injection layer 107 and electron transport layer 106.

A material forming cathode 108 is not particularly limited, as long as the material can efficiently inject electrons into an organic layer, and a material similar to the material forming anode 102 can be used. Particularly, metal such as tin, indium, calcium, aluminum, silver, copper, nickel, chromium, gold, platinum, iron, zinc, lithium, sodium, potassium, cesium and magnesium, or alloy thereof (such as magnesium-silver alloy, magnesium-indium alloy and aluminum-lithium alloy such as lithium fluoride/aluminum), or the like is preferred. In order to enhance electron injection efficiency to improve device characteristics, lithium, sodium, potassium, cesium, calcium, magnesium, or alloy containing the above low-work-function metals is effective. However, the above low-work-function metals are generally unstable in atmospheric air in many cases. In order to improve the above point, a method of doping a small amount of lithium, cesium and magnesium to an organic layer, and using an electrode having high stability is known, for example. As other dopants, inorganic salt such as lithium fluoride, cesium fluoride, lithium oxide and cesium oxide can also be used, but not limited thereto.

Further, preferred examples for protecting the electrode include lamination of metals such as platinum, gold, silver, copper, iron, tin, aluminum and indium, alloy using the above metals, inorganic substances such as silica, titania and silicon nitride, polyvinyl alcohol, polyvinyl chloride, a hydrocarbon-based polymer compound, or the like. A method of preparing the above electrodes is not particularly limited, as long as conduction, such as resistance heating, electron beam vapor deposition, sputtering, ion plating and coating, can be achieved.

Binding Agent that May be Used in Each Layer

The above materials used for the hole injection layer, the hole transport layer, the luminescent layer, the electron transport layer and the electron injection layer can form each layer alone, but can also be dispersed and used, as a polymer binding agent, in a solvent-soluble resin such as polyvinyl chloride, polycarbonate, polystyrene, poly(N-vinylcarbazole), polymethylmethacrylate, polybutylmethacrylate, polyester, polysulfone, polyphenylene oxide, polybutadiene, a hydrocarbon resin, a ketone resin, a phenoxy resin, polyamide, ethyl cellulose, a vinyl acetate resin, an ABS resin and a polyurethane resin; or a curable resin such as a phenolic resin, a xylene resin, a petroleum resin, a urea resin, a melamine resin, an unsaturated polyester resin, an alkyd resin, an epoxy resin and a silicone resin.

Method of Preparing an Organic Electroluminescent Device

Each layer constituting the organic EL device can be formed by forming the material to constitute each layer into a thin film according to a method such as a vapor deposition method, resistance heating vapor deposition, electron beam evaporation, sputtering, a molecule lamination method, a printing method, a spin coating method, a cast method and a coating method. A film thickness of each layer thus formed is not particularly limited, and can be appropriately set according to properties of the material, and is ordinarily in the range of about 2 nanometers to about 5000 nanometers. The film thickness can be ordinarily measured with a quartz crystal oscillation type thickness measuring apparatus or the like. When the thin film is formed by using the vapor deposition method, the vapor deposition conditions depend on a kind of the material, an objective crystal structure and association structure of the film, or the like. The vapor deposition conditions are preferably appropriately set to a board heating temperature of about +50 to about +400° C., a degree of vacuum of about $10^{-6}$ to about $10^{-3}$ Pa, a deposition rate of about 0.01 to about 50 nm/sec, a substrate temperature of about −150 to about +300° C., and a film thickness of about 2 nanometers to about 5 micrometers.

Next, as an example of the method for preparing the organic EL device, a method for preparing the organic EL device including anode/hole injection layer/hole transport layer/luminescent layer including host material and dopant material/electron transport layer/electron injection layer/cathode will be described. The anode is prepared by forming a thin film of an anode material on a suitable substrate by a vapor deposition method or the like, and then thin films of the hole injection layer and the hole transport layer are formed on the anode. A thin film is formed thereon by vapor codeposition of the host material and the dopant material, and is taken as the luminescent layer, and the electron transport layer and the electron injection layer are formed on the luminescent layer, and a thin film composed of a cathode substance is formed by a vapor deposition method or the like, and is taken as the cathode, and thus the objective organic EL device is obtained. In addition, in preparing the above organic EL device, the order can be reversed so as to be prepared in the order of the cathode, the electron injection layer, the electron transport layer, the luminescent layer, the hole transport layer, the hole injection layer and the anode.

When a DC voltage is applied to the organic EL device thus obtained, the voltage may be applied in such a manner that the anode has "+" polarity and the cathode has "−" polarity, and when a voltage of about 2 to about 40 V is applied, luminescence can be observed from a transparence or translucent electrode side (the anode or the cathode, or both). Moreover, the organic EL device also produces luminance in the case of application of a pulse current or an AC current. In addition, a waveform of the AC current to be applied may be arbitrary.

Application of an Organic Electroluminescent Device

The invention can be applied to a display apparatus equipped with the organic EL device, or a lighting apparatus equipped with the organic EL device, or the like.

The display apparatus or the lighting apparatus equipped with the organic EL device can be produced by a publicly-known method such as connecting the organic EL device according to the embodiment to a publicly-known driving device, and can be driven by appropriately using a publicly-known driving method such as a DC drive, a pulse drive and an AC drive.

Specific examples of the display apparatus include a panel display such as a color flat-panel display, and a flexible display such as a flexible color organic electroluminescence (EL) display (for example, refer to JP H10-335066 A, JP 2003-321546 A, JP 2004-281086 A and the like). Moreover, specific examples of a display type of the display include a matrix and/or a segment type. In addition, the matrix display and the segment display may coexist in the same panel.

In the matrix, pixels for display are two-dimensionally arranged in a grid shape, a mosaic shape or the like, and a character or an image is displayed by aggregation of the pixels. A shape or a size of the pixels is determined depending on an application. For example, a square pixel having a side of about 300 micrometers or less is ordinarily used for image and character display of a personal computer, a monitor and a television, and a pixel having a side on a millimeter order is used in the case of a large sized display such as a display panel. In the case of monochrome display, pixels having the same color may be arranged, but in the case of color display, red, green and blue pixels are arranged and allowed to display. In the above case, a delta type and a stripe type are typically applied. Then, as a driving method of the matrix, either a line sequential driving method or an active matrix may be applied. The line sequential drive has an advantage of a simple structure, but the active matrix may be superior in consideration of operating characteristics, and therefore both methods need to be selectively used according to an application.

In the segment type, a pattern is formed so as to display predetermined information, and a determined region is prepared to produce luminescence. Specific examples thereof include time or temperature display in a digital clock or a thermometer, operating status display in an audio device, an electromagnetic cooker or the like, and panel display in an automobile.

Specific examples of the lighting apparatus include a lighting apparatus in an interior illumination or the like, and a backlight in a liquid crystal display device (for example, refer to JP 2003-257621 A, JP 2003-277741 A, JP 2004-119211 A and the like). The backlight is used for the purpose of mainly improving visibility of the display apparatus having no spontaneous luminescence, and is used for a liquid crystal display device, a clock, an audio device, a car panel, a display board, a sign or the like. In particular, as a backlight for a liquid crystal display device, particularly for a personal computer in which thickness reduction becomes an issue, considering that the thickness reduction is difficult because a conventional type is formed of a fluorescent lamp or a lightguide plate, a backlight using the luminescent device according to the embodiment is characterized by a thin type and light weight.

EXAMPLES

Hereinafter, the invention will be described more specifically by way of Examples, but the invention is not limited by the Examples. First, Synthesis Examples of compounds used in Examples will be described below.

Synthesis Example (1)

Synthesis of Compound (1-199)

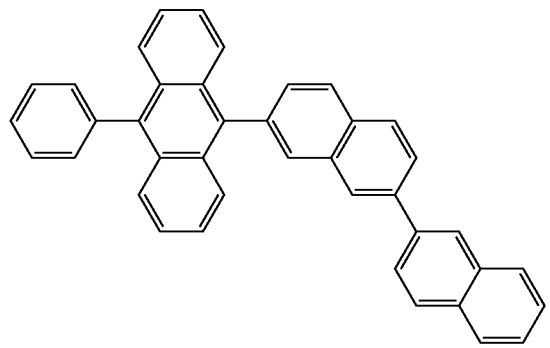

(1-199)

Compound (1-199) was prepared according to a method described in "Synthesis Example of compound represented by formula (1-55)" of JP 2012-104806 A.

Synthesis Example (2)

Synthesis of Compound (1-192)

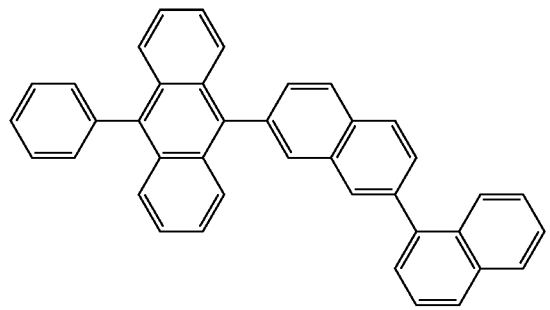

(1-192)

Compound (1-192) was prepared according to a method described in "Synthesis Example of compound represented by formula (1-46)" of JP 2012-104806 A.

Synthesis Example (3)

Synthesis of Compound (1-222)

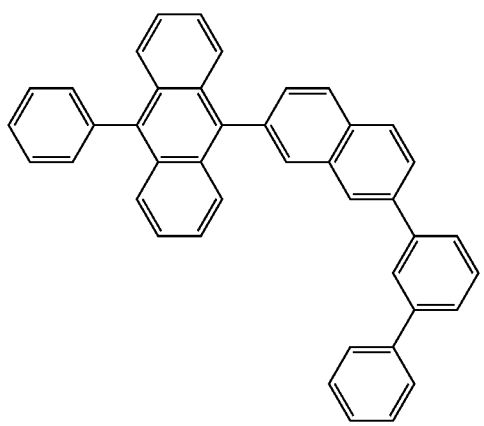
(1-222)

Compound (1-222) was prepared according to a method described in "Synthesis Example of compound represented by formula (1-2)" of JP 2012-104806 A.

Synthesis Example (4)

Synthesis of Compound (1-221)

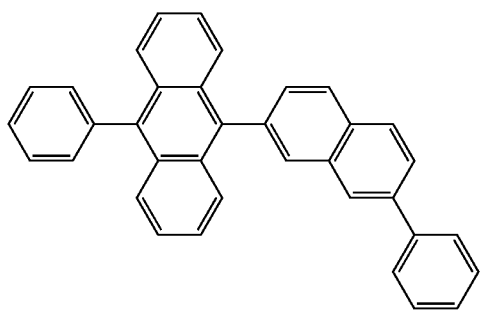
(1-221)

Compound (1-221) was prepared according to a method described in "Synthesis Example of compound represented by formula (1-1)" of JP 2012-104806 A.

Synthesis Example (5)

Synthesis of Compound (1-195)

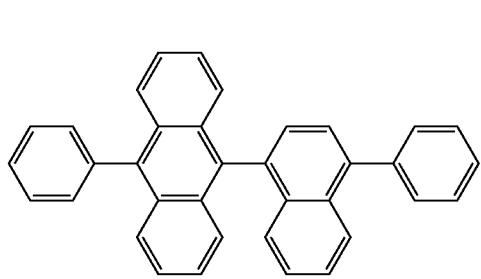
(1-195)

Compound (1-195) was prepared according to a method described in "Synthesis Example 30: Synthesis of compound (CH-AP41)" of JP 2016-88927 A.

Synthesis Example (6)

Synthesis of compound (1-134-O): 2-(10-phenylanthracene-9-yl)naphtho[2,3-b]benzofuran

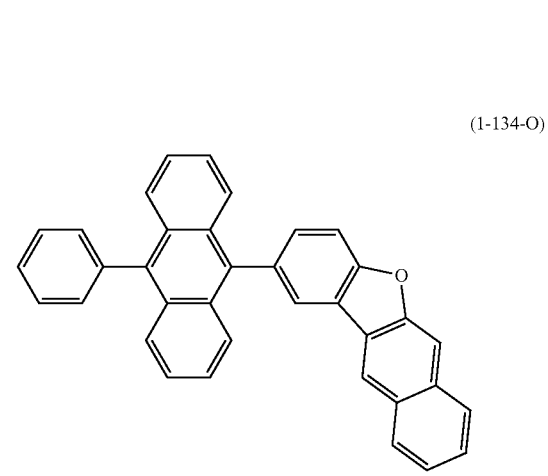 [SMILES: c1ccc(-c2c3ccccc3c(-c3ccc4oc5cc6ccccc6cc5c4c3)c3ccccc23)cc1]
(1-134-O)

Compound (1-134-O) was prepared according to a method described in the paragraph [0106] of WO 2014/141725 A.

Synthesis Example (7)

Synthesis of compound (2A-1): 15,15-dimethyl-N,N-diphenyl-15H-5,9-dioxa-16b-bolinedeno[1,2-b]naphtho[1,2,3-fg]anthracene-13-amine

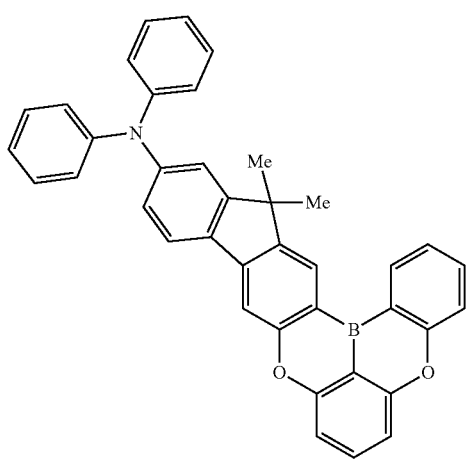

(2A-1)

Compound (2A-1) was prepared according to a method described in "Synthesis of compound represented by formula (1B-1)" of WO 2017/126443 A.

Structure of the compound obtained was identified by NMR measurement.

$^1$H-NMR (CDCl$_3$): δ=8.72 (d, 1H), 8.60 (s, 1H), 7.79-7.68 (m, 4H), 7.55 (d, 1H), 7.41 (t, 1H), 7.31-7.17 (m, 11H), 7.09-7.05 (m, 3H), 1.57 (s, 6H).

Synthesis Example (8)

Synthesis of compound (3-41): 2,12-di-t-butyl-5,9-bis(4-(t-butyl)phenyl)-7-methyl-5,9-dihydro-5,9-diaza-13b-boranaphtho[3,2,1-de]anthracene

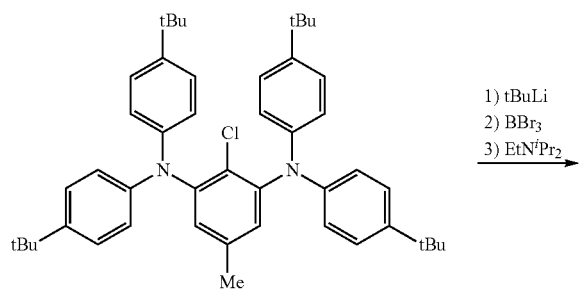

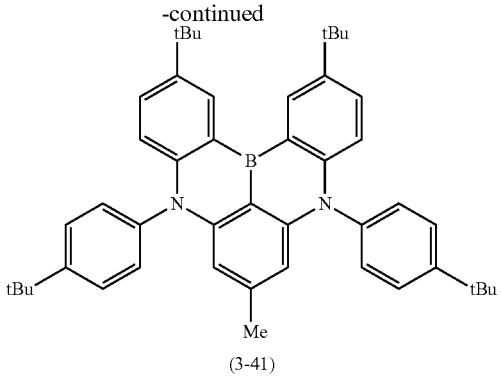

(3-41)

Compound (3-41) was prepared according to a method described in "Synthesis Example (32)" of WO 2015/102118 A.

Structure of the compound obtained was identified by NMR measurement.

$^1$H-NMR (CDCl$_3$): δ=1.47 (s, 36H), 2.17 (s, 3H), 5.97 (s, 2H), 6.68 (d, 2H), 7.28 (d, 4H), 7.49 (dd, 2H), 7.67 (d, 4H), 8.97 (d, 2H).

Synthesis Example (9)

Synthesis of compound (3-31): 2,12-di-t-butyl-5,9-bis(4-(t-butyl)phenyl)-5,9-dihydro-5,9-diaza-13b-boranaphtho[3,2,1-de]anthracene

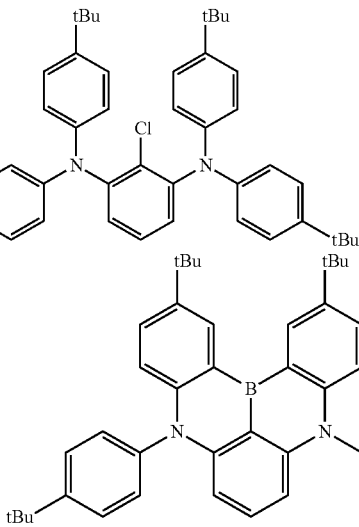

(3-31)

Compound (3-31) was prepared according to a method described in "Synthesis Example (32)" of WO 2015/102118 A.

Structure of the compound obtained was identified by NMR measurement.

$^1$H-NMR (CDCl$_3$): δ=1.46 (s, 18H), 1.47 (s, 18H), 6.14 (d, 2H), 6.75 (d, 2H), 7.24 (t, 1H), 7.29 (d, 4H), 7.52 (dd, 2H), 7.67 (d, 4H) 8.99 (d, 2H).

Synthesis Example (10)

Synthesis of compound (3-53): 2,12-di-t-butyl-5,9-bis(4-(t-butyl)phenyl)-7-(9H-carbazole-9-yl)-5,9-dihydro-5,9-diaza-13b-boranaphtho[3,2,1-de]anthracene

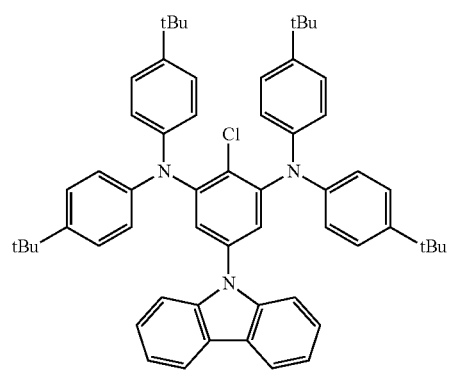

1) tBuLi
2) BBr₃
3) EtN$^i$Pr₂

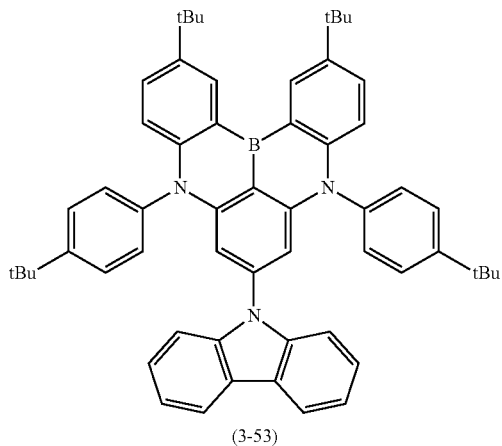

(3-53)

Compound (3-53) was prepared according to a method described in "Synthesis Example (32)" of WO 2015/102118 A.

Structure of the compound obtained was identified by NMR measurement.

$^1$H-NMR (CDCl₃): δ=1.35 (s, 18H), 1.50 (s, 18H), 6.34 (s, 2H), 6.85 (d, 2H), 7.16 (t, 2H), 7.23 (t, 2H), 7.32-7.35 (m, 6H), 7.56 (dd, 2H), 7.63 (d, 4H), 7.99 (d, 2H), 9.05 (d, 2H).

Synthesis Example (11)

Synthesis of compound (3-37): 3,12-di-t-butyl-9-(4-(t-butyl)phenyl)-5-(3,5-di-t-butylphenyl)-5,9-dihydro-5,9-diaza-13b-boranaphtho[3,2,1-de]anthracene

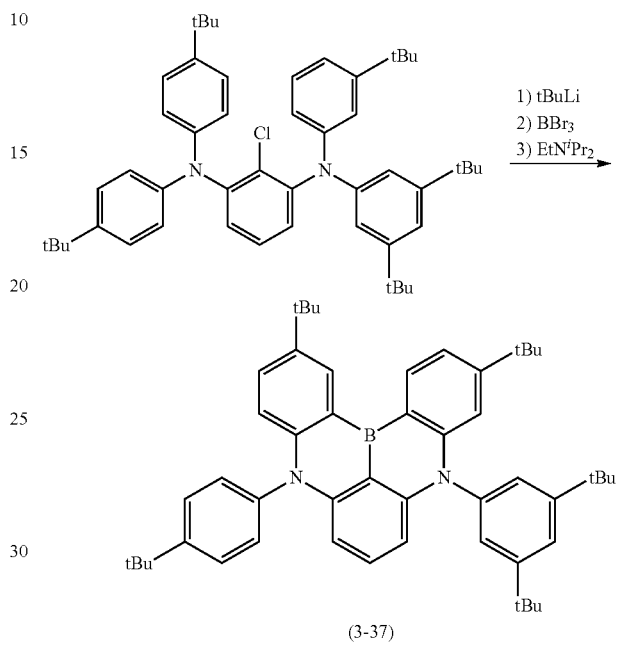

1) tBuLi
2) BBr₃
3) EtN$^i$Pr₂

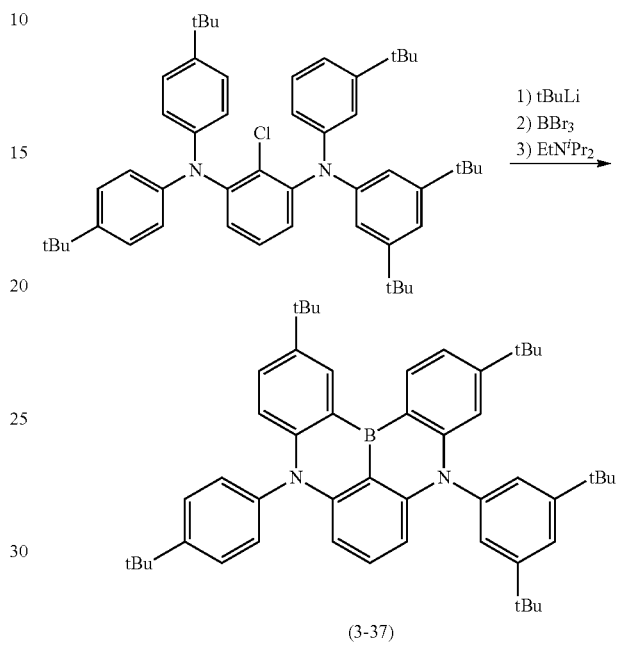

(3-37)

Compound (3-37) was prepared according to a method described in "Synthesis Example (32)" of WO 2015/102118 A.

Structure of the compound obtained was identified by NMR measurement.

$^1$H-NMR (CDCl₃): δ=1.20 (s, 9H), 1.36 (s, 18H), 1.46 (s, 9H), 1.47 (s, 9H), 6.14 (d, 1H), 6.25 (d, 1H), 6.68 (d, 1H), 6.73 (d, 1H), 7.21 (d, 2H), 7.29 (d, 3H), 7.34 (dd, 1H), 7.51 (dd, 1H), 7.61 (t, 1H), 7.67 (d, 2H), 8.86 (d, 1H), 8.96 (d, 1H).

Synthesis Example (12)

Synthesis of compound (3-46): 3,12-di-t-butyl-9-(4-(t-butyl)phenyl)-5-(3,5-di-t-butylphenyl)-7-methyl-5,9-dihydro-5,9-diaza-13b-boranaphtho[3,2,1-de]anthracene

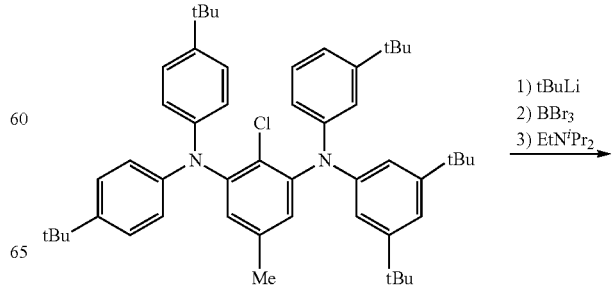

1) tBuLi
2) BBr₃
3) EtN$^i$Pr₂

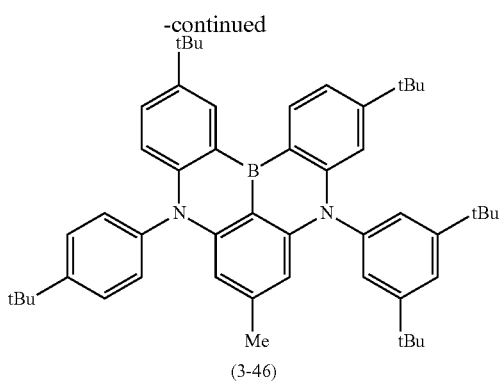

(3-46)

Compound (3-46) was prepared according to a method described in "Synthesis Example (32)" of WO 2015/102118 A.

Structure of the compound obtained was identified by NMR measurement.

$^1$H-NMR (CDCl$_3$): δ=1.20 (s, 9H), 1.37 (s, 18H), 1.46 (s, 9H), 1.47 (s, 9H), 2.18 (s, 3H), 5.97 (s, 1H), 6.08 (d, 1H), 6.63 (d, 1H), 6.66 (d, 1H), 7.20 (d, 2H), 7.27 (d, 2H), 7.32 (dd, 1H), 7.48 (dd, 1H), 7.61 (t, 1H), 7.67 (d, 2H), 8.84 (d, 1H), 8.94 (d, 1H).

Synthesis Example (13)

Synthesis of compound (3-50): 2,12-di-t-butyl-N,N,5,9-tetrakis(4-(t-butyl)phenyl)-5,9-dihydro-5,9-diaza-13b-boranaphtho[3,2,1-de]anthracene-7-amine

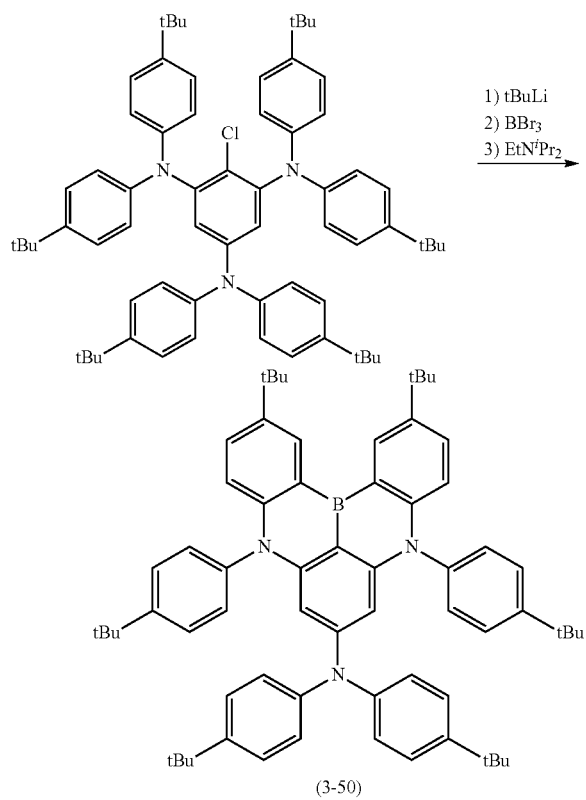

(3-50)

Compound (3-50) was prepared according to a method described in "Synthesis Example (32)" of WO 2015/102118 A.

Structure of the compound obtained was identified by NMR measurement.

$^1$H-NMR (CDCl$_3$): δ=1.3 (s, 18H), 1.3 (s, 18H), 1.5 (s, 18H), 5.8 (s, 2H), 6.6 (d, 2H), 6.8 (dd, 4H), 7.1 (dd, 4H), 7.1 (dd, 4H), 7.4-7.5 (m, 6H), 8.9 (d, 2H).

Synthesis Example (14)

Synthesis of compound (3-49): 2,12-di-t-butyl-5,9-bis(4-(t-butyl)phenyl)-N,N-diphenyl-5,9-dihydro-5,9-diaza-13b-boranaphtho[3,2,1-de]anthracene-7-amine

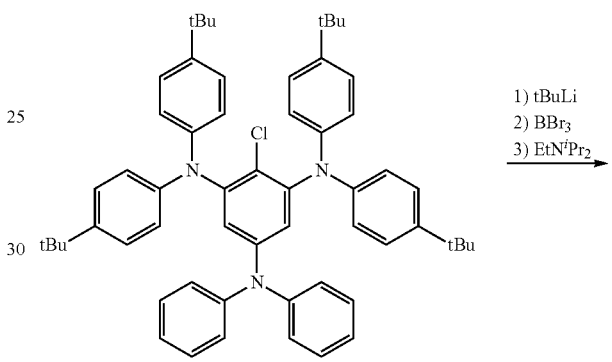

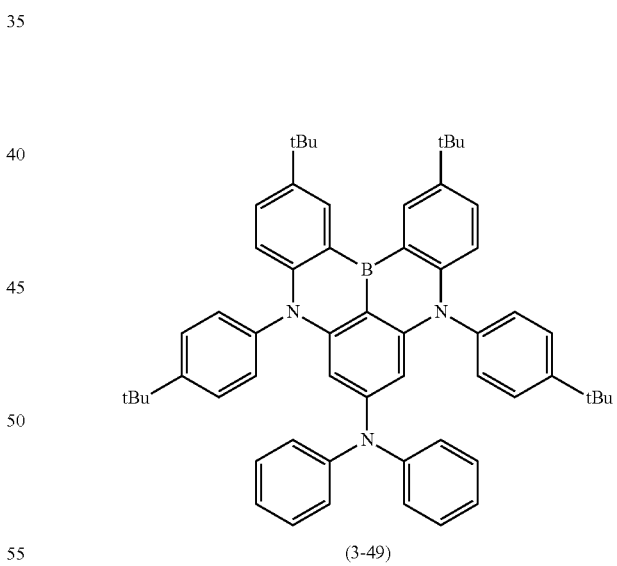

(3-49)

Compound (3-49) was prepared according to a method described in "Synthesis Example (32)" of WO 2015/102118 A.

Structure of the compound obtained was identified by NMR measurement.

$^1$H-NMR (CDCl$_3$): δ=1.33 (s, 18H), 1.46 (s, 18H), 5.55 (s, 2H), 6.75 (d, 2H), 6.89 (t, 2H), 6.94 (d, 4H), 7.06 (t, 4H), 7.13 (d, 4H), 7.43-7.46 (m, 6H), 8.95 (d, 2H).

Synthesis Example (15)

Synthesis of Compound (3-A-1)

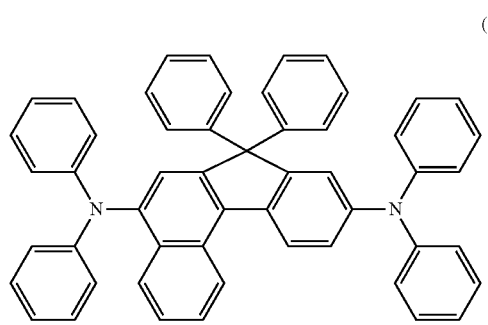
(3-A-1)

Compound (3-A-1) was prepared according to a method described in "Synthesis Example of compound (1'-1)" of JP 2008-291006 A.

Synthesis Example (16)

Synthesis of Compound (3-A-2)

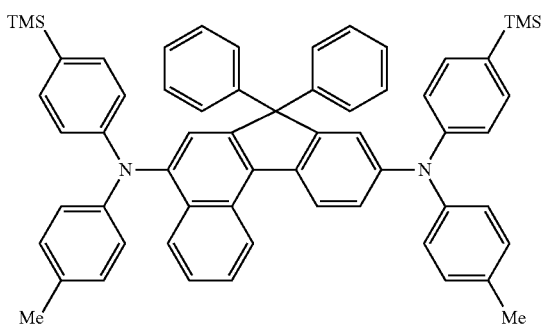
(3-A-2)

Compound (3-A-2) was prepared according to a method described in "Synthesis Example of compound represented by formula (1-20)" of JP 2011-37838 A.

Synthesis Example (17)

Synthesis of Compound (3-A-3)

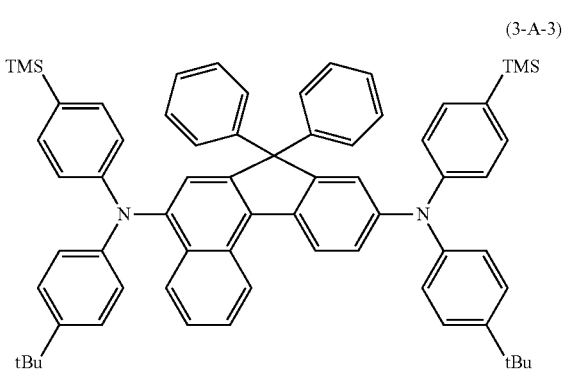 [SMILES: CC(C)(C)c1ccc(N(c2ccc([Si](C)(C)C)cc2)c2ccc3c(c2)C(c2ccccc2)(c2ccccc2)c2cc(N(c4ccc(C(C)(C)C)cc4)c4ccc([Si](C)(C)C)cc4)c4ccccc4c2-3)cc1]
(3-A-3)

Compound (3-A-3) was prepared according to a method described in "Synthesis Example of compound represented by formula (1-26)" of JP 2011-37838 A.

Synthesis Example (18)

Synthesis of Compound (3-A-4)

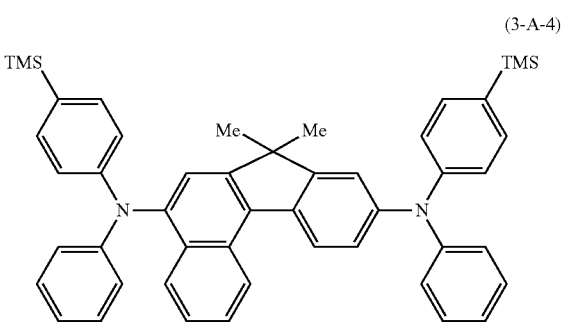 [SMILES: CC1(C)c2cc(N(c3ccccc3)c3ccc([Si](C)(C)C)cc3)ccc2-c2c1cc(N(c1ccccc1)c1ccc([Si](C)(C)C)cc1)c1ccccc21]
(3-A-4)

Compound (3-A-4) was prepared according to a method described in "Synthesis Example of compound represented by formula (1-62)" of JP 2011-37838 A.

Synthesis Example (19)

Synthesis of Compound (3-A-5)

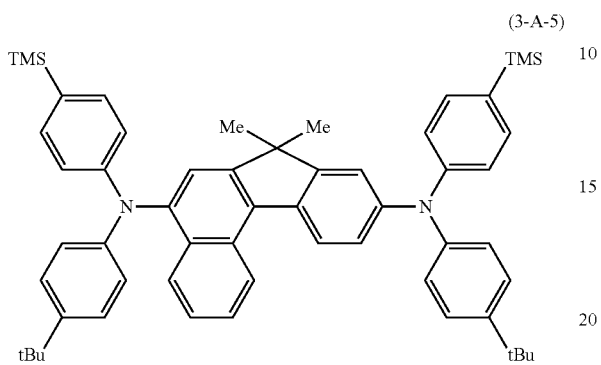

(3-A-5)

Compound (3-A-5) was prepared according to a method described in "Synthesis Example of compound represented by formula (1-101)" of JP 2011-037838 A.

Synthesis Example (20)

Synthesis of Compound (3-B-1)

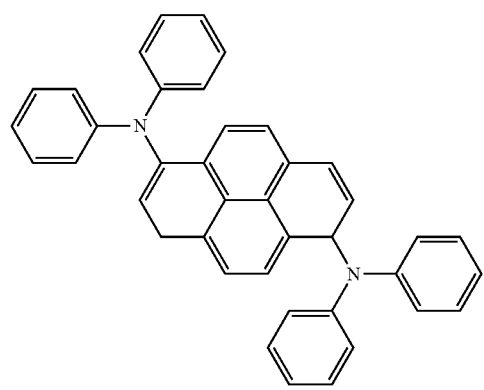

(3-B-1)

Compound (3-B-1) was prepared according to a method described in "Example 3: Preparation of compound D-8" of WO 2013/109030 A.

Synthesis Example (21)

Synthesis of Compound (3-B-2)

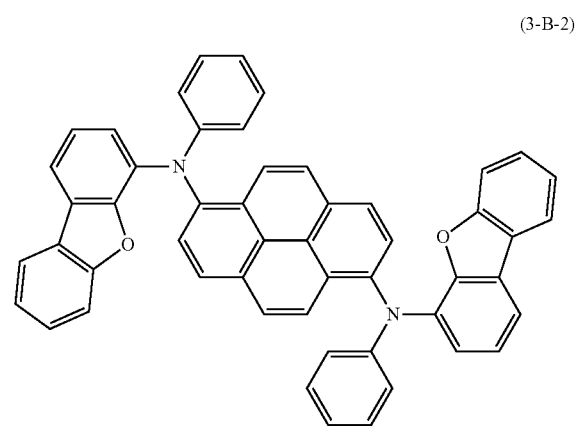 [SMILES: c1ccc(N(c2ccc3ccc4c(N(c5ccccc5)c5cccc6c5oc5ccccc56)ccc5ccc2c3c54)c2cccc3c2oc2ccccc23)cc1]

(3-B-2)

Compound (3-B-2) was prepared according to a method described in "Production Example 4" of JP 2013-080961 A.

Synthesis Example (22)

Synthesis of Compound (3-B-3)

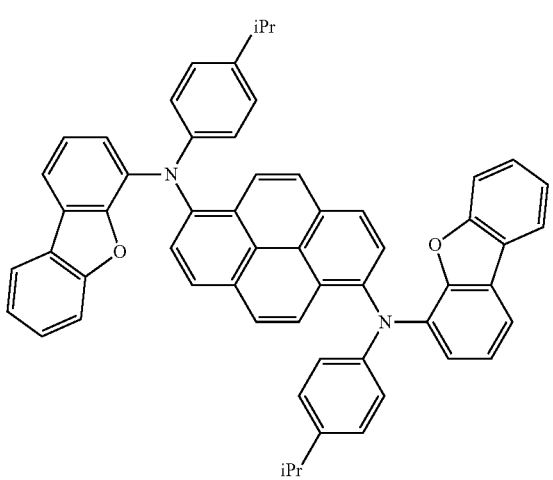

(3-B-3)

Compound (3-B-3) was prepared according to a method described in "Production Example 5" of JP 2013-080961 A.

Synthesis Example (23)

Synthesis of Compound (3-B-4)

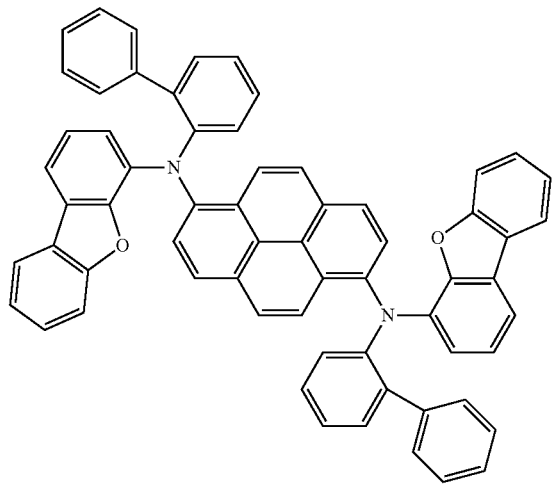

(3-B-4)

Compound (3-B-4) was prepared according to a method described in "Production Example 8" of JP 2013-080961 A.

Synthesis Example (24)

Synthesis of Compound (3-C-1)

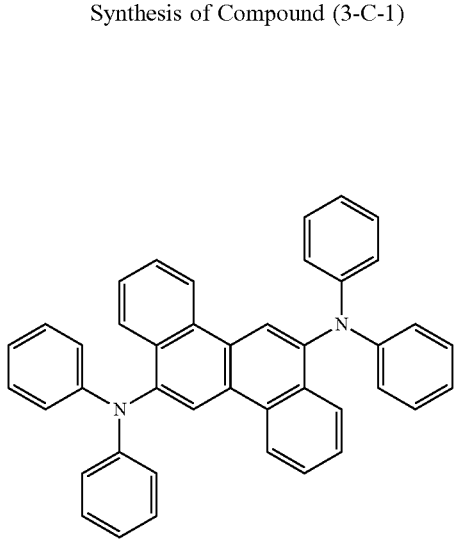

(3-C-1)

Compound (3-C-1) was prepared according to a method described in "Example 9: Preparation of compound D-69" of WO 2013/109030 A.

Synthesis Example (25)

Synthesis of Compound (3-C-2)

(3-C-2)

Compound (3-C-2) was prepared according to a method described in "Synthesis Example 8 (Synthesis of compound (11))" of WO 2004/044088 A.

Synthesis Example (26)

Synthesis of Compound (3-C-3)

(3-C-3)

Compound (3-C-3) was prepared according to a method described in "Synthesis Example 7 (Synthesis of compound (10))" of WO 2004/044088 A.

Other compounds of the invention can be synthesized by appropriately changing a raw material compound by a method according to the Synthesis Examples described above.

Hereinafter, in order to describe the invention in more specifically, Examples of an organic EL device using compounds of the invention will be described, but the invention is not limited thereto.

Organic EL devices according to Examples 1 to 10 and Comparative Examples 1 to 8 were prepared, and voltage (V), luminescence wavelength (nm), and external quantum efficiency (%) at specific luminance were measured, respectively.

The quantum efficiency of a luminescent device includes internal quantum efficiency and external quantum efficiency. The internal quantum efficiency represents a proportion at which external energy injected as electrons (or holes) into the luminescent layer of the luminescent device is converted into photons in a pure manner. On the other hand, the external quantum efficiency is calculated based on an amount of photons emitted to an outside of the luminescent device. The photons generated in the luminescent layer are continuously partly absorbed or reflected inside the luminescent device and are not emitted to the outside of the luminescent device, and therefore the external quantum efficiency becomes lower than the internal quantum efficiency.

A method of measuring the external quantum efficiency is as described below. Luminescence of a device was produced by applying a voltage at which luminance of the device reached 1000 cd/m$^2$ and 100 cd/m$^2$ by using a voltage/current generator R6144 made by Advantest Corporation. A spectral radiance in a visible light region was measured from a direction perpendicular to the luminescent surface by using a spectroradiometer SR-3AR made by Topcon Technohouse Corporation. A numerical value obtained by dividing a measured spectral radiance value of each wavelength component under assumption that the luminescent surface is a completely diffusing surface by wavelength energy and multiplying the resulting value with n is the number of photons at each wavelength. Next, the number of photons in the whole wavelength region observed was integrated, and the resulting value was taken as the total number of photons emitted from the device. A numerical value obtained by dividing an applied current value by an elementary charge was taken as the number of carriers injected into the device. Then, a numerical value obtained by dividing the total number of photons emitted from the device by the number of carriers injected into the device is the external quantum efficiency.

Tables 1 and 2 below show a material composition of each layer and EL characteristics data in the organic EL devices prepared in Examples 1 to 10 and Comparative Examples 1 to 8, respectively.

TABLE 1

| | | | | Luminescent layer (25 nm) | | | |
|---|---|---|---|---|---|---|---|
| Examples | Hole injection layer 1 (40 nm) | Hole injection layer 2 (5 nm) | Hole transport layer (25 nm) | Host (Concentration; mass %) | Dopant (Concentration; mass %) | Polycyclic aromatic compound (Concentration; mass %) | Electron transport layer 1 (5 nm) |
| 1 | HI | HAT-CN | HT-1 | 1-195 (86) | 3-41 (2) | 2A-1 (12) | ET-1 |
| 2 | HI | HAT-CN | HT-1 | 1-195 (90) | 3-41 (2) | 2A-1 (8) | ET-1 |
| 3 | HI | HAT-CN | HT-1 | 1-195 (93) | 3-41 (2) | 2A-1 (5) | ET-1 |
| 4 | HI | HAT-CN | HT-1 | 1-199 (90) | 3-41 (2) | 2A-1 (8) | ET-1 |
| 5 | HI | HAT-CN | HT-1 | 1-222 (90) | 3-41 (2) | 2A-1 (8) | ET-1 |
| 6 | HI | HAT-CN | HT-1 | 1-195 (90) | 3-31 (2) | 2A-1 (8) | ET-1 |
| 7 | HI | HAT-CN | HT-1 | 1-195 (90) | 3-49 (2) | 2A-1 (8) | ET-1 |
| 8 | HI | HAT-CN | HT-1 | 1-195 (90) | 3-B-4 (2) | 2A-1 (8) | ET-1 |
| 9 | HI | HAT-CN | HT-1 | 1-195 (93) | 3-B-4 (2) | 2A-1 (5) | ET-1 |
| 10 | HI | HAT-CN | HT-1 | 1-192 (90) | 3-B-4 (2) | 2A-1 (8) | ET-1 |

| | | | | | Device characteristics at 1000 cd/m$^2$ | | Device characteristics at 100 cd/m$^2$ |
|---|---|---|---|---|---|---|---|
| Examples | Electron transport layer 2 (25 nm) | Cathode (1 nm/ 100 nm) | Wavelength (nm) | Voltage (V) | External quantum efficiency (%) | | External quantum efficiency (%) |
| 1 | ET-2 + Liq | Liq/MgAg | 461 | 3.8 | 7.1 | | 7.7 |
| 2 | ET-2 + Liq | Liq/MgAg | 461 | 3.9 | 7.3 | | 7.8 |
| 3 | ET-2 + Liq | Liq/MgAg | 461 | 4.0 | 7.1 | | 7.8 |
| 4 | ET-2 + Liq | Liq/MgAg | 462 | 3.8 | 6.8 | | 7.0 |
| 5 | ET-2 + Liq | Liq/MgAg | 462 | 3.9 | 6.6 | | 6.9 |
| 6 | ET-2 + Liq | Liq/MgAg | 463 | 3.9 | 7.3 | | 7.7 |
| 7 | ET-2 + Liq | Liq/MgAg | 455 | 4.1 | 6.8 | | 7.0 |
| 8 | ET-2 + Liq | Liq/MgAg | 458 | 3.8 | 6.7 | | 7.5 |
| 9 | ET-2 + Liq | Liq/MgAg | 457 | 3.9 | 6.9 | | 7.3 |
| 10 | ET-2 + Liq | Liq/MgAg | 458 | 3.8 | 6.9 | | 7.5 |

TABLE 2

| Comparative Examples | Hole injection layer 1 (40 nm) | Hole injection layer 2 (5 nm) | Hole transport layer (25 nm) | Luminescent layer (25 nm) | | | Electron transport layer 1 (5 nm) |
|---|---|---|---|---|---|---|---|
| | | | | Host (Concentration; mass %) | Dopant (Concentration; mass %) | Polycyclic aromatic compound (Concentration; mass %) | |
| 1 | HI | HAT-CN | HT-1 | 1-195 (98) | 3-41 (2) | — | ET-1 |
| 2 | HI | HAT-CN | HT-1 | 1-199 (98) | 3-41 (2) | — | ET-1 |
| 3 | HI | HAT-CN | HT-1 | 1-222 (98) | 3-41 (2) | — | ET-1 |
| 4 | HI | HAT-CN | HT-1 | 1-195 (98) | 3-31 (2) | — | ET-1 |
| 5 | HI | HAT-CN | HT-1 | 1-195 (98) | 3-49 (2) | — | ET-1 |
| 6 | HI | HAT-CN | HT-1 | 1-195 (98) | 3-B-4 (2) | — | ET-1 |
| 7 | HI | HAT-CN | HT-1 | 1-192 (98) | 3-B-4 (2) | — | ET-1 |
| 8 | HI | HAT-CN | HT-1 | 1-195 (98) | — | 2A-1 (2) | ET-1 |

| Comparative Examples | Electron transport layer 2 (25 nm) | Cathode (1 nm/ 100 nm) | Device characteristics at 1000 cd/m$^2$ | | | Device characteristics at 100 cd/m$^2$ |
|---|---|---|---|---|---|---|
| | | | Wavelength (nm) | Voltage (V) | External quantum efficiency (%) | External quantum efficiency (%) |
| 1 | ET-2 + Liq | Liq/MgAg | 460 | 4.2 | 7.3 | 7.4 |
| 2 | ET-2 + Liq | Liq/MgAg | 462 | 4.1 | 6.8 | 6.7 |
| 3 | ET-2 + Liq | Liq/MgAg | 462 | 4.3 | 6.6 | 6.7 |
| 4 | ET-2 + Liq | Liq/MgAg | 463 | 4.2 | 7.4 | 7.5 |
| 5 | ET-2 + Liq | Liq/MgAg | 455 | 4.5 | 6.8 | 6.9 |
| 6 | ET-2 + Liq | Liq/MgAg | 457 | 4.1 | 6.9 | 7.4 |
| 7 | ET-2 + Liq | Liq/MgAg | 458 | 4.1 | 7.0 | 7.4 |
| 8 | ET-2 + Liq | Liq/MgAg | 449 | 4.2 | 6.7 | 7.1 |

In Tables 1 to 2, "HI" represents N4,N4'-diphenyl-N4,N4'-bis(9-phenyl-9H-carbazol-3-yl)-[1,1'-biphenyl]-4,4'-diamine, "HAT-CN" represents 1,4,5,8,9,12-hexaazatriphenylene hexacarbonitrile, "HT-1" represents N-([1,1'-biphenyl]-4-yl)-N-(4-(9-phenyl-9H-carbazol-3-yl)phenyl)-[1,1'-biphenyl]-4-amine, "ET-1" represents 9-{7-[bis(2,4,6-trimethylphenyl)boranyl]-9,9-dimethyl-9H-fluoren-2-yl}-3,6-dimethyl-9H-carbazole, and "ET-2" represents 3,3'-[(2-phenylanthracene-9,10-diyl)dibenzene-3,1-diyl]bis(5-methylpyridine). Chemical structures of these compounds are illustrated below together with a chemical structure of "Liq." In addition, hereinafter, "Me" is methyl.

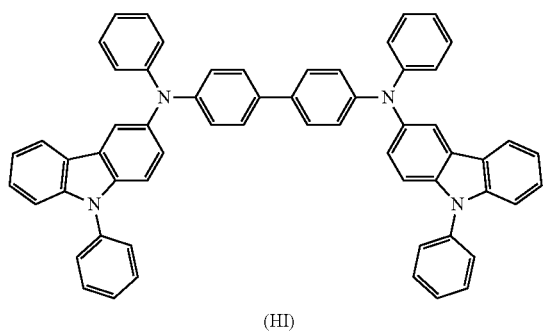

(HI)

-continued

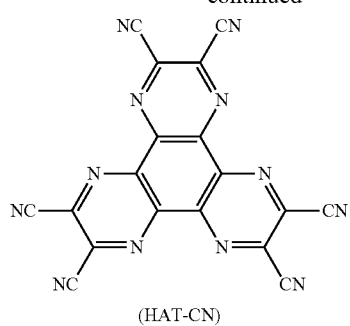
(HAT-CN)

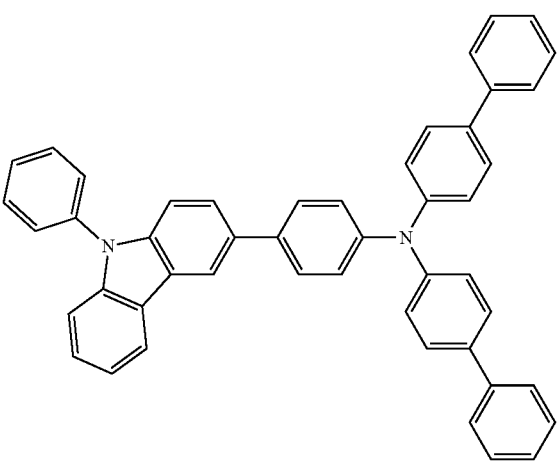
(HT-1)

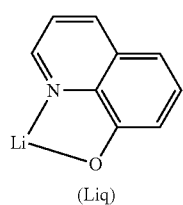
(Liq)

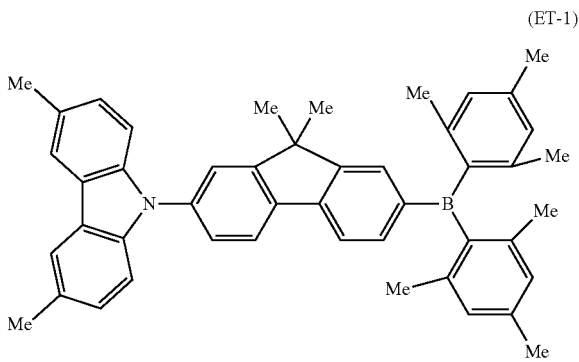
(ET-1)

-continued

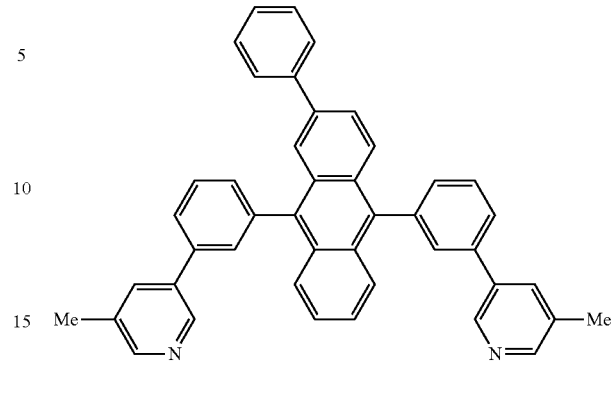
(ET-2)

Example 1

Device with Host Material: Compound (1-195), Dopant Material: Compound (3-41) and Polycyclic Aromatic Compound (2A-1)

A glass substrate having a size of 26 mm×28 mm×0.7 mm prepared by forming a film of ITO having a thickness of 180 nm by sputtering and polishing the ITO film to 150 nm (made by Opto Science, Inc.) was applied as a transparent supporting substrate. This transparent supporting substrate was fixed to a substrate holder of a commercially available vapor deposition apparatus (made by Showa Shinku Co., Ltd.), and a deposition boat made of molybdenum and containing each of HI, HAT-CN, HT-1, compound (1-195), compound (3-41), compound (2A-1), ET-1 and ET-2, and a deposition boat made of aluminum nitride and containing each of Liq, magnesium and silver were mounted in the apparatus, respectively.

As shown in Table 1, each layer as described below was formed sequentially on the ITO film of the transparent supporting substrate. A pressure in a vacuum chamber was reduced to $5 \times 10^{-4}$ Pa, and deposition was performed sequentially from HI, HAT-CN to HT-1. Thus, hole injection layer 1 (film thickness: 40 nm), hole injection layer 2 (film thickness: 5 nm) and hole transport layer (film thickness: 25 nm) were formed. Subsequently, compound (1-195), compound (3-41) and compound (2A-1) were simultaneously heated, and deposition was performed so as to obtain a film thickness of 25 nm to form a luminescent layer. A vapor deposition rate was adjusted to be approximately 86:2:12 in a mass ratio of compound (1-195) compound (3-41): compound (2A-1). Next, ET-1 was heated, and deposition was performed so as to obtain a film thickness of 5 nm to form electron transport layer 1. Next, ET-2 and Liq were simultaneously heated, and deposition was performed so as to obtain a film thickness of 25 nm to form an electron transport layer. A vapor deposition rate was adjusted to be approximately 50:50 in a mass ratio of ET-2 to Liq was. The vapor deposition rate for each layer was 0.01 to 1 nm/sec. Then, Liq was heated, and deposition was performed at a vapor deposition rate of 0.01 to 0.1 nm/sec so as to obtain a film thickness of 1 nm. Subsequently, magnesium and silver were simultaneously heated, and deposition was performed so as to obtain a film thickness of 100 nm to form a cathode to obtain an organic EL device. At this time, the vapor deposition rate was adjusted in the range between 0.1 nm to 10 nm/sec to be 10:1 in a ratio of the numbers of atoms for magnesium to silver.

When a direct current voltage was applied to the ITO electrode as a positive electrode and the magnesium/silver electrode as a negative electrode, and characteristics at luminescence of 1000 cd/m² were measured, as shown in Table 1, a driving voltage was 3.8 V, external quantum efficiency was 7.1%, and blue luminescence at 464 nm were obtained. The external quantum efficiency at luminescence of 100 cd/m² was 7.71.

Examples 2 to 10

According to Example 1, each organic EL device was prepared with the layer structure described in Table 1, and data of EL characteristics were obtained (Table 1).

Comparative Example 1

Device with Host Material: Compound (1-195) and Dopant Material: Compound (3-41)

A glass substrate having a size of 26 mm×28 mm×0.7 mm prepared by forming a film of ITO having a thickness of 180 nm by sputtering and polishing the ITO film to 150 nm (made by Opto Science, Inc.) was applied as a transparent supporting substrate. This transparent supporting substrate was fixed to a substrate holder of a commercially available vapor deposition apparatus (made by Showa Shinku Co., Ltd.), and a deposition boat made of molybdenum and containing each of HI, HAT-CN, HT-1, compound (1-195), compound (3-41), ET-1 and ET-2, and a deposition boat made of aluminum nitride and containing each of Liq, magnesium and silver were mounted in the apparatus, respectively.

As shown in Table 2, each layer as described below was formed sequentially on an ITO film of a transparent supporting substrate. A pressure in a vacuum chamber was reduced to $5 \times 10^{-4}$ Pa, and deposition was performed sequentially from HI, HAT-CN to HT-1. Thus, form hole injection layer 1 (film thickness: 40 nm), hole injection layer 2 (film thickness: 5 nm) and hole transport layer (film thickness: 25 nm) were formed. Subsequently, compound (1-195) and compound (3-41) were simultaneously heated, and deposition was performed so as to obtain a film thickness of 25 nm to form a luminescent layer. A vapor deposition rate was adjusted to be approximately 98:2 in a mass ratio of compound (1-195) to compound (3-41). Next, ET-1 was heated, and deposition was performed so as to obtain a film thickness of 5 nm to form electron transport layer 1. Next, ET-2 and Liq were simultaneously heated, and deposition was performed so as to obtain a film thickness of 25 nm to form an electron transport layer. A vapor deposition rate was adjusted to be approximately 50:50 in a mass ratio of ET-2 to Liq. The vapor deposition rate for each layer was 0.01 to 1 nm/sec. Thereafter, Liq was heated, and deposition was performed at a vapor deposition rate of 0.01 to 0.1 nm/sec so as to obtain a film thickness of 1 nm. Subsequently, magnesium and silver were simultaneously heated, and deposition was performed so as to obtain a film thickness of 100 nm to form a cathode to obtain an organic EL device. At this time, the vapor deposition rate was adjusted in the range between 0.1 nm to 10 nm/sec to be 10:1 in a ratio of the numbers of atoms of magnesium to silver.

When a direct current voltage was applied to the ITO electrode as a positive electrode and the magnesium/silver electrode as a negative electrode, and characteristics at luminescence of 1000 cd/m² were measured, a driving voltage was 4.2 V, external quantum efficiency was 7.3%, and blue luminescence at 460 nm were obtained. The external quantum efficiency at luminescence of 100 cd/m² was 7.4%.

Comparative Examples 2 to 7

According to Comparative Example 1, each organic EL device was produced with a layer structure as described in Table 2, and data of EL characteristics were obtained (Table 2).

Comparative Example 8

Device with Host Material: Compound (1-195) and Polycyclic Aromatic Compound (2A-1)

A glass substrate having a size of 26 mm×28 mm×0.7 mm prepared by forming a film of ITO having a thickness of 180 nm by sputtering and polishing the ITO film to 150 nm (made by Opto Science, Inc.) was applied as a transparent supporting substrate. This transparent supporting substrate was fixed to a substrate holder of a commercially available vapor deposition apparatus (made by Showa Shinku Co., Ltd.), and a deposition boat made of molybdenum and containing each of HI, HAT-CN, HT-1, compound (1-195), compound (2A-1), ET-1 and ET-2, and a deposition boat made of aluminum nitride and containing each of Liq, magnesium and silver were mounted in the apparatus, respectively.

As shown in Table 2, each layer as described below was formed sequentially on an ITO film of a transparent supporting substrate. A pressure in a vacuum chamber was reduced to 5×10-4 Pa, and deposition was performed sequentially from HI, HAT-CN to HT-1. Thus hole injection layer 1 (film thickness: 40 nm), hole injection layer 2 (film thickness: 5 nm) and hole transport layer (film thickness: 25 nm) were formed. Subsequently, compound (1-195) and compound (2A-1) were simultaneously heated, and deposition was performed so as to obtain a film thickness of 25 nm. Thus, a luminescent layer was formed. A vapor deposition rate was adjusted to be approximately 98:2 in a mass ratio of compound (1-195) to compound (2A-1) was. Next, ET-1 was heated, and deposition was performed so as to obtain a film thickness of 5 nm to form electron transport layer 1. Next, ET-2 and Liq were simultaneously heated, and deposition was performed so as to obtain a film thickness of 25 nm to form an electron transport layer. A vapor deposition rate was adjusted to be approximately 50:50 in a mass ratio of ET-2 to Liq. The vapor deposition rate for each layer was 0.01 to 1 nm/sec. Then, Liq was heated, and deposition was performed at a vapor deposition rate of 0.01 to 0.1 nm/sec so as to obtain a film thickness of 1 nm. Subsequently, magnesium and silver were simultaneously heated, and deposition was performed so as to obtain a film thickness of 100 nm to form a cathode to obtain an organic EL device. At this time, the vapor deposition rate was adjusted in the range between 0.1 nm to 10 nm/sec to be 10:1 in a ratio of the numbers of atoms of magnesium to silver.

When a direct current voltage was applied to the ITO electrode as a positive electrode and the magnesium/silver electrode as a negative electrode, and characteristics at luminescence of 1000 cd/m² were measured, a driving voltage was 4.2 V, external quantum efficiency was 6.7%, and blue luminescence at 449 nm were obtained. The external quantum efficiency at luminescence of 100 cd/m² was 7.1%.

As described above, evaluations were performed on part of the compounds according to the invention as the material for the luminescent layer of the organic EL device, and as a result, usability thereof was described above. However, other compounds in which evaluations were not performed also have the same basic skeleton, and have similar structures as a whole, and therefore a person skilled in the art can understand that other materials are similar materials for the luminescent layer having excellent characteristics.

What is claimed is:

1. An organic electroluminescent device, comprising a pair of electrode layers formed of an anode layer and a cathode layer, and a luminescent layer arranged between the pair of electrode layers, wherein the luminescent layer comprises a host material and a dopant material, the host material comprises an anthracene-based compound represented by formula (1), the dopant material is a polycyclic aromatic compound represented by formula (3), or a dimer or a trimer of a polycyclic aromatic compound having a plurality of structures represented by formula (3), or a compound represented by any one of formula (4-A), formula (4-B) and formula (4-C), and the luminescent layer further comprises a polycyclic aromatic compound represented by formula (2A) or a multimer of a polycyclic aromatic compound having a plurality of structures represented by formula (2A):

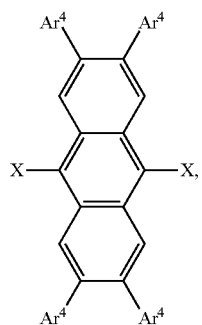

(I)

wherein, in formula (1), and $Ar^4$ are independently hydrogen, aryl which may be substituted, heteroaryl which may be substituted, diarylamino which may be substituted, diheteroarylamino which may be substituted, arylheteroarylamino which may be substituted, alkyl which may be substituted, alkenyl which may be substituted, alkoxy which may be substituted, aryloxy which may be substituted, arylthio which may be substituted, or silyl which may be substituted, and a case where all of X and $Ar^4$ simultaneously become hydrogen is excluded, and at least one hydrogen in the compound represented by formula (1) may be replaced by halogen, cyano, deuterium, or heteroaryl which may be substituted,

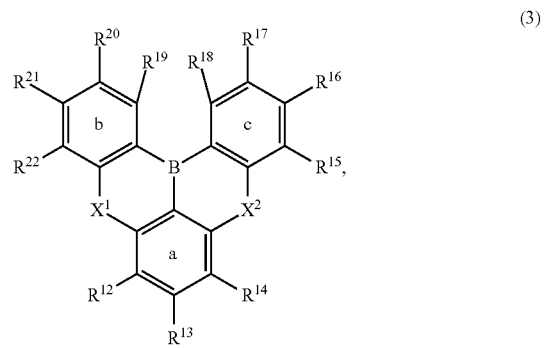

(3)

wherein, in formula (3), $R^{12}$, $R^{13}$, $R^{14}$, $R^{15}$, $R^{16}$, $R^{17}$, $R^{18}$, $R^{19}$, $R^{20}$, $R^{21}$ and $R^{22}$ are independently hydrogen, aryl, heteroaryl, diarylamino, diheteroarylamino, arylheteroarylamino, alkyl, cycloalkyl, alkoxy or aryloxy, wherein at least one hydrogen in the aryl, heteroaryl, diarylamino, diheteroarylamino, arylheteroarylamino, alkyl, cycloalkyl, alkoxy and aryloxy may be replaced by aryl, heteroaryl or alkyl, and adjacent groups of $R^{12}$, $R^{13}$, $R^{14}$, $R^{15}$, $R^{16}$, $R^{17}$, $R^{18}$, $R^{19}$, $R^{20}$, $R^{21}$ and $R^{22}$ may be bonded to each other to form an aryl ring or a heteroaryl ring together with an a ring, a b ring or a c ring, and at least one hydrogen in the ring formed may be replaced by aryl, heteroaryl, diarylamino, diheteroarylamino, arylheteroarylamino, alkyl, alkoxy or aryloxy, and wherein at least one hydrogen in the aryl, heteroaryl, diarylamino, diheteroarylamino, arylheteroarylamino, alkyl, alkoxy and aryloxy may be replaced by aryl, heteroaryl or alkyl, and $X^1$ and $X^2$ are independently >O, >N—R, >C(—R)$_2$, >S or >Se, in which, at least one of $X^1$ and $X^2$ is >N—R, and R of the >N—R is aryl having 6 to 12 carbons which may be substituted, heteroaryl having 2 to 15 carbons which may be substituted, or alkyl having 1 to 6 carbons, and R of the >C(—R)$_2$ is hydrogen, aryl having 6 to 12 carbons which may be substituted, or alkyl having 1 to 6 carbons, and R of the >N—R and/or R of the >C(—R)$_2$ may be bonded with the a ring, the b ring and/or the c ring by —O—, —S—, —C(—R)$_2$— or a single bond, and R of the —C(—R)$_2$— is alkyl having 1 to 6 carbons, and at least one hydrogen in the compound of formula (3) or the dimer or trimer of the polycyclic aromatic compound having the plurality of structures represented by formula (3) may be replaced by deuterium, cyano or halogen,

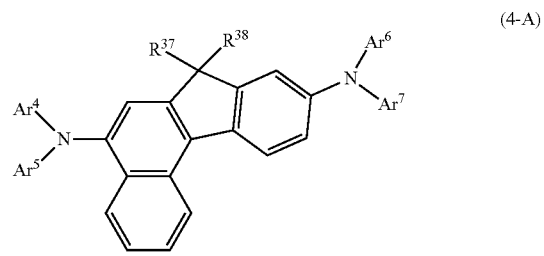

(4-A)

-continued

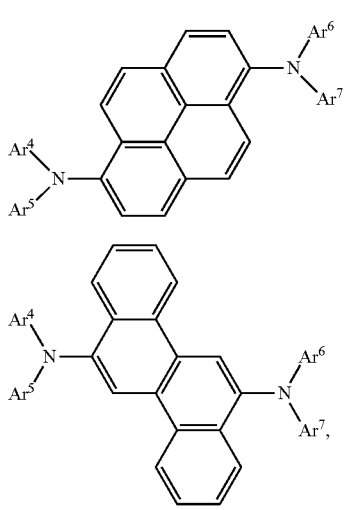

(4-B)

(4-C)

wherein, in formula (4-A), formula (4-B) and formula (4-C), $Ar^4$, $Ar^5$, $Ar^6$ and $Ar^7$ are independently aryl having 6 to 30 carbons or heteroaryl having 5 to 30 carbons, and at least one hydrogen in the aryl and heteroaryl may be replaced by aryl having 6 to 10 carbons, heteroaryl having 5 to 12 carbons, alkyl having 1 to 6 carbons, cycloalkyl having 3 to 10 carbons, alkoxy having 1 to 6 carbons, aryloxy having 6 to 10 carbon or trialkylsilyl having 3 to 12 carbons, and adjacent groups of $Ar^4$, $Ar^5$, $Ar^6$ and $Ar^7$ may be bonded to each other to form a ring, and $R^{37}$ and $R^{38}$ are independently hydrogen, aryl having 6 to 30 carbons, heteroaryl having 5 to 30 carbons, alkyl having 1 to 10 carbons, cycloalkyl having 3 to 12 carbons or trialkylsilyl having 3 to 12 carbons, and at least one hydrogen in the aryl, heteroaryl, alkyl, cycloalkyl and trialkylsilyl may be replaced by aryl having 6 to 10 carbons, heteroaryl having 5 to 12 carbons, alkyl having 1 to 6 carbons, cycloalkyl having 3 to 10 carbons or trialkylsilyl having 3 to 12 carbons, and $R^{37}$ and $R^{38}$ may be bonded to each other to form a ring, and at least one hydrogen in the compound represented by each of formula (4-A), formula (4-B) and formula (4-C) may be replaced by halogen, cyano or deuterium,

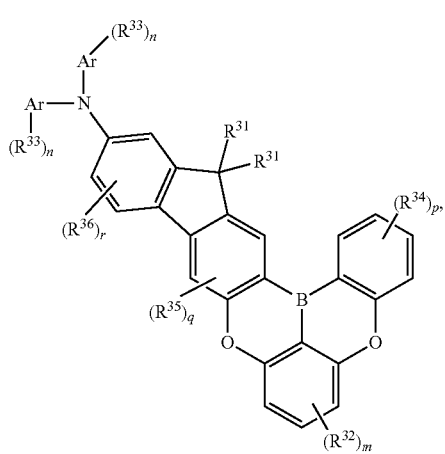

(2A)

wherein, in formula (2A),

Ar is independently aryl or heteroaryl, $R^{31}$, $R^{32}$, $R^{33}$, $R^{34}$, $R^{35}$ and $R^{36}$ are independently hydrogen, aryl, heteroaryl, diarylamino, diheteroarylamino, arylheteroarylamino, alkyl, cycloalkyl, alkoxy, trialkylsilyl or aryloxy, and at least one hydrogen in the aryl, heteroaryl, diarylamino, diheteroarylamino, arylheteroarylamino, alkyl, cycloalkyl, alkoxy, trialkylsilyl and aryloxy may be replaced by aryl, heteroaryl, diarylamino or alkyl, when $R^{34}$ is plural, adjacent $R^{34}$'s may be bonded to each other to form an aryl ring or a heteroaryl ring together with a c ring, and at least one hydrogen in the ring formed may be replaced by aryl, heteroaryl, diarylamino, diheteroarylamino, arylheteroarylamino, alkyl, alkoxy, trialkylsilyl or aryloxy, and at least one hydrogen in the aryl, heteroaryl, diarylamino, diheteroarylamino, arylheteroarylamino, alkyl, alkoxy, trialkylsilyl and aryloxy may be replaced by aryl, heteroaryl, diarylamino or alkyl, when $R^{33}$ and $R^{36}$ are adjacent to each other, both may be bonded by —O—, —S—, —C(—R)$_2$— or a single bond, and R of the —C(—R)$_2$— is hydrogen or alkyl having 1 to 6 carbons, m is an integer from 0 to 3, n is independently an integer of 0 to a maximum replaceable number to Ar, p is an integer from 0 to 4, q is independently an integer from 0 to 2, and r is an integer from 0 to 3, and at least one hydrogen in the compound represented by formula (2A) may be replaced by halogen or deuterium.

2. The organic electroluminescent device according to claim 1, wherein, in formula (1), X is independently a group represented by formula (1-X1), formula (1-X2) or formula (1-X3), $Ar^4$ is independently hydrogen, phenyl, biphenylyl, terphenylyl, naphthyl, or silyl which may be substituted, and at least one hydrogen in the compound represented by formula (1) may be replaced by halogen, cyano, deuterium, or a group represented by formula (A):

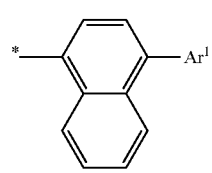

(1-X1)

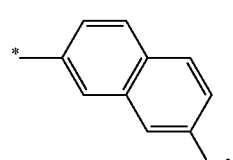

(1-X2)

*—$Ar^3$ (1-X3)

-continued

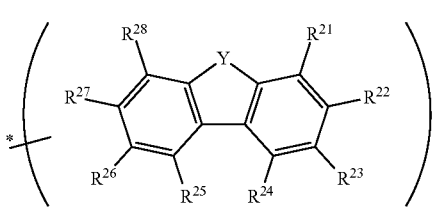
(A)

wherein, in formula (1-X1), formula (1-X2) and formula (1-X3), Ar¹, Ar² and Ar³ are independently hydrogen (excluding Ar³), phenyl, biphenylyl, terphenylyl, quaterphenylyl, naphthyl, phenanthryl, fluorenyl, benzofluorenyl, chrysenyl, triphenylenyl, pyrenyl, or a group represented by formula (A), and at least one hydrogen in AP may be further replaced by phenyl, biphenylyl, terphenylyl, naphthyl, phenanthryl, fluorenyl, chrysenyl, triphenylenyl, pyrenyl, or a group represented by formula (A), the naphthylene in formula (1-X1) and formula (1-X2) may be further fused with one benzene ring, a group represented by formula (1-X1), formula (1-X2) or formula (1-X3) is bonded to an anthracene ring of formula (1) at a position "*,"

in formula (A), Y is —O—, —S— or >N—$R^{29}$, and $R^{29}$ is hydrogen, or aryl which may be substituted, $R^{21}$, $R^{22}$, $R^{23}$, $R^{24}$, $R^{25}$, $R^{26}$, $R^{27}$ and $R^{28}$ are independently hydrogen, alkyl which may be substituted, aryl which may be substituted, heteroaryl which may be substituted, alkoxy which may be substituted, aryloxy which may be substituted, arylthio which may be substituted, trialkylsilyl, amino which may be substituted, halogen, hydroxy or cyano, adjacent groups of $R^{21}$, $R^{22}$, $R^{23}$, $R^{24}$, $R^{25}$, $R^{26}$, $R^{27}$ and $R^{28}$ may be bonded to each other to form a hydrocarbon ring, an aryl ring or a heteroaryl ring, and a group represented by formula (A) is bonded, by applying any of positions in the formula (A) as a bonding position "*," to a naphthalene ring of formula (1-X1) or formula (1-X2), a single bond of formula (1-X3) or Ar³ of formula (1-X3), or the group represented by formula (A) is bonded by replacing at least one hydrogen in the compound represented by formula (1).

3. The organic electroluminescent device according to claim 1, wherein, in formula (1), X is independently a group represented by formula (1-X1), formula (1-X2) or formula (1-X3), Ar⁴ is independently hydrogen, phenyl or naphthyl, and at least one hydrogen in the compound represented by formula (1) may be replaced by halogen, cyano or deuterium:

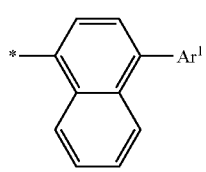
(1-X1)

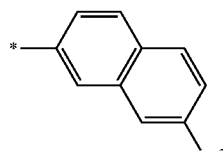
(1-X2)

(1-X3)

wherein, in formulas (1-X1), formula (1-X2) and formula (1-X3), Ar¹, Ar² and Ar³ are independently hydrogen (excluding Ar³), phenyl, biphenylyl, terphenylyl, naphthyl, phenanthryl, fluorenyl, chrysenyl, triphenylenyl, pyrenyl, or a group represented by any of formula (A-1), formula (A-2), formula (A-3), formula (A-4), formula (A-5), formula (A-6), formula (A-7), formula (A-8), formula (A-9), formula (A-10) and formula (A-11),

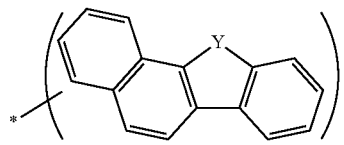
(A-1)

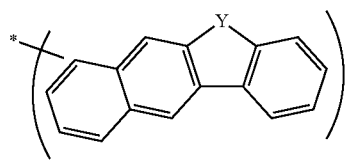
(A-2)

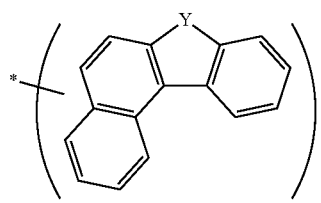
(A-3)

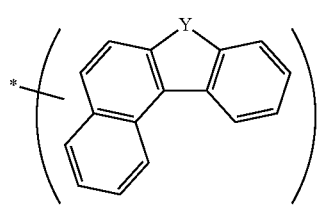
(A-4)

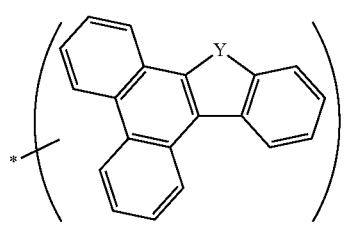
(A-5)

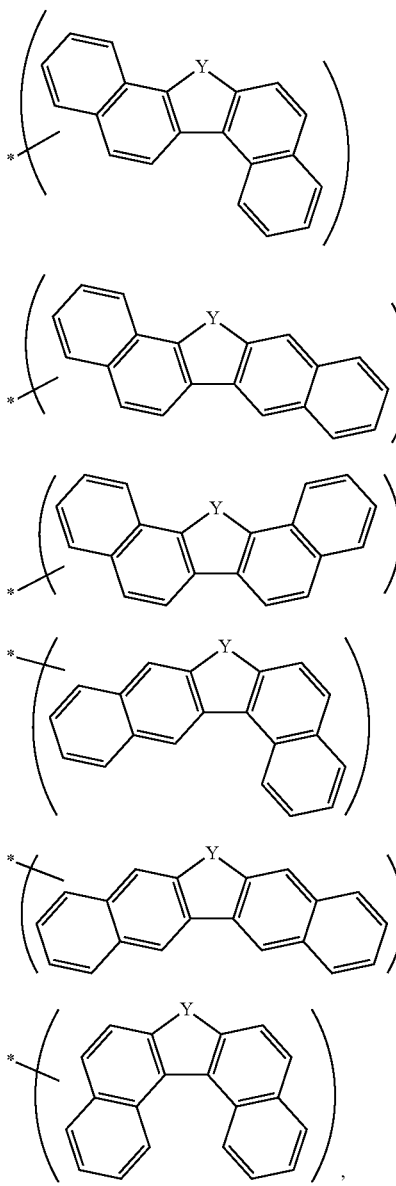

at least one hydrogen in Ar³ may be further replaced by phenyl, biphenylyl, terphenylyl, naphthyl, phenanthryl, fluorenyl, chrysenyl, triphenylenyl, pyrenyl, or a group represented by any of formula (A-1), formula (A-2), formula (A-3), formula (A-4), formula (A-5), formula (A-6), formula (A-7), formula (A-8), formula (A-9), formula (A-10) and formula (A-11), a group represented by formula (1-X1), formula (1-X2) or formula (1-X3) is bonded to an anthracene ring of formula (1) at a position "*,"

in formula (A-1), formula (A-2), formula (A-3), formula (A-4), formula (A-5), formula (A-6), formula (A-7), formula (A-8), formula (A-9), formula (A-10) and formula (A-11), Y is —O—, —S— or >N—R²⁹, and R²⁹ is hydrogen or aryl, and at least one hydrogen in the groups represented by formula (A-1), formula (A-2), formula (A-3), formula (A-4), formula (A-5), formula (A-6), formula (A-7), formula (A-8), formula (A-9), formula (A-10) and formula (A-11) may be replaced by alkyl, aryl, heteroaryl, alkoxy, aryloxy, arylthio, trialkylsilyl, diaryl-substituted amino, diheteroaryl-substituted amino, arylheteroaryl-substituted amino, halogen, hydroxy or cyano, and a group represented by formula (A-1), formula (A-2), formula (A-3), formula (A-4), formula (A-5), formula (A-6), formula (A-7), formula (A-8), formula (A-9), formula (A-10) and formula (A-11) is bonded, by applying any position in the groups represented by the formulas (A-1) to (A-11) as a bonding position "*," to a naphthalene ring of formula (1-X1) or formula (1-X2), a single bond of formula (1-X3), or Ar³ of formula (1-X3).

4. The organic electroluminescent device according to claim 3, wherein, in formula (1), X is independently a group represented by formula (1-X1), formula (1-X2) or formula (1-X3), and a group represented by formula (1-X1), formula (1-X2) or formula (1-X3) is bonded to an anthracene ring of formula (1) at a position "*," and Ar¹, Ar² and Ar³ are independently hydrogen (excluding Ar³), phenyl, biphenylyl, terphenylyl, naphthyl, phenanthryl, fluorenyl, or a group represented by any of formula (A-1), formula (A-2), formula (A-3) and formula (A-4) and at least one hydrogen in Ar³ may be further replaced by phenyl, naphthyl, phenanthryl, fluorenyl, or a group represented by any of formula (A-1), formula (A-2), formula (A-3) and formula (A-4), and Ar⁴ is independently hydrogen, phenyl or naphthyl.

5. The organic electroluminescent device according to claim 1, wherein the anthracene-based compound is represented by at least one structural formula selected from the group consisting of:

(1-199)

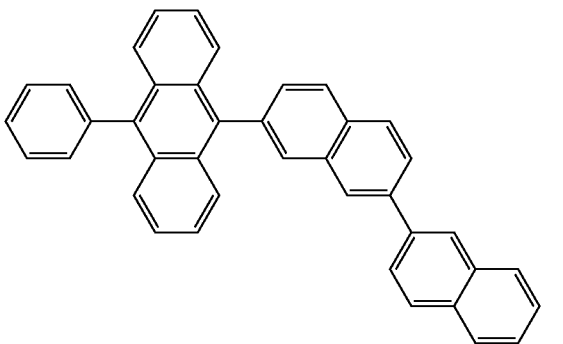

(1-192)

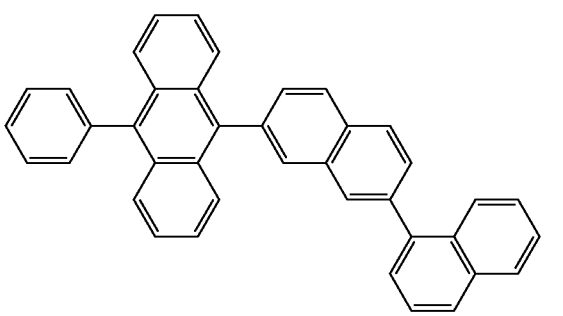

-continued (1-222)
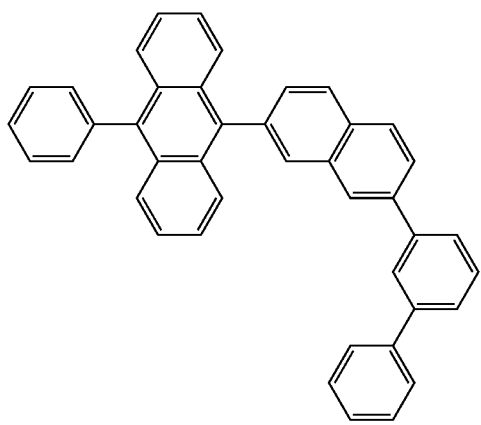

(1-221)
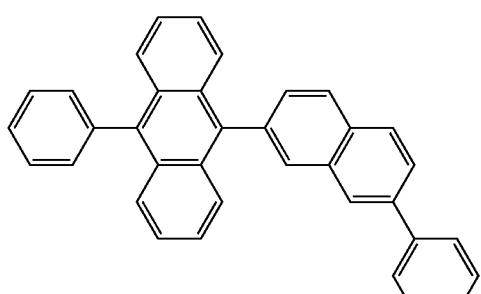

(1-195)
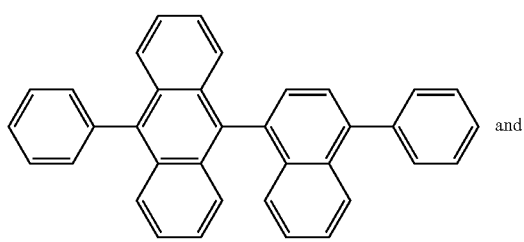

and (1-134-O)
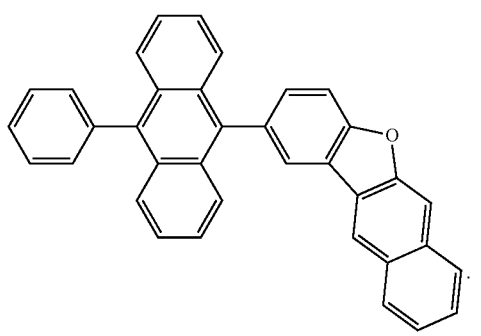

6. The organic electroluminescent device according to claim 1,
wherein, in formula (2A),
Ar is independently aryl,
$R^{31}$, $R^{32}$, $R^{33}$ and $R^{34}$ are independently hydrogen, aryl, heteroaryl, alkyl, cycloalkyl, alkoxy, trialkylsilyl or aryloxy, and at least one hydrogen in the groups may be replaced by aryl, heteroaryl or alkyl,
when $R^{34}$ is plural, adjacent $R^{34}$'s may be bonded to each other to form an aryl ring or a heteroaryl ring together with a c ring, and at least one hydrogen in the ring formed may be replaced by aryl, heteroaryl, alkyl, alkoxy, trialkylsilyl or aryloxy, and at least one hydrogen in the groups may be replaced by aryl, heteroaryl or alkyl, and
q is 0, and r is 0.

7. The organic electroluminescent device according to claim 1, wherein the polycyclic aromatic compound represented by formula (2A) is a polycyclic aromatic compound represented by formula (2A'):

(2A')
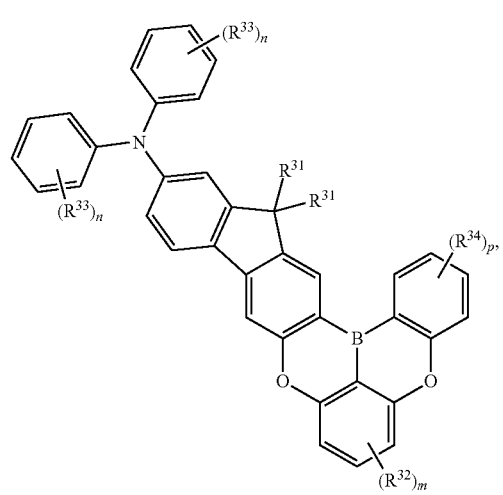

wherein, in formula (2A'),
$R^{31}$, $R^{32}$, $R^{33}$ and $R^{34}$ are independently hydrogen, aryl, heteroaryl, alkyl, cycloalkyl, alkoxy, trialkylsilyl or aryloxy, and at least one hydrogen in the aryl, heteroaryl, alkyl, cycloalkyl, alkoxy, trialkylsilyl and aryloxy may be replaced by aryl, heteroaryl or alkyl,
when $R^{34}$ is plural, adjacent $R^{34}$'s may be bonded to each other to form an aryl ring or a heteroaryl ring together with a c ring, and at least one hydrogen in the ring formed may be replaced by aryl, heteroaryl, alkyl, alkoxy, trialkylsilyl or aryloxy, and at least one hydrogen in the aryl, heteroaryl, alkyl, alkoxy, trialkylsilyl and aryloxy may be replaced by aryl, heteroaryl or alkyl, and
m is an integer from 0 to 3, n is independently an integer from 0 to the maximum replaceable number to Ar, and p is an integer from 0 to 4.

8. The organic electroluminescent device according to claim 7, wherein, in formula (2A'),
$R^{31}$ is independently hydrogen, aryl having 6 to 30 carbons or alkyl having 1 to 24 carbons,
$R^{32}$, $R^{33}$ and $R^{34}$ are independently hydrogen, aryl having 6 to 30 carbons, heteroaryl having 2 to 30 carbons, alkyl having 1 to 24 carbons, alkoxy having 1 to 24 carbons, trialkylsilyl having alkyl having 1 to 4 carbons, or aryloxy having 6 to 30 carbons, and at least one hydrogen in the aryl, heteroaryl, alkyl, alkoxy and trialkylsilyl may be replaced by aryl having 6 to 16 carbons, heteroaryl having 2 to 25 carbons or alkyl having 1 to 18 carbons, and
m is an integer from 0 to 3, n is independently an integer from 0 to 6, and p is an integer from 0 to 2.

9. The organic electroluminescent device according to claim 7, wherein, in formula (2A'),
$R^{31}$ is independently hydrogen, aryl having 6 to 12 carbons or alkyl having 1 to 12 carbons,
$R^{32}$, $R^{33}$ and $R^{34}$ are independently hydrogen, aryl having 6 to 30 carbons, heteroaryl having 2 to 30 carbons, alkyl having 1 to 24 carbons or trialkylsilyl having alkyl having 1 to 4 carbons, and
m is 0 or 1, n is independently 0 or 1, and p is 0 or 1.

10. The organic electroluminescent device according to claim 1, wherein the polycyclic aromatic compound represented by formula (2A) is a polycyclic aromatic compound represented by formula (2A-1):

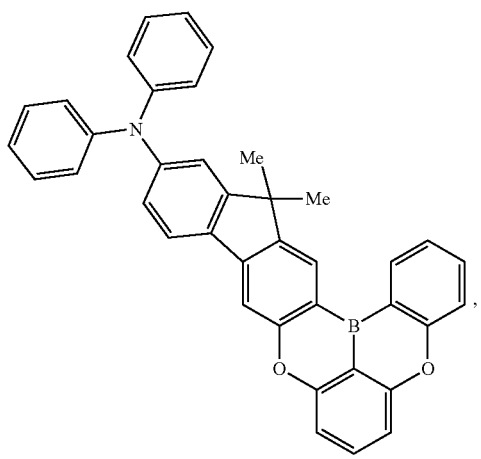

(2A-1)

wherein, in formula (2A-1), "Me" represents methyl.

11. The organic electroluminescent device according to claim 1, wherein the dopant material is the polycyclic aromatic compound represented by formula (3), or the dimer or the trimer of the polycyclic aromatic compound having the plurality of structures represented by formula (3).

12. The organic electroluminescent device according to claim 11, wherein, in formula (3),
$R^{12}$, $R^{13}$, $R^{14}$, $R^{15}$, $R^{16}$, $R^{17}$, $R^{18}$, $R^{19}$, $R^{20}$, $R^{21}$ and $R^{22}$ are independently hydrogen, aryl having 6 to 30 carbons, heteroaryl having 2 to 30 carbons, diarylamino (in which, aryl is aryl having 6 to 12 carbons), alkyl having 1 to 24 carbons or cycloalkyl having 3 to 24 carbons, and adjacent groups of $R^{12}$, $R^{13}$, $R^{14}$, $R^{15}$, $R^{16}$, $R^{17}$, $R^{18}$, $R^{19}$, $R^{20}$, $R^{21}$ and $R^{22}$ may be bonded to each other to form an aryl ring having 9 to 16 carbons or a heteroaryl ring having 6 to 15 carbons together with an a ring, a b ring or a c ring, and at least one hydrogen in the ring formed may be replaced by aryl having 6 to 30 carbons, a heteroaryl having 2 to 30 carbons, diarylamino (in which, aryl is aryl having 6 to 12 carbons), or alkyl having 1 to 24 carbons, and
$X^1$ and $X^2$ are independently >O, >N—R, >C(—R)$_2$ or >S, in which, at least one of $X^1$ and $X^2$ is >N—R, and R of the >N—R is aryl having 6 to 10 carbons which may be substituted, heteroaryl having 2 to 12 carbons which may be substituted, or alkyl having 1 to 4 carbons, and R of the >C(—R)$_2$ is hydrogen, aryl having 6 to 10 carbons which may be substituted, or alkyl having 1 to 4 carbons,
at least one hydrogen in the compound of formula (3) or the dimer of the polycyclic aromatic compound having the plurality of structures represented by formula (3) may be replaced by deuterium, cyano or halogen, and in the case of a multimer, the multimer is a dimer having two structures represented by formula (3).

13. The organic electroluminescent device according to claim 11, wherein the dopant material comprises at least one compound represented by a structural formula selected from the group consisting of:

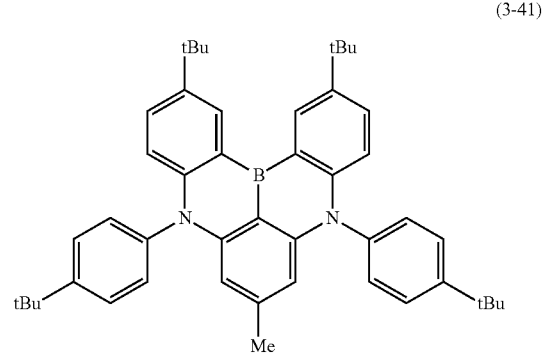

(3-41)

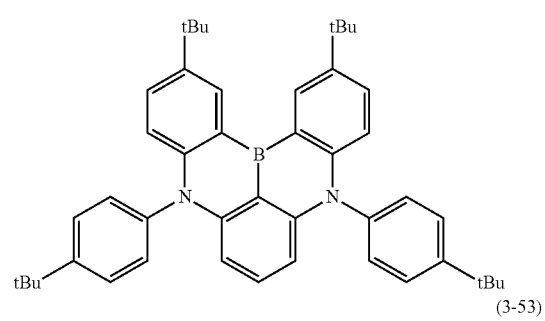

(3-31)

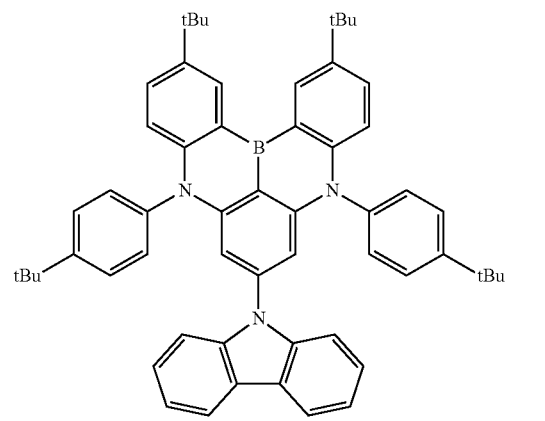

(3-53)

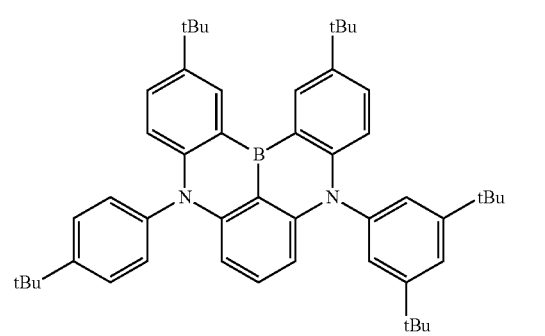

(3-37)

-continued (3-46)
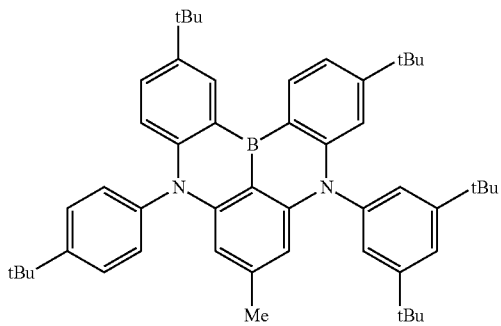

(3-50)
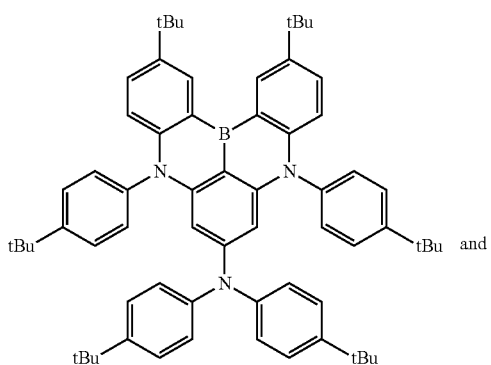
and (3-49)
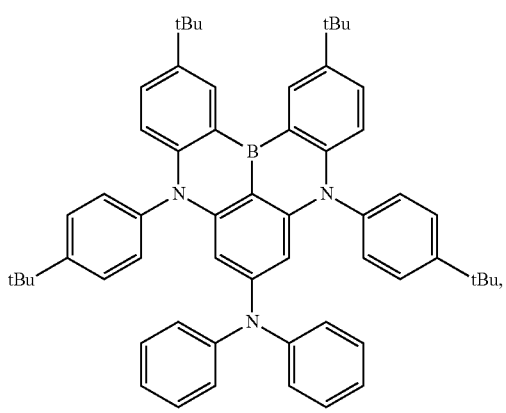

wherein, in the structural formulas, "Me" represents methyl, and "tBu" represents tertiary butyl.

14. The organic electroluminescent device according to claim 1, wherein the dopant material is the polycyclic aromatic compound represented by formula (4-B).

15. The organic electroluminescent device according to claim 1, wherein the dopant material comprises at least one compound represented by a structural formula selected from the group consisting of:

(3-A-1)
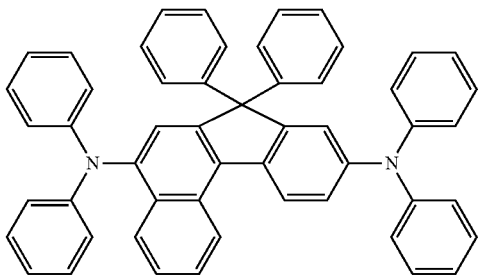

(3-A-2)
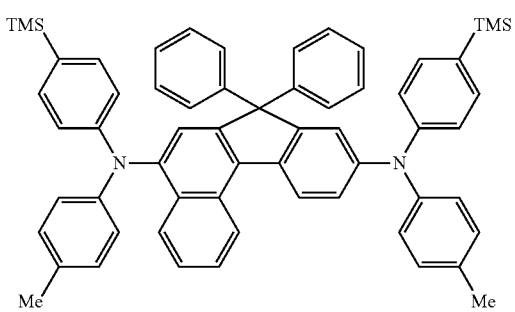

(3-A-3)
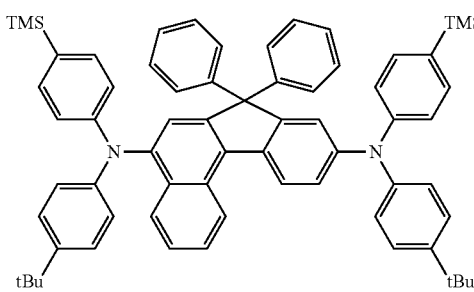

(3-A-4)
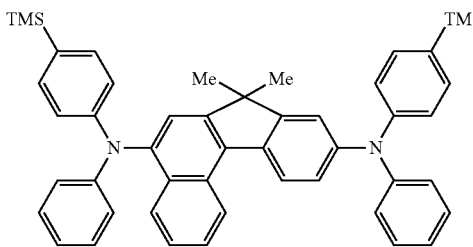

(3-A-5)
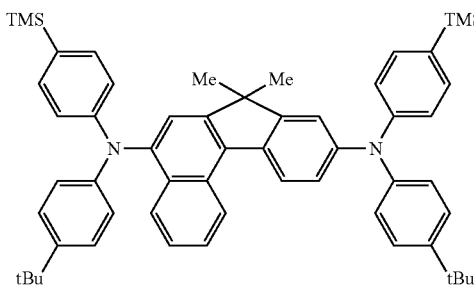

317

-continued (3-B-1)

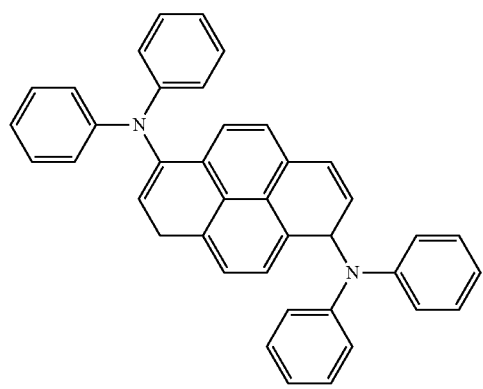

(3-B-2)

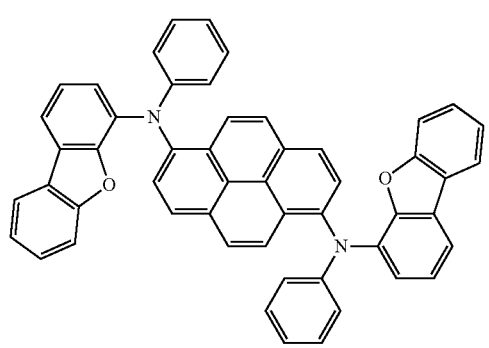

(3-B-3)

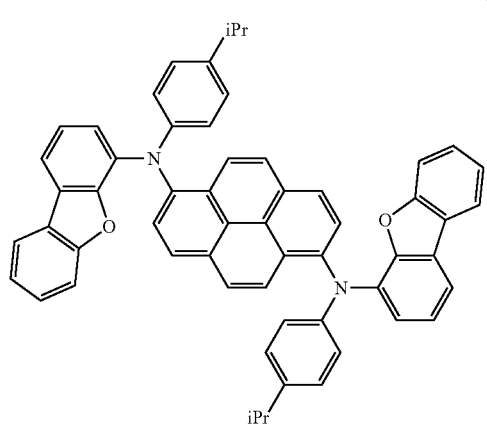

(3-B-4)

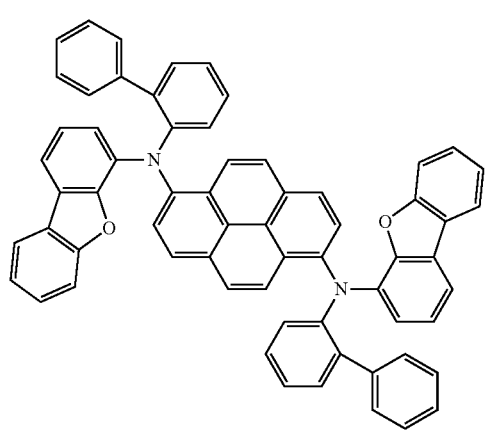

318

-continued (3-C-1)

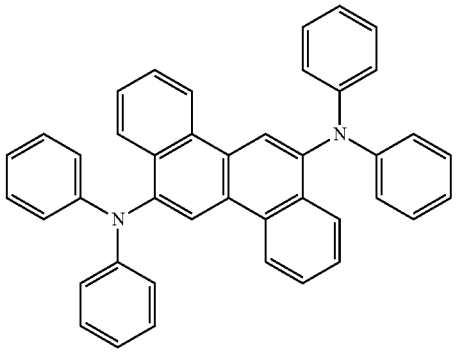

(3-C-2)

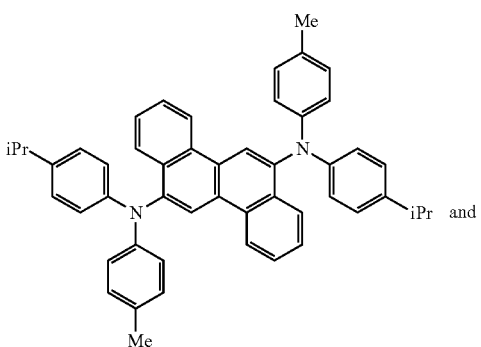

and (3-C-3)

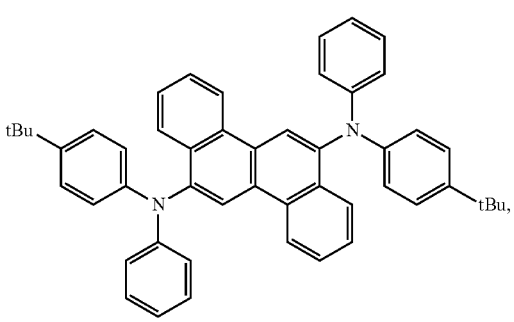

wherein, in the structural formulas, "Me" represents methyl, "iPr" represents isopropyl, "tBu" represents tertiary butyl, and "TMS" represents trimethylsilyl.

16. The organic electroluminescent device according to claim 1, comprising at least one of an electron transport layer and an electron injection layer arranged between the cathode and the luminescent layer, wherein at least one of the electron transport layer and the electron injection layer comprises at least one selected from the group of a borane derivative, a pyridine derivative, a fluoranthene derivative, a BO-based derivative, an anthracene derivative, a benzofluorene derivative, a phosphine oxide derivative, a pyrimidine derivative, a carbazole derivative, a triazine derivative, a benzimidazole derivative, a phenanthroline derivative and a quinolinol-based metal complex, wherein the BO-based derivative is a polycyclic aromatic compound represented by formula (ETM-4) or a multimer of a polycyclic aromatic compound having a plurality of structures represented by formula (ETM-4),

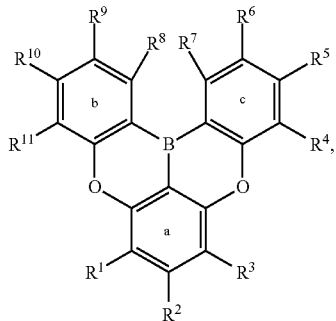

(ETM-4)

wherein $R^1$, $R^2$, $R^3$, $R^4$, $R^5$, $R^6$, $R^7$, $R^8$, $R^9$, $R^{10}$ and $R^{11}$ are independently hydrogen, aryl, heteroaryl, diarylamino, diheteroarylamino, arylheteroarylamino, alkyl, cycloalkyl, alkoxy, trialkylsilyl or aryloxy, and at least one hydrogen in the aryl, heteroaryl, diarylamino, diheteroarylamino, arylheteroarylamino, alkyl, cycloalkyl, alkoxy, trialkylsilyl and aryloxy may be replaced by aryl, heteroaryl or alkyl, and adjacent groups of $R^1$, $R^2$, $R^3$, $R^4$, $R^5$, $R^6$, $R^7$, $R^8$, $R^9$, $R^{10}$ and $R^{11}$ may be bonded to each other to form an aryl ring or a heteroaryl ring together with an a ring, a b ring or a c ring, and at least one hydrogen in the ring formed may be replaced by aryl, heteroaryl, diarylamino, diheteroarylamino, arylheteroarylamino, alkyl, alkoxy or aryloxy, and at least one hydrogen in the aryl, heteroaryl, diarylamino, diheteroarylamino, arylheteroarylamino, alkyl, alkoxy and aryloxy may be replaced by aryl, heteroaryl or alkyl, and at least one hydrogen in the compound represented by formula (ETM-4) may be replaced by halogen or deuterium.

17. The organic electroluminescent device according to claim 16, wherein at least one of the electron transport layer and the electron injection layer further comprises at least one selected from the group consisting of an alkali metal, an alkaline earth metal, a rare earth metal, an oxide of an alkali metal, a halide of an alkali metal, an oxide of an alkaline earth metal, a halide of an alkaline earth metal, an oxide of a rare earth metal, a halide of a rare earth metal, an organic complex of an alkali metal, an organic complex of an alkaline earth metal and an organic complex of a rare earth metal.

18. A display apparatus, comprising the organic electroluminescent device according to claim 1.

19. A lighting apparatus, comprising the organic electroluminescent device according to claim 1.

20. The organic electroluminescent device according to claim 1, wherein the anthracene-based compound is at least one compound represented a structural formula selected from the group consisting of:

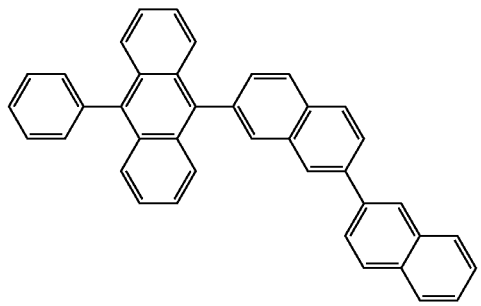

(1-199)

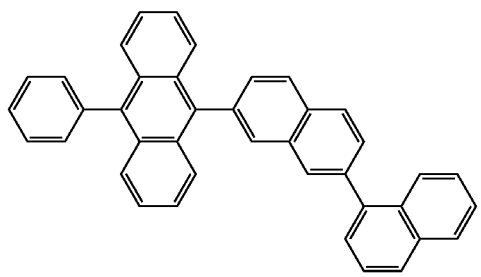

(1-192)

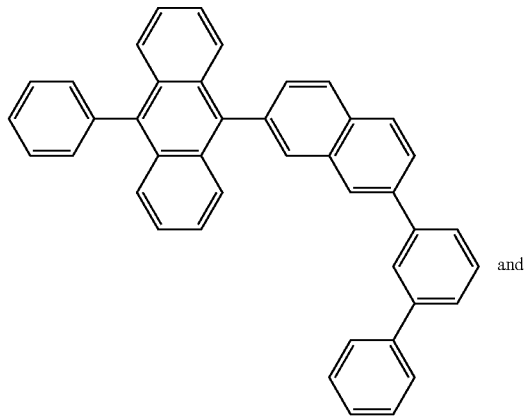

(1-222)

and

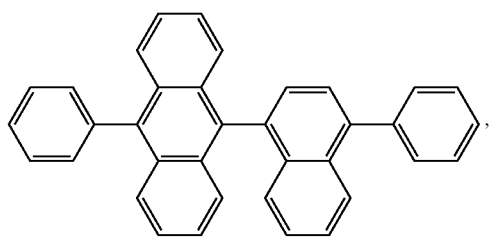

(1-195), and
the dopant material comprises at least one compound represented a structural formula selected from the group consisting of:
(3-41)
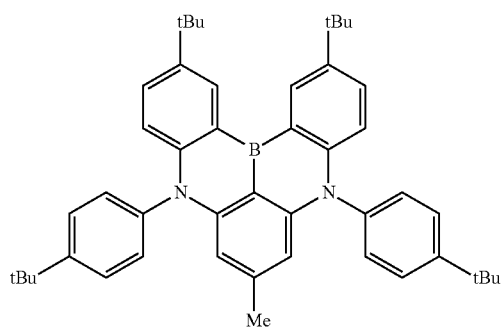
(3-31)
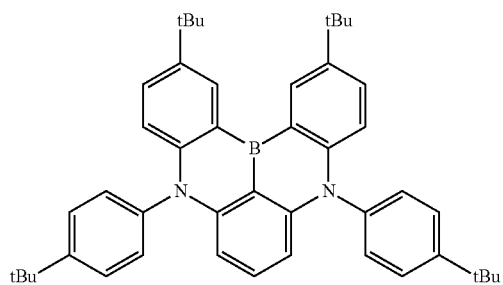
(3-49)
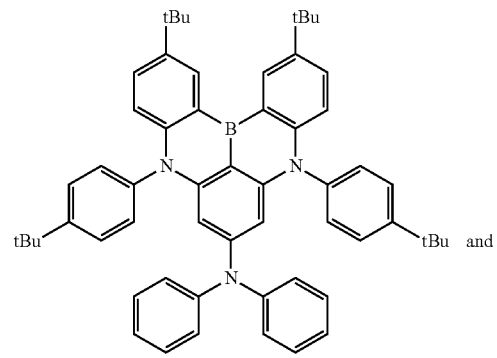
and
(3-B-4)
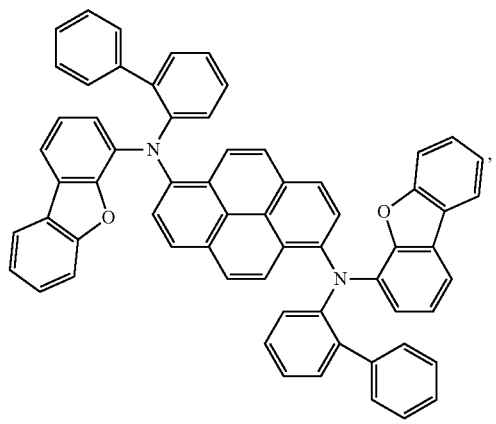
wherein, in the structural formulas, "Me" represents methyl, and "tBu" represents tertiary butyl.
* * * * *